US011300640B2

(12) United States Patent
Dmochowski et al.

(10) Patent No.: US 11,300,640 B2
(45) Date of Patent: Apr. 12, 2022

(54) PROTEIN REPORTERS FOR ULTRASENSITIVE DETECTION METHODS

(71) Applicant: The Trustees of the University of Pennsylvania, Philadelphia, PA (US)

(72) Inventors: Ivan J. Dmochowski, Philadelphia, PA (US); Yanfei Wang, Boston, MA (US); Benjamin W. Roose, Philadelphia, PA (US); Serge Zemerov, Cherry Hill, NJ (US); Zhuangyu Zhao, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/919,566

(22) Filed: Mar. 13, 2018

(65) Prior Publication Data
US 2019/0219646 A1    Jul. 18, 2019

Related U.S. Application Data

(60) Provisional application No. 62/470,704, filed on Mar. 13, 2017.

(51) Int. Cl.
| *A61K 49/00* | (2006.01) |
| *A61K 49/14* | (2006.01) |
| *G01R 33/28* | (2006.01) |
| *C01B 23/00* | (2006.01) |
| *A61K 49/18* | (2006.01) |
| *G01R 33/62* | (2006.01) |
| *G16H 50/20* | (2018.01) |
| *G01R 33/56* | (2006.01) |

(52) U.S. Cl.
CPC ........ *G01R 33/282* (2013.01); *A61K 49/0008* (2013.01); *A61K 49/0056* (2013.01); *A61K 49/14* (2013.01); *A61K 49/183* (2013.01); *C01B 23/0005* (2013.01); *G01R 33/5601* (2013.01); *G01R 33/62* (2013.01); *G16H 50/20* (2018.01)

(58) Field of Classification Search
CPC .... A61K 49/00; A61K 49/14; A61K 49/0008; A61K 49/0056; A61K 2121/00; A61K 2123/00; A61K 49/183; G01R 33/282; G01R 3/5601; G01R 33/62; C01B 23/0005; G16H 50/20
USPC .......... 424/1.11, 1.49, 1.65, 1.69, 1.73, 1.81, 424/1.85, 1.89, 9.1, 9.2, 9.3, 9.4, 9.5, 9.6; 530/300; 514/1, 1.1

See application file for complete search history.

(56) References Cited

U.S. PATENT DOCUMENTS 6,911,307 B1 *  6/2005  Dautel ................ C12Q 1/6897
                                                     435/6.16

OTHER PUBLICATIONS

Salverda et al, FEMS Microbiology Review, vol. 34, pp. 1015-1036 (Year: 2010).*
Antikainen and Martin, 2005, Altering protein specificity: techniques and applications, Bioorg. Med. Chem. 13:2701-2716.
Barsotti and Ipata, 2002, Pathways for alpha-D-ribose utilization for nucleobase salvage and 5-fluorouracil activation in rat brain, Biochem. Pharmacol, 63:117-122.
Benson et al., 2001, Design of Bioelectronic Interfaces by Exploiting Hinge-Bending Motions in Proteins, Science, 293:1641-1644.
Björkman et al., 1994, Probing protein-protein interactions. The ribose-binding protein in bacterial transport and chemotaxis, J. Biol. Chem, 269:30206-30211.
Bonardet et al., 1999, Nuclear Magnetic Resonance of Physisorbed 129Xe Used as a Probe to Investigate Porous Solids, Catal. Rev. Eng., 41:115-225.
Boos et al., 1998, Maltose/maltodextrin system of *Escherichia coli*: transport, metabolism, and regulation, Microbiol Mol Biol Rev, 62(1): 204-229.
Bouabe et al., 2011, Novel Highly Sensitive IL-10-β-Lactamase Reporter Mouse Reveals Cells of the Innate Immune System as a Substantial Source of IL-10 In Vivo, J Immunology, 187(6): 3165-3176.
Bowers et al., 1999, Exploring Surfaces and Cavities in Lipoxygenase and Other Proteins by Hyperpolarized Xenon-129 NMR, J Am Chem Soc, 121:9370-9377.
Bowman and Geissler, 2012, Equilibrium fluctuations of a single folded protein reveal a multitude of potential cryptic allosteric sites, Proc Natl Acad Sci USA, 109(29): 11681-11686.
Clark et al., 2014, Positron emission tomography probe demonstrates a striking concentration of ribose salvage in the liver, Proc. Natl. Acad. Sci. U. S. A. 111:E2866-E2874.
Conn, 1961, Equilibrium distribution of radioxenon in tissue: xenon-hemoglobin association curve, J Appl Physiol, 16:1065-1070.
Desvaux et al., 2005, Dynamics of Xenon Binding Inside the Hydrophobic Cavity of Pseudo-Wild-type Bacteriophage T4 Lysozyme Explored through Xenon-Based NMR Spectroscopy, J Am Chem Soc, 127:11676-11683.
Dubois et al., 2004, Probing the hydrophobic cavity of lipid transfer protein from Nicotiana tabacum through xenon-based NMR spectroscopy, J Am Chem Soc, 126:15738-15746.
Dwyer and Hellinga, 2004, Periplasmic binding proteins: a versatile superfamily for protein engineering, Curr. Opin. Struct. Biol. 14:495-504.
Ewing and Maestas, 1970, The Thermodynamics of Absorption of Xenon by Myoglobin, J Phys Chem, 74:2341-2344.
Fehr et al., 2002, Visualization of maltose uptake in living yeast cells by fluorescent nanosensors, Proc. Natl. Acad. Sci. U. S. A., 99:9846-9851.

(Continued)

*Primary Examiner* — D. L. Jones
(74) *Attorney, Agent, or Firm* — Riverside Law LLP

(57) ABSTRACT

The present invention relates to compositions and methods using protein reporters as imaging agents in ¹²⁹Xe NMR and MRI applications. It is described that bla and MBP are genetically-encoded proteins that induce a detectable chemical shift during ¹²⁹Xe NMR, allowing for use as protein reporters in research and clinical applications.

11 Claims, 61 Drawing Sheets

Specification includes a Sequence Listing.

(56) References Cited

OTHER PUBLICATIONS

Fukami-Kobayashi et al., 1999, Domain dislocation: a change of core structure in periplasmic binding proteins in their evolutionary history, J. Mol. Biol. 286:279-290.
Galarneau et al., 2002, Beta-lactamase protein fragment complementation assays as in vivo and in vitro sensors of protein protein interactions., Nat Biotechnol, 20:619-622.
Gao et al, 2003, Novel Fluorogenic Substrates for Imaging ă-Lactamase Gene Expression, J Am Chem Soc, 125:11146-11147.
Gilad et al., 2007, Artificial reporter gene providing MRI contrast based on proton exchange, Nat Biotech, 25(2): 217-219.
Guntas et al., 2005, Directed evolution of protein switches and their application to the creation of ligand-binding proteins, Proc. Natl. Acad. Sci. U. S. A., 102:11224-11229.
Harding et al., 2005, A B-lactamase with reduced immunogenicity for the targeted delivery of chemotherapeutics using antibody-directed enzyme prodrug therapy, Mol Cancer Ther, 4(11): 1791-1800.
Horn and Shoichet, 2004, Allosteric inhibition through core disruption, J Mol Biol, 336(5): 1283-1291.
Iordanova and Ahrens, 2012, In vivo magnetic resonance imaging of ferritin-based reporter visualizes native neuroblast migration, NeuroImage, 59:1004-1012.
Jelsch et al., 1993, Crystal structure of *Escherichia coli* TEM1 βlactamase at 1.8 Å resolution, 16(4): 364-383.
Kapust et al., 1999, *Escherichia coli* maltose-binding protein is uncommonly effective at promoting the solubility of polypeptides to which it is fusedProtein Sci, 8(8): 1668-1674.
Kather et al., 2008, Increased folding stability of TEM-1 beta-lactamase by in vitro selection, J Mol Biol, 383: 238-251.
Lager et al., 2003, Development of a fluorescent nanosensor for ribose, FEBS Lett, 553:85-89.
Landon et al., 2001, Magnetization transfer from laser-polarized xenon to protons located in the hydrophobic cavity of the wheat nonspecific lipid transfer protein, Prot Sci, 10:762-770.
Lippincott-Schwartz and Patterson, 2003, Development and use of fluorescent protein markers in living cells, Science, 300:87-91.
Lowery et al., 2004, Design of a conformation-sensitive xenon-binding cavity in the ribose-binding protein, Angew Chemie Int Ed, 43(46): 6320-6322.
Lowery et al., 2004, Design of a conformation-sensitive xenon-binding cavity in the ribose-binding protein, Angew. Chem. Int. Ed. Engl, 43:6320-6322.
Marvin and Hellinga, 2001, Conversion of a maltose receptor into a zinc biosensor by computational design, Proc. Natl. Acad. Sci. U. S. A., 98:4955-4960.
Marvin and Hellinga, 2001, Manipulation of ligand binding affinity by exploitation of conformational coupling, Nat. Struct. Biol., 8, 795-798.
Marvin et al., 2011, A genetically encoded, high-signal-to-noise maltose sensor, Proteins, 79:3025-3036.
Matagne et al., 1998, Catalytic properties of class A beta-lactamases: efficiency and diversity, Biochem J, 330:581-598.
McMahon et al., 2016, Cellular and Molecular Imaging Using Chemical Exchange Saturation Transfer, Top Magn Reson Imaging, 25(5): 197-204.
Medintz et al., 2006, Maltose-binding protein: a versatile platform for prototyping biosensing, Curr Opin Biotechnol, 17(1): 17-27.
Moschou et al., 2006, Binding Proteins: Unraveling Their Analytical Potential Anal. Chem. 2006, 78(19), 6692-6700.
Mugler and Altes, 2013, Hyperpolarized 129Xe MRI of the human lung, J Magn Reson Imaging, 37:313-331.
Park et al., 2007, Identification and characterization of human ribokinase and comparison of its properties with *E. coli* ribokinase and human adenosine kinase, FEBS Lett, 581:3211-3216.
Philippon et al., 1998, The diversity, structure and regulation of β-lactamases, Cell Mol Life Sci, 54:341-346.
Prange et al., 1998, Exploring hydrophobic sites in proteins with xenon or krypton, Proteins: Structure, Function, and Genetics, 30:61-73.

Quillin et al., 2002, Generation of noble-gas binding sites for crystallographic phasing using site-directed mutagenesis, Acta Crystallogr Sect D Biol Crystallogr, 58(1): 97-103.
Reuten et al., 2016, Maltose-Binding Protein (MBP), a SecretionEnhancing Tag for Mammalian Protein Expression Systems, PLoS One, 11(3): e0152386.
Riggs, 2000, Expression and purification of recombinant proteins by fusion to maltose-binding protein, Mol Biotechnol, 15(1): 51-63.
Ripmeester et al., 1988, The nuclear magnetic resonance of 129Xe trapped in clathrates and some other solids, J. Chem. Soc. Faraday Trans. 1 Phys. Chem. Condens. Phases, 84:3731-3745.
Rubin et al., 2000, Evidence of nonspecific surface interactions between laser-polarized xenon and myoglobin in solution, Proc Natl Acad Sci USA, 97:9472-9475.
Rubin et al., 2001, Characterization of the Effects of Nonspecific Xenon-Protein Interactions on 129Xe Chemical Shifts in Aqueous Solution: Further Development of Xenon as a Biomolecular Probe, J Magn Reson, 152:79-86.
Rubin et al., 2001, Detection of a conformational change in maltose binding protein by (129)Xe NMR spectroscopy, J Am Chem Soc, 123(35): 8616-8617.
Rubin et al., 2002, Detection and Characterization of Xenon-binding Sites in Proteins by 129Xe NMR Spectroscopy, J Mol Biol, 322:425-440.
Schnurr et al., 2015, Supramolecular Assays for Mapping Enzyme Activity by Displacement-Triggered Change in Hyperpolarized 129Xe Magnetization Transfer NMR Spectroscopy, Angew Chem Int Ed, 13444-13447.
Schroeder et al., 2006, Molecular imaging using a targeted magnetic resonance hyperpolarized biosensor, Science, 314:446-449.
Seo et al., 2014, Protein conformational dynamics dictate the binding affinity for a ligand, Nat. Commun., 5:3724.
Shapiro et al., 2014, Genetically encoded reporters for hyperpolarized xenon magnetic resonance imaging, Nat Chem, 6:629-634.
Sharff et al., 1993, Refined 1.8-A structure reveals the mode of binding of beta-cyclodextrin to the maltodextrin binding protein, Biochemistry, 32(40): 10553-10559.
Spence et al., 2001, Functionalized xenon as a biosensor, Proc Natl Acad Sci USA, 93:10654-10657.
Spotts et al., 2002, Time-lapse imaging of a dynamic phosphorylationdependent protein-protein interaction in mammalian cells, Proc Natl Acad Sci USA, 99(23): 15142-15147.
Swanson et al., 1997, Brain MRI with Laser-Polarized 129Xe, Magn Reson Med, 38:695-698.
Szmelcman et al., 1976, Maltose Transport in *Escherichia coli* K12, Eur J Biochem, 65(1): 13-19.
Taratula and Dmochowski, 2010, Functionalized 129Xe contrast agents for magnetic resonance imaging, Curr Opin Chem Biol, 14:97-104.
Telmer et al., 2003, Insights into the Conformational Equilibria of Maltose-binding Protein by Analysis of High Affinity Mutants, J Biol Chem, 278(36): 34555-34567.
Telmer et al., 2005, Structural studies of an engineered zinc biosensor reveal an unanticipated mode of zinc binding, J Mol Biol, 354:829-840.
Vercillo et al., 2007, Analysis of ligand binding to a ribose biosensor using site-directed mutagenesis and fluorescence spectroscopy, Protein Sci, 16:362-368.
Walker and Happer, 1997, Spin-exchange optical pumping of noble-gas nuclei, Rev Mod Phys, 69:629-642.
Wang and Dmochowski, 2015, Cucurbit[6]uril is an ultrasensitive 129Xe NMR contrast agent, Chem Commun, 51:8982-8985.
Wang et al., 2016, Programming A Molecular Relay for Ultrasensitive Biodetection via 129Xe NMR, Angew Chem Int Ed, 55(5): 1733-1736.
Waugh, 2016, Crystal structures of MBP fusion proteins, Protein Sci, 25(3): 559-571.
Wehrman et al., 2002, Protein-protein interactions monitored in mammalian cells via complementation of Beta-lactamase enzyme fragments, Proc Natl Acad Sci USA, 99(5): 3469-3474.
Whitney et al., 1998, A genome-wide functional assay of signal transduction in living mammalian cells, Nature Biotechnology, 16:1329-1333.

(56) References Cited

OTHER PUBLICATIONS

Willis and Furlong, 1974, Purification and properties of a ribose-binding protein from *Escherichia coli*, J. Biol. Chem. 249:6926-6929.
Wood et al., 2014, New trends and affinity tag designs for recombinant protein purification, Curr Opin Struct Biol, 26(1): 54-61.
Y. Bai, P. A. Hill and I. J. Dmochowski, 2012, Utilizing a Water-Soluble Cryptophane with Fast Xenon Exchange Rates for Picomolar Sensitivity NMR Measurements, Anal. Chem., 84:9935-9941.
Zlokarnik et al., 1998, Quantitation of transcription and clonal selection of single living cells with beta-lactamase as reporter, Science, 279:84-88.
Zlokarnik, 2000, Fusions to beta-lactamase as a reporter for gene expression in live mammalian cells, Methods Enzymol, 326:221-244.

* cited by examiner

**(SEQ ID NO:1) Native sequence of TEM-1 β-lactamase (TEM1) [UniProt ID P62593] expressed in *E. coli*
**
MSIQHFRVALIPFFAAFCLPVFAHPETLVKVKDAEDQLGARVGYIELDLNSGKILESFRPEERFPMMSTFKVLL
CGAVLSRVDAGQEQLGRRIHYSQNDLVEYSPVTEKHLTDGMTVRELCSAAITMSDNTAANLLLTTIGGPKELT
AFLHNMGDHVTRLDRWEPELNEAIPNDERDTTMPAAMATTLRKLLTGELLTLASRQQLIDWMEADKVAGP
LLRSALPAGWFIADKSGAGERGSRGIIAALGPDGKPSRIVVIYTTGSQATMDERNRQIAEIGASLIKHW
Note: residues that can be mutated to produce alternative protein reporters are underlined

(SEQ ID NO:7) Native sequence of mature TEM-1 β-lactamase (TEM1) [UniProt ID P62593] expressed in HEK293T cells
MHPETLVKVKDAEDQLGARVGYIELDLNSGKILESFRPEERFPMMSTFKVLLCGAVLSRVDAGQEQLGRRIH
YSQNDLVEYSPVTEKHLTDGMTVRELCSAAITMSDNTAANLLLTTIGGPKELTAFLHNMGDHVTRLDRWEPE
LNEAIPNDERDTTTPAAMATTLRKLLTGELLTLASRQQLIDWMEADKVAGPLLRSALPAGWFIADKSGAGER
GSRGIIAALGPDGKPSRIVVIYTTGSQATMDERNRQIAEIGASLIKHW

**(SEQ ID NO:8) Native sequence of mature maltose binding protein (MBP) [UniProt ID P0AEX9] expressed in *E. coli*
**
MKIEEGKLVIWINGDKGYNGLAEVGKKFEKDTGIKVTVEHPDKLEEKFPQVAATGDGPDIIFWAHDRFGGYA
QSGLLAEITPDKAFQDKLYPFTWDAVRYNGKLIAYPIAVEALSLIYNKDLLPNPPKTWEEIPALDKELKAKGKSA
LMFNLQEPYFTWPLIAADGGYAFKYENGKYDIKDVGVDNAGAKAGLTFLVDLIKNKHMNADTDYSIAEAAF
NKGETAMTINGPWAWSNIDTSKVNYGVTVLPTFKGQPSKPFVGVLSAGINAASPNKELAKEFLENYLLTDEG
LEAVNKDKPLGAVALKSYEEELAKDPRIAATMENAQKGEIMPNIPQMSAFWYAVRTAVINAASGRQTVDEA
LKDAQT
Note: residues that can be mutated to produce alternative protein reporters are underlined

**(SEQ ID NO:51) Native sequence of mature ribose binding protein (RBP) [UniProt ID P02925] expressed in *E. coli*
**
KDTIALVVSTLNNPFFVSLKDGAQKEADKLGYNLVVLDSQNNPAKELANVQDLTVRGTKILLINPTDSDAVGN
AVKMANQANIPVITLDRQATKGEVVSHIASDNVLGGKIAGDYIAKKAGEGAKVIELQGIAGTSAARERGEGF
QQAVAAHKFNVLASQPADFDRIKGLNVMQNLLTAHPDVQAVFAQNDEMALGALRALQTAGKSDVMVVG
FDGTPDGEKAVNDGKLAATIAQLPDQIGAKGVETADKVLKGEKVQAKYPVDLKLVVKQ
Note: residues that can be mutated to produce alternative protein reporters are underlined

SEQUENCE LISTING

<160> NUMBER OF SEQ ID NOS: 51

<210> SEQ ID NO 1
<211> LENGTH: 286
<212> TYPE: PRT
<213> ORGANISM: Artificial Sequence
<220> FEATURE:
<223> OTHER INFORMATION: Native sequence of TEM-1 beta-lactamase (TEM1)
      [UniProt ID P62593] expressed in E. coli

<400> SEQUENCE: 1

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 2
<211> LENGTH: 286
<212> TYPE: PRT
<213> ORGANISM: Artificial Sequence
<220> FEATURE:
<223> OTHER INFORMATION: TEM-1 beta-lactamase with a I263L mutation
      (mutation at residue 259)

<400> SEQUENCE: 2

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
         50                  55                  60

Pro Met Met Ser Thr Phe Lys Val Leu Leu Cys Gly Ala Val Leu Ser
 65                  70                  75                  80

Arg Val Asp Ala Gly Gln Glu Gln Leu Gly Arg Arg Ile His Tyr Ser
                 85                  90                  95

Gln Asn Asp Leu Val Glu Tyr Ser Pro Val Thr Glu Lys His Leu Thr
                100                 105                 110

Asp Gly Met Thr Val Arg Glu Leu Cys Ser Ala Ala Ile Thr Met Ser
                115                 120                 125

Asp Asn Thr Ala Ala Asn Leu Leu Leu Thr Thr Ile Gly Gly Pro Lys
130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
                180                 185                 190

Thr Gly Glu Leu Leu Thr Leu Ala Ser Arg Gln Gln Leu Ile Asp Trp
                195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Leu Tyr Thr Thr Gly Ser Gln Ala Thr Met Asp Glu Arg Asn
                260                 265                 270

Arg Gln Ile Ala Glu Ile Gly Ala Ser Leu Ile Lys His Trp
                275                 280                 285

<210> SEQ ID NO 3
<211> LENGTH: 286
<212> TYPE: PRT
<213> ORGANISM: Artificial Sequence
<220> FEATURE:
<223> OTHER INFORMATION: TEM-1 beta-lactamase with a I263L and I282A
      mutation (mutations at residues 259 and 278)

<400> SEQUENCE: 3

Met Ser Ile Gln His Phe Arg Val Ala Leu Ile Pro Phe Phe Ala Ala
 1               5                  10                  15

Phe Cys Leu Pro Val Phe Ala His Pro Glu Thr Leu Val Lys Val Lys
                 20                  25                  30

Asp Ala Glu Asp Gln Leu Gly Ala Arg Val Gly Tyr Ile Glu Leu Asp
                 35                  40                  45

Leu Asn Ser Gly Lys Ile Leu Glu Ser Phe Arg Pro Glu Glu Arg Phe
         50                  55                  60

Pro Met Met Ser Thr Phe Lys Val Leu Leu Cys Gly Ala Val Leu Ser
 65                  70                  75                  80

Arg Val Asp Ala Gly Gln Glu Gln Leu Gly Arg Arg Ile His Tyr Ser
                 85                  90                  95

Gln Asn Asp Leu Val Glu Tyr Ser Pro Val Thr Glu Lys His Leu Thr
                100                 105                 110

Asp Gly Met Thr Val Arg Glu Leu Cys Ser Ala Ala Ile Thr Met Ser

```
            115                 120                 125
Asp Asn Thr Ala Ala Asn Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Leu Tyr Thr Thr Gly Ser Gln Ala Thr Met Asp Glu Arg Asn
            260                 265                 270

Arg Gln Ile Ala Glu Ala Gly Ala Ser Leu Ile Lys His Trp
        275                 280                 285

<210> SEQ ID NO 4
<211> LENGTH: 286
<212> TYPE: PRT
<213> ORGANISM: Artificial Sequence
<220> FEATURE:
<223> OTHER INFORMATION: TEM-1 beta-lactamase with a I263N mutation
      (mutation at residue 259)

<400> SEQUENCE: 4

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190
```

Thr Gly Glu Leu Leu Thr Leu Ala Ser Arg Gln Gln Leu Ile Asp Trp
            195                 200                 205

Met Glu Ala Asp Lys Val Ala Gly Pro Leu Leu Arg Ser Ala Leu Pro
        210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Asn Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
            275                 280                 285

<210> SEQ ID NO 5
<211> LENGTH: 286
<212> TYPE: PRT
<213> ORGANISM: Artificial Sequence
<220> FEATURE:
<223> OTHER INFORMATION: TEM-1 beta-lactamase with a I263A mutation
      (mutation at residue 259)

<400> SEQUENCE: 5

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ala Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 6
<211> LENGTH: 286
<212> TYPE: PRT
<213> ORGANISM: Artificial Sequence
<220> FEATURE:
<223> OTHER INFORMATION: TEM-1 beta-lactamase with a I279N mutation
      (mutation at residue 275)

<400> SEQUENCE: 6

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Asn Ala Glu Ile Gly Ala Ser Leu Ile Lys His Trp
        275                 280                 285

<210> SEQ ID NO 7
<211> LENGTH: 264
<212> TYPE: PRT
<213> ORGANISM: Artificial Sequence
<220> FEATURE:
<223> OTHER INFORMATION: Native sequence of mature TEM-1 beta-lactamase
      (TEM1) [UniProt ID P62593] expressed in HEK293T cells

<400> SEQUENCE: 7

Met His Pro Glu Thr Leu Val Lys Val Lys Asp Ala Glu Asp Gln Leu
1               5                   10                  15

Gly Ala Arg Val Gly Tyr Ile Glu Leu Asp Leu Asn Ser Gly Lys Ile
            20                  25                  30

Leu Glu Ser Phe Arg Pro Glu Glu Arg Phe Pro Met Met Ser Thr Phe
        35                  40                  45

Lys Val Leu Leu Cys Gly Ala Val Leu Ser Arg Val Asp Ala Gly Gln
50                  55                  60

Glu Gln Leu Gly Arg Arg Ile His Tyr Ser Gln Asn Asp Leu Val Glu
65                  70                  75                  80

Tyr Ser Pro Val Thr Glu Lys His Leu Thr Asp Gly Met Thr Val Arg
                85                  90                  95

Glu Leu Cys Ser Ala Ala Ile Thr Met Ser Asp Asn Thr Ala Ala Asn
                100                 105                 110

Leu Leu Leu Thr Thr Ile Gly Gly Pro Lys Glu Leu Thr Ala Phe Leu
            115                 120                 125

His Asn Met Gly Asp His Val Thr Arg Leu Asp Arg Trp Glu Pro Glu
        130                 135                 140

Leu Asn Glu Ala Ile Pro Asn Asp Glu Arg Asp Thr Thr Thr Pro Ala
145                 150                 155                 160

Ala Met Ala Thr Thr Leu Arg Lys Leu Leu Thr Gly Glu Leu Leu Thr
                165                 170                 175

Leu Ala Ser Arg Gln Gln Leu Ile Asp Trp Met Glu Ala Asp Lys Val
                180                 185                 190

Ala Gly Pro Leu Leu Arg Ser Ala Leu Pro Ala Gly Trp Phe Ile Ala
            195                 200                 205

Asp Lys Ser Gly Ala Gly Glu Arg Gly Ser Arg Gly Ile Ile Ala Ala
210                 215                 220

Leu Gly Pro Asp Gly Lys Pro Ser Arg Ile Val Val Ile Tyr Thr Thr
225                 230                 235                 240

Gly Ser Gln Ala Thr Met Asp Glu Arg Asn Arg Gln Ile Ala Glu Ile
                245                 250                 255

Gly Ala Ser Leu Ile Lys His Trp
            260

<210> SEQ ID NO 8
<211> LENGTH: 366
<212> TYPE: PRT
<213> ORGANISM: Artificial Sequence
<220> FEATURE:
<223> OTHER INFORMATION: Native sequence of mature maltose binding
      protein (MBP) [UniProt ID P0AEX9] expressed in E. coli

<400> SEQUENCE: 8

Lys Ile Glu Glu Gly Lys Leu Val Ile Trp Ile Asn Gly Asp Lys Gly
1               5                   10                  15

Tyr Asn Gly Leu Ala Glu Val Gly Lys Lys Phe Glu Lys Asp Thr Gly
            20                  25                  30

Ile Lys Val Thr Val Glu His Pro Asp Lys Leu Glu Glu Lys Phe Pro
        35                  40                  45

Gln Val Ala Ala Thr Gly Asp Gly Pro Asp Ile Ile Phe Trp Ala His
50                  55                  60

Asp Arg Phe Gly Gly Tyr Ala Gln Ser Gly Leu Leu Ala Glu Ile Thr
65                  70                  75                  80

Pro Asp Lys Ala Phe Gln Asp Lys Leu Tyr Pro Phe Thr Trp Asp Ala

```
                    85                  90                  95
Val Arg Tyr Asn Gly Lys Leu Ile Ala Tyr Pro Ile Ala Val Glu Ala
                100                 105                 110

Leu Ser Leu Ile Tyr Asn Lys Asp Leu Leu Pro Asn Pro Pro Lys Thr
            115                 120                 125

Trp Glu Glu Ile Pro Ala Leu Asp Lys Glu Leu Lys Ala Lys Gly Lys
        130                 135                 140

Ser Ala Leu Met Phe Asn Leu Gln Glu Pro Tyr Phe Thr Trp Pro Leu
145                 150                 155                 160

Ile Ala Ala Asp Gly Gly Tyr Ala Phe Lys Tyr Glu Asn Gly Lys Tyr
                165                 170                 175

Asp Ile Lys Asp Val Gly Val Asp Asn Ala Gly Ala Lys Ala Gly Leu
            180                 185                 190

Thr Phe Leu Val Asp Leu Ile Lys Asn Lys His Met Asn Ala Asp Thr
        195                 200                 205

Asp Tyr Ser Ile Ala Glu Ala Ala Phe Asn Lys Gly Glu Thr Ala Met
210                 215                 220

Thr Ile Asn Gly Pro Trp Ala Trp Ser Asn Ile Asp Thr Ser Lys Val
225                 230                 235                 240

Asn Tyr Gly Val Thr Val Leu Pro Thr Phe Lys Gly Gln Pro Ser Lys
                245                 250                 255

Pro Phe Val Gly Val Leu Ser Ala Gly Ile Asn Ala Ala Ser Pro Asn
            260                 265                 270

Lys Glu Leu Ala Lys Glu Phe Leu Glu Asn Tyr Leu Leu Thr Asp Glu
        275                 280                 285

Gly Leu Glu Ala Val Asn Lys Asp Lys Pro Leu Gly Ala Val Ala Leu
        290                 295                 300

Lys Ser Tyr Glu Glu Glu Leu Ala Lys Asp Pro Arg Ile Ala Ala Thr
305                 310                 315                 320

Met Glu Asn Ala Gln Lys Gly Glu Ile Met Pro Asn Ile Pro Gln Met
                325                 330                 335

Ser Ala Phe Trp Tyr Ala Val Arg Thr Ala Val Ile Asn Ala Ala Ser
            340                 345                 350

Gly Arg Gln Thr Val Asp Glu Ala Leu Lys Asp Ala Gln Thr
        355                 360                 365

<210> SEQ ID NO 9
<211> LENGTH: 396
<212> TYPE: PRT
<213> ORGANISM: Artificial Sequence
<220> FEATURE:
<223> OTHER INFORMATION: maltose binding protein (MBP) comprising a
      V293L mutation

<400> SEQUENCE: 9

Met Gly Ser Ser His His His His His His Gly Ser Ser Met Lys Ile
1               5                   10                  15

Glu Glu Gly Lys Leu Val Ile Trp Ile Asn Gly Asp Lys Gly Tyr Asn
            20                  25                  30

Gly Leu Ala Glu Val Gly Lys Lys Phe Glu Lys Asp Thr Gly Ile Lys
        35                  40                  45

Val Thr Val Glu His Pro Asp Lys Leu Glu Glu Lys Phe Pro Gln Val
    50                  55                  60

Ala Ala Thr Gly Asp Gly Pro Asp Ile Ile Phe Trp Ala His Asp Arg
65                  70                  75                  80
```

```
Phe Gly Gly Tyr Ala Gln Ser Gly Leu Leu Ala Glu Ile Thr Pro Asp
                85                  90                  95

Lys Ala Phe Gln Asp Lys Leu Tyr Pro Phe Thr Trp Asp Ala Val Arg
            100                 105                 110

Tyr Asn Gly Lys Leu Ile Ala Tyr Pro Ile Ala Val Glu Ala Leu Ser
        115                 120                 125

Leu Ile Tyr Asn Lys Asp Leu Leu Pro Asn Pro Lys Thr Trp Glu
130                 135                 140

Glu Ile Pro Ala Leu Asp Lys Glu Leu Lys Ala Lys Gly Lys Ser Ala
145                 150                 155                 160

Leu Met Phe Asn Leu Gln Glu Pro Tyr Phe Thr Trp Pro Leu Ile Ala
                165                 170                 175

Ala Asp Gly Gly Tyr Ala Phe Lys Tyr Glu Asn Gly Lys Tyr Asp Ile
            180                 185                 190

Lys Asp Val Gly Val Asp Asn Ala Gly Ala Lys Ala Gly Leu Thr Phe
        195                 200                 205

Leu Val Asp Leu Ile Lys Asn Lys His Met Asn Ala Asp Thr Asp Tyr
210                 215                 220

Ser Ile Ala Glu Ala Ala Phe Asn Lys Gly Glu Thr Ala Met Thr Ile
225                 230                 235                 240

Asn Gly Pro Trp Ala Trp Ser Asn Ile Asp Thr Ser Lys Val Asn Tyr
                245                 250                 255

Gly Val Thr Val Leu Pro Thr Phe Lys Gly Gln Pro Ser Lys Pro Phe
            260                 265                 270

Val Gly Val Leu Ser Ala Gly Ile Asn Ala Ala Ser Pro Asn Lys Glu
        275                 280                 285

Leu Ala Lys Glu Phe Leu Glu Asn Tyr Leu Leu Thr Asp Glu Gly Leu
290                 295                 300

Glu Ala Leu Asn Lys Asp Lys Pro Leu Gly Ala Val Ala Leu Lys Ser
305                 310                 315                 320

Tyr Glu Glu Glu Leu Ala Lys Asp Pro Arg Ile Ala Ala Thr Met Glu
                325                 330                 335

Asn Ala Gln Lys Gly Glu Ile Met Pro Asn Ile Pro Gln Met Ser Ala
            340                 345                 350

Phe Trp Tyr Ala Val Arg Thr Ala Val Ile Asn Ala Ala Ser Gly Arg
        355                 360                 365

Gln Thr Val Asp Glu Ala Leu Lys Asp Ala Gln Thr Asn Gly Ile Glu
370                 375                 380

Glu Asn Leu Tyr Phe Gln Ser Asn Ile Gly Ser Gly
385                 390                 395

<210> SEQ ID NO 10
<211> LENGTH: 396
<212> TYPE: PRT
<213> ORGANISM: Artificial Sequence
<220> FEATURE:
<223> OTHER INFORMATION: maltose binding protein (MBP) comprising a
      V293A mutation

<400> SEQUENCE: 10

Met Gly Ser Ser His His His His His Gly Ser Ser Met Lys Ile
1               5                   10                  15

Glu Glu Gly Lys Leu Val Ile Trp Ile Asn Gly Asp Lys Gly Tyr Asn
                20                  25                  30

Gly Leu Ala Glu Val Gly Lys Lys Phe Glu Lys Asp Thr Gly Ile Lys
            35                  40                  45
```

```
Val Thr Val Glu His Pro Asp Lys Leu Glu Glu Lys Phe Pro Gln Val
        50                  55                  60

Ala Ala Thr Gly Asp Gly Pro Asp Ile Ile Phe Trp Ala His Asp Arg
 65                  70                  75                  80

Phe Gly Gly Tyr Ala Gln Ser Gly Leu Leu Ala Glu Ile Thr Pro Asp
                 85                  90                  95

Lys Ala Phe Gln Asp Lys Leu Tyr Pro Phe Thr Trp Asp Ala Val Arg
                100                 105                 110

Tyr Asn Gly Lys Leu Ile Ala Tyr Pro Ile Ala Val Glu Ala Leu Ser
                115                 120                 125

Leu Ile Tyr Asn Lys Asp Leu Leu Pro Asn Pro Lys Thr Trp Glu
130                 135                 140

Glu Ile Pro Ala Leu Asp Lys Glu Leu Lys Ala Lys Gly Lys Ser Ala
145                 150                 155                 160

Leu Met Phe Asn Leu Gln Glu Pro Tyr Phe Thr Trp Pro Leu Ile Ala
                165                 170                 175

Ala Asp Gly Gly Tyr Ala Phe Lys Tyr Glu Asn Gly Lys Tyr Asp Ile
                180                 185                 190

Lys Asp Val Gly Val Asp Asn Ala Gly Ala Lys Ala Gly Leu Thr Phe
                195                 200                 205

Leu Val Asp Leu Ile Lys Asn Lys His Met Asn Ala Asp Thr Asp Tyr
210                 215                 220

Ser Ile Ala Glu Ala Ala Phe Asn Lys Gly Glu Thr Ala Met Thr Ile
225                 230                 235                 240

Asn Gly Pro Trp Ala Trp Ser Asn Ile Asp Thr Ser Lys Val Asn Tyr
                245                 250                 255

Gly Val Thr Val Leu Pro Thr Phe Lys Gly Gln Pro Ser Lys Pro Phe
                260                 265                 270

Val Gly Val Leu Ser Ala Gly Ile Asn Ala Ala Ser Pro Asn Lys Glu
                275                 280                 285

Leu Ala Lys Glu Phe Leu Glu Asn Tyr Leu Leu Thr Asp Glu Gly Leu
290                 295                 300

Glu Ala Ala Asn Lys Asp Lys Pro Leu Gly Ala Val Ala Leu Lys Ser
305                 310                 315                 320

Tyr Glu Glu Glu Leu Ala Lys Asp Pro Arg Ile Ala Ala Thr Met Glu
                325                 330                 335

Asn Ala Gln Lys Gly Glu Ile Met Pro Asn Ile Pro Gln Met Ser Ala
                340                 345                 350

Phe Trp Tyr Ala Val Arg Thr Ala Val Ile Asn Ala Ala Ser Gly Arg
                355                 360                 365

Gln Thr Val Asp Glu Ala Leu Lys Asp Ala Gln Thr Asn Gly Ile Glu
                370                 375                 380

Glu Asn Leu Tyr Phe Gln Ser Asn Ile Gly Ser Gly
385                 390                 395
```

<210> SEQ ID NO 11
<211> LENGTH: 396
<212> TYPE: PRT
<213> ORGANISM: Artificial Sequence
<220> FEATURE:
<223> OTHER INFORMATION: maltose binding protein (MBP) comprising V321A and Q325A mutations

<400> SEQUENCE: 11

```
Met Gly Ser Ser His His His His His His Gly Ser Ser Met Lys Ile
```

```
            1               5                  10                   15
         Glu Glu Gly Lys Leu Val Ile Trp Ile Asn Gly Asp Lys Gly Tyr Asn
                        20                  25                  30

Gly Leu Ala Glu Val Gly Lys Lys Phe Glu Lys Asp Thr Gly Ile Lys
                        35                  40                  45

Val Thr Val Glu His Pro Asp Lys Leu Glu Lys Phe Pro Gln Val
                 50                  55                  60

Ala Ala Thr Gly Asp Gly Pro Asp Ile Ile Phe Trp Ala His Asp Arg
         65                  70                  75                  80

Phe Gly Gly Tyr Ala Gln Ser Gly Leu Leu Ala Glu Ile Thr Pro Asp
                             85                  90                  95

Lys Ala Phe Gln Asp Lys Leu Tyr Pro Phe Thr Trp Asp Ala Val Arg
                         100                 105                 110

Tyr Asn Gly Lys Leu Ile Ala Tyr Pro Ile Ala Val Glu Ala Leu Ser
                         115                 120                 125

Leu Ile Tyr Asn Lys Asp Leu Leu Pro Asn Pro Pro Lys Thr Trp Glu
                         130                 135                 140

Glu Ile Pro Ala Leu Asp Lys Glu Leu Lys Ala Lys Gly Lys Ser Ala
         145                 150                 155                 160

Leu Met Phe Asn Leu Gln Glu Pro Tyr Phe Thr Trp Pro Leu Ile Ala
                         165                 170                 175

Ala Asp Gly Gly Tyr Ala Phe Lys Tyr Glu Asn Gly Lys Tyr Asp Ile
                         180                 185                 190

Lys Asp Val Gly Val Asp Asn Ala Gly Ala Lys Ala Gly Leu Thr Phe
                         195                 200                 205

Leu Val Asp Leu Ile Lys Asn Lys His Met Asn Ala Asp Thr Asp Tyr
                         210                 215                 220

Ser Ile Ala Glu Ala Ala Phe Asn Lys Gly Glu Thr Ala Met Thr Ile
         225                 230                 235                 240

Asn Gly Pro Trp Ala Trp Ser Asn Ile Asp Thr Ser Lys Val Asn Tyr
                         245                 250                 255

Gly Val Thr Val Leu Pro Thr Phe Lys Gly Gln Pro Ser Lys Pro Phe
                         260                 265                 270

Val Gly Val Leu Ser Ala Gly Ile Asn Ala Ala Ser Pro Asn Lys Glu
                         275                 280                 285

Leu Ala Lys Glu Phe Leu Glu Asn Tyr Leu Leu Thr Asp Glu Gly Leu
                         290                 295                 300

Glu Ala Val Asn Lys Asp Lys Pro Leu Gly Ala Val Ala Leu Lys Ser
         305                 310                 315                 320

Tyr Glu Glu Glu Leu Ala Lys Asp Pro Arg Ile Ala Ala Thr Ala Glu
                         325                 330                 335

Asn Ala Ala Lys Gly Glu Ile Met Pro Asn Ile Pro Gln Met Ser Ala
                         340                 345                 350

Phe Trp Tyr Ala Val Arg Thr Ala Val Ile Asn Ala Ala Ser Gly Arg
                         355                 360                 365

Gln Thr Val Asp Glu Ala Leu Lys Asp Ala Gln Thr Asn Gly Ile Glu
                         370                 375                 380

Glu Asn Leu Tyr Phe Gln Ser Asn Ile Gly Ser Gly
         385                 390                 395

<210> SEQ ID NO 12
<211> LENGTH: 367
<212> TYPE: PRT
<213> ORGANISM: Artificial Sequence
```

<220> FEATURE:
<223> OTHER INFORMATION: Native sequence of mature MBP expressed in
      HEK293T cells

<400> SEQUENCE: 12

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr
        355                 360                 365
```

<210> SEQ ID NO 13
<211> LENGTH: 861
<212> TYPE: DNA

<213> ORGANISM: Artificial Sequence
<220> FEATURE:
<223> OTHER INFORMATION: Nucleotide sequence encoding native sequence of
    TEM-1 beta-lactamase (TEM1) [UniProt ID P62593] expressed in E.
    coli

<400> SEQUENCE: 13

```
atgtctatcc agcactttcg cgtcgcgctc attccgttct ttgccgcttt ctgtctgcct    60
gtctttgcac atccggaaac cctggtcaag gttaaagacg ctgaagatca gcttggtgcg   120
cgtgtgggtt acatcgaact ggacctgaat tcgggcaaaa ttctggagag cttccgtcca   180
gaagaacgct tcccgatgat gagcaccttc aaggttctgc tgtgcggtgc ggttctgtcc   240
cgtgttgatg ccggtcaaga gcaactgggt cgccgtattc actatagcca gaatgacctg   300
gtggagtaca gcccggtgac ggagaagcac ctgacggacg gcatgaccgt ccgtgagctg   360
tgctccgcag ccattacgat gtctgacaat actgcggcga acctgttgtt gacgaccatc   420
ggtggcccga agaattgac gcgtttctg cataacatgg gcgatcacgt gactcgcctg   480
gatcgttggg agccggagct gaacgaagcc attccgaatg atgagagaga cacgaccacc   540
ccggcagcga tggcgacgac cctgcgcaag ctgttaaccg gtgagttgct gaccctggca   600
agccgtcaac agctgatcga ttggatggaa gctgacaaag ttgcgggtcc gctgctgcgt   660
agcgcgttgc cggcaggctg gtttatcgcg gacaaaagcg gcgcaggcga gcgtggcagc   720
cgtggtatta tcgccgcact gggtccggac ggtaaaccga gccgcattgt tgtgatctat   780
accaccggta gccaggccac gatggatgag cgtaaccgtc agattgctga aatcggtgcg   840
agcctgatca gcattggta a                                              861
```

<210> SEQ ID NO 14
<211> LENGTH: 795
<212> TYPE: DNA
<213> ORGANISM: Artificial Sequence
<220> FEATURE:
<223> OTHER INFORMATION: Nucleotide sequence encoding native sequence of
    mature TEM-1 beta-lactamase (TEM1) [UniProt ID P62593] expressed
    in HEK293T cells

<400> SEQUENCE: 14

```
atgcatccgg aaaccctcgt gaaggtcaaa gacgcagaag atcaacttgg agccagagtc    60
ggatacattg agctcgacct gaacagcggg aagatcctgg aatcctttcg gcctgaggag   120
cgcttcccga tgatgtccac attcaaagtg ttgctgtgcg gtgccgtgct gtcaagggtg   180
gacgccggac aggagcaact gggtcggcgc attcactact cccaaaacga cctcgtggag   240
tactcccccg tgactgagaa gcacctgacg gacggcatga ctgtgcggga actgtgttcc   300
gcggcgatca ccatgtccga taacaccgcc gccaatttgc tgctgaccac catcggtggc   360
cccaaggagc tgaccgcttt cctgcacaac atgggcgacc acgtgacccg cctggacaga   420
tgggaacccg aactgaacga ggccatcccc aacgatgaac gcgataccac taccccctgct   480
gccatggcaa ccaccctgag gaagctgctg actggcgaac tgctgaccct ggcctcgagg   540
cagcagctga tcgactggat ggaggccgac aaggtcgccg gaccactcct gcgctcagcc   600
cttcctgccg gatggttcat tgcggacaag agcggagccg gagagagagg tcccggggt   660
atcattgcgg cccttggacc agacggaaag ccgtcgcgga tcgtcgtgat ctacaccact   720
gggtcgcagg ctaccatgga cgagcggaat agacagatcg ccgaaattgg cgcctccctc   780
atcaagcact ggtag                                                    795
```

<210> SEQ ID NO 15
<211> LENGTH: 1098
<212> TYPE: DNA
<213> ORGANISM: Artificial Sequence
<220> FEATURE:
<223> OTHER INFORMATION: Nucleotide sequence encoding mature maltose binding protein (MBP) expressed in E. coli

<400> SEQUENCE: 15

```
aaaatcgaag aaggtaaaact ggtaatctgg attaacggcg ataaaggcta taacggtctc      60
gctgaagtcg gtaagaaatt cgagaaagat accggaatta agtcaccgt tgagcatccg       120
gataaactgg aagagaaatt cccacaggtt gcggcaactg gcgatgggcc tgacattatc     180
ttctgggcac acgaccgctt tggtggctac gctcaatctg gcctgttggc tgaaatcacc     240
ccggacaaag cgttccagga caagctgtat ccgtttacct gggatgccgt acgttacaac     300
ggcaagctga ttgcttaccc gatcgctgtt gaagcgttat cgctgattta aacaaagat     360
ctgctgccga cccgccaaa aacctgggaa gagatcccgg cgctggataa agaactgaaa     420
gcgaaaggta gagcgcgct gatgttcaac ctgcaagaac gtacttcac ctggccgctg      480
attgctgctg acggggtta tgcgttcaag tatgaaaacg gcaagtacga cattaaagac     540
gtgggcgtgg ataacgctgg cgcgaaagcg ggtctgacct tcctggttga cctgattaaa     600
aacaaacaca tgaatgcaga caccgattac tccatcgcag aagctgcctt taataaaggc     660
gaaacagcga tgaccatcaa cggcccgtgg gcatggtcca acatcgacac cagcaaagtg     720
aattatggtg taacggtact gccgaccttc aagggtcaac catccaaacc gttcgttggc     780
gtgctgagcg caggtattaa cgccgccagt ccgaacaaag agctggcaaa agagttcctc     840
gaaaactatc tgctgactga tgaaggtctg gaagcggtta taaagacaa accgctgggt     900
gccgtagcgc tgaagtctta cgaggaagag ttggcgaaag atccacgtat tgccgccact     960
atggaaaacg cccagaaagg tgaaatcatg ccgaacatcc gcagatgtc cgctttctgg    1020
tatgccgtgc gtactgcggt gatcaacgcc gccagcggtc gtcagactgt cgatgaagcc    1080
ctgaaagacg cgcagact                                                  1098
```

<210> SEQ ID NO 16
<211> LENGTH: 1107
<212> TYPE: DNA
<213> ORGANISM: Artificial Sequence
<220> FEATURE:
<223> OTHER INFORMATION: Nucleotide sequence encoding mature MBP expressed in HEK293T cells

<400> SEQUENCE: 16

```
atgaagattg aagaggggaa gctcgtgatt tggattaacg gcgacaaggg ctacaacggg      60
ctggccgaag tcgaaagaa attcgaaaag gacactggca tcaaggtcac cgtggaacac     120
ccggacaagc tcgaggaaaa gttcccacaa gtcgccgcta ctggggacgg acccgatatc     180
atcttctggg cccatgatcg cttcggtgga tatgcgcagt ccggtctgtt ggccgaaatc     240
acgcccgata aggccttcca agacaagctg tacccgttta cttgggacgc cgtgcggtac     300
aacggaaagc tcatcgcgta ccccatcgct gtggaagccc ttagcctcat ctacaacaag     360
gatctcctgc ccaaccccc taagacttgg gaagagattc agccctgga caaggaactg     420
aaggccaagg gaaagtccgc cctgatgttc aacttgcaag agccgtactt cacctggcct     480
ctcattgcgg ccgatggggg ttacgccttc aaatatgaga acgggaaata cgacattaag     540
gacgtgggcg tggacaacgc cggagcgaaa gccggcctga ccttcctggt ggacctgatc     600
```

-continued

```
aagaacaagc acatgaacgc cgacaccgac tactccatcg ctgaagcggc cttcaacaag    660
ggcgaaaccg ccatgaccat caatggaccc tgggcatggt ccaacatcga cacctccaag    720
gtcaactacg gcgtcaccgt gctgccgact ttcaagggcc agccttccaa gcctttcgtg    780
ggagtgcttt cggccggcat taacgccgcc agccccaata aggagctggc gaaggagttc    840
cttgagaact acctcctgac cgatgagggt ctggaagccg tgaacaagga caaaccgctg    900
ggagcagtgg ccctgaagtc atacgaagag gaactggcca aggacccgag aatcgcggcc    960
accatggaga acgcgcagaa gggcgaaatc atgccgaaca tcccgcagat gtcggccttt   1020
tggtacgcag tgcggactgc agtgatcaat gctgctagcg gtcgccagac agtggacgaa   1080
gccctgaagg atgcacagac ctgatag                                       1107
```

<210> SEQ ID NO 17
<211> LENGTH: 25
<212> TYPE: DNA
<213> ORGANISM: Artificial Sequence
<220> FEATURE:
<223> OTHER INFORMATION: Site-directed mutagenesis forward primer for
      introduction of a bla I263A mutation

<400> SEQUENCE: 17
gcattgttgt ggcgtatacc accgg                                          25

<210> SEQ ID NO 18
<211> LENGTH: 25
<212> TYPE: DNA
<213> ORGANISM: Artificial Sequence
<220> FEATURE:
<223> OTHER INFORMATION: Site-directed mutagenesis reverse primer for
      introduction of a bla I263A mutation

<400> SEQUENCE: 18
ccggtggtat acgccacaac aatgc                                          25

<210> SEQ ID NO 19
<211> LENGTH: 25
<212> TYPE: DNA
<213> ORGANISM: Artificial Sequence
<220> FEATURE:
<223> OTHER INFORMATION: Site-directed mutagenesis forward primer for
      introduction of a bla I263D mutation

<400> SEQUENCE: 19
gcattgttgt ggactatacc accgg                                          25

<210> SEQ ID NO 20
<211> LENGTH: 25
<212> TYPE: DNA
<213> ORGANISM: Artificial Sequence
<220> FEATURE:
<223> OTHER INFORMATION: Site-directed mutagenesis reverse primer for
      introduction of a bla I263D mutation

<400> SEQUENCE: 20
ccggtggtat agtccacaac aatgc                                          25

<210> SEQ ID NO 21
<211> LENGTH: 36
<212> TYPE: DNA
<213> ORGANISM: Artificial Sequence
<220> FEATURE:
<223> OTHER INFORMATION: Site-directed mutagenesis forward primer for
      introduction of a bla I263N mutation

<400> SEQUENCE: 21
ccgagccgca ttgttgtgaa ctataccacc ggtagc    36

<210> SEQ ID NO 22
<211> LENGTH: 36
<212> TYPE: DNA
<213> ORGANISM: Artificial Sequence
<220> FEATURE:
<223> OTHER INFORMATION: Site-directed mutagenesis reverse primer for
      introduction of a bla I263N mutation

<400> SEQUENCE: 22
gctaccggtg gtatagttca caacaatgcg gctcgg    36

<210> SEQ ID NO 23
<211> LENGTH: 25
<212> TYPE: DNA
<213> ORGANISM: Artificial Sequence
<220> FEATURE:
<223> OTHER INFORMATION: Site-directed mutagenesis forward primer for
      introduction of a bla I263L mutation

<400> SEQUENCE: 23
gcattgttgt gctgtatacc accgg    25

<210> SEQ ID NO 24
<211> LENGTH: 25
<212> TYPE: DNA
<213> ORGANISM: Artificial Sequence
<220> FEATURE:
<223> OTHER INFORMATION: Site-directed mutagenesis reverse primer for
      introduction of a bla I263L mutation

<400> SEQUENCE: 24
ccggtggtat acagcacaac aatgc    25

<210> SEQ ID NO 25
<211> LENGTH: 48
<212> TYPE: DNA
<213> ORGANISM: Artificial Sequence
<220> FEATURE:
<223> OTHER INFORMATION: Site-directed mutagenesis forward primer for
      introduction of a bla I279N mutation

<400> SEQUENCE: 25
gccacgatgg atgagcgtaa ccgtcagaac gctgaaatcg gtgcgagc    48

<210> SEQ ID NO 26
<211> LENGTH: 48
<212> TYPE: DNA
<213> ORGANISM: Artificial Sequence
<220> FEATURE:
<223> OTHER INFORMATION: Site-directed mutagenesis reverse primer for
      introduction of a bla I279N mutation

<400> SEQUENCE: 26
gctcgcaccg atttcagcgt tctgacggtt acgctcatcc atcgtggc    48

<210> SEQ ID NO 27
<211> LENGTH: 27
<212> TYPE: DNA
<213> ORGANISM: Artificial Sequence
<220> FEATURE:
<223> OTHER INFORMATION: Site-directed mutagenesis forward primer for
      introduction of a bla I282A mutation

<400> SEQUENCE: 27
cagattgctg aagccggtgc gagcctg                                          27

<210> SEQ ID NO 28
<211> LENGTH: 27
<212> TYPE: DNA
<213> ORGANISM: Artificial Sequence
<220> FEATURE:
<223> OTHER INFORMATION: Site-directed mutagenesis reverse primer for
      introduction of a bla I282A mutation

<400> SEQUENCE: 28
caggctcgca ccggcttcag caatctg                                          27

<210> SEQ ID NO 29
<211> LENGTH: 33
<212> TYPE: DNA
<213> ORGANISM: Artificial Sequence
<220> FEATURE:
<223> OTHER INFORMATION: Site-directed mutagenesis forward primer for
      introduction of a MBP V293L mutation

<400> SEQUENCE: 29
gaaggtctgg aagcgctgaa taaagacaaa ccg                                   33

<210> SEQ ID NO 30
<211> LENGTH: 33
<212> TYPE: DNA
<213> ORGANISM: Artificial Sequence
<220> FEATURE:
<223> OTHER INFORMATION: Site-directed mutagenesis reverse primer for
      introduction of a MBP V293L mutation

<400> SEQUENCE: 30
cggtttgtct ttattcagcg cttccagacc ttc                                   33

<210> SEQ ID NO 31
<211> LENGTH: 33
<212> TYPE: DNA
<213> ORGANISM: Artificial Sequence
<220> FEATURE:
<223> OTHER INFORMATION: Site-directed mutagenesis forward primer for
      introduction of a MBP V293A mutation

<400> SEQUENCE: 31
gaaggtctgg aagcggcgaa taaagacaaa ccg                                   33

<210> SEQ ID NO 32
<211> LENGTH: 33
<212> TYPE: DNA
<213> ORGANISM: Artificial Sequence
<220> FEATURE:
<223> OTHER INFORMATION: Site-directed mutagenesis reverse primer for
      introduction of a MBP V293A mutation

<400> SEQUENCE: 32
cggtttgtct ttattcgccg cttccagacc ttc                                   33

<210> SEQ ID NO 33
<211> LENGTH: 54
<212> TYPE: DNA
<213> ORGANISM: Artificial Sequence
<220> FEATURE:
<223> OTHER INFORMATION: Site-directed mutagenesis forward primer for
      introduction of a MBP M321A mutation

<400> SEQUENCE: 33
gcgaaagatc cacgtattgc cgccactgcg gaaaacgccc agaaaggtga aatc         54

<210> SEQ ID NO 34
<211> LENGTH: 54
<212> TYPE: DNA
<213> ORGANISM: Artificial Sequence
<220> FEATURE:
<223> OTHER INFORMATION: Site-directed mutagenesis reverse primer for
      introduction of a MBP M321A mutation

<400> SEQUENCE: 34
gatttcacct ttctgggcgt tttccgcagt ggcggcaata cgtggatctt tcgc         54

<210> SEQ ID NO 35
<211> LENGTH: 39
<212> TYPE: DNA
<213> ORGANISM: Artificial Sequence
<220> FEATURE:
<223> OTHER INFORMATION: Site-directed mutagenesis forward primer for
      introduction of a MBP Q325A mutation

<400> SEQUENCE: 35
gccactgcgg aaaacgccgc gaaaggtgaa atcatgccg                          39

<210> SEQ ID NO 36
<211> LENGTH: 39
<212> TYPE: DNA
<213> ORGANISM: Artificial Sequence
<220> FEATURE:
<223> OTHER INFORMATION: Site-directed mutagenesis reverse primer for
      introduction of a MBP Q325A mutation

<400> SEQUENCE: 36
cggcatgatt tcacctttcg cggcgttttc cgcagtggc                          39

<210> SEQ ID NO 37
<211> LENGTH: 39
<212> TYPE: DNA
<213> ORGANISM: Artificial Sequence
<220> FEATURE:
<223> OTHER INFORMATION: Forward primer for MBP-GFP cloning

<400> SEQUENCE: 37
tacttccaat ccaatgcaag caagggcgag gagctgttc                          39

<210> SEQ ID NO 38
<211> LENGTH: 43
<212> TYPE: DNA
<213> ORGANISM: Artificial Sequence
<220> FEATURE:
<223> OTHER INFORMATION: Reverse primer for MBP-GFP cloning

<400> SEQUENCE: 38
ttatccactt ccaatgttat tacttgtaca gctcgtccat gcc                     43

<210> SEQ ID NO 39
<211> LENGTH: 35
<212> TYPE: DNA
<213> ORGANISM: Artificial Sequence
<220> FEATURE:
<223> OTHER INFORMATION: Site-directed mutagenesis forward primer for
      introduction of a MBP I329Y mutation

<400> SEQUENCE: 39
cgcccagaaa ggtgaataca tgccgaacat cccgc                              35

```
<210> SEQ ID NO 40
<211> LENGTH: 35
<212> TYPE: DNA
<213> ORGANISM: Artificial Sequence
<220> FEATURE:
<223> OTHER INFORMATION: Site-directed mutagenesis reverse primer for
      introduction of a MBP I329Y mutation

<400> SEQUENCE: 40
gcgggatgtt cggcatgtat tcacctttct gggcg                              35

<210> SEQ ID NO 41
<211> LENGTH: 29
<212> TYPE: DNA
<213> ORGANISM: Artificial Sequence
<220> FEATURE:
<223> OTHER INFORMATION: Site-directed mutagenesis forward primer for
      introduction of a RBP L19V mutation

<400> SEQUENCE: 41
gttctttgtc tctgtgaagg acggcgcgc                                     29

<210> SEQ ID NO 42
<211> LENGTH: 29
<212> TYPE: DNA
<213> ORGANISM: Artificial Sequence
<220> FEATURE:
<223> OTHER INFORMATION: Site-directed mutagenesis reverse primer for
      introduction of a RBP L19V mutation

<400> SEQUENCE: 42
gcgcgccgtc cttcacagag acaaagaac                                     29

<210> SEQ ID NO 43
<211> LENGTH: 813
<212> TYPE: DNA
<213> ORGANISM: Artificial Sequence
<220> FEATURE:
<223> OTHER INFORMATION: Nucleotide sequence encoding RBP(L19A)

<400> SEQUENCE: 43
aaagatacca tcgcgctggt cgtgagcacc ctgaataacc cgttctttgt ctctgcgaag     60
gacggcgcgc aaaaggaagc cgataaactg gctataaact tggttgtcct ggacagccag    120
aacaacccgg ccaaagaact ggcgaacgtt caagatttga cggtccgtgg caccaagatt    180
ctgctgatca atccgacgga ttcggacgct gtcggcaacg cagtcaaaat ggcaaatcaa    240
gcaaacatcc cggttattac gctggatcgt caagcaacca agggtgaagt tgtgtcccac    300
atcgcgagcg acaatgtgct gggtggcaag attgcgggtg attacattgc aaaaaaagct    360
ggcgagggtg ccaaggttat tgagttgcag ggtatcgcgg gtaccagcgc tgcgcgcgag    420
cgcggcgagg gtttccaaca agctgttgcg gcacataagt ttaacgtttt ggcaagccag    480
ccggctgact cgaccgtat caagggcctg aatgtaatgc agaatctgct gaccgcccac    540
ccagacgtgc aagccgtgtt tgcccagaat gatgaaatgg cgctgggcgc gctgcgtgca    600
ctgcaaacgg ctggtaagtc cgatgtgatg gttgtgggtt tcgacggtac cccggatggt    660
gaaaaagccg ttaatgacgg taaactggcg gcgacgattg cacaactgcc ggaccagatc    720
ggtgcgaagg tgtggagac tgcggataaa gtgctgaagg gcgaaaaagt ccaagcgaaa    780
taccctgtgg acctgaaact ggttgtcaaa cag                                813

<210> SEQ ID NO 44
<211> LENGTH: 271
```

```
<212> TYPE: PRT
<213> ORGANISM: Artificial Sequence
<220> FEATURE:
<223> OTHER INFORMATION: Amino acid sequence of RBP(L19A)

<400> SEQUENCE: 44

Lys Asp Thr Ile Ala Leu Val Val Ser Thr Leu Asn Asn Pro Phe Phe
1               5                   10                  15

Val Ser Ala Lys Asp Gly Ala Gln Lys Glu Ala Asp Lys Leu Gly Tyr
            20                  25                  30

Asn Leu Val Val Leu Asp Ser Gln Asn Asn Pro Ala Lys Glu Leu Ala
        35                  40                  45

Asn Val Gln Asp Leu Thr Val Arg Gly Thr Lys Ile Leu Leu Ile Asn
    50                  55                  60

Pro Thr Asp Ser Asp Ala Val Gly Asn Ala Val Lys Met Ala Asn Gln
65                  70                  75                  80

Ala Asn Ile Pro Val Ile Thr Leu Asp Arg Gln Ala Thr Lys Gly Glu
                85                  90                  95

Val Val Ser His Ile Ala Ser Asp Asn Val Leu Gly Gly Lys Ile Ala
            100                 105                 110

Gly Asp Tyr Ile Ala Lys Lys Ala Gly Glu Gly Ala Lys Val Ile Glu
        115                 120                 125

Leu Gln Gly Ile Ala Gly Thr Ser Ala Ala Arg Glu Arg Gly Glu Gly
    130                 135                 140

Phe Gln Gln Ala Val Ala Ala His Lys Phe Asn Val Leu Ala Ser Gln
145                 150                 155                 160

Pro Ala Asp Phe Asp Arg Ile Lys Gly Leu Asn Val Met Gln Asn Leu
                165                 170                 175

Leu Thr Ala His Pro Asp Val Gln Ala Val Phe Ala Gln Asn Asp Glu
            180                 185                 190

Met Ala Leu Gly Ala Leu Arg Ala Leu Gln Thr Ala Gly Lys Ser Asp
        195                 200                 205

Val Met Val Val Gly Phe Asp Gly Thr Pro Asp Gly Glu Lys Ala Val
    210                 215                 220

Asn Asp Gly Lys Leu Ala Ala Thr Ile Ala Gln Leu Pro Asp Gln Ile
225                 230                 235                 240

Gly Ala Lys Gly Val Glu Thr Ala Asp Lys Val Leu Lys Gly Glu Lys
                245                 250                 255

Val Gln Ala Lys Tyr Pro Val Asp Leu Lys Leu Val Val Lys Gln
            260                 265                 270

<210> SEQ ID NO 45
<211> LENGTH: 13
<212> TYPE: PRT
<213> ORGANISM: Artificial Sequence
<220> FEATURE:
<223> OTHER INFORMATION: His tag

<400> SEQUENCE: 45

Met Gly Ser Ser His His His His His His Gly Ser Ser
1               5                   10

<210> SEQ ID NO 46
<211> LENGTH: 534
<212> TYPE: PRT
<213> ORGANISM: Artificial Sequence
<220> FEATURE:
<223> OTHER INFORMATION: Amino acid sequence of GFP-RBP(L19A) fusion
      reporter protein
```

<400> SEQUENCE: 46

| | | | | | | | | | | | | | | |
|---|---|---|---|---|---|---|---|---|---|---|---|---|---|---|
| Met | Gly | Ser | Ser | His | His | His | His | His | Gly | Ser | Ser | Val | Ser | Lys |
| 1 | | | | 5 | | | | | 10 | | | | | 15 |
| Gly | Glu | Glu | Leu | Phe | Thr | Gly | Val | Val | Pro | Ile | Leu | Val | Glu | Leu | Asp |
| | | | 20 | | | | | 25 | | | | | 30 | | |
| Gly | Asp | Val | Asn | Gly | His | Lys | Phe | Ser | Val | Arg | Gly | Glu | Gly | Glu | Gly |
| | | | 35 | | | | | 40 | | | | | 45 | | |
| Asp | Ala | Thr | Asn | Gly | Lys | Leu | Thr | Leu | Lys | Phe | Ile | Cys | Thr | Thr | Gly |
| | 50 | | | | | 55 | | | | | 60 | | | | |
| Lys | Leu | Pro | Val | Pro | Trp | Pro | Thr | Leu | Val | Thr | Thr | Leu | Thr | Tyr | Gly |
| 65 | | | | | 70 | | | | | 75 | | | | | 80 |
| Val | Gln | Cys | Phe | Ser | Arg | Tyr | Pro | Asp | His | Met | Lys | Gln | His | Asp | Phe |
| | | | | 85 | | | | | 90 | | | | | 95 | |
| Phe | Lys | Ser | Ala | Met | Pro | Glu | Gly | Tyr | Val | Gln | Glu | Arg | Thr | Ile | Ser |
| | | | | 100 | | | | | 105 | | | | | 110 | |
| Phe | Lys | Asp | Asp | Gly | Thr | Tyr | Lys | Thr | Arg | Ala | Glu | Val | Lys | Phe | Glu |
| | | | | 115 | | | | | 120 | | | | | 125 | |
| Gly | Asp | Thr | Leu | Val | Asn | Arg | Ile | Glu | Leu | Lys | Gly | Ile | Asp | Phe | Lys |
| | | | 130 | | | | | 135 | | | | | 140 | | |
| Glu | Asp | Gly | Asn | Ile | Leu | Gly | His | Lys | Leu | Glu | Tyr | Asn | Phe | Asn | Ser |
| 145 | | | | | 150 | | | | | 155 | | | | | 160 |
| His | Asn | Val | Tyr | Ile | Thr | Ala | Asp | Lys | Gln | Lys | Asn | Gly | Ile | Lys | Ala |
| | | | | 165 | | | | | 170 | | | | | 175 | |
| Asn | Phe | Lys | Ile | Arg | His | Asn | Val | Glu | Asp | Gly | Ser | Val | Gln | Leu | Ala |
| | | | 180 | | | | | 185 | | | | | 190 | | |
| Asp | His | Tyr | Gln | Gln | Asn | Thr | Pro | Ile | Gly | Asp | Gly | Pro | Val | Leu | Leu |
| | | | 195 | | | | | 200 | | | | | 205 | | |
| Pro | Asp | Asn | His | Tyr | Leu | Ser | Thr | Gln | Ser | Lys | Leu | Ser | Lys | Asp | Pro |
| | 210 | | | | | 215 | | | | | 220 | | | | |
| Asn | Glu | Lys | Arg | Asp | His | Met | Val | Leu | Leu | Glu | Phe | Val | Thr | Ala | Ala |
| 225 | | | | | 230 | | | | | 235 | | | | | 240 |
| Gly | Ile | Thr | Leu | Gly | Met | Asp | Glu | Leu | Tyr | Lys | Gly | Ile | Glu | Glu | Asn |
| | | | | 245 | | | | | 250 | | | | | 255 | |
| Leu | Tyr | Phe | Gln | Ser | Asn | Ala | Lys | Asp | Thr | Ile | Ala | Leu | Val | Val | Ser |
| | | | | 260 | | | | | 265 | | | | | 270 | |
| Thr | Leu | Asn | Asn | Pro | Phe | Phe | Val | Ser | Ala | Lys | Asp | Gly | Ala | Gln | Lys |
| | | | 275 | | | | | 280 | | | | | 285 | | |
| Glu | Ala | Asp | Lys | Leu | Gly | Tyr | Asn | Leu | Val | Val | Leu | Asp | Ser | Gln | Asn |
| | 290 | | | | | 295 | | | | | 300 | | | | |
| Asn | Pro | Ala | Lys | Glu | Leu | Ala | Asn | Val | Gln | Asp | Leu | Thr | Val | Arg | Gly |
| 305 | | | | | 310 | | | | | 315 | | | | | 320 |
| Thr | Lys | Ile | Leu | Leu | Ile | Asn | Pro | Thr | Asp | Ser | Asp | Ala | Val | Gly | Asn |
| | | | | 325 | | | | | 330 | | | | | 335 | |
| Ala | Val | Lys | Met | Ala | Asn | Gln | Ala | Asn | Ile | Pro | Val | Ile | Thr | Leu | Asp |
| | | | 340 | | | | | 345 | | | | | 350 | | |
| Arg | Gln | Ala | Thr | Lys | Gly | Glu | Val | Val | Ser | His | Ile | Ala | Ser | Asp | Asn |
| | | | 355 | | | | | 360 | | | | | 365 | | |
| Val | Leu | Gly | Gly | Lys | Ile | Ala | Gly | Asp | Tyr | Ile | Ala | Lys | Lys | Ala | Gly |
| | | | 370 | | | | | 375 | | | | | 380 | | |
| Glu | Gly | Ala | Lys | Val | Ile | Glu | Leu | Gln | Gly | Ile | Ala | Gly | Thr | Ser | Ala |
| 385 | | | | | 390 | | | | | 395 | | | | | 400 |
| Ala | Arg | Glu | Arg | Gly | Glu | Gly | Phe | Gln | Gln | Ala | Val | Ala | Ala | His | Lys |

```
                405                 410                 415
Phe Asn Val Leu Ala Ser Gln Pro Ala Asp Phe Asp Arg Ile Lys Gly
        420                 425                 430

Leu Asn Val Met Gln Asn Leu Leu Thr Ala His Pro Asp Val Gln Ala
        435                 440                 445

Val Phe Ala Gln Asn Asp Glu Met Ala Leu Gly Ala Leu Arg Ala Leu
    450                 455                 460

Gln Thr Ala Gly Lys Ser Asp Val Met Val Gly Phe Asp Gly Thr
465                 470                 475                 480

Pro Asp Gly Glu Lys Ala Val Asn Asp Gly Lys Leu Ala Ala Thr Ile
                485                 490                 495

Ala Gln Leu Pro Asp Gln Ile Gly Ala Lys Gly Val Glu Thr Ala Asp
            500                 505                 510

Lys Val Leu Lys Gly Glu Lys Val Gln Ala Lys Tyr Pro Val Asp Leu
        515                 520                 525

Lys Leu Val Val Lys Gln
    530
```

<210> SEQ ID NO 47
<211> LENGTH: 1602
<212> TYPE: DNA
<213> ORGANISM: Artificial Sequence
<220> FEATURE:
<223> OTHER INFORMATION: nucleotide sequence encoding a GFP-RBP(L19A)
      fusion reporter protein

<400> SEQUENCE: 47

| | | |
|---|---|---|
| atgggttctt ctcaccatca ccatcaccat ggttcttctg tgagcaaggg cgaggagctg | 60 |
| ttcaccgggg tggtgcccat cctggtcgag ctggacggcg acgtaaacgg ccacaagttc | 120 |
| agcgtgcgcg gcgagggcga gggcgatgcc accaacggca agctgaccct gaagttcatc | 180 |
| tgcaccaccg gcaagctgcc cgtgccctgg cccaccctcg tgaccaccct gacctacggc | 240 |
| gtgcagtgct tcagccgcta ccccgaccac atgaagcagc acgacttctt caagtccgcc | 300 |
| atgcccgaag gctacgtcca ggagcgcacc atctccttca aggacgacgg cacctacaag | 360 |
| acccgcgccg aggtgaagtt cgagggcgac accctggtga accgcatcga gctgaagggc | 420 |
| atcgacttca aggaggacgg caacatcctg ggcacaagc tggagtacaa cttcaacagc | 480 |
| cacaacgtct atatcacggc cgacaagcag aagaacggca tcaaggcgaa cttcaagatc | 540 |
| cgccacaacg tcgaggacgg cagcgtgcag ctcgccgacc actaccagca gaacaccccc | 600 |
| atcggcgacg gccccgtgct gctgcccgac aaccactacc tgagcaccca gtccaagctg | 660 |
| agcaaagacc ccaacgagaa gcgcgatcac atggtcctgc tggagttcgt gaccgccgcc | 720 |
| gggatcactc tcggcatgga cgagctgtac aaggggatcg aggaaaacct gtacttccaa | 780 |
| tccaatgcaa agataccat cgcgctggtc gtgagcaccc tgaataaccc gttctttgtc | 840 |
| tctgcgaagg acgcgcgca aaaggaagcc gataaactgg ctataacttg gttgtcctg | 900 |
| gacagccaga caacccggc caaagaactg gcgaacgttc aagatttgac ggtccgtggc | 960 |
| accaagattc tgctgatcaa tccgacggat tcggacgctg tcggcaacgc agtcaaaatg | 1020 |
| gcaaatcaag caaacatccc ggttattacg ctggatcgtc aagcaaccaa gggtgaagtt | 1080 |
| gtgtcccaca tcgcgagcga caatgtgctg ggtggcaaga ttgcgggtga ttacattgca | 1140 |
| aaaaagctg gcgagggtgc caaggttatt gagttcaggg tatcgcgggg taccagcgct | 1200 |
| gcgcgcgagc gcggcgaggg tttccaacaa gctgttgcgg cacataagtt taacgttttg | 1260 |

-continued

```
gcaagccagc cggctgactt cgaccgtatc aagggcctga atgtaatgca gaatctgctg   1320
accgcccacc cagacgtgca agccgtgttt gcccagaatg atgaaatggc gctgggcgcg   1380
ctgcgtgcac tgcaaacggc tggtaagtcc gatgtgatgg ttgtgggttt cgacggtacc   1440
ccggatggtg aaaagccgt taatgacggt aaactggcgg cgacgattgc acaactgccg    1500
gaccagatcg gtgcgaaggg tgtggagact gcggataaag tgctgaaggg cgaaaaagtc   1560
caagcgaaat accctgtgga cctgaaactg gttgtcaaac ag                      1602
```

<210> SEQ ID NO 48
<211> LENGTH: 25
<212> TYPE: PRT
<213> ORGANISM: Artificial Sequence
<220> FEATURE:
<223> OTHER INFORMATION: MBP leader sequence

<400> SEQUENCE: 48

Met Asn Met Lys Lys Leu Ala Thr Leu Val Ser Ala Val Ala Leu Ser
1               5                   10                  15

Ala Thr Val Ser Ala Asn Ala Met Ala
            20                  25

<210> SEQ ID NO 49
<211> LENGTH: 396
<212> TYPE: PRT
<213> ORGANISM: Artificial Sequence
<220> FEATURE:
<223> OTHER INFORMATION: Amino acid sequence of MBP for expression in E.
      coli

<400> SEQUENCE: 49

Met Gly Ser Ser His His His His His His Gly Ser Ser Met Lys Ile
1               5                   10                  15

Glu Glu Gly Lys Leu Val Ile Trp Ile Asn Gly Asp Lys Gly Tyr Asn
            20                  25                  30

Gly Leu Ala Glu Val Gly Lys Lys Phe Glu Lys Asp Thr Gly Ile Lys
        35                  40                  45

Val Thr Val Glu His Pro Asp Lys Leu Glu Glu Lys Phe Pro Gln Val
    50                  55                  60

Ala Ala Thr Gly Asp Gly Pro Asp Ile Ile Phe Trp Ala His Asp Arg
65                  70                  75                  80

Phe Gly Gly Tyr Ala Gln Ser Gly Leu Leu Ala Glu Ile Thr Pro Asp
                85                  90                  95

Lys Ala Phe Gln Asp Lys Leu Tyr Pro Phe Thr Trp Asp Ala Val Arg
            100                 105                 110

Tyr Asn Gly Lys Leu Ile Ala Tyr Pro Ile Ala Val Glu Ala Leu Ser
        115                 120                 125

Leu Ile Tyr Asn Lys Asp Leu Leu Pro Asn Pro Pro Lys Thr Trp Glu
    130                 135                 140

Glu Ile Pro Ala Leu Asp Lys Glu Leu Lys Ala Lys Gly Lys Ser Ala
145                 150                 155                 160

Leu Met Phe Asn Leu Gln Glu Pro Tyr Phe Thr Trp Pro Leu Ile Ala
                165                 170                 175

Ala Asp Gly Gly Tyr Ala Phe Lys Tyr Glu Asn Gly Lys Tyr Asp Ile
            180                 185                 190

Lys Asp Val Gly Val Asp Asn Ala Gly Ala Lys Ala Gly Leu Thr Phe
        195                 200                 205

Leu Val Asp Leu Ile Lys Asn Lys His Met Asn Ala Asp Thr Asp Tyr

```
                210                 215                 220
Ser Ile Ala Glu Ala Ala Phe Asn Lys Gly Glu Thr Ala Met Thr Ile
225                 230                 235                 240

Asn Gly Pro Trp Ala Trp Ser Asn Ile Asp Thr Ser Lys Val Asn Tyr
            245                 250                 255

Gly Val Thr Val Leu Pro Thr Phe Lys Gly Gln Pro Ser Lys Pro Phe
                260                 265                 270

Val Gly Val Leu Ser Ala Gly Ile Asn Ala Ala Ser Pro Asn Lys Glu
            275                 280                 285

Leu Ala Lys Glu Phe Leu Glu Asn Tyr Leu Leu Thr Asp Glu Gly Leu
                290                 295                 300

Glu Ala Ala Asn Lys Asp Lys Pro Leu Gly Ala Val Ala Leu Lys Ser
305                 310                 315                 320

Tyr Glu Glu Glu Leu Ala Lys Asp Pro Arg Ile Ala Ala Thr Met Glu
                325                 330                 335

Asn Ala Gln Lys Gly Glu Ile Met Pro Asn Ile Pro Gln Met Ser Ala
            340                 345                 350

Phe Trp Tyr Ala Val Arg Thr Ala Val Ile Asn Ala Ala Ser Gly Arg
                355                 360                 365

Gln Thr Val Asp Glu Ala Leu Lys Asp Ala Gln Thr Asn Gly Ile Glu
            370                 375                 380

Glu Asn Leu Tyr Phe Gln Ser Asn Ile Gly Ser Gly
385                 390                 395
```

<210> SEQ ID NO 50
<211> LENGTH: 1191
<212> TYPE: DNA
<213> ORGANISM: Artificial Sequence
<220> FEATURE:
<223> OTHER INFORMATION: Nucleotide sequence of MBP for expression in E. coli

<400> SEQUENCE: 50

```
atgggttctt ctcaccatca ccatcaccat ggttcttcta tgaaaatcga agaaggtaaa    60
ctggtaatct ggattaacgg cgataaaggc tataacggtc tcgctgaagt cggtaagaaa   120
ttcgagaaag ataccggaat taaagtcacc gttgagcatc cggataaact ggaagagaaa   180
ttcccacagg ttgcggcaac tggcgatggc cctgacatta tcttctgggc acacgaccgc   240
tttggtggct acgctcaatc tggcctgttg gctgaaatca ccccggacaa agcgttccag   300
gacaagctgt atccgtttac ctgggatgcc gtacgttaca acggcaagct gattgcttac   360
ccgatcgctg ttgaagcgtt atcgctgatt tataacaaag atctgctgcc gaacccgcca   420
aaaacctggg aagagatccc ggcgctggat aaagaactga agcgaaaggt aagagcgcg    480
ctgatgttca acctgcaaga accgtacttc acctggccgc tgattgctgc tgacggggggt   540
tatgcgttca gtatgaaaaa cggcaagtac gacattaaag acgtgggcgt ggataacgct   600
ggcgcgaaag cgggtctgac cttcctggtt gacctgatta aaaacaaaca catgaatgca   660
gacaccgatt actccatcgc agaagctgcc tttaataaag gcgaaacagc gatgaccatc   720
aacggcccgt gggcatggtc caacatcgac accagcaaag tgaattatgg tgtaacggta   780
ctgccgacct tcaagggtca accatccaaa ccgttcgttg gcgtgctgag cgcaggtatt   840
aacgccgcca gtccgaacaa agagctggca aaagagttcc tcgaaaacta tctgctgact   900
gatgaaggtc tggaagcggt taataaagac aaaccgctgg gtgccgtagc gctgaagtct   960
tacgaggaag agttggcgaa agatccacgt attgccgcca ctatggaaaa cgcccagaaa  1020
```

```
ggtgaaatca tgccgaacat cccgcagatg tccgctttct ggtatgccgt gcgtactgcg    1080
gtgatcaacg ccgccagcgg tcgtcagact gtcgatgaag ccctgaaaga cgcgcagact    1140
aatgggatcg aggaaaacct gtacttccaa tccaatattg gaagtggata a             1191

<210> SEQ ID NO 51
<211> LENGTH: 271
<212> TYPE: PRT
<213> ORGANISM: Artificial Sequence
<220> FEATURE:
<223> OTHER INFORMATION: Native amino acid sequence of RBP for
      expression in E. coli

<400> SEQUENCE: 51

Lys Asp Thr Ile Ala Leu Val Val Ser Thr Leu Asn Asn Pro Phe Phe
1               5                   10                  15

Val Ser Leu Lys Asp Gly Ala Gln Lys Glu Ala Asp Lys Leu Gly Tyr
            20                  25                  30

Asn Leu Val Val Leu Asp Ser Gln Asn Asn Pro Ala Lys Glu Leu Ala
        35                  40                  45

Asn Val Gln Asp Leu Thr Val Arg Gly Thr Lys Ile Leu Leu Ile Asn
    50                  55                  60

Pro Thr Asp Ser Asp Ala Val Gly Asn Ala Val Lys Met Ala Asn Gln
65                  70                  75                  80

Ala Asn Ile Pro Val Ile Thr Leu Asp Arg Gln Ala Thr Lys Gly Glu
                85                  90                  95

Val Val Ser His Ile Ala Ser Asp Asn Val Leu Gly Gly Lys Ile Ala
            100                 105                 110

Gly Asp Tyr Ile Ala Lys Lys Ala Gly Glu Gly Ala Lys Val Ile Glu
        115                 120                 125

Leu Gln Gly Ile Ala Gly Thr Ser Ala Ala Arg Glu Arg Gly Glu Gly
    130                 135                 140

Phe Gln Gln Ala Val Ala Ala His Lys Phe Asn Val Leu Ala Ser Gln
145                 150                 155                 160

Pro Ala Asp Phe Asp Arg Ile Lys Gly Leu Asn Val Met Gln Asn Leu
                165                 170                 175

Leu Thr Ala His Pro Asp Val Gln Ala Val Phe Ala Gln Asn Asp Glu
            180                 185                 190

Met Ala Leu Gly Ala Leu Arg Ala Leu Gln Thr Ala Gly Lys Ser Asp
        195                 200                 205

Val Met Val Val Gly Phe Asp Gly Thr Pro Asp Gly Glu Lys Ala Val
    210                 215                 220

Asn Asp Gly Lys Leu Ala Ala Thr Ile Ala Gln Leu Pro Asp Gln Ile
225                 230                 235                 240

Gly Ala Lys Gly Val Glu Thr Ala Asp Lys Val Leu Lys Gly Glu Lys
                245                 250                 255

Val Gln Ala Lys Tyr Pro Val Asp Leu Lys Leu Val Val Lys Gln
            260                 265                 270
```

PROTEIN REPORTERS FOR ULTRASENSITIVE DETECTION METHODS

CROSS REFERENCE TO RELATED APPLICATIONS

This application claims priority to U.S. Provisional Application No. 62/470,704, filed Mar. 13, 2017 which is hereby incorporated by reference herein in its entirety.

STATEMENT REGARDING FEDERALLY SPONSORED RESEARCH OR DEVELOPMENT

This invention was made with government support under RO 1 GM097478 awarded by the National Institutes of Health. The government has certain rights in the invention.

BACKGROUND OF THE INVENTION

Genetically encoded optical reporters such as green fluorescent protein (GFP) have enabled biomolecular imaging, making it possible to connect cellular processes with quantitative, real-time measurements of localized gene expression (Lippincott-Schwartz and Patterson, 2003, Science, 300(5616): 87-91). However, owing to the strong scattering of light by living tissue, optical reporters are mostly limited to studies of single cells and transparent, model organisms. Alternate non-invasive imaging methods such as magnetic resonance imaging (MRI) are thus needed for monitoring gene expression and tracking cell migration in larger organisms (Iordanova and Ahrens, 2012, NeuroImage, 59(2): 1004-1012). MRI offers excellent spatiotemporal resolution; however, $^1$H MRI reporter genes are limited by low detection sensitivity and by high background $^1$H signals from water and fat. This has motivated investigation of hyperpolarized (HP)$^{129}$Xe (I=½) to generate MR contrast, which can provide Xe-specific molecular information within the context of $^1$H NMR signals.

HP $^{129}$Xe with long $T_1$ gives rise to $10^4$-$10^5$ signal enhancement over the room-temperature Boltzmann population of nuclear spins and is readily obtained by a process of spin-exchange optical pumping (Walker and Happer, 1997, Rev Mod Phys, 69(2): 629-642). HP $^{129}$Xe is non-toxic, can be delivered to living organisms via inhalation or Xe-solution injection, and has been employed for imaging the lungs and brain of living mammals, including humans (Swanson et al., 1997, Magn Reson Med, 38(5): 695-698; Mugler and Altes, 2013, J Magn Reson Imaging, 37(2): 313-331). Xenon has high affinity for hydrophobic void spaces, including host molecules such as water-soluble cryptophane and cucurbituril (Bai et al., 2012, Anal Chem, 9935-9941; Wang and Dmochowski, 2015, Chem Commun, 51: 8982-8985; Schnurr et al., 2015, Angew Chem Int Ed, 13444-13447), and its highly polarizable electron cloud affords xenon high sensitivity to its local environment. The interactions between xenon and small molecules have led to many biosensing applications (Spence et al., 2001, Proc Natl Acad Sci USA, 93: 10654-10657; Taratula and Dmochowski, 2010, Curr Opin Chem Biol, 14: 97-104). Using an NMR technique known as HP $^{129}$Xe chemical exchange saturation transfer (hyper-CEST) (Schroeder et al., 2006, Science, 314(5798): 446-449), many structures with low-affinity Xe binding sites can be identified that are otherwise invisible by direct detection of HP $^{129}$Xe NMR peaks. By hyper-CEST, host-encapsulated HP $^{129}$Xe is selectively depolarized by radiofrequency (RF) saturation pulses, and the depolarized $^{129}$Xe rapidly exchanges with HP $^{129}$Xe in aqueous solvent, where Xe is soluble (~5 mM/atm at room temperature) and loss of signal is readily observed. Recently, Shapiro et al. reported the use of genetically encoded bacterial gas vesicles (GVs) as ultrasensitive hyper-CEST contrast agents (Shapiro et al., 2014, Nat Chem, 6(7): 629-634). While providing a pioneering example, GVs are very large (0.1-2 micron long) multimeric protein assemblies from complex gene clusters and are therefore difficult to reconstitute in many eukaryotic systems.

The small size (D=4.3 Å) and hydrophobicity of xenon allow it to interact with proteins via both non-specific and specific binding events (Rubin et al., 2001, J Magn Reson, 152(1): 79-86; Rubin et al., 2002, J Mol Biol, 322(2): 425-440; Rubin et al., 2000, Proc Natl Acad Sci USA, 97(17): 9472-9475). Previous $^{129}$Xe NMR studies have probed hydrophobic cavities within globular proteins (Landon et al., 2001, Prot Sci, 10(4): 762-770; Bowers et al., 1999, J Am Chem Soc, 121(40): 9370-9377; Dubois et al., 2004, J Am Chem Soc, 126(48): 15738-15746; Desvaux et al., 2005, J Am Chem Soc, 127(33): 11676-11683). The promiscuous interactions of xenon with many proteins have also been investigated by X-ray diffraction in protein crystals under high Xe pressure, where xenon can occupy hydrophobic cavities, substrate-binding sites, and channel pores (Prange et al., 1998, 30(1): 61-73). Notably, these are weak interactions, with hemoglobin and myoglobin exhibiting the highest reported xenon association constants of around 200 $M^{-1}$ at room temperature (Conn, 1961, J Appl Physiol, 16(5): 1065-1070; Ewing and Maestas, 1970, J Phys Chem, 74(11): 2341-2344).

Current molecular imaging methods utilize gadolinium-based contrast agents, however these agents are typically required at high concentration (approaching 1 mM), whereas many targets (cancer biomarkers and the like) are more typically present at nM-µM concentrations.

Thus, there is a need in the art for improved agents that can serve as contrast agents in molecular imaging methods. The present invention satisfies this unmet need.

SUMMARY OF THE INVENTION

In one embodiment, the invention relates to a composition comprising an imaging agent comprising one or more protein reporters. In one embodiment, one or more protein reporters are TEM-1 β-lactamase (bla), maltose-binding protein (MBP), ribose-binding protein (RBP), a fragment thereof, or a mutant thereof.

In one embodiment, the imaging agent is configured to bind to hyperpolarized $^{129}$Xe.

In one embodiment, the one or more protein reporters comprise an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO:44, SEQ ID NO:46 or SEQ ID NO:49.

In one embodiment, the mutant of bla comprises a point mutation located at a residue selected from I263, I279, I282, and M182 or a combination thereof.

In one embodiment, the mutant of MBP comprises a point mutation located at D14, K15, A63, R66, A96, E111, Y155, W230, L262, V293, M321, Q325, I329, W340, or a combination thereof.

In one embodiment, the mutant of RBP comprises a point mutation located at L19.

In one embodiment, one or more protein reporters comprise a targeting domain that binds to a biomolecule or analyte of interest.

In one embodiment, the invention relates to a composition comprising an isolated nucleic acid molecule encoding a protein reporter.

In one embodiment, the nucleic acid molecule comprises a nucleotide sequence encoding TEM-1 β-lactamase (bla), a fragment of bla, or a mutant of bla. In one embodiment, the nucleotide sequence encodes bla comprising an amino acid sequence of SEQ ID NO: 1, SEQ ID NO: 2, SEQ ID NO: 3, SEQ ID NO: 4, SEQ ID NO: 5, SEQ ID NO: 6, and SEQ ID NO: 7. In one embodiment, the nucleotide sequence encodes a bla mutant having a point mutation located at I263, I279, I282, M182 or a combination thereof. In one embodiment, the nucleic acid further comprises a nucleotide sequence encoding a targeting domain, wherein the targeting domain binds to a biomolecule or analyte of interest.

In one embodiment, the nucleic acid molecule comprises a nucleotide sequence encoding maltose-binding protein (MBP), a fragment of MBP, or a mutant of MBP. In one embodiment, the nucleotide sequence encodes MBP comprising an amino acid sequence of SEQ ID NO: 8, SEQ ID NO: 9, SEQ ID NO: 10, SEQ ID NO: 11, SEQ ID NO: 12 and SEQ ID NO:49. In one embodiment, the nucleotide sequence encodes a MBP mutant having a point mutation located at D14, K15, A63, R66, A96, E111, Y155, W230, L262, V293, M321, Q325, I329, W340 or a combination thereof. In one embodiment, the nucleic acid further comprises a nucleotide sequence encoding a targeting domain, wherein the targeting domain binds to a biomolecule or analyte of interest.

In one embodiment, the nucleic acid molecule comprises a nucleotide sequence encoding, ribose-binding protein (RBP), a fragment of RBP, or a mutant of RBP. In one embodiment, the nucleotide sequence encodes RBP comprising an amino acid sequence of SEQ ID NO: 44 or SEQ ID NO:46. In one embodiment, the nucleotide sequence encodes a RBP mutant having a point mutation located at L19. In one embodiment, the nucleic acid further comprises a nucleotide sequence encoding a targeting domain, wherein the targeting domain binds to a biomolecule or analyte of interest.

In one embodiment, the invention relates to a method comprising the steps of: a) administering to a cell or subject one or more protein reporters comprising bla, MBP, RBP, a fragment thereof, a mutant thereof, or combination thereof; b) administering hyperpolarized xenon to the cell or subject; c) obtaining magnetic resonance data of a target site of the cell or subject; and d) analyzing the data to produce a magnetic resonance image of the target site.

In one embodiment, the method further comprises administering a saturating radio frequency pulse to the target site.

In one embodiment, the protein reporter comprises bla and the data comprises a chemical shift of about 60 ppm indicating the presence and location of bla at the target site.

In one embodiment, the protein reporter comprises MBP and the data comprises a chemical shift of about 100 ppm indicating the presence and location of MBP at the target site.

In one embodiment, the protein reporter comprises a mutant MBP wherein the mutant MBP is a MBP-based zinc sensor.

In one embodiment, the method comprises multiplexed detection of a combination of protein reporters comprising administering a combination of bla and MBP protein reporters.

In one embodiment, the protein reporter is administered at a concentration in the range of about 0.001 µM-100 µM.

In one embodiment, the cell is in an in vitro or ex vivo environment.

In one embodiment, the subject is a mammal.

In one embodiment, the protein reporter further comprises a targeting domain that binds a biomolecule or analyte of interest.

In one embodiment, the method is used to detect the presence of a tumor in the subject.

In one embodiment, the method comprises administering a ligand or analyte for the reporter protein, wherein the ligand or analyte is maltose, ribose, an amino acid, zinc, a metal ion, sucrose, trinitrotoluene (TNT), L-lactate, L-leucine or serotonin.

In one embodiment, maltose is administered at a concentration of about 1 mM.

In one embodiment, the invention relates to a method comprising the steps of: a) administering to a cell or subject one or more isolated nucleic acid molecules comprising one or more nucleotide sequences encoding one or more protein reporters comprising bla, MBP, RBP, a fragment thereof, a mutant thereof, or combination thereof; b) administering hyperpolarized xenon to the cell or subject; c) obtaining magnetic resonance data of a target site of the cell or subject; and d) analyzing the data to produce a magnetic resonance image of the target site.

In one embodiment, the method further comprises administering a saturating radio frequency to the target site.

In one embodiment, the protein reporter comprises bla, and the data comprises a chemical shift of about 60 ppm indicating the presence and location of the protein reporter at the target site.

In one embodiment, the nucleic acid molecule induces the expression of the protein reporter at a concentration of about 0.001 µM-100 µM.

In one embodiment, the method comprises administering a ligand for the reporter protein, wherein the ligand is selected from the group consisting of maltose, ribose, an amino acid, zinc, a metal ion, sucrose, trinitrotoluene (TNT), L-lactate, L-leucine or serotonin.

In one embodiment, maltose is administered at a concentration of about 1 mM.

In one embodiment, the method is used to evaluate the gene expression of a gene of interest in the cell or subject.

In one embodiment, the method is used to detect the presence of a ligand or analyte of interest in the cell or subject.

In one embodiment, the one or more administered isolated nucleic acids induces expression of a combination of protein reporters, wherein the combination comprises bla and MBP.

In one embodiment, the invention relates to a method for detecting the presence of an analyte in a cell or subject, the method comprising the steps of: a) administering to a cell or subject one or more isolated nucleic acid molecules comprising one or more nucleotide sequences encoding one or more protein reporters, a fragment thereof, a mutant thereof, or combination thereof; b) administering hyperpolarized xenon to the cell or subject; c) obtaining a hyper-CEST image of a target site of the cell or subject; and d) detecting a detectable signal during hyper-CEST imaging. In one embodiment, the protein reporter comprises bla, MBP, RBP, a fragment thereof, a mutant thereof, or combination thereof.

In one embodiment, the method further comprises administering a saturating radio frequency to the target site.

In one embodiment, the nucleic acid molecule induces the expression of the protein reporter at a concentration of about 0.001 µM-100 µM.

In one embodiment, the method further comprises detecting an increase in the detectable signal during hyper-CEST imaging when the protein reporter is bound to an analyte relative to when the protein reporter is not bound to the analyte.

In one embodiment, the method further comprises detecting a decrease in the detectable signal during hyper-CEST imaging when the protein reporter is bound to an analyte relative to when the protein reporter is not bound to the analyte.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2, comprising FIG. 2A depicts a cartoon representation of bla showing the major secondary structure elements; the position of each residue along the primary structure: from N-terminus to C-terminus is highlighted. The volumes indicate regions of high Xe occupancy. FIG. 2B depicts selected snapshots from the molecular dynamics trajectory after 0.6 μs (top panel) and 1 μs (bottom panel), highlighting only Xe atoms occupying the main allosteric site. The sidechains of the residues lining the pocket are represented as sticks, while bound Xe atoms are shown as spheres. Note how Xe atoms first occupy the entrance of the allosteric pocket before proceeding toward the innermost region.

FIG. 3, comprising FIG. 3A depicts a close-up of the main Xe-binding site. Secondary structure elements (helices 1 and 12 and the flanking beta sheet) are shown. Xe atoms (spheres) establish van der Waals interactions with many sidechains (sticks). FIG. 3B depicts a hyper-CEST z-spectra for wt-bla and I263A, 80 μm in pH 7.2 PBS.

FIG. 7, comprising

FIG. 7A depicts the number of Xe atoms in contact with the protein (closer than 3 Å from any protein atom) is shown as a function of time. The line shows the centered moving average using a window length of 0.2 s; the dotted and dashed lines highlight the values 13 and 18, respectively. Note how after 0.6 μs the number of Xe atoms increases on average by approximately five units. Apart from this stepwise increment, fluctuations in the number of Xe atoms (binding and unbinding events) occur on time scales smaller than the smoothing window (approximately 0.1 μs). FIG. 7B depicts the number of Xe atoms bound to the main binding site (defined as the region surrounded by the sidechains of residues 33, 44, 244, 246, 261, 263, 265, 286 and 279). The number of ions bound to this region increases by two or three units after 0.6 s. FIG. 7C depicts the same plot as in FIG. 7B for a different binding region (cavity surrounded by sidechains of residues 68, 72 and 172). Note how in this case the binding is only transient.

FIG. 16, comprising FIG. 16A depicts Xe shown as spheres (van der Waals radii enlarged for clarity). FIG. 16B depicts the Xe1 binding site, with surrounding protein sidechains shown as sticks. Dashes indicate protein-Xe contacts within 4.5 Å. The isomorphous difference Fourier map for Xe1 is shown as mesh contoured at 10σ.

FIG. 18 comprising FIG. 18A through FIG. 18C depicts a comparison of an "open" bla structure complexed with an allosteric ligand (PDB ID 1PZO) to unliganded bla complexed with Xe, and shows that while the positions of A36, L40, V44, and I263 do not change between the open and closed conformations of bla, I279 shifts roughly 2 Å away from I263.

FIG. 19 comprises FIG. 19A and FIG. 19B.

FIG. 20 comprises FIG. 20A and FIG. 20B.

FIG. 21, comprising FIG. 21A depicts the Xe occupancy maps calculated by "flooding" simulations for each mutant (shading) overlaid onto that of the WT. The positions of Xe atoms determined by X-ray crystallography are indicated by spheres for WT and mutants (the structure of I263A was not solved experimentally). FIG. 21B illustrates a comparison of the occupancy maps calculated by single Xe simulation vs "flooding" simulations.

FIG. 22, comprising FIG. 22A illustrates a close up of the WT binding trajectories. FIG. 22B illustrates pathways for the WT and mutants.

FIG. 25, comprising FIG. 25A depicts Xe1 map contoured at 5σ. FIG. 25B depicts Xe2 map contoured at 3σ. FIG. 25C depicts Xe3 map contoured at 2σ.

FIG. 26, comprising FIG. 26A In FIG. 26B, Xe3 is shown as a sphere and the isomorphous difference Fourier map is shown as mesh contoured at 4σ.

FIG. 30, comprising FIG. 30A depicts Xe (sphere) bound to MBP$_{open}$ (PDB ID 1LLS), with the N-domain (residues 1-109 and 364-309), C-domain (residues 114-258 and 316-370), and linking segments (residues 110-113, 259-263, and 310-315). FIG. 30B depicts the Xe-binding cavity of MBP. Xe (sphere) is surrounded by primarily hydrophobic residues (Ile-11, Leu-20, Phe-61, Ile-108, Leu-262, Leu-284, Leu-290, Val-293, Leu-299). Lys-15 acts as a "cap", shielding bound Xe from solvent. A single water molecule is positioned 5.4 Å away, indicating the Xe pocket's proximity to the surface. FIG. 30C depicts a comparison of Xe-binding pockets of MBP$_{open}$ (PDB ID 1OMP (Sharff et al., 1992, Biochemistry, 31(44): 10657-10663), MBP$_{open}$ derivatized with Xe (PDB ID 1LLS), MBP$_{open}$ bound to β-cyclodextrin (PDB ID 1DMB), and MBP$_{closed}$ bound to maltose (PDB ID 1ANF (Quiocho et al., 1997, Structure, 5(8): 997-1015).

FIG. 31 comprises FIG. 31A and FIG. 31B. FIG. 30B depicts time-dependent saturation transfer data of 100 nM MBP in PBS pH 7.2 at 300 K. The observed saturation contrast is 0.26±0.01. Saturation frequencies of Dsnob-shaped pulses were positioned at +99 ppm and −99 ppm, referenced to the Xe$_{(aq)}$ peak, for on- and off-resonance, respectively. Pulse length, $\tau_{pulse}$=1.0496 ms; field strength, B1$_{max}$=279 μT. Both on-resonance and off-resonance data were fitted with first-order exponential decay curves, with T1$_{on}$=21.8±0.6 s and T1$_{off}$=55±3 s.

FIG. 36, comprising FIG. 36A depicts results without maltose and FIG. 36B depicts results with 1 mM maltose.

FIG. 38, comprising FIG. 38A depicts the saturation contrast=0.21±0.04; T$_{1on}$=7.4±0.2 s; T$_{1off}$=9.7±0.3 s. FIG. 38B depicts the saturation contrast for 15±6 μM MBP, saturation contrast=0.40±0.06; T$_{1on}$=5.35±0.17 s; T$_{1off}$=9.3±0.3 s. FIG. 38C depicts the saturation contrast=0.32±0.03; T$_{1on}$=7.1±0.3 s; T$_{1off}$=12.1±0.3 s.

FIG. 38D depicts the saturation contrast for 6±4 μM MBP, saturation contrast=0.60±0.02; T$_{1on}$=4.94±0.10 s; T$_{1off}$=16.7±0.6 s.

FIG. 39, comprising

FIG. 44, comprising FIG. 44A depicts time-dependent saturation transfer data for 0 μM maltose: saturation contrast=0.022±0.004; T$_{1on}$=41±2 s and T$_{1off}$=44±3 seconds (s). FIG. 44B depicts time-dependent saturation transfer data for 0.1 μM maltose: saturation contrast=0.050±0.007; T$_{1on}$=34±1 s and T$_{1off}$=41±3 s. FIG. 44C depicts time-dependent saturation transfer data for 0.3 μM maltose: saturation contrast=0.05±0.01; T$_{1on}$=35±1 s and T$_{1off}$=43±1 s. FIG. 44D depicts time-dependent saturation transfer data for 0.5 µM maltose: saturation contrast=0.11±0.01; $T_{1on}$=26.3±0.9 s and $T_{1off}$=39±1 s. FIG. 44E depicts time-dependent saturation transfer data for 1 µM maltose: saturation contrast=0.118±0.007; $T_{1on}$=32.7±0.7 s and $T_{1off}$=50±1 s. FIG. 44F depicts time-dependent saturation transfer data for 3 µM maltose: saturation contrast=0.161±0.004; $T_{1on}$=26±1 s and $T_{1off}$=46±2 s. FIG. 44G depicts time-dependent saturation transfer data for 1 mM maltose: saturation contrast=0.26±0.01; $T_{1on}$=21.8±0.7 s and $T_{1off}$=55±3 s. All measurements taken in pH 7.2 PBS at 300 K. Pulse length, $\tau_{pulse}$=1.0496 ms; field strength, $B_{1,max}$=279 µT. The number of pulses increased linearly from 0 to 15000.

FIG. 47, comprising FIG. 47A depicts time-dependent saturation transfer data for 0 nM maltose: saturation contrast=0.01±0.01; $T_{1on}$=19.0±0.5 s and $T_{1off}$=18.8±0.6 s. FIG. 47B depicts time-dependent saturation transfer data for 32 nM maltose: saturation contrast=0.07±0.01; $T_{1on}$=17.1±0.4 s and $T_{1off}$=19.0±0.6 s. FIG. 47C depicts time-dependent saturation transfer data for 72 nM maltose: saturation contrast=0.12±0.02; $T_{1on}$=19.3±0.7 s and $T_{1off}$=25.3±0.6 s. FIG. 47D depicts time-dependent saturation transfer data for 140 nM maltose: saturation contrast=0.173±0.006; $T_{1on}$=15.2±0.5 s and $T_{1off}$=22.3±0.9 s. FIG. 47E depicts time-dependent saturation transfer data for 5 µM maltose: saturation contrast=0.24±0.01; $T_{1on}$=16.2±0.6 s and $T_{1off}$=29.4±0.8 s. All measurements taken in pH 7.2 PBS at 300 K. Pulse length, $\tau_{pulse}$=1.0496 ms; field strength, $B_{1,max}$=279 µT. The number of pulses increased linearly from 0 to 15000.

FIG. 48, comprising FIG. 48A depicts time-dependent saturation transfer data for [MBP-GFP]<0.001 µM, no maltose; saturation contrast=0.09±0.01. FIG. 48B depicts time-dependent saturation transfer data for [MBP-GFP]<0.001 µM, 1 mM maltose; saturation contrast=0.11±0.01. FIG. 48C depicts time-dependent saturation transfer data for [MBP-GFP]=1.0±0.2 µM, no maltose; saturation contrast=0.14±0.01. FIG. 48D depicts time-dependent saturation transfer data for [MBP-GFP]=1.00±0.02 µM, 1 mM maltose; saturation contrast=0.25±0.02. All measurements taken in pH 7.2 PBS at 300 K. Pulse length, $\tau_{pulse}$=1.0496 ms; $B_{1,max}$=279 µT. The number of pulses increased linearly from 0 to 10000.

FIG. 60 depicts sequences of exemplary proteins reporters of the invention.

DETAILED DESCRIPTION

Figure 1:
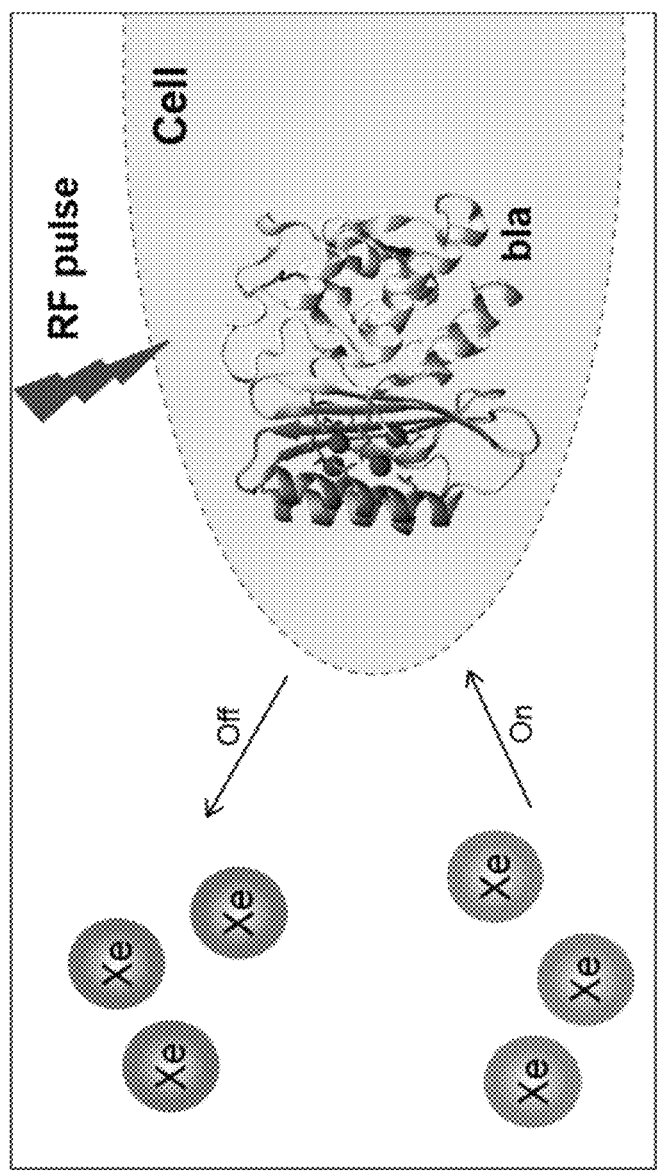
FIG. 1 is an illustration depicting that hyperpolarized $^{129}$Xe chemical exchange saturation transfer (hyper-CEST) occurs between aqueous solvent (left) and TEM-1 β-lactamase in solution or inside a cell. Hyperpolarized $^{129}$Xe exchanges into bla, where the unique resonance frequency can be saturated by shaped RF pulses. Saturated xenon returns to the bulk, leading to a decrease in Xe-aq signal.

The present invention relates to compositions and methods using one or more genetically-encoded detection agents. In one embodiment the detection agents function as molecular reporters for NMR and MRI applications. In one embodiment the detection agents function as biosensors for detection of a ligand (for example, maltose, ribose or zinc).

In certain embodiments the present invention relates to a detection agent comprising one or more genetically-encoded protein reporters or isolated nucleic acid molecules encoding the same. Exemplary genetically encoded protein reporters include, but are not limited to, TEM-1 β-lactamase (bla), and periplasmic binding proteins (PBPs) including, but not limited to, maltose binding protein (MBP), and ribose binding protein (RBP). In certain instances, bla is referred to herein as TEM1. For example, in one embodiment, the composition comprises bla, a fragment thereof, a mutant thereof, or an isolated nucleic acid molecule encoding the same. In one embodiment, the composition comprises a PBP, a fragment thereof, a mutant thereof, or an isolated nucleic acid molecule encoding the same. In one embodiment, the composition comprises MBP, a fragment thereof, a mutant thereof, or an isolated nucleic acid molecule encoding the same. In one embodiment, the composition comprises RBP, a fragment thereof, a mutant thereof, or an isolated nucleic acid molecule encoding the same. In certain embodiments, the invention provides methods comprising administering the imaging agent to a cell, tissue, or subject, and detecting the presence, abundance, or location of the imaging agent at a site of interest with the cell, tissue, or subject. In certain embodiments, the method comprises the use of $^{129}$Xe NMR or MRI to detect the imaging agent. In certain embodiments, the invention relates to compositions and methods relating to the use of both bla and MBP, fragments thereof, mutants thereof, or isolated nucleic acids encoding the same, to allow for multiplexed detection of both protein reporters.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent homology between two sequences is a function of the number of matching or homologous positions shared by the two sequences divided by the number of positions compared×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The terms "patient," "subject," "individual," and the like are used interchangeably herein, and refer to any animal, or cells thereof whether in vitro or in situ, amenable to the methods described herein. In certain non-limiting embodiments, the patient, subject, or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one that expresses the gene product in a tissue-specific manner.

A "constitutive" promoter is a nucleotide sequence which, when operably linked with a polynucleotide that encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The terms "precursor cell," "progenitor cell," and "stem cell" are used interchangeably in the art and as used herein refer either to a pluripotent or lineage-uncommitted progenitor cell, which is potentially capable of an unlimited number of mitotic divisions to either renew itself or to produce progeny cells which will differentiate into the desired cell type. In contrast to pluripotent stem cells, lineage-committed progenitor cells are generally considered to be incapable of giving rise to numerous cell types that phenotypically differ from each other. Instead, progenitor cells give rise to one or possibly two lineage-committed cell types.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

As used herein, the terms "subject" and "patient" are used interchangeably. As used herein, a subject is preferably a mammal such as a non-primate (e.g., cows, pigs, horses, cats, dogs, rats, etc.) and a primate (e.g., monkey and human), most preferably a human.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to compositions and methods using a genetically-encoded molecular reporter for NMR and MRI applications. For example, in certain embodiments the present invention relates to a genetically encoded protein reporter for ultrasensitive imaging. In certain embodiments, the present invention provides a composition comprising one or more protein reporters, such as bla, MBP, RBP and/or mutants thereof. In certain embodiments, the protein reporter provides significant saturation contrast. In certain embodiments, the protein reporter is used in $^{129}$Xe NMR or MRI applications, including hyper-CEST. In certain embodiments, in hyper-CEST, the protein reporter gives rise to a unique saturation peak. In certain embodiments, each protein reporter gives rise to a unique saturation peak distinguishing the reporters from each other. In certain embodiments, each protein reporter gives rise to a unique saturation peak distinguishing the reporters from the $^{129}$Xe-H$_2$O peak.

The invention also provides methods that include administering to a cell, cell population, tissue, organism, or subject, one or more protein reporters comprising bla, MBP, RBP, a fragment thereof, or mutant thereof. In certain embodiments, the method comprises obtaining magnetic resonance data of a target site of interest within the cell, cell population, tissue, organism, or subject, and analyzing the data to produce a magnetic resonance image of the target site. In certain embodiments, the method comprises the use of $^{129}$Xe NMR or MRI modalities to detect the presence, abundance, or location of the one or more protein reporters. In one embodiment, the method comprises the use of hyper-CEST. In one embodiment, the method comprises the administration of a plurality of protein reporters, thereby providing multiplexed detection of the plurality of protein reporters.

Compositions

In one aspect, the present invention provides a composition comprising a reporter for NMR and MRI applications. In certain instances, the composition comprises a genetically-encoded reporter. In one embodiment, the genetically-encoded reporter is TEM-1 β-lactamase (bla), a fragment thereof, or a mutant thereof. In one embodiment, the genetically-encoded reporter is a periplasmic binding protein (PBP), a fragment thereof, or a mutant thereof. In one embodiment, the composition comprises a combination of protein reporters. For example, in one embodiment, the composition comprises a combination of bla and at least one PBP, fragments thereof, or mutants thereof. In one embodiment, the protein reporter comprises one or more allosteric binding sites for Xe, where protein reporter-bound Xe induces a detectable shift in saturation contrast peak, as compared to aqueous Xe.

In certain embodiments, the invention comprises a composition comprising an isolated nucleic acid molecule encoding a genetically-encoded reporter for NMR and MRI applications. For example, in certain instances the composition comprises an isolated nucleic acid molecule encoding bla or a PBP, a fragment thereof, or a mutant thereof.

The present invention provides a composition comprising a protein reporter, a nucleic acid molecule encoding a protein reporter, a cell comprising a protein reporter, a cell encoding a protein reporter, or a combination thereof. The protein reporter can employ any protein that undergoes a conformational change upon binding to a ligand (analyte). The nature of the protein used is dependent upon the analyte to be detected. Examples of proteins suitable for use in the invention include members of the periplasmic-binding protein superfamily such as glucose/galactose-binding protein (GGBP), MBP, RBP, arabinose-binding protein (ABP), histidine-binding protein (HBP), glutamine-binding protein (QBP), ferric-siderophore binding PBPs, BtuF (a PBP for the vitamin B12 transporter), Bt-thiaminase I, TbpA, dipeptide-binding protein (DPBP), leucine-binding protein (LBP), leucine-, isoleucine-, valine-binding protein (LIVBP), oligopeptide-binding protein (OPBP), and arginine-binding protein (ArgBP).

The ligand-binding sites can be naturally evolved, or engineered using rational design or directed evolution, and therefore interact with natural or non-natural ligands. Periplasmic binding proteins such as MBP, RBP, and engineered versions thereof (e.g., zinc sensor variants (ZSFs)) are merely examples, as are all homologues, analogues and/or paralogues of members of this superfamily. Other examples include hexokinase, phosphofructokinase, DNA polymerase, etc.

In certain embodiments, the invention comprises a cell, cell population, tissue, 3-dimensional cell culture, tissue engineering scaffold, or organism, comprising bla, MBP, RBP a fragment thereof, or mutant thereof. In certain embodiments, the invention comprises a cell, cell population, tissue, or 3-dimensional cell culture, tissue engineering scaffold or organism, comprising an isolated nucleic acid molecule encoding bla, MBP, RBP a fragment thereof, or mutant thereof.

In certain embodiments, the invention relates to other versions or isoforms of β-lactamase, other than the TEM-1 version exemplified herein. For example, the present invention encompasses the use of other β-lactamases that bind $^{129}$Xe and induce a detectable chemical shift during hyper-CEST imaging.

In certain embodiments, the invention relates to multiplexing protein reporters. For example, the present invention comprises the use of bla and PBP reporters used in combination at varying concentrations and inducing unique detectable chemical shifts during hyper-CEST imaging.

Peptide

In certain embodiments, the composition comprises a peptide or protein comprising bla, a bla fragment, or a bla mutant.

In one embodiment, bla comprises the amino acid sequence of:

(SEQ ID NO: 1)
MSIQHFRVALIPFFAAFCLPVFAHPETLVKVKDAEDQLGARVGYIEL

DLNSGKILESFRPEERFPMMSTFKVLLCGAVLSRVDAGQEQLGRRIH

YSQNDLVEYSPVTEKHLTDGMTVRELCSAAITMSDNTAANLLLTTIG

GPKELTAFLHNMGDHVTRLDRWEPELNEAIPNDERDTTMPAAMATTL

RKLLTGELLTLASRQLIDWMEADKVAGPLLRSALPAGWFIADKSGAG

ERGSRGIIAALGPDGKPSRIVVIYTTGSQATMDERNRQIAEIGASLI

KHW

In certain embodiments, the peptide comprises bla having one or more mutations. In certain embodiments, the peptide comprises bla having one or more mutations. In certain embodiments, the peptide comprises bla having one or more mutations at M182 (residue 180 relative to the sequence of SEQ ID NO: 1), I263 (residue 259 relative to the sequence of SEQ ID NO: 1), I279 (residue 275 relative to the sequence of SEQ ID NO: 1, I282 (residue 278 relative to the sequence of SEQ ID NO: 1.) For example, in certain embodiments, the peptide comprises bla having one or more mutations selected from: M182T, I263L, I263N, I263A, I279N, and I282A.

In one embodiment, the peptide comprises bla having an I263L mutation (residue 259 relative to the sequence of SEQ ID NO: 1). In one embodiment, the peptide comprising bla having an I263L mutation comprises the amino acid sequence of:

(SEQ ID NO. 2)
MSIQHFRVALIPFFAAFCLPVFAHPETLVKVKDAEDQLGARVGYIEL

DLNSGKILESFRPEERFPMMSTFKVLLCGAVLSRVDAGQEQLGRRIH

-continued
```
YSQNDLVEYSPVTEKHLTDGMTVRELCSAAITMSDNTAANLLLTTIG

GPKELTAFLHNMGDHVTRLDRWEPELNEAIPNDERDTTMPAAMATTL

RKLLTGELLTLASRQQLIDWMEADKVAGPLLRSALPAGWFIADKSGA

GERGSRGIIAALGPDGKPSRIVVLYTTGSQATMDERNRQIAEIGASL

IKHW
```

In one embodiment, the peptide comprises bla having an I282A mutation (residue 278 relative to the sequence of SEQ ID NO: 1). In one embodiment, the peptide comprising bla having an I263L and I282A mutation comprises the amino acid sequence of:

```
                                            (SEQ ID NO: 3)
MSIQHFRVALIPFFAAFCLPVFAHPETLVKVKDAEDQLGARVGYIEL

DLNSGKILESFRPEERFPMMSTFKVLLCGAVLSRVDAGQEQLGRRIH

YSQNDLVEYSPVTEKHLTDGMTVRELCSAAITMSDNTAANLLLTTIG

GPKELTAFLHNMGDHVTRLDRWEPELNEAIPNDERDTTMPAAMATTL

RKLLTGELLTLASRQQLIDWMEADKVAGPLLRSALPAGWFIADKSGA

GERGSRGIIAALGPDGKPSRIVVLYTTGSQATMDERNRQIAEAGASL

IKHW
```

In one embodiment, the peptide comprises bla having an I263N mutation (residue 259 relative to the sequence of SEQ ID NO: 1). In one embodiment, the peptide comprising bla having an I263N mutation comprises the amino acid sequence of:

```
                                            (SEQ ID NO: 4)
MSIQHFRVALIPFFAAFCLPVFAHPETLVKVKDAEDQLGARVGYIEL

DLNSGKILESFRPEERFPMMSTFKVLLCGAVLSRVDAGQEQLGRRIH

YSQNDLVEYSPVTEKHLTDGMTVRELCSAAITMSDNTAANLLLTTIG

GPKELTAFLHNMGDHVTRLDRWEPELNEAIPNDERDTTMPAAMATTL

RKLLTGELLTLASRQQLIDWMEADKVAGPLLRSALPAGWFIADKSGA

GERGSRGIIAALGPDGKPSRIVVNYTTGSQATMDERNRQIAEIGASL

IKHW.
```

In one embodiment, the peptide comprises bla having an I263A mutation (residue 259 relative to the sequence of SEQ ID NO: 1). In one embodiment, the peptide comprising bla having an I263A mutation comprises the amino acid sequence of:

```
                                            (SEQ ID NO: 5)
MSIQHFRVALIPFFAAFCLPVFAHPETLVKVKDAEDQLGARVGYIEL

DLNSGKILESFRPEERFPMMSTFKVLLCGAVLSRVDAGQEQLGRRIH

YSQNDLVEYSPVTEKHLTDGMTVRELCSAAITMSDNTAANLLLTTIG

GPKELTAFLHNMGDHVTRLDRWEPELNEAIPNDERDTTMPAAMATTL

RKLLTGELLTLASRQQLIDWMEADKVAGPLLRSALPAGWFIADKSGA

GERGSRGIIAALGPDGKPSRIVVAYTTGSQATMDERNRQIAEIGASL

IKHW.
```

In one embodiment, the peptide comprises bla having an I279N mutation (residue 275 relative to the sequence of SEQ ID NO: 1). In one embodiment, the peptide comprising bla having an I279N mutation comprises the amino acid sequence of:

```
                                            (SEQ ID NO: 6)
MSIQHFRVALIPFFAAFCLPVFAHPETLVKVKDAEDQLGARVGYIEL

DLNSGKILESFRPEERFPMMSTFKVLLCGAVLSRVDAGQEQLGRRIH

YSQNDLVEYSPVTEKHLTDGMTVRELCSAAITMSDNTAANLLLTTIG

GPKELTAFLHNMGDHVTRLDRWEPELNEAIPNDERDTTMPAAMATTL

RKLLTGELLTLASRQQLIDWMEADKVAGPLLRSALPAGWFIADKSGA

GERGSRGIIAALGPDGKPSRIVVIYTTGSQATMDERNRQNAEIGASL

IKHW.
```

In certain embodiments, SEQ ID NO: 1, SEQ ID NO: 2, SEQ ID NO: 3, SEQ ID NO: 4, SEQ ID NO: 5, and SEQ ID NO: 6 refer to bla protein reporters for expression in bacterial cells.

In one embodiment, bla comprises the amino acid sequence of:

```
                                            (SEQ ID NO: 7)
MHPETLVKVKDAEDQLGARVGYIELDLNSGKILESFRPEERFPMMST

FKVLLCGAVLSRVDAGQEQLGRRIHYSQNDLVEYSPVTEKHLTDGMT

VRELCSAAITMSDNTAANLLLTTIGGPKELTAFLHNMGDHVTRLDRW

EPELNEAIPNDERDTTTPAAMATTLRKLLTGELLTLASRQQLIDWME

ADKVAGPLLRSALPAGWFIADKSGAGERGSRGIIAALGPDGKPSRIV

VIYTTGSQATMDERNRQIAEIGASLIKHW.
```

In certain embodiments, SEQ ID NO: 7 refers to bla for expression in HEK293T cells.

In one embodiment, composition comprises a peptide comprising a fragment of any of SEQ ID NOs: 1-7 that mimics the utility of bla as a reporter in NMR and MRI applications. In one embodiment, composition comprises a peptide comprising a mutant of any of SEQ ID NOs: 1-7 that mimics the utility of bla as a reporter in NMR and MRI applications.

Exemplary bla mutants include those having point mutations, substitutions, deletions, and truncations that alter the chemical shift of $^{129}$Xe, as compared to aqueous $^{129}$Xe. For example, in certain embodiments, the mutant comprises a mutation that increases or decreases the affinity of Xe to bla. The presence of various bla mutants having different xenon affinities allows for the ability to multiplex in various applications. Exemplary point mutations include mutations at residues at I263, I279, and I282, with respect to the bacterial bla of SEQ ID NOs: 1-6.

In certain embodiments, the composition comprises a peptide or protein comprising MBP, an MBP fragment, or an MBP mutant.

In one embodiment, MBP comprises the amino acid sequence of:

```
                                            (SEQ ID NO: 8)
KIEEGKLVIWINGDKGYNGLAEVGKKFEKDTGIKVTVEHPDKLEEKF

PQVAATGDGPDIIFWAHDRFGGYAQSGLLAEITPDKAFQDKLYPFTW

DAVRYNGKLIAYPIAVEALSLIYNKDLLPNPPKTWEEIPALDKELKA
```

KGKSALMFNLQEP<u>Y</u>FTWPLIAADGGYAFKYENGKYDIKDVGVDNAGA

KAGLTFLVDLIKNKHMNADTDYSIAEAAFNKGETAMTINGP<u>W</u>AWSNI

DTSKVNYGVTVLPTFKGQPSKPFVGV<u>L</u>SAGINAASPNKELAKEFLEN

YLLTDEGLEA<u>V</u>NKDKPLGAVALKSYEEELAKDPRIAAT<u>M</u>ENAQKGE<u>I</u>

MPNIPQMSAF<u>W</u>YAVRTAVINAASGRQTVDEALKDAQT.

In one embodiment, the MBP comprises the amino acid sequence of SEQ ID NO:8 operably linked to at least one regulatory element. In one embodiment, at least one regulatory element is a start codon (e.g., a methionine) at the N terminus. In one embodiment, at least one regulatory element is a leader sequence at the N terminus. In one embodiment, the MBP comprises the amino acid sequence of SEQ ID NO:8 operably linked to a peptide tag (e.g., a His tag). In one embodiment, a His tag comprises an amino acid sequence as set forth in SEQ ID NO:45. Therefore, in one embodiment, the MBP comprises SEQ ID NO:8 operably linked to the amino acid sequence of SEQ ID NO:45 at the N terminus. In one embodiment, the MBP comprises SEQ ID NO:49.

Exemplary MBP mutants include those having point mutations, substitutions, deletions, and truncations that alter the chemical shift of $^{129}$Xe, as compared to aqueous $^{129}$Xe. For example, in certain embodiments, the mutant comprises a mutation that increases or decreases the affinity of Xe to MBP. The presence of various MBP mutants having different xenon affinities allows for the ability to multiplex in various applications. Exemplary point mutations include mutations at residues at D14, K15, A63, R66, A96, E111, Y155, W230, L262, V293, M321, Q325, I329 and W340 with respect to the bacterial MBP of SEQ ID NO: 8 (underlined residues in SEQ ID NO:8). In one embodiment, the peptide comprises MBP having a V293L mutation relative to the sequence of SEQ ID NO: 8. In one embodiment, the peptide comprising MBP having a V293L mutation comprises the amino acid sequence of:

(SEQ ID NO: 9)
MGSSHHHHHHGSSMKIEEGKLVIWINGDKGYNGLAEVGKKFEKDTGI

KVTVEHPDKLEEKFPQVAATGDGPDIIFWAHDRFGGYAQSGLLAEIT

PDKAFQDKLYPFTWDAVRYNGKLIAYPIAVEALSLIYNKDLLPNPPK

TWEEIPALDKELKAKGKSALMFNLQEPYFTWPLIAADGGYAFKYENG

KYDIKDVGVDNAGAKAGLTFLVDLIKNKHMNADTDYSIAEAAFNKGE

TAMTINGPWAWSNIDTSKVNYGVTVLPTFKGQPSKPFVGVLSAGINA

ASPNKELAKEFLENYLLTDEGLEALNKDKPLGAVALKSYEEELAKDP

RIAATMENAQKGEIMPNIPQMSAFWYAVRTAVINAASGRQTVDEALK

DAQTNGIEENLYFQSNIGSG

In one embodiment, the peptide comprises MBP having a V293A relative to the sequence of SEQ ID NO: 8. In one embodiment, the peptide comprising MBP having a V293A mutation comprises the amino acid sequence of:

(SEQ ID NO: 10)
MGSSHHHHHHGSSMKIEEGKLVIWINGDKGYNGLAEVGKKFEKDTGIKVT

VEHPDKLEEKFPQVAATGDGPDIIFWAHDRFGGYAQSGLLAEITPDKAFQ

DKLYPFTWDAVRYNGKLIAYPIAVEALSLIYNKDLLPNPPKTWEEIPALD

KELKAKGKSALMFNLQEPYFTWPLIAADGGYAFKYENGKYDIKDVGVDNA

GAKAGLTFLVDLIKNKHMNADTDYSIAEAAFNKGETAMTINGPWAWSNID

TSKVNYGVTVLPTFKGQPSKPFVGVLSAGINAASPNKELAKEFLENYLLT

DEGLEAANKDKPLGAVALKSYEEELAKDPRIAATMENAQKGEIMPNIPQM

SAFWYAVRTAVINAASGRQTVDEALKDAQTNGIEENLYFQSNIGSG

In one embodiment, the peptide comprises MBP having a M321A/Q325A mutation relative to the sequence of SEQ ID NO: 8. In one embodiment, the peptide comprising MBP having a M321A/Q325A mutation comprises the amino acid sequence of:

(SEQ ID NO: 11)
MGSSHHHHHHGSSMKIEEGKLVIWINGDKGYNGLAEVGKKFEKDTGIKVT

VEHPDKLEEKFPQVAATGDGPDIIFWAHDRFGGYAQSGLLAEITPDKAFQ

DKLYPFTWDAVRYNGKLIAYPIAVEALSLIYNKDLLPNPPKTWEEIPALD

KELKAKGKSALMFNLQEPYFTWPLIAADGGYAFKYENGKYDIKDVGVDNA

GAKAGLTFLVDLIKNKHMNADTDYSIAEAAFNKGETAMTINGPWAWSNID

TSKVNYGVTVLPTFKGQPSKPFVGVLSAGINAASPNKELAKEFLENYLLT

DEGLEAVNKDKPLGAVALKSYEEELAKDPRIAATAENAAKGEIMPNIPQM

SAFWYAVRTAVINAASGRQTVDEALKDAQTNGIEENLYFQSNIGSG.

In certain embodiments, SEQ ID NO: 8, SEQ ID NO: 9, SEQ ID NO: 10, and SEQ ID NO: 11 refer to MBP for expression in bacterial cells.

In one embodiment, MBP comprises the amino acid sequence of:

(SEQ ID NO: 12)
MKIEEGKLVIWINGDKGYNGLAEVGKKFEKDTGIKVTVEHPDKLEEKFPQ

VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYENGKYDIKDVGVDNAGAKAGLTFLVDLI

KNKHMNADTDYSIAEAAFNKGETAMTINGPWAWSNIDTSKVNYGVTVLPT

FKGQPSKPFVGVLSAGINAASPNKELAKEFLENYLLTDEGLEAVNKDKPL

GAVALKSYEEELAKDPRIAATMENAQKGEIMPNIPQMSAFWYAVRTAVIN

AASGRQTVDEALKDAQT.

In certain embodiments, SEQ ID NO: 12 refers to MBP for expression in HEK293T cells.

In one embodiment, composition comprises a peptide comprising a fragment of any of SEQ ID NOs: 8-12 that mimics the utility of MBP as a reporter in NMR and MRI applications. In one embodiment, composition comprises a peptide comprising a mutant of any of SEQ ID NOs: 8-12 that mimics the utility of MBP as a reporter in NMR and MRI applications.

In certain embodiments, the composition comprises a peptide or protein comprising RBP, an RBP fragment, or an RBP mutant.

In one embodiment, RBP comprises a mutant of RBP comprising a mutation at residue L19 relative to SEQ ID NO:51. In one embodiment, the mutation at residue L19 is a L19A mutation. In one embodiment, the peptide comprising RBP having a L19A mutation comprises the amino acid sequence of:

```
                                            (SEQ ID NO: 44)
KDTIALVVSTLNNPFFVSAKDGAQKEADKLGYNLVVLDSQNNPAKELANV

QDLTVRGTKILLINPTDSDAVGNAVKMANQANIPVITLDRQATKGEVVSH

IASDNVLGGKIAGDYIAKKAGEGAKVIELQGIAGTSAARERGEGFQQAVA

AHKFNVLASQPADFDRIKGLNVMQNLLTAHPDVQAVFAQNDEMALGALRA

LQTAGKSDVMVVGFDGTPDGEKAVNDGKLAATIAQLPDQIGAKGVETADK

VLKGEKVQAKYPVDLKLVVKQ.
```

In one embodiment, the RBP comprises the amino acid sequence of SEQ ID NO:44 operably linked to at least one regulatory element. In one embodiment, at least one regulatory element is a start codon (e.g., a methionine) at the N terminus. In one embodiment, at least one regulatory element is a leader sequence at the N terminus. In one embodiment, a leader sequence is set forth in SEQ ID NO:48. Therefore, in one embodiment, the RBP comprises SEQ ID NO:44 operably linked to the amino acid sequence of SEQ ID NO:48 at the N terminus.

In one embodiment, the RBP comprises the amino acid sequence of SEQ ID NO:44 operably linked to a peptide tag (e.g., a His tag). In one embodiment, a His tag comprises an amino acid sequence as set forth in SEQ ID NO:45. Therefore, in one embodiment, the RBP comprises SEQ ID NO:44 operably linked to the amino acid sequence of SEQ ID NO:45 at the N terminus.

In one embodiment, RBP reporter protein is a fusion protein comprising a fusion of GFP and RBP(L19A). In one embodiment, a GFP-RBP(L19A) fusion protein reporter comprises the amino acid sequence of:

```
                                            (SEQ ID NO: 46)
MGSSHHHHHHGSSVSKGEELFTGVVPILVELDGDVNGHKFSVRGEGEGDA

TNGKLTLKFICTTGKLPVPWPTLVTTLTYGVQCFSRYPDHMKQHDFFKSA

MPEGYVQERTISFKDDGTYKTRAEVKFEGDTLVNRIELKGIDFKEDGNIL

GHKLEYNFNSHNVYITADKQKNGIKANFKIRHNVEDGSVQLADHYQQNTP

IGDGPVLLPDNHYLSTQSKLSKDPNEKRDHMVLLEFVTAAGITLGMDELY

KGIEENLYFQSNAKDTIALVVSTLNNPFFVSAKDGAQKEADKLGYNLVVL

DSQNNPAKELANVQDLTVRGTKILLINPTDSDAVGNAVKMANQANIPVIT

LDRQATKGEVVSHIASDNVLGGKIAGDYIAKKAGEGAKVIELQGIAGTSA

ARERGEGFQQAVAAHKFNVLASQPADFDRIKGLNVMQNLLTAHPDVQAVF

AQNDEMALGALRALQTAGKSDVMVVGFDGTPDGEKAVNDGKLAATIAQLP

DQIGAKGVETADKVLKGEKVQAKYPVDLKLVVKQ.
```

The amino acid sequence of RBP denoted in SEQ ID NO: 44 comprises a L19A mutation compared to the native RBP sequence.

In one embodiment, composition comprises a peptide comprising a fragment of SEQ ID NO:44 that mimics the utility of RBP as a reporter in NMR and MRI applications. In one embodiment, composition comprises a peptide comprising a mutant of SEQ ID NO:44 that mimics the utility of RBP as a reporter in NMR and MRI applications.

Exemplary RBP mutants include those having point mutations, substitutions, deletions, and truncations that alter the chemical shift of $^{129}$Xe, as compared to aqueous $^{129}$Xe. For example, in certain embodiments, the mutant comprises a mutation that increases or decreases the affinity of Xe to RBP.

In one embodiment, the reporter proteins of the invention include one or more mutations to promote sensing of non-native ligands. For example, in one embodiment, the invention provides PBP mutants have one or more mutations to allow for detection of a non-native ligand or analyte including, but not limited to, an amino acid, zinc, a metal ion, sucrose, trinitrotoluene (TNT), L-lactate, L-leucine or serotonin.

In one embodiment, the MBP reporter protein of the invention comprises one or more mutation at residue D14, K15, A63, R66, A96, E111, Y155, W230, L262, V293, M321, Q325, I329 or W340 with respect to the bacterial MBP of SEQ ID NO: 8, or an equivalent residue of SEQ ID NO:9-12. In one embodiment, the MBP reporter protein of the invention comprises one or more mutation selected from D14C, A63H, R66H, A96F, E111M, Y155E, Y155C, Y155H, W230C, L262M, I329F, W340E, W340H and W340C with respect to the bacterial MBP of SEQ ID NO: 8, or an equivalent residue of SEQ ID NO:9-12.

The invention should also be construed to include any form of a peptide having substantial homology to a protein reporter, protein reporter fragment, or protein reporter mutant disclosed herein. Preferably, a peptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of protein reporter, protein reporter fragment, or protein reporter mutant disclosed herein.

The peptide of the present invention may be made using chemical methods. For example, peptides can be synthesized by solid phase techniques (Roberge J Y et al (1995) Science 269: 202-204), cleaved from the resin, and purified by preparative high performance liquid chromatography. Automated synthesis may be achieved, for example, using the ABI 431 Å Peptide Synthesizer (Perkin Elmer) in accordance with the instructions provided by the manufacturer.

The peptide may alternatively be made by recombinant means or by cleavage from a longer polypeptide. The composition of a peptide may be confirmed by amino acid analysis or sequencing.

The variants of the peptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two peptides is determined by comparing the amino acid sequence and its conserved amino acid substitutes of one polypeptide to a sequence of a second polypeptide. Variants are defined to include peptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to stimulate the differentiation of a stem cell into the osteoblast lineage. The present invention includes amino acid sequences that are at least 60%, 65%, 70%, 72%, 74%, 76%, 78%, 80%, 90%, or 95% similar or identical to the original amino acid sequence. The degree of identity between two peptides is determined using computer algorithms and methods that are widely known for the persons skilled in the art. The identity between two amino acid sequences is preferably determined by using the BLASTP algorithm (BLAST Manual, Altschul, S., et al., NCBI NLM NIH Bethesda, Md. 20894, Altschul, S., et al., J. Mol. Biol. 215: 403-410, 1990).

The peptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The peptides of the invention may include unnatural amino acids formed by post-translational modification or by introducing unnatural amino acids during translation. A variety of approaches are available for introducing unnatural amino acids during protein translation.

A peptide or protein of the invention may be conjugated with other molecules, such as proteins, to prepare fusion proteins. This may be accomplished, for example, by the synthesis of N-terminal or C-terminal fusion proteins provided that the resulting fusion protein retains the functionality of bla as a reporter for NMR and MRI. A peptide or protein of the invention may be phosphorylated using conventional methods such as the method described in Reedijk et al. (The EMBO Journal 11(4): 1365, 1992).

Cyclic derivatives of the peptides of the invention are also part of the present invention. Cyclization may allow the peptide to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position.

It may be desirable to produce a cyclic peptide which is more flexible than the cyclic peptides containing peptide bond linkages as described above. A more flexible peptide may be prepared by introducing cysteines at the right and left position of the peptide and forming a disulfide bridge between the two cysteines. The two cysteines are arranged so as not to deform the beta-sheet and turn. The peptide is more flexible as a result of the length of the disulfide linkage and the smaller number of hydrogen bonds in the beta-sheet portion. The relative flexibility of a cyclic peptide can be determined by molecular dynamics simulations.

The invention also relates to peptides comprising protein reporter, protein reporter fragment, or protein reporter mutant fused to, or integrated into, a target protein, and/or a targeting domain capable of directing the chimeric protein to a desired cellular component or cell type or tissue. The chimeric proteins may also contain additional amino acid sequences or domains. The chimeric proteins are recombinant in the sense that the various components are from different sources, and as such are not found together in nature (i.e., are heterologous).

In one embodiment, the targeting domain can be a membrane spanning domain, a membrane binding domain, or a sequence directing the protein to associate with, for example, vesicles or with the nucleus. In one embodiment, the targeting domain can target a peptide to a particular cell type or tissue. For example, the targeting domain can be a cell surface ligand or an antibody against cell surface antigens of a target tissue. A targeting domain may target the peptide of the invention to a cellular component.

Exemplary chimeric proteins may comprise a targeting domain, which targets the protein reporter-containing chimeric protein to a site of interest within a cell, tissue, or organism. For example, in certain embodiments, the targeting domain binds to an exogenous or endogenous biomolecule of the cell, tissue, or organism. For example, the targeting domain may bind to an epitope, ligand, antigen, or binding pair member. In certain embodiments, the targeting domain binds to an antigen; for example, a bacterial antigen, viral antigen, tumor-associated antigen, or tumor-specific antigen, thus targeting the chimeric protein to a site in which the antigen may be present. Such fusion peptides can be used in MRI applications to specifically detect the presence or abundance of the antigen with spatial and temporal resolution.

In certain embodiments, the targeting domain comprises an antibody or antibody fragment. Antibodies or antibody fragments include, but are not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may also include Fab', Fv, F(ab')2, and or other antibody fragments that retain specific binding to antigen.

A peptide of the invention may be synthesized by conventional techniques. For example, the peptides or chimeric proteins may be synthesized by chemical synthesis using solid phase peptide synthesis. These methods employ either solid or solution phase synthesis methods (see for example, J. M. Stewart, and J. D. Young, Solid Phase Peptide Synthesis, $2^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis). By way of example, a peptide of the invention may be synthesized using 9-fluorenyl methoxycarbonyl (Fmoc) solid phase chemistry with direct incorporation of phosphothreonine as the N-fluorenylmethoxy-carbonyl-O-benzyl-L-phosphothreonine derivative.

N-terminal or C-terminal fusion proteins comprising a peptide or chimeric protein of the invention conjugated with other molecules may be prepared by fusing, through recombinant techniques, the N-terminal or C-terminal of the peptide or chimeric protein, and the sequence of a selected protein or selectable marker with a desired biological function. The resultant fusion proteins contain the protein reporter fused to the selected protein as described herein. In certain embodiments, the fusion or chimeric protein comprises a protein reporter and a marker or reporter peptide. Examples of marker or reporter peptides include immunoglobulins, glutathione-S-transferase (GST), hemagglutinin (HA), GFP, and truncated myc.

The protein reporters of the invention may be modified to increase protease stability/increase circulation time/increase specific targeting efficiency. In one embodiment, the protein reporters of the invention are pegylated.

Peptides of the invention may be developed using a biological expression system. Exemplary biological expression systems include, for example, bacterial, yeast, insect, or mammalian cell or cell populations modified to express the peptide described herein.

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Nucleic Acids

In one embodiment, the present invention provides a composition comprising an isolated nucleic acid encoding bla, a fragment thereof, or a mutant thereof. For example, in certain embodiments, the composition comprises a nucleotide sequence encoding bla, a bla fragment, or a bla mutant, in combination with a nucleotide sequence encoding a protein or nucleic acid of interest. As such, the bla, bla fragment, or bla mutant functions as a reporter gene used in hyper-CEST imaging, to evaluate the expression of the isolated nucleic acid molecule.

In one embodiment, the isolated nucleic acid sequence encodes bla. In various embodiments, the isolated nucleic acid sequence encodes bla comprising an amino acid sequence selected from SEQ ID NOs: 1-7.

Further, the invention encompasses an isolated nucleic acid encoding a peptide having substantial homology to bla, a bla fragment, or a bla mutant disclosed herein. In certain embodiments, the isolated nucleic acid sequence encodes bla having at least 75%, 80%, 85%, 90%, 95%, 96%, 97%, 98%, or 99% sequence homology with an amino acid sequence selected from SEQ ID NOs: 1-7.

In one embodiment, the isolated nucleic acid molecule comprises the nucleotide sequence of:

(SEQ ID NO: 13)
ATGTCTATCCAGCACTTTCGCGTCGCGCTCATTCCGTTCTTTGCCGCTTT

CTGTCTGCCTGTCTTTGCACATCCGGAAACCCTGGTCAAGGTTAAAGACG

CTGAAGATCAGCTTGGTGCGCGTGTGGGTTACATCGAACTGGACCTGAAT

TCGGGCAAAATTCTGGAGAGCTTCCGTCCAGAAGAACGCTTCCCGATGAT

GAGCACCTTCAAGGTTCTGCTGTGCGGTGCGGTTCTGTCCCGTGTTGATG

CCGGTCAAGAGCAACTGGGTCGCCGTATTCACTATAGCCAGAATGACCTG

GTGGAGTACAGCCCGGTGACGGAGAAGCACCTGACGGACGGCATGACCGT

CCGTGAGCTGTGCTCCGCAGCCATTACGATGTCTGACAATACTGCGGCGA

ACCTGTTGTTGACGACCATCGGTGGCCCGAAAGAATTGACCGCGTTTCTG

CATAACATGGGCGATCACGTGACTCGCCTGGATCGTTGGGAGCCGGAGCT

GAACGAAGCCATTCCGAATGATGAGAGAGACACGACCACCCCGGCAGCGA

TGGCGACGACCCTGCGCAAGCTGTTAACCGGTGAGTTGCTGACCCTGGCA

AGCCGTCAACAGCTGATCGATTGGATGGAAGCTGACAAAGTTGCGGGTCC

GCTGCTGCGTAGCGCGTTGCCGGCAGGCTGGTTTATCGCGGACAAAAGCG

GCGCAGGCGAGCGTGGCAGCCGTGGTATTATCGCCGCACTGGGTCCGGAC

GGTAAACCGAGCCGCATTGTTGTGATCTATACCACCGGTAGCCAGGCCAC

GATGGATGAGCGTAACCGTCAGATTGCTGAAATCGGTGCGAGCCTGATCA

AGCATTGGTAA

The nucleotide sequence of SEQ ID NO: 13 encodes the amino acid sequence of SEQ ID NO: 1. In certain embodiments, the composition comprises an isolated nucleic acid molecule comprising a nucleotide sequence having substantial homology to SEQ ID NO: 13. For example, in certain embodiments, the composition comprises an isolated nucleic acid molecule comprising a nucleotide sequence that is about 50% homologous, more preferably about 70% homologous, even more preferably about 80% homologous, more preferably about 90% homologous, even more preferably, about 95% homologous, and even more preferably about 99% homologous to SEQ ID NO: 13.

In one embodiment, the isolated nucleic acid molecule comprises the nucleotide sequence of:

(SEQ ID NO: 14)
ATGCATCCGGAAACCCTCGTGAAGGTCAAAGACGCAGAAGATCAACTTGG

AGCCAGAGTCGGATACATTGAGCTCGACCTGAACAGCGGGAAGATCCTGG

AATCCTTTCGGCCTGAGGAGCGCTTCCCGATGATGTCCACATTCAAAGTG

TTGCTGTGCGGTGCCGTGCTGTCAAGGGTGGACGCCGGACAGGAGCAACT

GGGTCGGCGCATTCACTACTCCCAAAACGACCTCGTGGAGTACTCCCCCG

TGACTGAGAAGCACCTGACGGACGGCATGACTGTGCGGGAACTGTGTTCC

GCGGCGATCACCATGTCCGATAACACCGCCGCCAATTTGCTGCTGACCAC

CATCGGTGGCCCCAAGGAGCTGACCGCTTTCCTGCACAACATGGGCGACC

ACGTGACCCGCCTGGACAGATGGGAACCCGAACTGAACGAGGCCATCCCC

AACGATGAACGCGATACCACTACCCCTGCTGCCATGGCAACCACCCTGAG

GAAGCTGCTGACTGGCGAACTGCTGACCCTGGCCTCGAGGCAGCAGCTGA

TCGACTGGATGGAGGCCGACAAGGTCGCCGGACCACTCCTGCGCTCAGCC

-continued
CTTCCTGCCGGATGGTTCATTGCGGACAAGAGCGGAGCCGGAGAGAGG

GTCCCGGGGTATCATTGCGGCCCTTGGACCAGACGGAAAGCCGTCGCGGA

TCGTCGTGATCTACACCACTGGGTCGCAGGCTACCATGGACGAGCGGAAT

AGACAGATCGCCGAAATTGGCGCCTCCCTCATCAAGCACTGGTAG

The nucleotide sequence of SEQ ID NO: 14 encodes the amino acid sequence of SEQ ID NO: 7. In certain embodiments, the composition comprises an isolated nucleic acid molecule comprising a nucleotide sequence having substantial homology to SEQ ID NO: 14. For example, in certain embodiments, the composition comprises an isolated nucleic acid molecule comprising a nucleotide sequence that is about 50% homologous, more preferably about 70% homologous, even more preferably about 80% homologous, more preferably about 90% homologous, even more preferably, about 95% homologous, and even more preferably about 99% homologous to SEQ ID NO: 14.

In one embodiment, the isolated nucleic acid molecule comprises the nucleotide sequence of:

(SEQ ID NO: 15)
AAAATCGAAGAAGGTAAACTGGTAATCTGGATTA

ACGGCGATAAAGGCTATAACGGTCTCGCTGAAGTCGGTAAGAAATTCGAG

AAAGATACCGGAATTAAAGTCACCGTTGAGCATCCGGATAAACTGGAAGA

GAAATTCCCACAGGTTGCGGCAACTGGCGATGGCCCTGACATTATCTTCT

GGGCACACGACCGCTTTGGTGGCTACGCTCAATCTGGCCTGTTGGCTGAA

ATCACCCCGGACAAAGCGTTCCAGGACAAGCTGTATCCGTTTACCTGGGA

TGCCGTACGTTACAACGGCAAGCTGATTGCTTACCCGATCGCTGTTGAAG

CGTTATCGCTGATTTATAACAAAGATCTGCTGCCGAACCCGCCAAAAACC

TGGGAAGAGATCCCGGCGCTGGATAAAGAACTGAAAGCGAAAGGTAAGAG

CGCGCTGATGTTCAACCTGCAAGAACCGTACTTCACCTGGCCGCTGATTG

CTGCTGACGGGGGTTATGCGTTCAAGTATGAAAACGGCAAGTACGACATT

AAAGACGTGGGCGTGGATAACGCTGGCGCGAAAGCGGGTCTGACCTTCCT

GGTTGACCTGATTAAAAACAAACACATGAATGCAGACACCGATTACTCCA

TCGCAGAAGCTGCCTTTAATAAAGGCGAAACAGCGATGACCATCAACGGC

CCGTGGGCATGGTCCAACATCGACACCAGCAAAGTGAATTATGGTGTAAC

GGTACTGCCGACCTTCAAGGGTCAACCATCCAAACCGTTCGTTGGCGTGC

TGAGCGCAGGTATTAACGCCGCCAGTCCGAACAAAGAGCTGGCAAAAGAG

TTCCTCGAAAACTATCTGCTGACTGATGAAGGTCTGGAAGCGGTTAATAA

AGACAAACCGCTGGGTGCCGTAGCGCTGAAGTCTTACGAGGAAGAGTTGG

CGAAAGATCCACGTATTGCCGCCACTATGGAAAACGCCCAGAAAGGTGAA

ATCATGCCGAACATCCCGCAGATGTCCGCTTTCTGGTATGCCGTGCGTAC

TGCGGTGATCAACGCCGCCAGCGGTCGTCAGACTGTCGATGAAGCCCTGA

AAGACGCGCAGACT.

The nucleotide sequence of SEQ ID NO: 15 encodes the amino acid sequence of SEQ ID NO: 8. In one embodiment, the MBP comprises the nucleotide sequence of SEQ ID NO: 15 operably linked to at least one regulatory element. In one embodiment, at least one regulatory element is a start codon (e.g., a sequence encoding methionine) at the 5' terminus. In one embodiment, at least one regulatory element is a stop codon at the 3' terminus. In one embodiment, at least one regulatory element is a sequence encoding a leader sequence at the 5' terminus. In one embodiment, a leader sequence is set forth in SEQ ID NO:45. Therefore, in one embodiment, the MBP comprises SEQ ID NO: 15 operably linked to a sequence encoding the amino acid sequence of SEQ ID NO:45 at the 5' terminus. In one embodiment, the MBP is encoded by the nucleotide sequence of SEQ ID NO:50. The nucleotide sequence of SEQ ID NO: 50 encodes the amino acid sequence of SEQ ID NO: 49.

In certain embodiments, the composition comprises an isolated nucleic acid molecule comprising a nucleotide sequence having substantial homology to SEQ ID NO: 15. For example, in certain embodiments, the composition comprises an isolated nucleic acid molecule comprising a nucleotide sequence that is about 50% homologous, more preferably about 70% homologous, even more preferably about 80% homologous, more preferably about 90% homologous, even more preferably, about 95% homologous, and even more preferably about 99% homologous to SEQ ID NO: 15.

In one embodiment, the isolated nucleic acid molecule comprises the nucleotide sequence of:

(SEQ ID NO: 16)
ATGAAGATTGAAGAGGGGAAGCTCGTGATTTGGATTAACGGCGACAAGGG

CTACAACGGGCTGGCCGAAGTCGGAAAGAAATTCGAAAAGGACACTGGCA

TCAAGGTCACCGTGGAACACCCGGACAAGCTCGAGGAAAGTTCCCACAA

GTCGCCGCTACTGGGGACGGACCCGATATCATCTTCTGGGCCCATGATCG

CTTCGGTGGATATGCGCAGTCCGGTCTGTTGGCCGAAATCACGCCCGATA

AGGCCTTCCAAGACAAGCTGTACCCGTTTACTTGGGACGCCGTGCGGTAC

AACGGAAAGCTCATCGCGTACCCCATCGCTGTGGAAGCCCTTAGCCTCAT

CTACAACAAGGATCTCCTGCCCAACCCCCCTAAGACTTGGGAAGAGATTC

CAGCCCTGGACAAGGAACTGAAGGCCAAGGGAAAGTCCGCCCTGATGTTC

AACTTGCAAGAGCCGTACTTCACCTGGCCTCTCATTGCGGCCGATGGGGG

TTACGCCTTCAAATATGAGAACGGGAAATACGACATTAAGGACGTGGGCG

TGGACAACGCCGGAGCGAAAGCCGGCCTGACCTTCCTGGTGGACCTGATC

AAGAACAAGCACATGAACGCCGACACCGACTACTCCATCGCTGAAGCGGC

CTTCAACAAGGGCGAAACCGCCATGACCATCAATGGACCCTGGGCATGGT

CCAACATCGACACCTCCAAGGTCAACTACGGCGTCACCGTGCTGCCGACT

TTCAAGGGCCAGCCTTCCAAGCCTTTCGTGGGAGTGCTTTCGGCCGGCAT

TAACGCCGCCAGCCCCAATAAGGAGCTGGCGAAGGAGTTCCTTGAGAACT

ACCTCCTGACCGATGAGGGTCTGGAAGCCGTGAACAAGGACAAACCGCTG

GGAGCAGTGGCCCTGAAGTCATACGAAGAGGAACTGGCCAAGGACCCGAG

AATCGCGGCCACCATGGAGAACGCGCAGAAGGGCGAAATCATGCCGAACA

TCCCGCAGATGTCGGCCTTTTGGTACGCAGTGCGGACTGCAGTGATCAAT

GCTGCTAGCGGTCGCCAGACAGTGGACGAAGCCCTGAAGGATGCACAGAC

CTGATAG.

The nucleotide sequence of SEQ ID NO: 16 encodes the amino acid sequence of SEQ ID NO: 12. In certain embodiments, the composition comprises an isolated nucleic acid molecule comprising a nucleotide sequence having substantial homology to SEQ ID NO: 16. For example, in certain embodiments, the composition comprises an isolated nucleic acid molecule comprising a nucleotide sequence that is about 50% homologous, more preferably about 70% homologous, even more preferably about 80% homologous, more preferably about 90% homologous, even more preferably, about 95% homologous, and even more preferably about 99% homologous to SEQ ID NO: 16.

In one embodiment, the isolated nucleic acid molecule comprises the nucleotide sequence of:

(SEQ ID NO: 43)
AAAGATACCATCGCGCTGGTCGTGAGCACCCTGAATAACCCGTTCTTTGT

CTCTGCGAAGGACGGCGCGCAAAAGGAAGCCGATAAACTGGGCTATAACT

TGGTTGTCCTGGACAGCCAGAACAACCCGGCCAAAGAACTGGCGAACGTT

CAAGATTTGACGGTCCGTGGCACCAAGATTCTGCTGATCAATCCGACGGA

TTCGGACGCTGTCGGCAACGCAGTCAAAATGGCAAATCAAGCAAACATCC

CGGTTATTACGCTGGATCGTCAAGCAACCAAGGGTGAAGTTGTGTCCCAC

ATCGCGAGCGACAATGTGCTGGGTGGCAAGATTGCGGGTGATTACATTGC

AAAAAAAGCTGGCGAGGGTGCCAAGGTTATTGAGTTGCAGGGTATCGCGG

GTACCAGCGCTGCGCGCGAGCGCGGCGAGGGTTTCCAACAAGCTGTTGCG

GCACATAAGTTTAACGTTTTGGCAAGCCAGCCGGCTGACTTCGACCGTAT

CAAGGGCCTGAATGTAATGCAGAATCTGCTGACCGCCCACCCAGACGTGC

AAGCCGTGTTTGCCCAGAATGATGAAATGGCGCTGGGCGCGCTGCGTGCA

CTGCAAACGGCTGGTAAGTCCGATGTGATGGTTGTGGGTTTCGACGGTAC

CCCGGATGGTGAAAAAGCCGTTAATGACGGTAAACTGGCGGCGACGATTG

CACAACTGCCGGACCAGATCGGTGCGAAGGGTGTGGAGACTGCGGATAAA

GTGCTGAAGGGCGAAAAAGTCCAAGCGAAATACCCTGTGGACCTGAAACT

GGTTGTCAAACAG.

The nucleotide sequence of SEQ ID NO: 43 encodes the amino acid sequence of SEQ ID NO: 44.

In one embodiment, the isolated nucleic acid molecule comprises the nucleotide sequence of:

(SEQ ID NO: 43)
ATGGGTTCTTCTCACCATCACCATCACCATGGTTCTTCTGTGAGCAAGGG

CGAGGAGCTGTTCACCGGGGTGGTGCCCATCCTGGTCGAGCTGGACGGCG

ACGTAAACGGCCACAAGTTCAGCGTGCGCGGCGAGGGCGAGGGCGATGCC

ACCAACGGCAAGCTGACCCTGAAGTTCATCTGCACCACCGGCAAGCTGCC

CGTGCCCTGGCCCACCCTCGTGACCACCCTGACCTACGGCGTGCAGTGCT

TCAGCCGCTACCCCGACCACATGAAGCAGCACGACTTCTTCAAGTCCGCC

ATGCCCGAAGGCTACGTCCAGGAGCGCACCATCTCCTTCAAGGACGACGG

CACCTACAAGACCCGCGCCGAGGTGAAGTTCGAGGGCGACACCCTGGTGA

ACCGCATCGAGCTGAAGGGCATCGACTTCAAGGAGGACGGCAACATCCTG

GGGCACAAGCTGGAGTACAACTTCAACAGCCACAACGTCTATATCACGGC

CGACAAGCAGAAGAACGGCATCAAGGCGAACTTCAAGATCCGCCACAACG

TCGAGGACGGCAGCGTGCAGCTCGCCGACCACTACCAGCAGAACACCCCC

ATCGGCGACGGCCCCGTGCTGCTGCCCGACAACCACTACCTGAGCACCCA

GTCCAAGCTGAGCAAAGACCCCAACGAGAAGCGCGATCACATGGTCCTGC

TGGAGTTCGTGACCGCCGCCGGGATCACTCTCGGCATGGACGAGCTGTAC

AAGGGGATCGAGGAAAACCTGTACTTCCAATCCAATGCAAAAGATACCAT

CGCGCTGGTCGTGAGCACCCTGAATAACCCGTTCTTTGTCTCTGCGAAGG

ACGGCGCGCAAAAGGAAGCCGATAAACTGGGCTATAACTTGGTTGTCCTG

GACAGCCAGAACAACCCGGCCAAAGAACTGGCGAACGTTCAAGATTTGAC

GGTCCGTGGCACCAAGATTCTGCTGATCAATCCGACGGATTCGGACGCTG

TCGGCAACGCAGTCAAAATGGCAAATCAAGCAAACATCCCGGTTATTACG

CTGGATCGTCAAGCAACCAAGGGTGAAGTTGTGTCCCACATCGCGAGCGA

CAATGTGCTGGGTGGCAAGATTGCGGGTGATTACATTGCAAAAAAAGCTG

GCGAGGGTGCCAAGGTTATTGAGTTGCAGGGTATCGCGGGTACCAGCGCT

GCGCGCGAGCGCGGCGAGGGTTTCCAACAAGCTGTTGCGGCACATAAGTT

TAACGTTTTGGCAAGCCAGCCGGCTGACTTCGACCGTATCAAGGGCCTGA

ATGTAATGCAGAATCTGCTGACCGCCCACCCAGACGTGCAAGCCGTGTTT

GCCCAGAATGATGAAATGGCGCTGGGCGCGCTGCGTGCACTGCAAACGGC

TGGTAAGTCCGATGTGATGGTTGTGGGTTTCGACGGTACCCCGGATGGTG

AAAAAGCCGTTAATGACGGTAAACTGGCGGCGACGATTGCACAACTGCCG

GACCAGATCGGTGCGAAGGGTGTGGAGACTGCGGATAAAGTGCTGAAGGG

CGAAAAAGTCCAAGCGAAATACCCTGTGGACCTGAAACTGGTTGTCAAAC

AG.

The nucleotide sequence of SEQ ID NO: 47 encodes the amino acid sequence of SEQ ID NO: 46 comprising a GFP-RBP(L19A) fusion reporter protein.

In certain embodiments, the composition comprises an isolated nucleic acid molecule comprising a nucleotide sequence having substantial homology to SEQ ID NO:43 or SEQ ID NO: 47. For example, in certain embodiments, the composition comprises an isolated nucleic acid molecule comprising a nucleotide sequence that is about 50% homologous, more preferably about 70% homologous, even more preferably about 80% homologous, more preferably about 90% homologous, even more preferably, about 95% homologous, and even more preferably about 99% homologous to SEQ ID NO:43 or SEQ ID NO: 47.

SEQ ID NOs: 13-16 are codon optimized sequences, which are optimized for increased levels of protein expression. However, a skilled artisan would recognize that other nucleic acid sequences which encode a protein reporter, protein reporter fragment, or protein reporter mutant described herein may also be effective for use as an imaging agent.

The isolated nucleic acid sequence encoding protein reporter, protein reporter fragment, or protein reporter mutant can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The isolated nucleic acid may comprise any type of nucleic acid, including, but not limited to DNA and RNA.

For example, in one embodiment, the composition comprises an isolated DNA molecule, including for example, an isolated cDNA molecule, encoding protein reporter, protein reporter fragment, or protein reporter mutant. In one embodiment, the composition comprises an isolated RNA molecule encoding protein reporter, protein reporter fragment, or protein reporter mutant.

The nucleic acid molecules of the present invention can be modified to improve stability in serum or in growth medium for cell cultures. Modifications can be added to enhance stability, functionality, and/or specificity and to minimize immunostimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In certain backbone-modified ribonucleotides, the phosphoester group connecting to adjacent ribonucleotides is replaced by a modified group, e.g., a phosphorothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Other examples of modifications are nucleobase-modified ribonucleotides, i.e., ribonucleotides containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In some instances, the nucleic acid molecule comprises at least one of the following chemical modifications: 2'-H, 2'-O-methyl, or 2'-OH modification of one or more nucleotides. In certain embodiments, a nucleic acid molecule of the invention can have enhanced resistance to nucleases. For increased nuclease resistance, a nucleic acid molecule can include, for example, 2'-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the invention can include 2'-O-methyl, 2'-fluoro, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

In certain embodiments, the nucleic acid molecule of the invention preferably has one or more of the following properties:

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. (Nucleic Acids Res., 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone.

Modifications of the nucleic acid of the invention may be present at one or more of, a phosphate group, a sugar group, backbone, N-terminus, C-terminus, or nucleobase.

The present invention also includes a vector in which the isolated nucleic acid of the present invention is inserted. The art is replete with suitable vectors that are useful in the present invention.

In brief summary, the expression of natural or synthetic nucleic acids encoding a protein reporter, protein reporter fragment, or protein reporter mutant is typically achieved by operably linking a nucleic acid encoding the protein reporter, protein reporter fragment, or protein reporter mutant to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method.

In certain embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter, leader and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence to which it is operatively linked when such expression is desired, or turning off the expression when expression is not desired. Examples of inducible promoters include, but are not limited to a metallothionein promoter, a glucocorticoid promoter, a progesterone promoter, and a tetracycline promoter.

Enhancer sequences found on a vector also regulate expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of the protein reporter, protein reporter fragment, or protein reporter mutant, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Delivery Vehicles

In one embodiment, the present invention provides a delivery vehicle comprising a protein reporter or a nucleic acid molecule encoding a protein reporter. Exemplary delivery vehicles include, but are not limited to, microspheres, microparticles, nanoparticles, polymersomes, liposomes, and micelles. For example, in certain embodiments, the delivery vehicle is loaded with a protein reporter or a nucleic acid molecule encoding a protein reporter. In certain embodiments, the delivery vehicle provides for controlled release, delayed release, or continual release of its loaded cargo. In certain embodiments, the delivery vehicle comprises a targeting moiety that targets the delivery vehicle to a target site.

Cells

In one embodiment, the present invention provides a cell or population of cells comprising a protein reporter. In one embodiment, the cell or cell population is contacted with a protein reporter or nucleic acid molecule encoding a protein reporter. In one embodiment, the cell or cell population is contacted with a fusion protein or chimeric protein comprising a protein reporter. For example, in one embodiment, the cell or cell population can be modified to express a protein reporter. In one embodiment, the cell or cell population can be modified to express a fusion protein or chimeric protein comprising a protein reporter.

Exemplary cells include eukaryotic and prokaryotic cells. For example, the cells may be bacterial cells, yeast cells, insect cells, mammalian cells, reptilian cells, avian cells, and the like. In certain embodiments, the cells are human.

In certain embodiments, the invention provides an in vitro or ex vivo cell population comprising a protein reporter. In certain embodiments, the in vitro or ex vivo cell population is a 3-dimensional cell culture population. Use of a protein reporter as an NMR or MRI reporter in such a model is advantageous as traditional markers are difficult to detect at increased tissue depths.

Substrates

The present invention provides a scaffold or substrate composition comprising a protein reporter, a nucleic acid molecule encoding a protein reporter, a cell comprising a protein reporter, a cell encoding a protein reporter, or a combination thereof. The scaffold of the invention may be of any type known in the art. Non-limiting examples of such a scaffold include a hydrogel, electrospun scaffold, foam, mesh, sheet, patch, and sponge.

Analytes

Analytes detectable using the reporter proteins of the invention include organic and inorganic molecules, including biomolecules. The analyte can be an environmental pollutant (e.g., a pesticide, insecticide, toxin, etc.); a therapeutic molecule (e.g., a low molecular weight drug); a biomolecule (e.g., a protein or peptide, nucleic acid, lipid or carbohydrate, for example, a hormone, cytokine, membrane antigen, receptor (e.g., neuronal, hormonal, nutrient or cell surface receptor) or analyte therefor, or nutrient and/or metabolite such as glucose); a whole cell (including a prokaryotic cell, such as pathogenic bacterium, and eukaryotic cell, such as a mammalian tumor cell); a virus (including a retrovirus, herpesvirus, adenovirus, lentivirus, etc.); and a spore. In one embodiment, the analyte is zinc or a metal ion such as ferric ion.

In one embodiment, the reporter proteins of the invention may be used to detect their native (wild-type) analyte, or they may be used to detect a non-native analyte. The invention also contemplates that the mutant reporter proteins may be able to only bind a analyte or analytes that the wild-type binding protein does not bind. Methods of generating mutant proteins, in general, are well-known in the art (e.g., Looger, et al., (2003) Nature 423:185-190, which is hereby incorporated by reference). These mutant binding proteins retain the ability to undergo conformational change, which can produce a directly generated signal upon analyte-binding. By introducing one or more amino acid changes, mutant proteins can be constructed with selectivities for one or more amino acid, TNT (trinitrotoluene), L-lactate, or serotonin. These and other mutant PBPs could be used in the methods of the invention for detecting binding of a non-native PBP analyte to a reporter protein.

In certain embodiments, the method comprises detecting the presence of an analyte by administering a protein reporter, or nucleic acid encoding protein reporter, to a subject or cell, wherein the protein reporter exhibits an altered detectable signal during hyper-CEST imaging when the protein reporter binds to an analyte. In certain embodiments, the method comprises detecting an increase in the detectable signal during hyper-CEST imaging when the protein reporter is bound to an analyte relative to when the protein reporter is not bound to the analyte. In certain embodiments, the method comprises detecting a decrease in the detectable signal during hyper-CEST imaging when the protein reporter is bound to an analyte relative to when the protein reporter is not bound to the analyte.

Biosensors

In one embodiment, the present invention relates to biosensors that use ligand-mediated macromolecular structural changes to link molecular recognition and signal transduction. Biosensors of the invention can be used to precisely and accurately sense a diverse set of analytes having numerous medical, environmental and defense applications (Willner et al, Angew. Chem. Int. Ed. 39:1180 (2000), Laval et al, Analyst 125:29 (2000), Lowe, Curr. Op. Chem. Biol. 10:428 (2000) and Hellinga et al, Trends Biotech. 16:1983 (1998)). The biosensor can employ any protein that undergoes a conformational change upon binding to a ligand (analyte). The nature of the protein used is dependent upon the analyte to be detected. In one embodiment, the biosensor comprises a PBP or mutant thereof having a binding specificity for a non-native ligand. For example, the biosensor of the invention may comprise a PBP or mutant thereof having a binding specificity for zinc, sucrose, trinitrotoluene (TNT), L-lactate, or serotonin.

The protein of the biosensor can be attached directly or indirectly to a conductive layer. The conductive layer of the present biosensor can be any conducting or semiconducting substance in any form. Examples of suitable forms include foils, wires, wafers, chips, micro- or nano-particles, semiconductor devices and coatings deposited by any known deposition process. Gold, silver, and copper conductive layers chemisorb thiol, sulfide or disulfide functional compounds, while other conductive layers can chemisorb these or other SAM-forming compounds (that include oxygen-containing compounds for etched silicon [SiH] and silicon-derivative compounds [trichiorosilanes, trimethoxysilanes, for example] for metal oxides). Preferred conductive materials include gold, silver, copper, aluminum, platinum, iridium, palladium, rhodium, mercury, silicon, osmium, ruthenium, gallium arsenide, indium phosphide, mercury, cadmium telluride, carbon and the like. Gold, silver, aluminum foil, and doped silicon wafers are particularly preferred.

In one embodiment, the reporter protein is attached via a tether, for example, a tether comprising a peptide, nucleic acid, lipid or carbohydrate. The protein can also be modified so as to contain one member of a binding pair (e.g., the protein can be biotinylated) and the surface to which it is attached can be derivatized with the other member of the binding pair (e.g., the surface can be streptavidin-derivatized) (Rao et al, Mikrochimica Acta 128:127-143 (1998)).

In operation, the biosensor of the invention can be deployed in situ to monitor continuously fluctuations in analyte, e.g., in the blood stream of a patient to monitor blood glucose, etc., in water samples to monitor for toxins, pollutants, or in a bioreactor or chemical reactor to monitor reaction progress.

Pharmaceutical Compositions

The present invention also provides pharmaceutical compositions comprising one or more of the compositions described herein. Formulations may be employed in admixtures with conventional excipients, i.e., pharmaceutically acceptable organic or inorganic carrier substances suitable for administration to the wound or treatment site. The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., other analgesic agents.

In vivo administration of the compositions of this invention may be carried out, for example, by parenteral, by intravenous, intratumoral, subcutaneous, intramuscular, or intraperitoneal injection, by infusion, by inhalation or by any other acceptable systemic method.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

In certain aspects, the protein reporter is aerosolized to allow for the inhalation of the composition for delivery to the lung. Methods to formulate aerosolized compositions comprising the protein reporter are known in the art, and are described for example, in Brown et al., 1995, J Aerosol Med, 8(1): 43-58 and Bustami et al., 2000, Pharm Res, 17(11): 1360-1366.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Methods

In one embodiment, the reporter proteins of the invention are capable of providing a detectable signal upon target analyte binding to the reporter protein. To "provide a detectable signal", as used herein refers to the ability to recognize a change in a property of a reporter group within the reporter protein in a manner that enables the detection of analyte-protein binding. In one embodiment, therefore, the reporter protein may comprise one or more "reporter groups," e.g., a fluorescent protein or dye, that are responsible for generating the detectable signal which is altered upon a change in binding molecule conformation or reporter group environment which occurs, for example, upon analyte binding. Thus, in one embodiment of providing a detectable signal, the reporter protein will generate a signal directly upon binding of the target analyte to the reporter protein. As used herein, "generating a signal directly upon binding" is used to mean that the act of binding of the analyte to the binding molecule itself is responsible for generating the detectable signal, without any additional reactions or processes. For example, a directly generated signal can be a signal that is produced when a conformational change occurs in a reporter protein, such as when the reporter protein binds specifically to its target.

The one or more protein reporters described herein may be used as an imaging agent in a variety of research, clinical or diagnostic applications.

In certain embodiments, the present invention provides methods of detecting a molecule of interest, for example in the determination of a diagnosis or prognosis of a pathology. In certain embodiments, the method comprises administering an imaging agent comprising a protein reporter to a cell, tissue, organ (e.g., lung or brain) or organism. In certain embodiments, the imaging agent comprises a fusion protein or chimeric protein comprising a protein reporter, and further comprising a targeting domain that binds to the molecule of interest. As described elsewhere herein, the targeting domain may bind to an epitope or antigen that is associated with a given pathology. Exemplary antigens include bacterial antigens, viral antigens, tumor-associated antigens, and tumor-specific antigens. In clinical applications, imaging agents comprising a protein reporter may be used in molecular imaging applications in cancer, immunology, regenerative medicine and other areas where nanoparticle reporters are desired.

In one embodiment, the present invention provides research methods using the imaging agents comprising a protein reporter. For example, the imaging agent may be used to label and quantify gene expression in bacteria and mammalian cells. For example, in certain embodiments, the method comprises the use of a nucleic acid molecule encoding a protein reporter in studies evaluating the function of various components of the transcription or translation process, including, for example, the function of promoters, enhancers, untranslated regions, transcription factors, and the like. Since a protein reporter is genetically encoded, the present invention provides non-invasive research methods to evaluate cell function, migration, proliferation, differentiation, de-differentiation, and the like in various areas of study. For example, the imaging agent may be used to study organ development, tumor growth, tumor metastasis, immune response, stem cell biology, and the like.

As hyperpolarized xenon is readily delivered to the lungs, and xenon rapidly diffuses from the lungs to the brain, it is envisioned that genetically encoded reporters that interact with xenon may be similarly imaged in the lungs and/or brain to assess the structure and function of these organs.

In addition, hyperpolarized xenon is very soluble and has long magnetization lifetime in many bio-compatible fluids, such as perfluorooctyl bromide (PFOB). Therefore in one embodiment, hyperpolarized xenon can be injected locally at a site or into a tissue of interest for imaging of the site or tissue. Thus, it is envisioned that genetically encoded reporters that interact with xenon may be similarly imaged in other tissues or organs, including, but not limited to, the eye, knee cap, and breast.

In certain embodiments, the imaging agents and methods find use in hyper-CEST imaging. In some cases, hyper-CEST imaging is ratiometric, making it suitable for imaging even under conditions where the absolute concentration of xenon and reporter may be inhomogeneous. In certain instances, the imaging agents and methods find use in applications where the use of lower magnetic fields is desired. For instance, $^{129}Xe$ can be polarized without the use of high magnetic fields, allowing molecular imaging and biological assays with comparatively inexpensive low-to-moderate-field MRI magnets.

In certain embodiments, the imaging agent comprising a protein reporter is configured to be compatible for use in NMR or MRI, for example NMR or MRI that uses hyperpolarized xenon. In one embodiment, the method comprises the use of $^{129}$Xe NMR or MRI. For example, the spin polarization of $^{129}$Xe can be increased to a non-equilibrium state ("hyperpolarized") by optical pumping, increasing its NMR signal by approximately $10^4$-$10^{54}$. In certain instances, hyperpolarization of $^{129}$Xe is carried out by spin-exchange with optically pumped alkali metal vapor. In these instances, the electron spin of atomic nuclei of an alkali metal, such as Rb, is initially polarized by irradiating the alkali metal vapor with polarized light.

$^{129}$Xe is a substantially inert and biocompatible element that rapidly distributes into tissues such as the lungs, brain, heart and kidneys after being introduced into a subject in gaseous form, where its polarization decays exponentially with a magnetization lifetime ($T_1$) of 4-6 seconds. Because of its high spin polarization, sub-millimolar local concentrations of $^{129}$Xe are sufficient for imaging. As a result, in certain embodiments, imaging agents that include xenon may be detectable at low concentrations, e.g., nanomolar, picomolar or lower concentrations.

In certain aspects, hyperpolarized $^{129}$Xe NMR operates on the basis of chemical exchange saturation transfer (hyper-CEST). Because of its high polarizability, xenon's NMR frequency is sensitive to its local chemical environment. Hyper-CEST contrast agents may produce a distinct chemical shift in $^{129}$Xe. When radiofrequency (RF) saturation pulses are applied at this frequency, rapid exchange between protein reporter bound-xenon and dissolved xenon in the surrounding media may result in saturation transfer between these two compartments, reducing the signal in the xenon in the surrounding media. In certain instances, during use, $^{129}$Xe specifically binds to one or more allosteric binding sites of a protein resulting in a chemical shift change compared to aqueous Xe. This detectable shift allows for the use of the imaging agent comprising a protein reporter in NMR and MRI applications.

Embodiments of the methods are directed to MRI methods. In certain instances, the method includes imaging a target site using an imaging agent, for example an imaging agent comprising a protein reporter, protein reporter fragment, or protein reporter mutant, as described above.

A target site may be in vivo or in vitro. As such, a target site may include, for example, any molecule, cell, tissue, body part, body cavity, organ system, whole organism, collection of any number of organisms, etc., that are of interest. For example, target sites may include a vessel or container containing a solution comprising a collection of organisms, including bacteria or archaea. In certain instances, target sites may include a vessel or container containing a solution comprising cells grown in culture, including primary mammalian cells, immortalized cell lines, tumor cells, stem cells, and the like. In certain embodiments, the target site may include a 3-dimensional in vitro population of cells grown in culture. In certain embodiments, target sites of interest include tissue and organs in culture. In certain embodiments, target sites of interest include tissue, organs, or organ systems in a subject, for example, lungs, brain, kidneys, liver, heart, the central nervous system, the peripheral nervous system, the gastrointestinal system, the circulatory system, the immune system, the skeletal system, the sensory system, and the like.

In certain embodiments, the method comprises administering a composition comprising a protein reporter. In one embodiment, the method comprises administering a composition comprising a nucleic acid encoding a protein reporter. The protein reporter may be administered at any dose or concentration that is sufficient to provide a detectable signal. In one embodiment, the protein reporter is administered at a concentration in the range of about 0.001 μM to about 1000 μM. In one embodiment, the reporter is administered at a concentration in the range of about 0.01 μM to about 100 μM. In one embodiment, the reporter is administered at a concentration in the range of about 0.1 μM to about 100 μM. In one embodiment, the reporter is administered at a concentration in the range of about 1 μM to about 10 μM. It is described herein that a concentration of about 0.1 μM is able to generate a detectable signal. In certain instances, a protein reporter can be detected at concentrations in the nanomolar or picomolar ranges.

In certain embodiments, the method comprises administering a composition comprising a protein reporter in combination with a compound. In one embodiment, the method comprises administering a protein reporter in combination with maltose. In one embodiment, the compound is administered at a concentration in the range of about 0.001 μM to about 100 mM. In one embodiment, the compound is administered at a concentration in the range of about 0.01 μM to about 10 mM. In one embodiment, the compound is administered at a concentration in the range of about 0.1 μM to about 10 mM. In one embodiment, the compound is administered at a concentration in the range of about 100 μM to about 10 mM. In one embodiment, the compound is administered at a concentration in the range of about 1 mM to about 10 mM. It is described herein that a concentration of about 1 mM is able to generate a detectable signal. In certain instances, a protein reporter in combination with a compound can be detected at compound concentrations in the micromolar or millimolar ranges.

In certain embodiments, the method comprises administering a noble gas to the cell, container, tissue, organism, or subject. In certain embodiments, the noble gas may be xenon gas. For example, the noble gas may be $^{129}$Xe gas, such as hyperpolarized $^{129}$Xe gas. In certain embodiments, the noble gas is administered locally or systemically. The noble gas may be administered by any conventional means known in the art. For example, in one embodiment, the noble gas may be administered to the subject by dissolving the noble gas in the medium in which the subject resides. In certain embodiments, the noble gas may be administered to the subject by inhalation. In yet another embodiment, the noble gas is administered to the subject parenterally in a lipid emulsion. In certain instances, the noble gas is administered to the subject parenterally in a microfoam. In certain instances, the noble gas is administered to the subject by infusion, for example, systemically, or regionally or locally by e.g. intra-arterial, intra-tumoral, intra-venous, or parenteral infusion. In yet other embodiments, the noble gas is administered to the subject by extracorporeal membrane gas exchange.

In certain embodiments, the method includes obtaining an MRI image of the target site. In some cases, the method includes applying an external magnetic field to the target site, transmitting a radio frequency (RF) signal from a transmitter to the target site, and receiving MRI data at a receiver. The MRI data may be analyzed using a processor, such as a processor configured to analyze the MRI data and produce an MRI image from the MRI data. In certain embodiments, the MRI data detected by the receiver includes an MRI signal (e.g., a radio frequency MRI signal of the target site of the subject). Additional aspects of MRI systems and methods are found, for example, in U.S. Pat. Nos. 7,307,421, 7,295,008, 7,050,617, 6,556,010, 6,242, 916, 4,307,343 the disclosures of each of which are incorporated herein by reference. In certain embodiments, the method includes obtaining MRI data (e.g., signal) of the target site, and analyzing the MRI data (e.g., signal) to produce an MRI image of the target site. The MRI data (e.g., signal) may be obtained using a standard MRI device, or may be obtained using an MRI device configured to specifically detect the protein reporter used. Obtaining the MRI data (e.g., signal) may include detecting the MRI data (e.g., signal) with an MRI detector.

In certain embodiments, MRI data is obtained by applying a strong static magnetic field, a rapidly switching gradient field for spatial coding, and RF pulses that are frequency matched such that the RF pulses trigger magnetic resonance signals from excited atomic nuclei at the target site. For example, an atomic nucleus may produce magnetic resonance signals when the RF pulse has a frequency that matches the resonance frequency (measured in chemical shifts (δ) in parts per million (ppm)) of the atomic nucleus. In such cases, the nucleus absorbs the RF pulse energy to become excited, and releases a magnetic resonance signal when the excited nucleus subsequently relaxes to an unexcited state after characteristic time periods. The magnetic resonance signals are detected by RF receiving antennas and digitized to generate the MRI data. The MRI data are analyzed using any known method of analyzing MRI data. In certain instances, the MRI data are analyzed to reconstruct the MRI image. For example, the MRI image is reconstructed from the MRI data by decoding the spatial information encoded in the MRI data using a linear reconstruction algorithm, such as Fourier transformation.

In certain embodiments, the method includes methods for enhancing contrast in the MRI image. In certain embodiments, methods for enhancing contrast in the MRI image include administering the protein reporter to the target site. For example, the MRI method using a contrast mechanism may be chemical exchange saturation transfer (CEST) MRI. CEST MRI relies on the dependence of the resonance of an atomic nucleus, such as a proton, on the chemical environment of the nucleus, and the ability of the atomic nucleus to exchange at a sufficient rate with another atomic nucleus in a different chemical environment. In other words, the resonance frequency (or chemical shift) of a first exchangeable pool of nuclei in a first chemical environment is offset relative to the resonance frequency of a second exchangeable pool of nuclei in a second chemical environment. In CEST MRI, selective saturation of the first pool of nuclei by applying saturation RF pulses at the resonance frequency of the first pool of nuclei causes a reduction in the signal from the second pool of nuclei between which the first nuclei can exchange. For example, a proton in an amide group (—NH) of a protein and protons in water molecules surrounding the protein have distinct resonance frequencies, and the proton in an amide group in a protein may exchange sufficiently rapidly with protons in the water molecules. Selective saturation of protons in a protein in solution causes progressive saturation of, and thus a decrease in, the MR signal from the protons in the surrounding water due to CEST. As a result, the signal from the protons in the protein is enhanced relative to the surrounding water.

For example, in certain instances, the method includes applying to the target site a saturating radio frequency pulse having a frequency offset relative to the resonance frequency of the noble gas used, such as xenon (e.g., hyperpolarized $^{129}$Xe), dissolved in the surrounding media. In certain instances, the noble gas is dissolved in adjacent tissue. In certain instances, the method includes applying to the target site a saturating radio frequency pulse having a frequency offset relative to the resonance frequency of the noble gas dissolved in the adjacent tissue. In certain embodiments, the frequency offset is 350 ppm or less, or 300 ppm or less, or 250 ppm or less, or 200 ppm or less, or 150 ppm or less, or 100 ppm or less, or 75 ppm or less, or 50 ppm or less relative to the resonance frequency of the noble gas dissolved in the surrounding media. For example, the frequency offset may range from 50 ppm to 350 ppm relative to the resonance frequency of the noble gas dissolved in the surrounding media.

In some instances, the frequency offset is correlated to the type of protein reporter, protein reporter fragment, or protein reporter mutant used. In certain instances, different forms of protein reporter, protein reporter fragment, or protein reporter mutant have different frequency offsets that may be individually detectable, thereby allowing for multiplexed detection.

In some embodiments, the method includes the uniplex analysis of a target site. By "uniplex analysis" it is meant that a protein reporter is administered to a target site and the target site is analyzed to detect an MRI image of the target site. For example, a single type of protein reporter may be administered to the target site and an MRI image of the target site obtained. In some cases, the method includes the uniplex analysis of the target site to determine an MRI image of the target site.

As described herein, different types of protein reporters may have different chemical shifts when observed by MRI (or NMR), e.g., hyper-CEST imaging, enabling multiplexed imaging. As such, certain embodiments include the multiplex analysis of two or more protein reporters at one or more target sites. By "multiplex analysis" it is meant that the presence of two or more distinct protein reporters, in which the two or more protein reporters are different from each other, is determined. For example, protein reporters may be specifically targeted to different target sites using different targeting domains. In these instances, a first and second protein reporter may be administered to a target site. A first MRI signal may be obtained at a first chemical shift, and a second MRI signal may be obtained at a second chemical shift. The first and second MRI signals may be analyzed individually or together to produce individual MRI images of the signals or composite images of two or more of the signals. In certain embodiment, the method comprises the use of 2 or more, 3 or more, 4 or more, 5 or more, 10 or more, or more distinct protein reporters.

In certain embodiments, the method includes obtaining one or more images of the target site using the resonance frequency of one nucleus, such as $^1$H, to obtain images of the anatomy, then obtaining one or more images using the resonance frequency of the hyperpolarized xenon to obtain an image produced by the imaging agent comprising a protein reporter, protein reporter fragment, or protein reporter mutant.

Methods of Detecting a Molecule

The present invention also relates to methods of detecting the presence of an analyte or ligand in a sample using the reporter protein of the present invention. As used herein, the terms "ligand" and "analyte" are used to indicate the molecule to which the reporter protein will specifically bind. The analyte or ligand measured in the methods described herein is not labeled with a reporter group. As used herein, a sample can be any environment that may be suspected of containing the analyte to be measured. Thus, a sample includes, but is not limited to, a solution, a cell, a body fluid, a tissue or portion thereof, and an organ or portion thereof.

When a sample includes a cell, the cell can be a prokaryotic or eukaryotic cell, for example, an animal cell. Examples of animal cells include, but are not limited to, insect, avian, and mammalian such as, for example, bovine, equine, porcine, canine, feline, human, and nonhuman primates. The scope of the invention should not be limited by the cell type assayed. Examples of biological fluids to be assayed include, but are not limited to, blood, urine, saliva, synovial fluid, interstitial fluid, cerebrospinal fluid, lymphatic fluids, semen, ocular fluid, bile and amniotic fluid. The scope of the methods of the present invention should not be limited by the type of body fluid assayed.

In one embodiment, for measuring the concentrations of a target analyte, the reporter protein of the present invention may be contacted with analyte-free solutions (control), such as buffers, and the directly generated signal measured. The value of the detectable signal measured may be, but is not limited to, intensity, rate-based or lifetime. The detectable signal measurement can, in turn, be directly or indirectly tied to the concentration of measured analyte. For example, the reporter protein can be contacted with a sample suspected of containing an analyte to be measured, and the intensity of the directly generated signal is measured at least once. The sequence in measuring the intensity of the control and experimental signals is not important and can be performed in any order. Any differences in the generated signals are an indication of the presence or absence of the analyte in the sample or control. Furthermore, measurements of the generated signal can be taken either continuously, episodically, or sequentially to monitor changes in the concentration of the analyte in the sample. Once the control or baseline signal is established, the subsequently measured signals can be measured continuously or at discrete times.

The comparison of the signals can be qualitative or quantitative. Furthermore, the quantitative differences can be relative or absolute. Of course, the differences in signal may be equal to zero, indicating the absence of the analyte sought. The quantity may simply be the measured signal without any additional measurements or manipulations. Alternatively, the difference in signals may be manipulated mathematically or in an algorithm, with the algorithm designed to correlate the measured signal value to the quantity of analyte in the sample. The quantity may be expressed as a difference, percentage or ratio of the measured value of the analyte to a measured value of another compound including, but not limited to, a standard. The difference may be negative, indicating a decrease in the amount of measured analyte. The quantity may also be expressed as a difference or ratio of the analyte to itself, measured at a different point in time.

Kits

The present invention provides kits that can be used in the above-described methods. In one embodiment, a kit comprises a composition of the invention, in one or more containers. In another embodiment, a kit comprises one or more imaging agents of the invention, in one or more containers, and one or more other agents useful for NMR or MRI applications in one or more other containers. In certain embodiments, the kit comprises a plurality of imaging agents, each comprising different protein reporters, wherein the different imaging agents exhibit different detectable chemical shifts, thereby allowing for multiplexing. Preferably, the kit further comprises instructions for using the imaging agents or other agents, as well as dosage information for method of administration. Optionally associated with such container(s) can be a notice in the form prescribed by a governmental agency regulating the manufacture, use or sale of pharmaceuticals or biological products, which reflects approval by the agency of manufacture, use or sale for human administration.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: A Genetically Encoded β-Lactamase Reporter for Ultrasensitive $^{129}$Xe NMR in Mammalian Cells Molecular imaging holds considerable promise for elucidating biological processes in normal physiology as well as disease states, but requires noninvasive methods for identifying analytes at sub-micromolar concentrations. Particularly useful are genetically encoded, single-protein reporters that harness the power of molecular biology to visualize specific molecular processes, but such reporters have been conspicuously lacking for in vivo magnetic resonance imaging (MRI). Reported herein is TEM-1 β-lactamase (bla), a single-protein reporter for hyperpolarized (HP)$^{129}$Xe NMR, with significant saturation contrast at 0.1 µM. This 29 kDa protein derived from E. coli can function as a genetically-encoded single-protein contrast agent for hyper-CEST, and gives useful contrast when expressed in both bacterial and mammalian cells (FIG. 1). As demonstrated herein, HP $^{129}$Xe chemical exchange saturation transfer (hyper-CEST) interactions with allosteric sites in bla give rise to a unique saturation peak at 255 ppm, well removed (~60 ppm downfield) from the $^{129}$Xe-H$_2$O peak. Useful saturation contrast was also observed for bla expressed in bacterial cells and mammalian cells.

Bla is a small, monomeric bacterial enzyme that hydrolyzes β-lactam antibiotics and confers antibiotic resistance to its host. Importantly, bla is not normally found in eukaryotic cells and is nontoxic when overexpressed in eukaryotic cells (Matagne et al., 1998, Biochem J, 330(Pt 2): 581-598; Philippon et al., 1998, Cell Mol Life Sci, 54(4): 341-346). The activity that bla confers motivated the development of fluorogenic substrates for studies of gene expression in mammalian cell culture (Zlokarnik et al., 1998, Science, 279(5347): 84-88; Zlokarnik, 2000, Methods Enzymol, 326: 221-244; Whitney et al., 1998, 16(13): 1329-1333; Gao et al, 2003, 125(37): 11146-11147). Bla has since been widely applied in biotechnology, e.g., in protein fragment complementation assays for studying protein-protein interactions in vitro and in vivo (Galarneau et al., 2002, Nat Biotechnol, 20(6): 619-622; Wehrman et al., 2002, Proc Natl Acad Sci USA, 99(5): 3496-3474; Spotts et al., 2002, Proc Natl Acad Sci USA, 99(23): 15142-15147), with constructs engineered to be minimally immunogenic (Harding et al., 2005, Mol Cancer Ther, 4(11): 1791-1800), and in transgenic bla-mouse reporters (Bouabe et al., 2011, J Immunology, 187(6): 3165-3176).

The materials and methods employed in these experiments are now described.

MD Simulation.

The molecular dynamics simulation was initialized using the X-ray crystal structure of bla (Jelsch et al., 1993, 16(4): 364-383). The molecular system contained a total of 67970 atoms, including bla, 21238 water molecules, 127 ions in solution and 60 Xe atoms. The resulting initial aqueous concentration of Xe is 155 mM. The simulation was performed using the CHARMM22-CMAP force field with torsional cross-terms for the protein (MacKerell et al., 2001, Biopolymers, 56(4): 257-265; Mackerell et al., 2004, J Comput Chem, 25(11): 1400-1415). The water molecules were described using the TIP3P model (Jorgensen et al., 1983, J Chem Phys, 79(2): 926-935). Periodic boundary conditions were employed for all of the MD simulations and the electrostatic potential was evaluated using the particle-mesh Ewald method (Essmann et al., 1995, J Chem Phys, 103(19): 8577-8593). The lengths of all bonds containing hydrogen were constrained with the SHAKE/RATTLE algorithm (Ryckaert et al., 1977, J Comput Phys, 23(3): 327-341. The system was maintained at a temperature of 300 K and pressure of 1 atm using the Langevin thermostat and barostat methods as implemented in the MD code NAMD2.10 (Phillips et al., 2005, J Comput Chem, 26(16): 1781-1802). The rRESPA multiple time step method was employed, with a high frequency timestep of 2.0 fs and a low frequency time step of 4.0 fs.

Sample Preparation

A pJ411 vector containing a codon-optimized coding sequence for $E.$ $coli$ TEM-1 β-lactamase (UniProt accession number P62593) was purchased from DNA 2.0. The bla plasmid was transformed into $E.$ $coli$ BL21(DE3) competent cells (New England BioLabs) and grown on LB-agar plates supplemented with 50 μg/mL kanamycin. 1 L cultures of transformed cells were grown in LB media supplemented with 50 μg/mL kanamycin at 37° C. until reaching an $OD_{600}$ of approximately 0.8. Protein expression was induced with 2 mM isopropyl-β-thiogalactopyranoside (IPTG) (Carbosynth) overnight at 18° C.

For expression of bla in HEK293T cells, a transient-expression vector with a CMV promoter and SV40 enhancer (vector name pD2610-v12) containing a codon-optimized coding sequence for $E.$ $coli$ TEM-1 β-lactamase was purchased from DNA 2.0. The HEK293T/17 cells were cultured in a T25 flask in high L-glutamine DMEM media supplemented with fetal bovine serum (FBS) and antibiotics until reaching about 80% confluency. Cells were subsequently transfected with the pD2610 plasmid using Lipofectamine 3000 reagent (Thermo Fisher). After 3 days, cells were harvested and resuspended in PBS.

Hyperpolarized $^{129}$Xe Chemical Exchange Saturation Transfer.

Hyper-CEST experiments were performed using an 11.7-T spectrometer with a 10-mm probe. HP $^{129}$Xe was generated using the spin-exchange optical pumping (SEOP) method with a home-built $^{129}$Xe hyperpolarizer generating roughly 10% hyperpolarized $^{129}$Xe, as described elsewhere (Wang et al., 2016, Angew Chem Int Ed, 55(5): 1733-1736). A gas mixture of 10% nitrogen, 89% helium, and 1% natural abundance xenon (Linde Group, N.J.) was used as the hyperpolarizer input. For each data point in the hyper-CEST spectrum, the output gas mixture from the hyperpolarizer was bubbled into an NMR tube through capillaries for 20 seconds, followed by a 3-second delay to allow bubbles to collapse. For hyper-CEST z-spectra (FIG. 3B and FIG. 8 (left)), a saturation train of 600 dSNOB pulses (690 Hz bandwidth) with a 0.1 ms delay in between was used: Pulse length $\tau_{pulse}$=3.80 ms, field strength $B_{1,max}$=77 μT, number of pulses $n_{pulse}$=600. Saturation contrast is calculated according to Equation 1 as previously reported (Bai et al., 2014, Chem Sci, 5(8): 3197-3203) and represents the normalized difference between on- and off-resonance signals in saturation time dependent hyper-CEST experiments. For all experiments, 0.01-0.1% (v/v) Pluronic L81 (Aldrich) was added to mitigate foaming.

The calculation of saturation transfer (ST) was based on the equation below, where I represents the acquired post saturation Xe(aq) signal with set saturation frequency, duration, and power. L represents the duration of hyper-CEST pulse sequences. The index k indicates each data point.

$$ST = \sum_k \frac{I_{off}^k - I_{on}^k}{I_{off}^k} \frac{L^k}{\sum_{k'} L^{k'}} \tag{1}$$

TEM-1 Bla Expression and Purification

A pJ411 vector containing the codon-optimized coding sequence for TEM-1 β-lactamase (bla) from $Escherichia$ $coli$ (UniProt accession P62593) was purchased from DNA 2.0. A M182T substitution was incorporated into the bla gene to stabilize the native state of the protein (Kather et al., 2008, J Mol Biol, 383: 238-251).

BL21(DE3) $E.$ $coli$ competent cells were transformed with the bla-pJ411 plasmid and cultured on a LB-agar plate supplemented with 50 μg/mL kanamycin. Single colonies of transformed cells were used to inoculate 5 mL of LB medium supplemented with 50 μg/mL kanamycin. The 5 mL cultures were incubated overnight at 37° C. with shaking at 250 rpm. The 5 mL cultures were used to inoculate 6×1 L of LB medium supplemented with 50 μg/mL kanamycin in baffled culture flasks. The 1 L cell cultures were incubated at 37° C. with shaking at 250 rpm until $OD_{600}$ reached ~0.7. Protein expression was induced by adding isopropyl-β-D-thiogalactopyranoside (IPTG) to a final concentration of 1 mM. The induced cultures were incubated overnight at 18° C. with shaking at 250 rpm. The cells were pelleted by centrifugation and frozen at −80° C. for long-term storage.

The cells were lysed by one round of freeze-thaw lysis (Johnson et al., 1994, Biotechnology, 12: 1357-130) in 50 mM Tris (pH 8.0), 10% (v/v) glycerol. The lysate was clarified by centrifugation and the supernatant was loaded onto three 5 mL HiTrap Q HP anion-exchange columns (GE Healthcare Life Sciences) connected in series and pre-equilibrated with 50 mM Tris (pH 8.0), 10% (v/v) glycerol. Protein was eluted from the column with 50 mM Tris (pH 8.0), 10% (v/v) glycerol supplemented with 3.0 M NaCl. The flow-through and eluted fractions were evaluated by SDS-PAGE, and fractions containing bla were pooled, concentrated, and then loaded onto a HiLoad 16/600 Superdex size-exclusion column (GE Healthcare Life Sciences) pre-equilibrated with 50 mM Tris (pH 7.4). Fractions containing pure bla were pooled, and analysis by SDS-PAGE indicated that the protein was over 95% pure. Protein concentration was determined by measuring absorbance at 280 nm using the extinction coefficient ($\varepsilon_{280}$=28 085 $M^{-1}$ $cm^{-1}$) calculated by the PROTPARAM server (Wilkins et al., 1999, Methods Mol Biol, 112: 531-552).

Bla(I263A) Preparation

The I263A mutation to bla was introduced into the bla-pJ411 plasmid via site-directed mutagenesis. The oligonucleotide primers used were: 5'-GCAT-TGTTGTGGCGTATACCACCGG-3' (SEQ ID NO: 17) (sense) and 5'-CCGGTGGTATACGCCACAACAATGC-3' (SEQ ID NO: 18) (antisense). The mutated bla gene was sequenced to confirm the incorporation of the I263A mutation and verify the integrity of the rest of the gene sequence. The blaI263A mutant was expressed and purified following the same procedure used for wt-bla.

Circular Dichroism (CD) Spectroscopy

The CD spectra of wt-bla and bla(I263A) were collected on a AVIV model 425 circular dichroism spectrometer using a 1 mm quartz cuvette. The samples consisted of 10 µM enzyme in 10 mM sodium phosphate (pH 8.0) buffer. The CD spectra were acquired at 25° C. with a wavelength step of 1 nm.

Activity Assay of Bla(I263A) Pre- and Post-CEST

The hydrolase activity of 5 nM bla(I263A) was measured in 50 mM Tris (pH 7.4), 5% (v/v) DMSO using 450 µM nitrocefin (EMD Millipore) as a substrate. The hydrolysis of nitrocefin was monitored at A482 using an Infinite M1000 Pro plate reader (Tecan). The activity assays were performed in triplicate for pre- and post-CEST bla(I263A). The initial rates measured for pre- and post-CEST bla(I263A) were 0.142±0.002 A482 min$^{-1}$ and 0.153±0.009 A482 min$^{-1}$, respectively.

Expression of TEM-1 Bla in E. coli

BL21(DE3) E. coli competent cells were transformed with the bla-pJ411 plasmid and cultured on a LB-agar plate supplemented with 50 µg/mL kanamycin. A single colony of transformed cells was used to inoculate 5 mL of LB medium supplemented with 50 µg/mL kanamycin. The 5 mL culture was incubated overnight at 25° C. with shaking at 250 rpm. The next morning the cells were pelleted and resuspended in 2 mL of fresh LB. The resuspended cells were used to inoculate 2×1 L of LB medium supplemented with 50 µg/mL kanamycin in baffled culture flasks. The 1 L cell cultures were incubated at 37° C. with shaking at 250 rpm until $OD_{600}$ reached ~0.7, at which point the control flask was stored at 4° C. and the other flask was induced by adding IPTG to a final concentration of 2 mM. The induced culture flask was incubated overnight at 18° C. with shaking at 250 rpm and then stored at 4° C. Aliquots from the control and induced cultures were centrifuged and the cell pellets were resuspended in PBS buffer. To measure the concentration of bla present in the E. coli cell suspension, the cells were diluted to an $OD_{600}$ of 3 in PBS buffer and then lysed by five rounds of freeze/thaw lysis. The lysate was clarified and the supernatants were stored at 4° C. The concentration of bla was measured by both quantitative SDS-PAGE (FIG. 12) and by measuring enzyme activity. For the SDS-PAGE analysis, the supernatants from the control and induced growths were ran on a NuPAGE 12% Bis-Tris gel (Invitrogen). Previously-purified bla at known concentrations served as standards. The gel was developed using a Pierce Silver Stain Kit (Thermo Scientific) and imaged on a Typhoon FLA 7000 laser scanner (GE Healthcare Life Sciences). The intensity of the bla bands were quantified using the ImageQuant TL software package (GE Healthcare Life Sciences).

Bla activity was measured in 50 mM Tris (pH 7.4), 5% (v/v) DMSO using 500 µM nitrocefin (EMD Millipore) as a substrate. The hydrolysis of nitrocefin was monitored for absorbance at 482 nm using an Infinite M1000 Pro plate reader (Tecan), with the hydrolase activity of 2 nM bla serving as a standard. The activity assays were performed in triplicate, and gave the same bla expression level as seen by SDS-PAGE, which in one instance was 0.7 µM normalized to $OD_{600}$=1.

Transient Expression of TEM-1 Bla in HEK 293T Cells

A pD2610-v12 vector containing the HEK293 T codon-optimized coding sequence for mature bla (i.e. without the N-terminal signal peptide) was purchased from DNA 2.0. This construct also contained the M182T stabilizing mutation. The bla-pD2610-v12 plasmid was amplified in DH10B E. coli and purified using a Qiagen Megaprep kit. Plasmid concentration was measured by A260, and the A260/A280 ratio indicated that the plasmid was of high purity.

Figure 14:
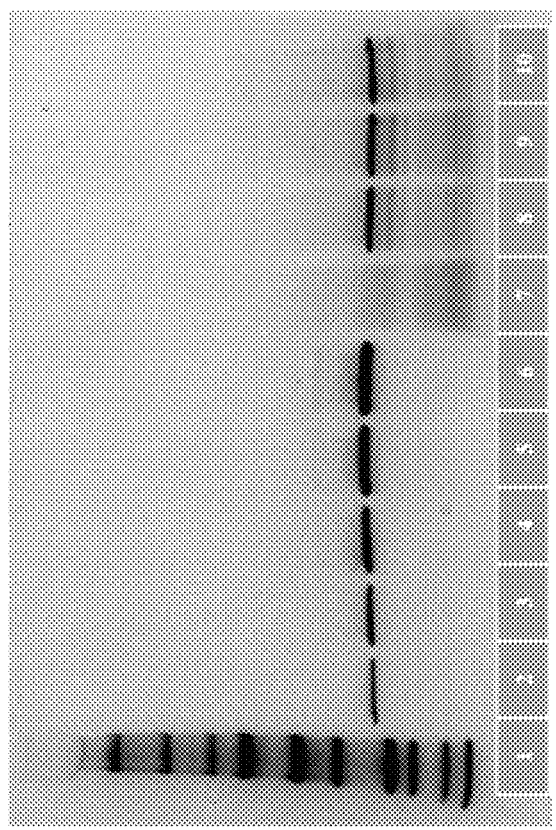
FIG. 14 depicts an image of an SDS-PAGE gel to quantify bla expression level in HEK293T cells. Lane 1: Precision plus protein standards (Bio-Rad). Lanes 2-6 contain 0.3, 0.6, 1.2, 2.4, 3.6 µg of purified bla. Lane 7: 20 µL lysate of control HEK cells at 0.6 million/mL. Lanes 8-10: 20 µL lysate of transfected HEK cells at 0.6 million/ml. Gel was developed using Coomassie Blue and imaged on a Typhoon FLA 7000 laser scanner. Analysis of band intensity showed that Lanes 8-10 contain 1.25±0.16 µg bla corresponding to a 3.6±0.5 µM bla expression level for 1 million/mL transfected HEK cells.
Figure 15:
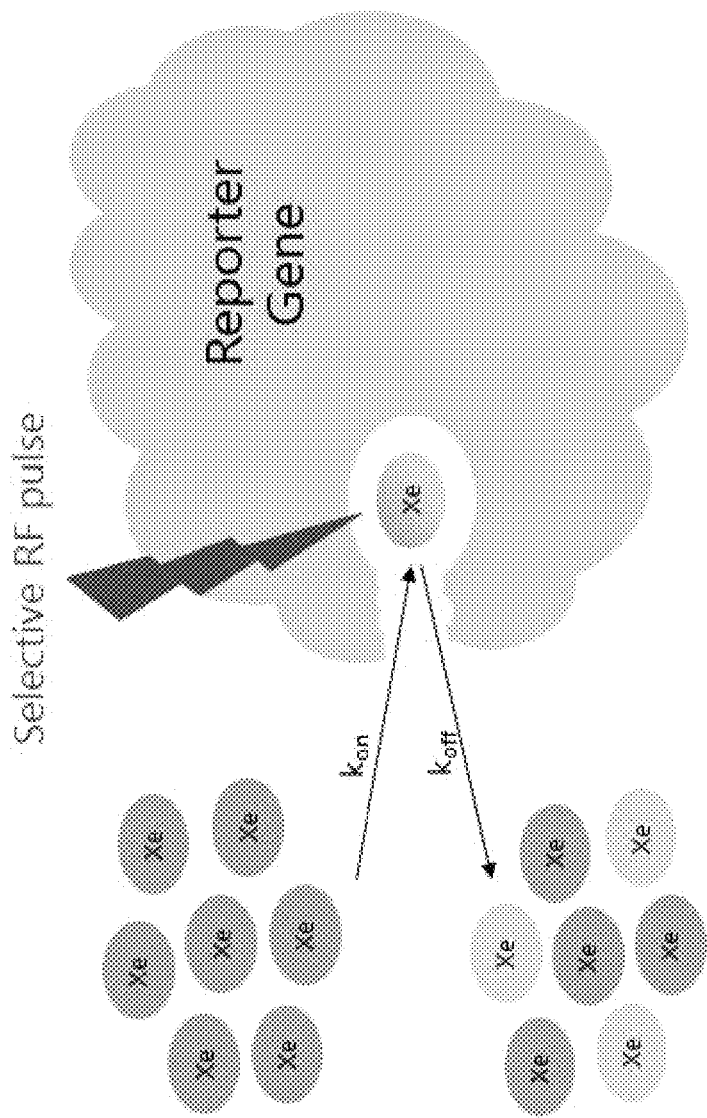
FIG. 15 depicts a schematic illustrating that during $^{129}$Xe hyper-CEST exchangeable solute-bound Xe atoms that resonate at a frequency different from bulk hyperpolarized Xe are selectively spin-flipped using RF irradiation. Rapid exchange leads to the depolarization of bulk Xe, thereby generating MR contrast.

HEK293T/17 cells were cultured in T25 flasks in DMEM supplemented with L-glutamine, 10% fetal bovine serum, and 1% penicillin/streptomycin until 80% confluency. The medium was then removed and the cells were washed with phosphate-buffered saline. Cells were then transfected with 6.25 µg plasmid per flask using lipofectamine 3000 reagent (Thermo Fisher). Cells were incubated in the DNA-lipid complex at 37° C. for 3 days. Prior to hyper-CEST experiments, cells were washed with PBS, harvested, and counted with a hemocytometer. In order to determine the expression level of bla, HEK293T cells were lysed by three freeze-thaw cycles. The lysate was clarified by centrifugation and the supernatant was analyzed by colorimetric assay and SDS-PAGE. The bla expression level of 0.2 million/mL transfected HEK cells was determined to be equivalent to 0.7 µM bla in the cell suspension, which agrees with the level determined by SDS-PAGE gel (FIG. 14).

Figure 13:
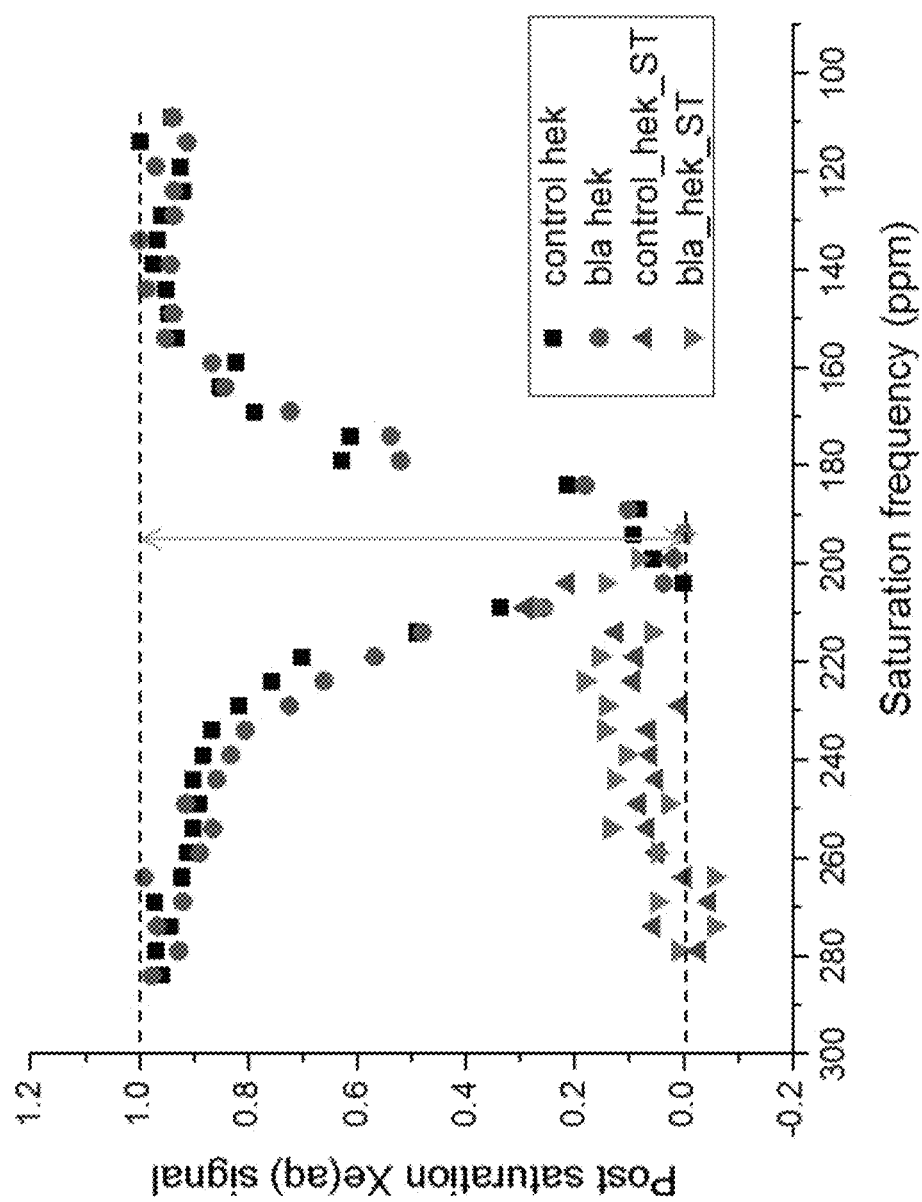
FIG. 13 depicts a hyper-CEST frequency-scan profile of transfected and control HEK293T cells at 4.4 million/mL concentration. Control_hek_ST (upward pointing triangle) and bla_hek_ST (downward pointing triangle) represent the difference of signal intensity for each pair of offset frequencies with reference to the $^{129}$Xe-H$_2$O peak, $S_{-\Delta w}$–$S_{+\Delta w}$ ($\Delta w$=5, 10, . . . 85 ppm), for control HEK cells and transfected cells, respectively.

Cells transfected with a pD2529-CMV vector without SV40 gave an expression level of 2.7 µM bla for 4.4 million/mL cells, and were used in FIG. 13.

The results of the experiments are now described.

Molecular Dynamics Simulations Reveal Xenon Binding Sites in Bla.

To explore whether bla is able to accommodate Xe atoms, "flooding" molecular dynamics (MD) simulations were performed. In this procedure, the protein is simulated in the presence of a large number of solute moieties to increase the rate of collisions between the solute and protein and thus enhance the sampling of binding events. In particular, bla in the presence of Xe atoms (0.15 M) dissolved in water was simulated. Characterization of the protein regions visited by Xe atoms during the simulation gives information about the putative binding sites, pathways and, to some extent, binding kinetics.

Figures 2A, 2B:
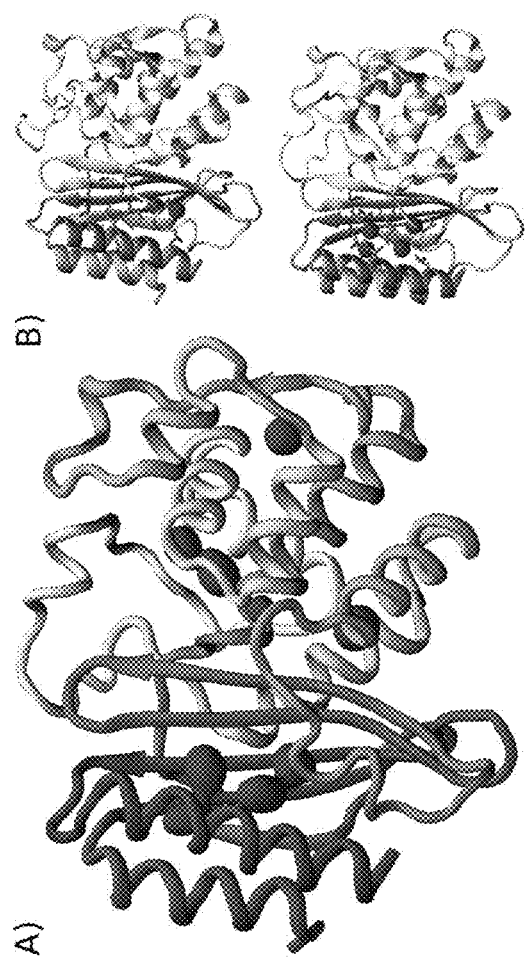
FIG. 2A and FIG. 2B, illustrate the structure of bla and results from molecular dynamics simulations.
Figures 3A, 3B:
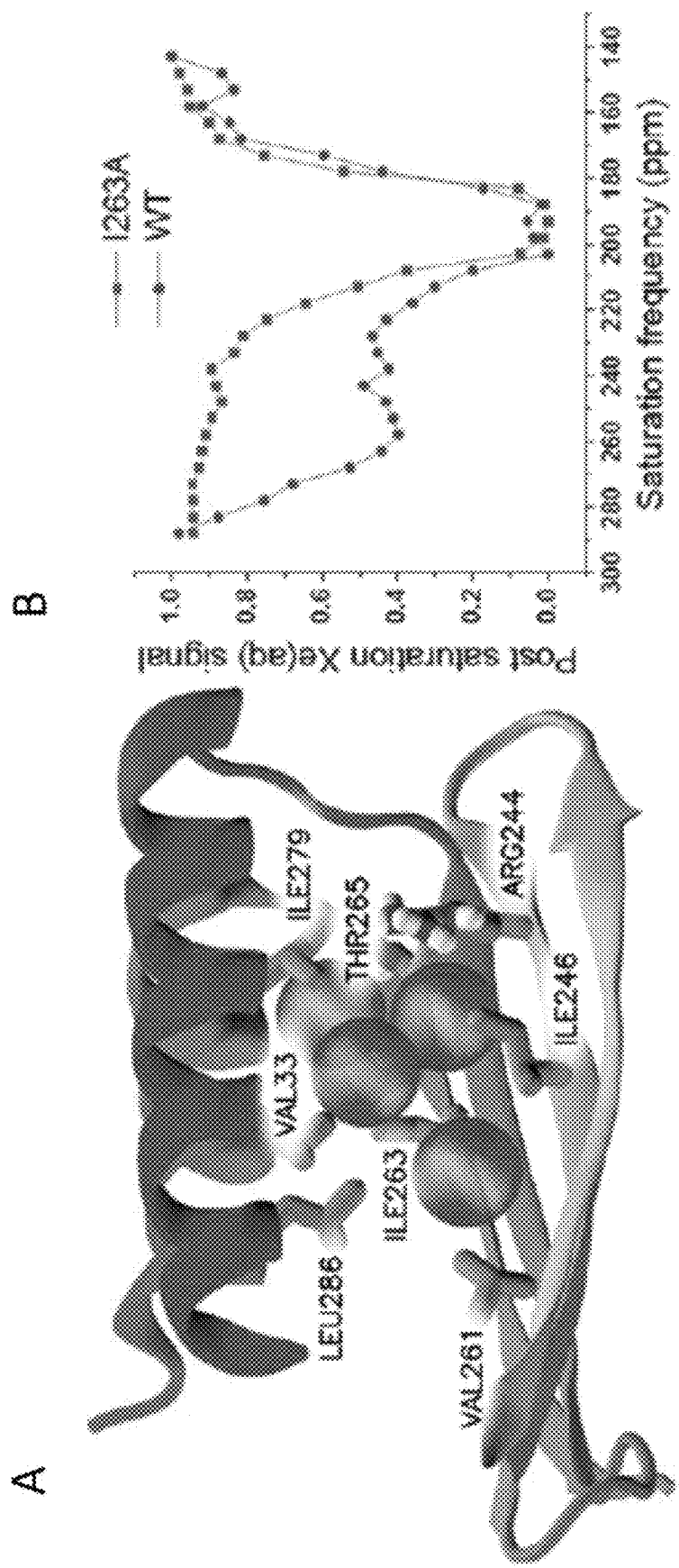
FIG. 3A and FIG. 3B, depict the results of example experiments.
Figure 5:
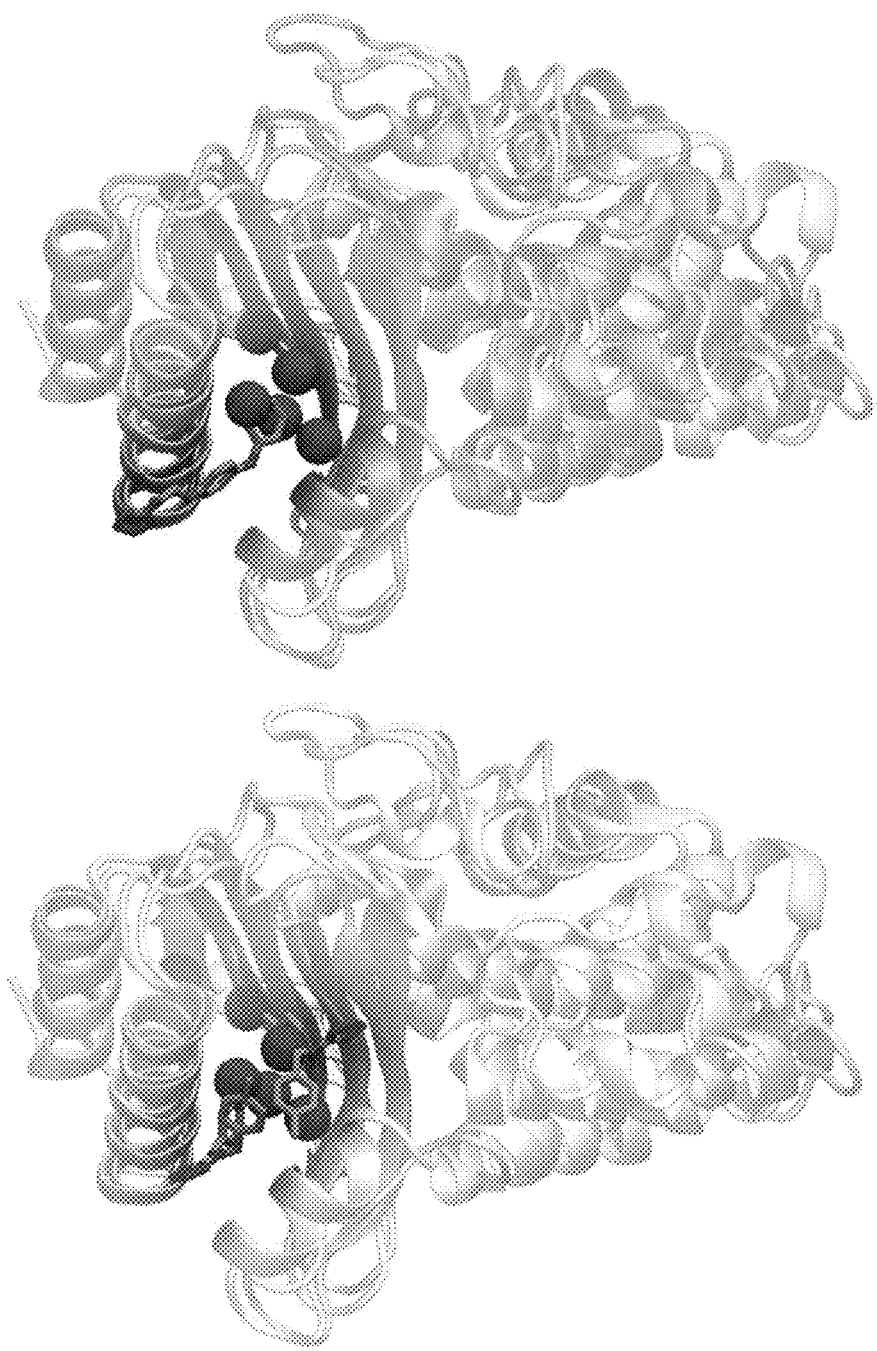
FIG. 5 depicts the structural comparison between the Xe binding site and the crystallographically determined allosteric binding sites. The structure of bla after 1-μs of molecular dynamics simulation is superimposed to the structure of bla in complex with 3-(4-PHENYLAMINO-PHENYLAMINO)-2-(1H-TETRAZOL-5-YL)-ACRYLONITRILE (upper—PDB code: 1PZP) and N,N-BIS(4-CHLOROBENZYL)-1H-1,2,3,4-TETRAAZOL-5-AMINE (lower—PDB code: 1PZO). Xe atoms are shown as spheres, while the allosteric inhibitors are shown as sticks. Note how Xe atoms are found in the regions of space occupied by the bulky phenyl moieties.
Figure 6:
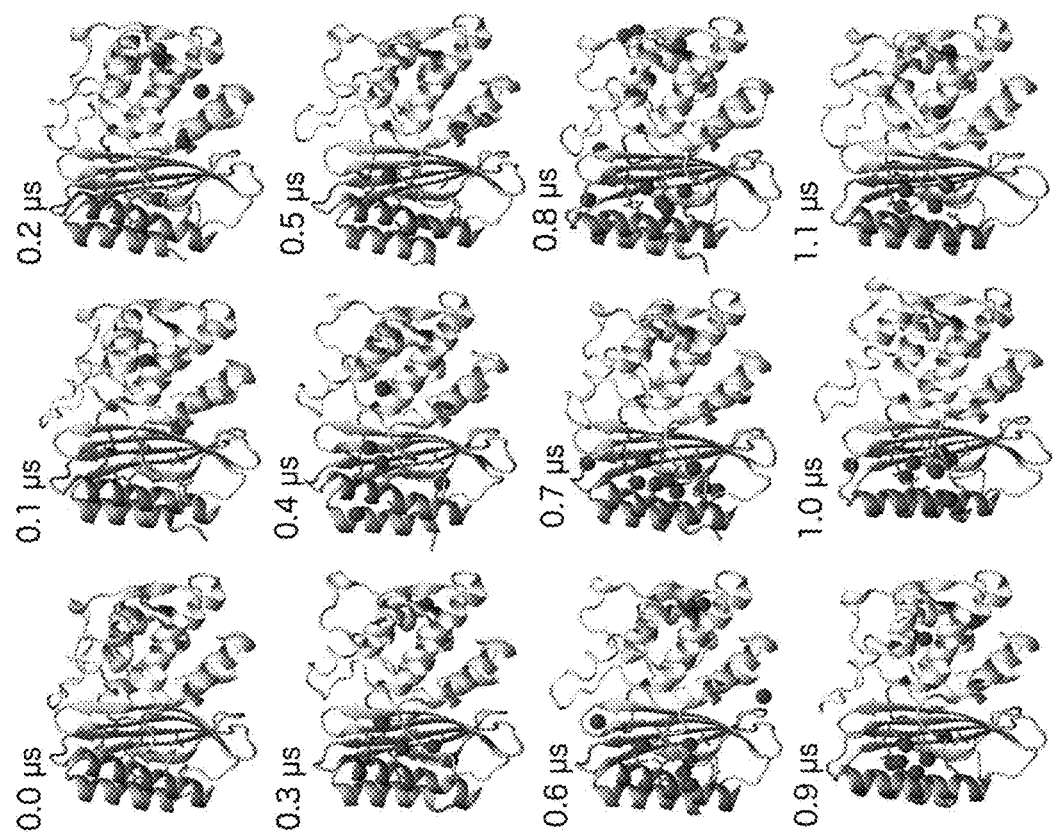
FIG. 6 depicts representative snapshots from the "flooding" MD simulation trajectory. Xe atoms are shown as spheres. After 0.6 μs, Xe atoms engage in stable interactions with the sidechains from the region close to helices 1 and 12.

The analysis of a 1-µs trajectory reveals a complex landscape with numerous bla regions characterized by a large value of Xe occupancy (FIG. 2A). The most prominent binding region is located between the two terminal α-helices (one at the N-terminus and the other at the C-terminus: residues 26 to 41 and 272 to 290, respectively) and the flanking β sheet; where Xe atoms are observed to form a cluster of up to 4 atoms (FIG. 2 and FIG. 3A). Strikingly, this is the same allosteric site that had been characterized crystallographically (FIG. 5) (Horn and Shoichet, 2004, J Mol Biol, 336(5): 1283-1291). Five other regions with comparable occupancy but smaller size are detected throughout the protein, all of them in proximity of helix 2 (residues 67 to 87).

The location and extension of these high-Xe-occupancy regions (FIG. 5) bear striking resemblance to the cryptic allosteric sites detected by Bowman and Geissler (Bowman and Geissler, 2012, Proc Natl Acad Sci USA, 109(29): 11681-11686) on a large sampling of protein conformations collected via Markov State Models, which included the experimentally validated allosteric binding site. In this relatively large, hydrophobic cavity, Xe atoms establish van der Waals interactions with the sidechains of several residues (V33, V44, R244, I246, V261, I263, T265, I279, L286). R244 and T265 are the only polar residues in this pocket (FIG. 3A). As previously noted, (Bowman and Geissler, 2012, Proc Natl Acad Sci USA, 109(29): 11681-11686) the side chains that form this primary cavity also interact with allosteric bla inhibitors (Horn and Shoichet, 2004, J Mol Biol, 336: 1283-1291)

Figures 7A, 7B, 7C:
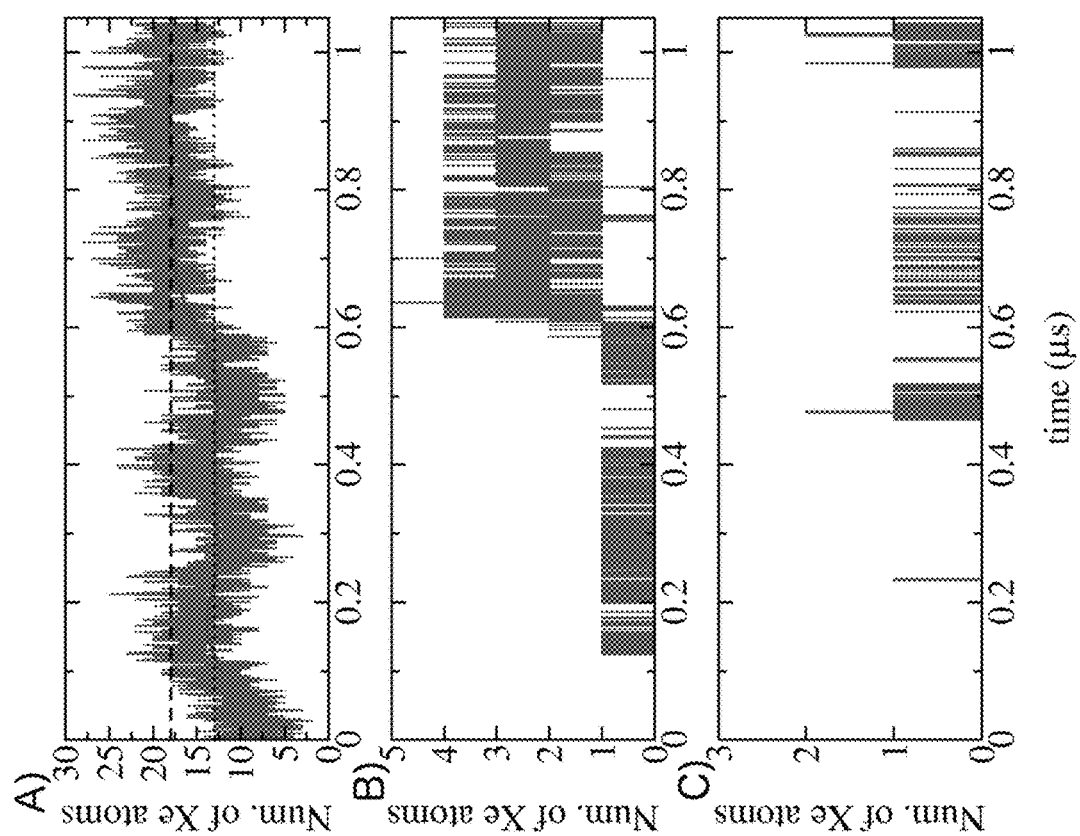
FIG. 7A through FIG. 7C, depicts the results of simulations of Xe atom binding events sampled during the "flooding" MD simulation.

The present simulations provide insight into the relative binding kinetics of Xe to this allosteric site. Indeed, it was found that binding to the innermost section of this cavity (located between helix 1 and 12) occurs after ~0.6 μs and only after the most solvent accessible part of the cavity (lined by helix 11 and 12) is fully occupied by two Xe atoms (FIG. 2B). Thus, in spite of the high concentration of Xe atoms, binding to the allosteric pocket is a relatively slow process, slower than binding to any other pocket present in bla (FIG. 7).

Bla Produces Hyper-CEST Signals at Sub-Micromolar Concentrations.

Figure 8:
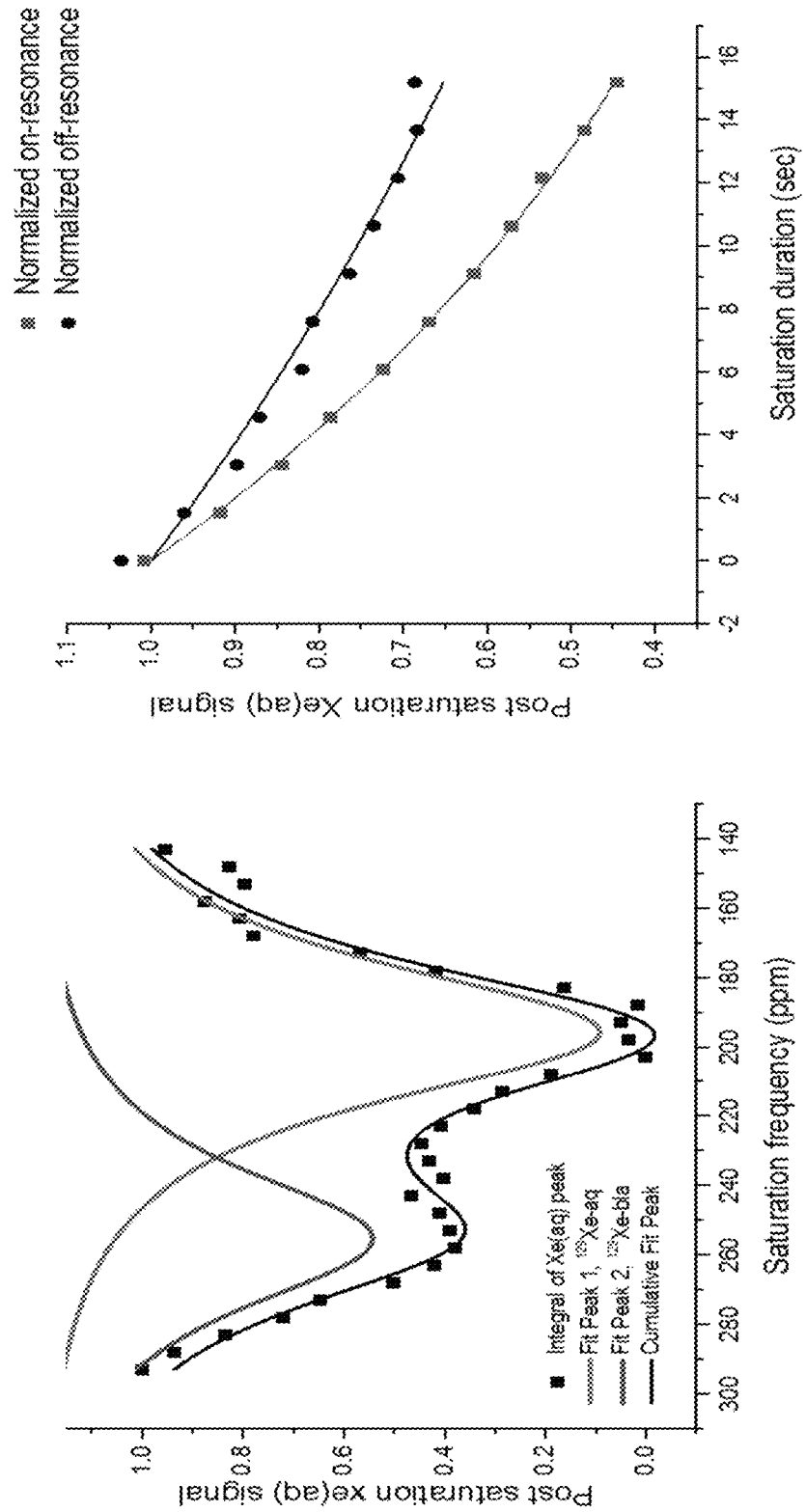
FIG. 8 depicts hyper-CEST spectra of wt-bla. Left: Hyper-CEST frequency-scan profile of 80 μM bla in pH 7.2 PBS at 300 K. The black squares show the experimental data, and the lines show the exponential Lorentzian fits. Right: Representative hyper-CEST profile of 0.1 μM bla in pH 7.2 PBS at 300 K. Saturation frequencies of Dsnob-shaped pulses were positioned +60 ppm and −60 ppm referenced to the Xe-aq peak, for on- and off-resonance. Pulse length, $\tau_{pulse}$=0.759 ms; field strength, $B_{1,max}$=385 μT. Both on-resonance and off-resonance data were fitted with first-order exponential decay curves, with $t_{on}$=18.9±0.1 sec and $t_{off}$=35.5±1.1 sec.

For in vitro studies, recombinant bla was expressed in BL21(DE3) *E. coli* and purified with column chromatography. Bla (80 μM) was used to obtain a hyper-CEST z-spectrum, where multiple selective Dsnob-shaped saturation pulses were scanned over the chemical shift range of 143-293 ppm in 5-ppm steps, and the aqueous $^{129}$Xe signal was measured as a function of saturation pulse offset (FIG. 3B and FIG. 8). Two saturation responses were observed: one free $^{129}$Xe in solution peak centered at 195 ppm, and a second peak centered at 255 ppm that was attributed to xenon-bla interaction. Both peaks in the hyper-CEST z-spectrum appeared broad, indicating that xenon undergoes fast exchange between the aqueous state and the transient protein-binding state. Importantly, the unique $^{129}$Xe-bla peak cannot be directly observed by HP $^{129}$Xe NMR spectroscopy even with high-concentration (~mM) bla, due to the low population of protein-bound xenon and high exchange rate of xenon between different sites. This scenario was observed previously with spores (Bai et al., 2014, Chem Sci, 5: 3197-3203) and also CB (Kunth et al., Chem Sci, 2015, 6069-6075).

Figure 9:
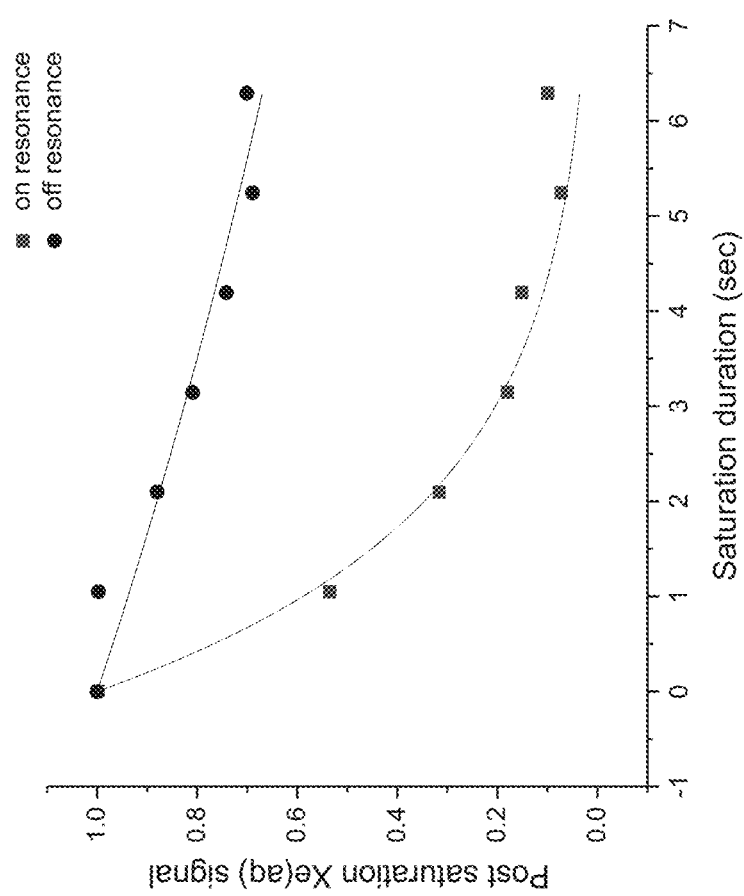
FIG. 9 depicts a representative hyper-CEST profile of 0.5 μM bla in pH 7.2 PBS at 300 K. Saturation frequencies of Dsnob-shaped pulses were positioned +60 ppm and −60 ppm referenced to Xe-aq peak, for on- and off-resonance. Pulse length, $\tau_{pulse}$=1.0496 ms; field strength, $B_{1,max}$=279 μT

Hyper-CEST measurements were then carried out by varying saturation time to determine the molecular sensitivity of bla. Shaped saturation pulses were applied at the chemical shift of $^{129}$Xe-bla, and the residual aqueous $^{129}$Xe signal after spin transfer was measured as on-resonance CEST response (FIG. 8 and FIG. 9). Off-resonance pulses were applied at 135 ppm, to mirror the 60-ppm frequency interval observed for Xe-bla and Xe-aq signals. The observed depolarization response in hyper-CEST experiments arose from both self-relaxation of HP $^{129}$Xe and bla-mediated saturation transfer. The normalized difference between on-resonance and off-resonance signals was represented by the saturation contrast. Using this method, 0.1 μM (2.9 μg/mL) bla was able to produce 0.23±0.02 saturation contrast (Equation 1). The in vitro detection limit of single protein bla is comparable to previously reported GVs in terms of protein mass concentration (Shapiro et al., 2014, Nat Chem, 6(7): 629-634), and represents a 100-fold improvement compared to $^1$H-CEST reporter genes (Gilad et al., 2007, Nat Biotech, 25(2): 217-219).

Figure 10:
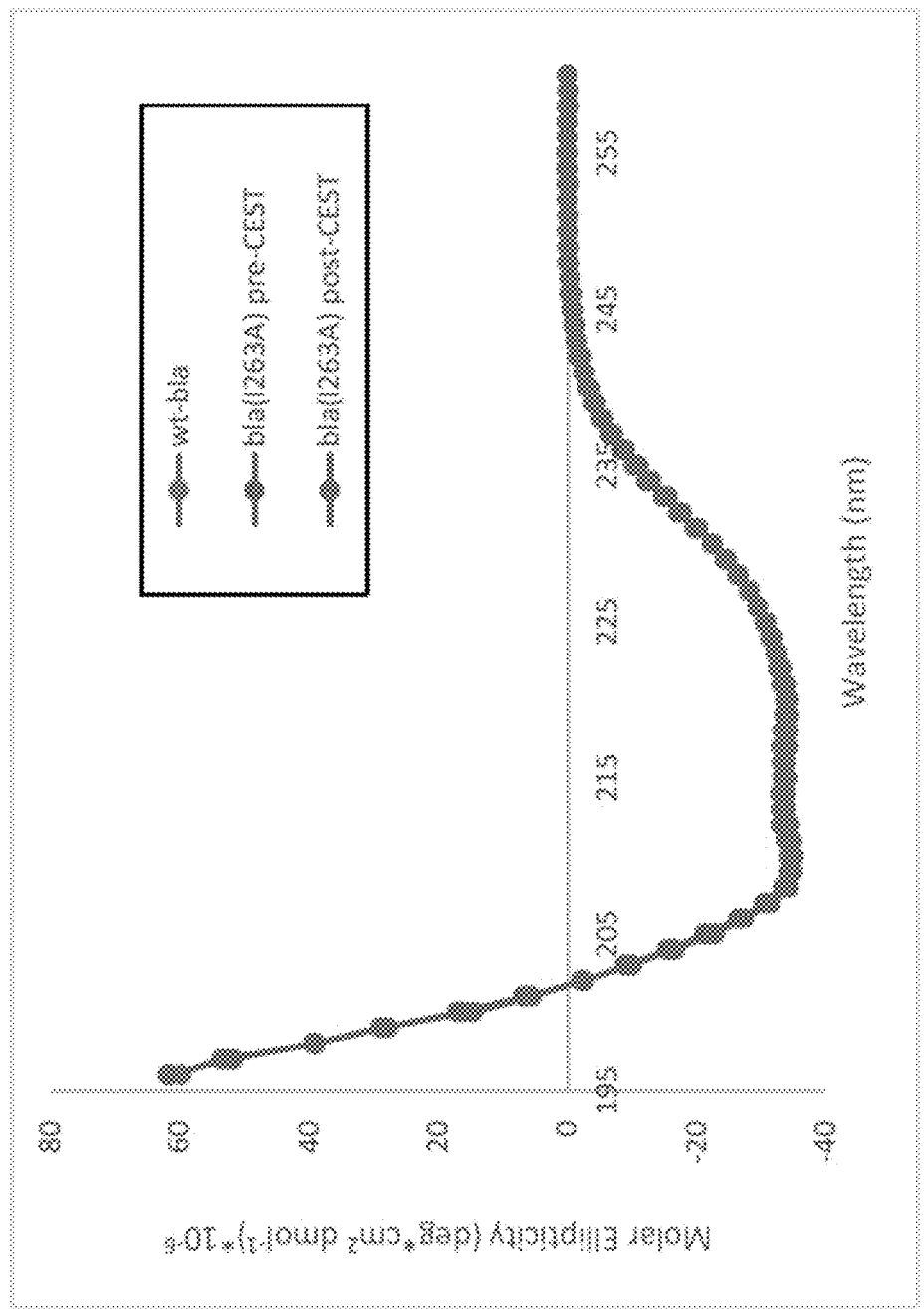
FIG. 10 depicts CD spectra of bla(I263A) before and after Xe hyper-CEST experiment. The CD spectrum of wt-bla is shown as a reference.

It was examined whether the 255 ppm peak observed in the hyper-CEST spectrum may originate from the allosteric cavity (FIG. 2B) identified by MD simulations. Ile-263 is positioned at the entrance of this Xe-binding site and lies in close proximity to the bound Xe (FIG. 3A). Thus, Ile-263 was mutated to alanine, and the I263A mutant was expressed and purified following the same procedure used for wild-type (wt) bla. The hyper-CEST z-spectrum for I263A showed almost complete loss of the Xe-bla signal (FIG. 3B). Following hyper-CEST, an activity assay confirmed that the I263A enzyme was not denatured by Xe bubbling during the hyper-CEST experiments. Additionally, circular dichroism (CD) spectroscopy confirmed that the secondary structure of the I263A mutant was maintained (FIG. 10). The loss of hyper-CEST signal at 255 ppm is attributed to faster Xe exchange and/or lower Xe affinity for the larger I263A cavity. This highlights that the architecture of the wt-bla allosteric site is crucial for producing a hyper-CEST signal.

Cells Expressing Recombinant Bla Produce Hyper-CEST Contrast.

Figure 4:
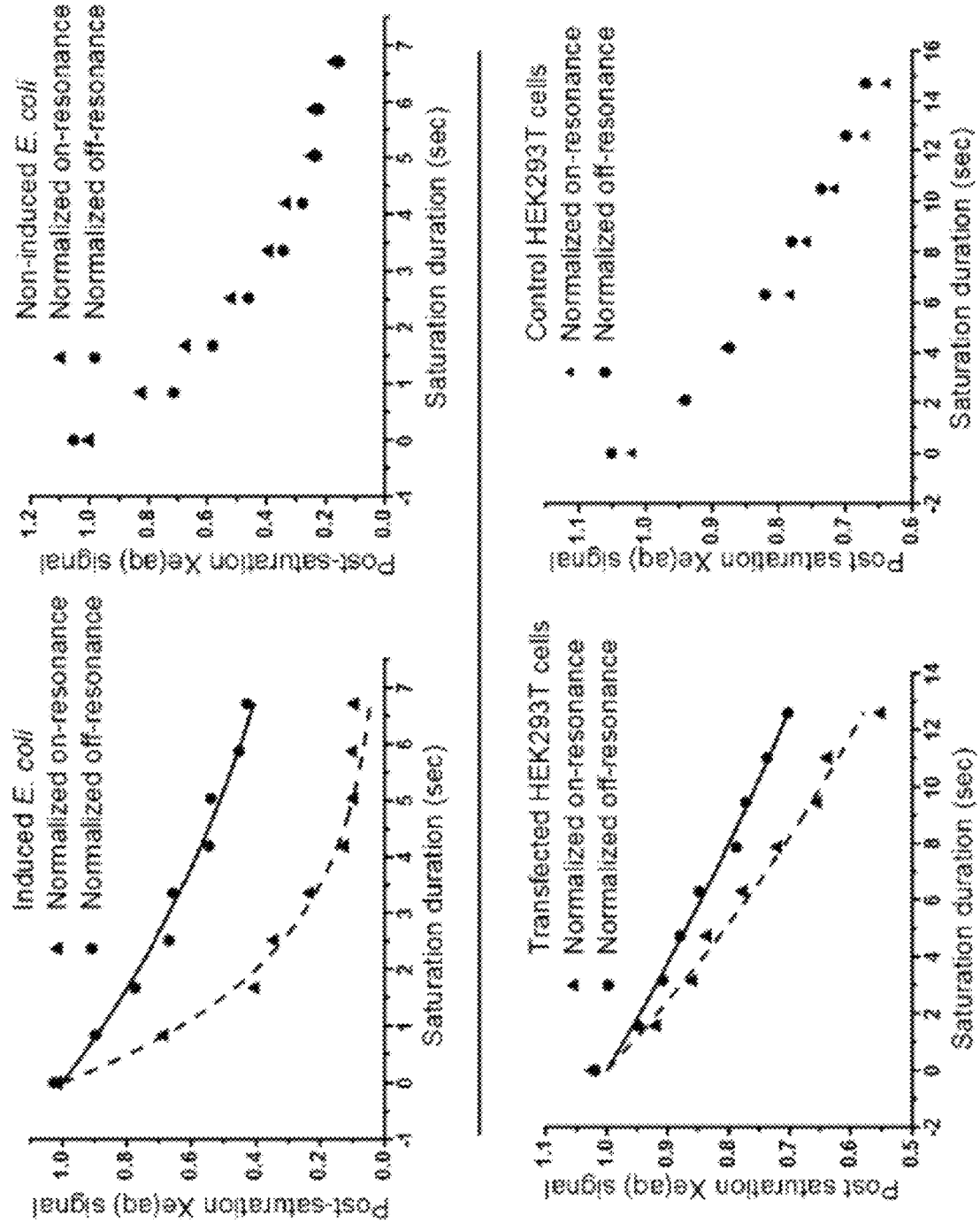
FIG. 4 depicts the results of hyper-CEST experiments with bla-expressing bacterial and mammalian cells. Top: Time-dependent saturation transfer data for induced (left) and non-induced (right) *E. coli*. Bottom: Time-dependent saturation transfer data for transfected (left) and control (right) HEK293T/17 cells. Saturation frequencies of Dsnob-shaped pulses were positioned +60 ppm and −60 ppm referenced to the Xe-aq peak, for on- and off-resonance. Pulse length, $\tau_{pulse}$=1.0496 ms; field strength, $B_{1,max}$=279 μT. The number of pulses linearly increased from 0 to 6000, 12 000 or 14 000.
Figure 11:
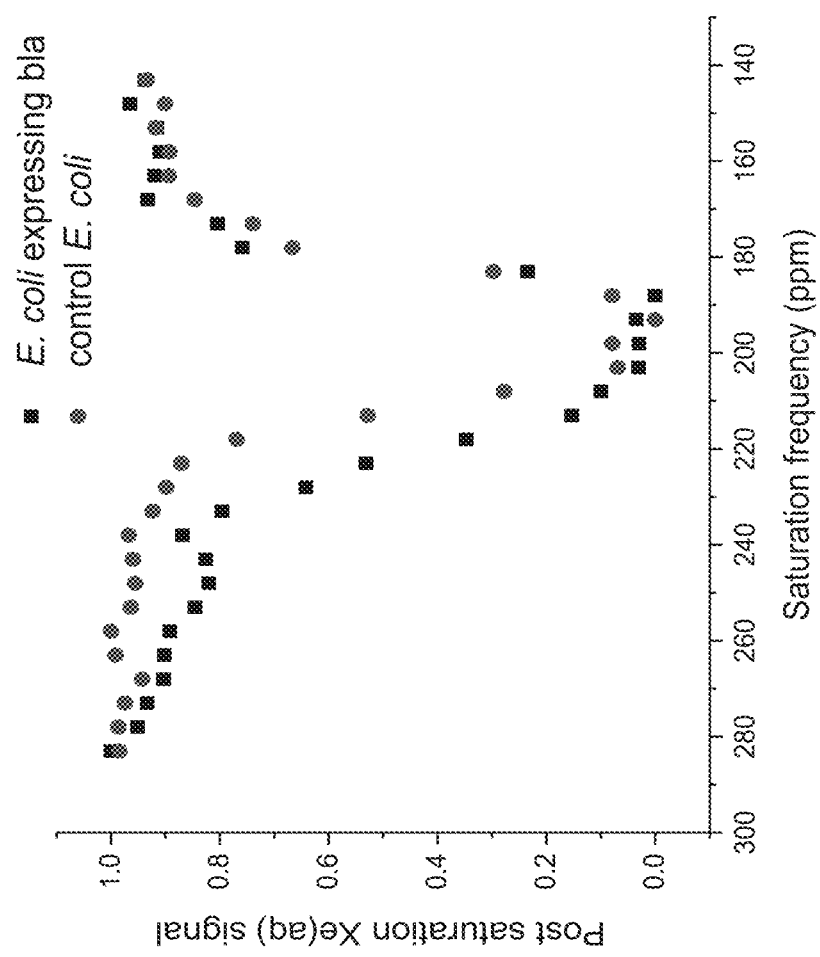
FIG. 11 depicts a representative hyper-CEST frequency-scan profile of induced and control *E. coli* at $OD_{600}$=9.2.
Figure 12:
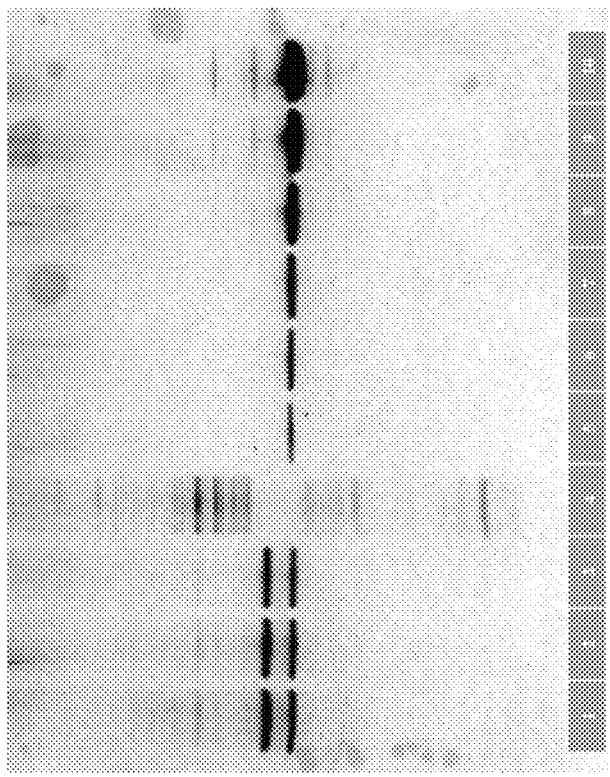
FIG. 12 depicts an image of an SDS-PAGE gel to quantify bla expression level in *E. coli*. Lanes 1-3: Lysate from induced *E. coli* (normalized to $OD_{600}$=3). The heavier bands right above mature bla bands correspond to the bla with N-terminal signal peptide uncleaved; Lane 4: Lysate from non-induced *E. coli* (normalized to $OD_{600}$=3. Lanes 5-10 contain 0.0725, 0.145, 0.29, 0.58, 0.87, 1.16 μg of purified bla. Analysis of band intensity showed that Lanes 1-3 contain 0.62±0.13 μg bla, which corresponds to 0.71±0.15 μM bla for *E. coli* cell suspension at $OD_{600}$=1.

The possibility of using bla as a $^{129}$Xe NMR reporter in cellular environments was then examined. BL21(DE3) *E. coli* cells expressing recombinant wt-bla were cultured in LB medium and induced with 2 mM isopropyl-β-thiogalactopyranoside (IPTG). Cells were then pelleted, washed, resuspended in phosphate buffered saline (PBS), and used in hyper-CEST experiments. *E. coli* transformed with the same plasmid but not induced by IPTG were prepared following the same procedure as a negative control. Saturation time-dependent hyper-CEST experiments showed that bla-expressing *E. coli* grown to an $OD_{600}$ of 9.2 produced a saturation contrast of 0.72±0.03 (FIG. 4A). After 6.7-sec exposure to saturation pulse, the $^{129}$Xe-aq peak was almost completely saturated. By contrast, the on-resonance and off-resonance curves were almost identical for the control *E. coli* sample at the same $OD_{600}$. The same result was observed in the z-spectra of induced and non-induced *E. coli* (FIG. 11). In these *E. coli* experiments, bla was readily detected at the equivalent of 6.4 M concentration in the cell suspension, as confirmed by gel and colorimetric assay (FIG. 12).

Having established that bla can be used as a genetically-encoded reporter in a bacterial system, it was set out to test whether it can also function in mammalian cells. HEK293T/17 cells were transfected with a transient-expression plasmid incorporating SV40 enhancer, harvested, and resuspended in PBS for hyper-CEST experiments. Control cells were sub-cultured from the same flask but not transfected. At 4.4 million cells per mL concentration, without optimization for bla expression, both transfected and non-transfected cells produced obvious saturation contrast, and both z-spectra had a slight shoulder appearing in the downfield region of the $^{129}$Xe-aq peak (FIG. 13). While not wishing to be bound by any particular theory, it is thought that this background signal arises from the interaction of xenon with membranes enclosing the organelles in eukaryotic cells (Riggle et al., 2015, J Am Chem Soc, 137(16): 5542-5548; Klippel et al., 2014, Angew Chem Int Ed, 53(2): 493-496), which are absent in prokaryotic cells. In order to minimize background contrast, the hyper-CEST signal of samples at lower cell density was compared while increasing the bla expression level. As illustrated by FIG. 4C, 0.2 million/ml transfected HEK cells producing the equivalent of 0.7 μM bla in the cell suspension (FIG. 14) was sufficient to produce a saturation contrast of 0.13±0.01, compared to minimal contrast observed for control HEK cells.

Lower detection sensitivity was observed for bla expressed in cellular environments compared to pure bla in buffer. For example, the saturation contrast produced by approximately 6.5 μM bla expressed in *E. coli* was considerably less than that produced by 0.5 μM pure bla in buffer under the same saturation pulse conditions (FIG. 9). This decrease in saturation contrast can be attributed to the diffusion barriers imposed by cells, which can result in tens-of-millisecond xenon penetration time (Bifone et al., 1996, Proc Natl Acad Sci USA, 93: 12932-12936; Boutin et al., 2001, NMR Biomed, 24: 1264-1269). Nevertheless, 0.7 LM bla expressed by 0.2 million/mL transfected HEK cells was readily detected using hyper-CEST.

TEM-1 Bla can Function as a Genetically Encoded Single-Protein Reporter for Hyper-CEST NMR MD simulation identified multiple regions with high xenon occupancy, displaying different binding kinetics, and suggests a specific xenon pathway for the primary allosteric site in bla. It is surmised that the observed 'stepwise' binding mechanism affords bla hyper-CEST capability by slowing the exchange interaction between xenon and bla and thus allowing for a longer Xe residence time inside the protein. In addition, the pooling of several Xe atoms at the primary allosteric site may be important for the slow exchange interactions, and also contribute to the unique bla-$^{129}$Xe NMR chemical shift observed at 255 ppm. X-ray crystallography and hyper-CEST studies with wild-type bla and bla mutants have confirmed the primary Xe binding site in bla. MD simulations have further identified Xe entry and exit path(s).

In summary, it is demonstrated herein that TEM-1 bla can function as a genetically encoded single-protein reporter for hyper-CEST NMR, with molecular sensitivity of at least 0.1 µM in vitro. The *E. coli* experiments confirmed the ability to detect bla expression in a bacterial system, where hyper-CEST data indicate no competing background signal from endogenous proteins. The feasibility of bla-based in vivo hyper-CEST biomolecular imaging was further supported by HEK cell experiments, where sub-micromolar levels of bla produced useful contrast. Bla has been well established as a fluorogenic reporter for in vivo studies, which lends support to its further development as a hyper-CEST reporter for biomolecular imaging. For example, bla mutagenesis should make it possible to increase Xe affinity at the primary site and also shift the hyper-CEST response peak, either to achieve multiplexing or to discriminate further against $^{129}$Xe-mammalian cell background signals.

Example 2: A Structural Basis for $^{129}$Xe Hyper-CEST Signal in TEM1 β-Lactamase Experiments presented herein were conducted to characterize the interaction between Xe and β-lactamase (bla) by X-ray crystallography. Further, protein mutagenesis combined with additional X-ray crystallography and molecular dynamics (MD) simulations were performed to elucidate the structural basis for the hyper-CEST NMR signal. The crystal structure of bla reveals a major Xe binding site, with entry and egress pathways identified through MD simulations. Mutations made to the major Xe binding site confirm its role in generating the 60-ppm downfield shift observed in the $^{129}$Xe hyper-CEST z-spectrum of bla, and further analysis of Xe exchange with these mutants by X-ray crystallography and MD simulations sheds further insights regarding the relationship between Xe-protein interactions and CEST.

The materials and methods employed in these experiments are now described.

MD Simulations

All MD simulations were performed using CHARMM36 force field (Huang et al., 2013, J Comput Chem, 34(25): 2135-2145). The water molecules were described using the TIP3P model (Jorgensen et al., 1983, J Chem Phys, 79(2): 926-935). Periodic boundary conditions were employed for all of the MD simulations and the electrostatic potential was evaluated using the particle-mesh Ewald method (Essmann et al, 1995, J Chem Phys, 103(19): 8577-8593). The lengths of all bonds containing hydrogen were constrained with the SHAKE algorithm (Rykeart et al, 1977, J Comput Phys, 23(3): 327-341). The system was maintained at a temperature of 300 K and pressure of 1 atm using the Langevin thermostat and barostat methods as implemented in the MD code NAMD2.12 (Phillips et al., 2005, J Comput Phys, 26(16): 1781-1802), which was used for the simulations with a 2.0 fs time step.

Plasmid Preparation and Mutagenesis

The codon-optimized gene for TEM-1 β-lactamase (bla) from *Escherichia coli* (UniProt accession P62593) was synthesized and cloned into a pJ411 vector by DNA 2.0, as described previously (Wang et al., 2016, Angew Chemie Int Ed, 55(31): 8984-8987). A M182T substitution was incorporated into the bla gene to stabilize the native state of the protein (Kather et al., 2008, J Mol Biol, 383: 238-251). Mutations to bla were introduced via site-directed mutagenesis using the forward and reverse primers listed in Table 1. The mutated plasmids were amplified in NEB-5a competent cells (New England Biolabs) and then purified using a miniprep kit (Qiagen). All mutated bla genes were sequenced to verify the incorporation of the desired mutation and the integrity of the entire gene sequence.

TABLE 1

Oligonucleotide primers used in site-directed mutagenesis of bla

| | | |
|---|---|---|
| I263D | Forward primer | 5'-GCATTGTTGTGGACTATACCACCGG-3' (SEQ ID NO: 19) |
| | Reverse primer | 5'-CCGGTGGTATAGTCCACAACAATGC-3' (SEQ ID NO: 20) |
| I263N | Forward primer | 5'-CCGAGCCGCATTGTTGTGAACTATACCACCGGTAGC-3' (SEQ ID NO: 21) |
| | Reverse primer | 5'-GCTACCGGTGGTATAGTTCACAACAATGCGGCTCGG-3' (SEQ ID NO: 22) |
| I263A | Forward primer | 5'-GCATTGTTGTGGCGTATACCACCGG-3' (SEQ ID NO: 17) |
| | Reverse primer | 5'-CCGGTGGTATACGCCACAACAATGC-3' (SEQ ID NO: 18) |
| I263L | Forward primer | 5'-GCATTGTTGTGCTGTATACCACCGG-3' (SEQ ID NO: 23) |

TABLE 1-continued

Oligonucleotide primers used in site-directed mutagenesis of bla

| | | |
|---|---|---|
| | Reverse primer | 5'-CCGGTGGTATACAGCACAACAATGC-3' (SEQ ID NO: 24) |
| I279N | Forward primer | 5'-GCCACGATGGATGAGCGTAACCGTCAGAACGCTGAAATCGGTGCGAGC-3' (SEQ ID NO: 25) |
| | Reverse primer | 5'-GCTCGCACCGATTTCAGCGTTCTGACGGTTACGCTCATCCATCGTGGC-3' (SEQ ID NO: 26) |
| I282A | Forward primer | 5'-CAGATTGCTGAAGCCGGTGCGAGCCTG-3' (SEQ ID NO: 27) |
| | Reverse primer | 5'-CAGGCTCGCACCGGCTTCAGCAATCTG-3' (SEQ ID NO: 28) |

Plasmid Expression and Purification

WT bla and its mutants were expressed and purified as described previously (Wang et al., 2016, Angew Chemie Int Ed, 55(31): 8984-8987). Briefly, bla was transformed into BL21(DE3) competent cells (New England Biolabs) and grown in 6×1 L of LB medium supplemented with 50 μg/mL kanamycin. Protein expression was induced by adding isopropyl-β-D-thiogalactopyranoside (IPTG) to a final concentration of 1 mM. The induced cells were incubated overnight at 18° C., harvested by centrifugation, then lysed by freeze-thaw lysis. Bla was purified via anion-exchange followed by size-exclusion chromatography. Purified bla was evaluated by SDS-PAGE and observed to be over 95% pure. Protein concentration was determined by measuring absorbance at 280 nm using the extinction coefficient ($\varepsilon_{280}$=28 100 M$^{-1}$ cm$^{-1}$) calculated by the PROTPARAM server (Wilkins et al., 1999, Methods Mol Biol, 112: 531-552).

$^{129}$Xe Hyper-CEST Spectroscopy $^{129}$Xe was hyperpolarized and z-spectra of bla were acquired as described previously (Wang et al., 2016, Angew Chemie Int Ed, 55(31): 8984-8987). Briefly, HP $^{129}$Xe was generated using the spin-exchange optical pumping (SEOP) method with a home-built $^{129}$Xe polarizer based on the IGI.Xe.2000 commercial model by GE. A Shark 65 W tunable ultra-narrow band diode laser (OptiGrate) set to 795 nm was used for optical pumping of Rb vapor. A gas mixture of 89% helium, 10% nitrogen, and 1% natural abundance xenon (Linde Group, N.J.) was used as the hyperpolarizer input. $^{129}$Xe hyperpolarization level was roughly 10-15%. For each data point in the hyper-CEST z-spectra, hp $^{129}$Xe was bubbled into the NMR tube through capillaries for 20 seconds, followed by a 3-second delay to allow bubbles to collapse. A Dsnob saturation pulse with 690 Hz bandwidth was used. Pulse length $\tau_{pulse}$=3.80 ms, field strength $B_{1, max}$=77 μT, number of pulses $n_{pulse}$=400, saturation time $T_{sat}$=1.52 s. NMR experiments were performed using a Bruker BioDRX 500 MHz NMR spectrometer and 10-mm PABBO probe, at 300 K. A 900 hard pulse of this probe has a pulse length of 22 as. For all experiments, the protein concentration was 80 μM, with 0.1% (v/v) Pluronic L81 (Aldrich) added to mitigate foaming.

Protein Crystallization and Xe Derivatization

Crystals of WT bla were grown at 21° C. by the hanging drop vapor diffusion method in which 4 μL of 5 mg/mL bla in 10-50 mM Tris (pH 7.0) buffer was mixed with 4 μL of precipitant solution consisting of 2% (v/v) tacsimate (pH 6.0), 0.1 M Bis-Tris (pH 6.5), 20% (w/v) PEG 3350 and suspended over a 1 mL reservoir of precipitant solution. The hanging drop was streak seeded with WT bla microcrystals. Crystals of I263L bla were also grown at 21° C. by the hanging drop vapor diffusion method in which 5 μL of 7 mg/mL I263L bla in 50 mM Tris (pH 7.4) buffer were mixed with 5 μL of the same precipitant solution used to crystallize WT bla and suspended over a 1 mL reservoir of precipitant solution. Crystals of I263N bla were initially grown at 21° C. by the sitting drop vapor diffusion method in which 500 nL of 7 mg/mL I263N bla in 50 mM Tris (pH 7.4) buffer was mixed with 500 nL of precipitant solution consisting of 0.2 M sodium formate (pH 7.0), 20% (w/v) PEG 3350 and suspended over a 80 μL reservoir of precipitant solution. The I263N bla crystals used for Xe derivatization were grown at 21° C. by the hanging drop vapor diffusion method in which 1 μL of 5 mg/mL I263N bla in 50 mM Tris (pH 7.4) was mixed with 1 μL of the same precipitant solution and suspended over a 1 mL reservoir of precipitant solution. Crystals of native bla were flash-cooled in liquid nitrogen after being briefly immersed in cryoprotectant solution consisting of precipitant solution supplemented with either 30% (v/v) glycerol or 15% (w/v) MPD and 15% (v/v) PEG 400. Xe derivatives of bla were prepared by sealing a cryoprotected crystal inside a xenon derivatization chamber (Hampton Research) and incubating the crystal with pressurized Xe (AirGas) at 1.2-2.0 MPa. Following Xe incubation, the derivatized crystal was removed from the chamber and immediately flash-cooled in liquid nitrogen.

Diffraction Data Collection and Structure Refinement

X-ray diffraction data were collected remotely at beamline 4.2.2 of the Advanced Light Source (ALS) synchrotron at the Lawrence Berkeley National Laboratory, beamlines 24ID-C and 24ID-E of the Advanced Photon Source (APS) synchrotron at the Argonne National Laboratory, and beamline 14-1 at Stanford Synchrotron Radiation Lightsource (SSRL) of the National Accelerator Laboratory. All X-ray diffraction data were collected at 100 K. Diffraction images were indexed and integrated with either XDS (Kabsch, 2010, Acta Crystallogr Sect D Biol Crystallogr, 66: 125-132) or iMosflm (Battye et al, 2011, Acta Crystallogr Sect D Biol Crystallogr, 67(4): 271-281) and then processed by AIMLESS (Evans, 2011, Acta Crystallogr Sect D Biol Crystallogr, 67(4): 282-292) from the CCP4 suite of programs (Winn et al., 2011, Acta Crystallogr Sect D Biol Crystallogr, 67(4): 235-242). The structure of native bla was solved by molecular replacement in Phaser (McCoy et al, 2007, J Appl Crystallogr, 40(4): 658-674) using a high-resolution bla structure (PDB ID 1BTL) (Jelsch et al., 1993, Proteins, 16(4): 364-383) less the solvent and ions as a search model. All other structures in this study, in turn, were phased by molecular replacement using the refined model of native bla (PDB ID 5HVI) less the solvent and ions as the search model. Iterative cycles of refinement and manual model adjustments were performed using PHENIX (version 1.9) (Adams et al., 2010, Acta Crystallogr, Sect D Biol Crystallogr, 66(2): 213-221, Afonine et al, 2012, Acta Crystallogr, Sect D Biol Crystallogr, 68(4): 352-367) and COOT (version 0.8.1) (Emsley et al., 2010, Acta Crystallogr Sect D Biol Crystallogr, 66(4): 486-501), respectively. Translationlibration-screw (TLS) refinement was performed in the later stages of refinement using TLS groups determined by PHENIX. Xe atoms were identified by inspection of electron density peaks in the isomorphous Fourier difference maps. The isomorphous difference Fourier map was generated from the structure factor amplitudes $|F_{xe}|-|F_{native}|$ and phases from the refined model of the native structure. The occupancies of Xe atoms were calculated using a combination of occupancy and B-factor refinement. Disordered protein atoms showing no electron density in the 2Fo-Fc map were deleted from the protein model, and electron density peaks that were not confidently interpretable were left unmodeled. Refinement proceeded until $R_{free}$ converged at its lower limit. The quality of the final model was assessed using MolProbity (Chen et al., 2010, Acta Crystallogr Sect D Biol Crystallogr, 66(1): 12-21). Data collection and refinement statistics are presented in Table 2. All structure figures were generated using PyMOL (The PyMOL Molecular Graphics System, Version 1.3 Schrödinger, LLC).

TABLE 2

| | | | | | | | |
|---|---|---|---|---|---|---|---|
| | | | | Data collection and refinement statistics | | | |
| | bla | bla-Xe (1.2 MPa) | bla-Xe (2.0 MPa) | I263L bla | I263L bla-Xe | I263N bla | I263N bla-Xe |
| beamline | ALS 4.2.2 | APS 24ID-E | SSRL 14-1 | SSRL 14-1 | SSRL 14-1 | APS 24ID-C | SSRL 14-1 |
| wavelength (Å) | 1.000 | 0.979 | 0.980 | 1.181 | 1.181 | 0.979 | 1.181 |
| resolution limits (Å) | 63.20-1.64 (1.67-1.64) | 51.27-1.70 (1.73-1.70) | 51.38-1.41 (1.43-1.41) | 62.92-1.82 (1.85-1.82) | 43.65-1.50 (1.53-1.50) | 95.78-1.75 (1.78-1.75) | 63.36-1.95 (2.00-1.95) |
| unit cell | | | | | | | |
| space group | $P2_1$ | $P2_1$ | $P2_1$ | $P2_1$ | $P2_1$ | $P2_1$ | $P2_1$ |
| a, b, c (Å) | 60.7, 84.2, 95.7 | 60.7, 84.6, 95.9 | 60.4, 84.6, 96.0 | 60.5, 84.0, 94.9 | 60.4, 84.1, 95.6 | 60.0, 83.5, 95.8 | 60.1, 84.2, 96.2 |
| α, β, γ (°) | 90.0, 90.1, 90.0 | 90.0, 90.1, 90.0 | 90.0, 90.6, 90.0 | 90.0, 90.4, 90.0 | 90.0, 90.0, 90.0 | 90.0, 90.1, 90.0 | 90.0, 90.0, 90.0 |
| no. of total/unique reflections | 409738/113836 | 752752/106586 | 574332/180127 | 314492/82018 | 544324/148928 | 635352/93490 | 258898/68222 |
| redundancy[a] | 3.6 (3.4) | 7.1 (7.1) | 3.2 (3.2) | 3.8 (3.8) | 3.7 (3.6) | 6.8 (6.6) | 3.8 (3.8) |
| $R_{merge}$[a,b] | 0.05 (0.30) | 0.09 (0.32) | 0.09 (0.52) | 0.11 (0.40) | 0.07 (0.32) | 0.15 (0.75) | 0.14 (0.56) |
| $R_{pim}$[a,c] | 0.05 (0.26) | 0.06 (0.20) | 0.08 (0.49) | 0.10 (0.35) | 0.06 (0.27) | 0.06 (0.34) | 0.12 (0.48) |
| $CC_{1/2}$[a,d] | 0.998 (0.927) | 0.998 (0.962) | 0.995 (0.732) | 0.987 (0.848) | 0.996 (0.904) | 0.995 (0.868) | 0.985 (0.875) |
| $I/\sigma(I)$[a] | 15.1 (3.4) | 13.1 (5.6) | 6.0 (1.5) | 6.3 (2.3) | 9.0 (2.8) | 10.3 (3.1) | 7.2 (3.1) |
| completeness (%)[a] | 96.9 (89.6) | 100.0 (100.0) | 97.2 (95.3) | 96.5 (94.8) | 97.7 (95.6) | 98.3 (97.7) | 97.8 (96.3) |
| $R_{work}$[e] | 0.17 | 0.15 | 0.18 | 0.18 | 0.17 | 0.17 | 0.18 |
| $R_{free}$[f] | 0.21 | 0.19 | 0.22 | 0.23 | 0.19 | 0.22 | 0.22 |
| protein chains[g] | 4 | 4 | 4 | 4 | 4 | 4 | 4 |
| protein atoms[g] | 8082 | 8038 | 8067 | 8056 | 8079 | 8042 | 7998 |
| water molecules[g] | 967 | 812 | 859 | 558 | 1210 | 806 | 608 |
| Xe atoms[g] | 0 | 13 | 13 | 0 | 13 | 0 | 8 |
| root-mean-square deviations | | | | | | | |
| bonds (Å) | 0.008 | 0.009 | 0.009 | 0.011 | 0.008 | 0.007 | 0.005 |
| angles (°) | 1.13 | 1.20 | 1.24 | 1.14 | 0.99 | 1.06 | 0.85 |
| average B factors (Å$^2$) | | | | | | | |
| protein | 11 | 9 | 11 | 11 | 10 | 14 | 12 |
| water | 22 | 18 | 23 | 15 | 19 | 24 | 21 |
| Xe | — | 15 | 18 | — | 15 | — | 21 |
| Ramachandran plot (%)[h] | | | | | | | |
| favored | 98.1 | 98.0 | 97.5 | 97.2 | 97.5 | 98.0 | 97.1 |
| allowed | 1.9 | 2.0 | 2.5 | 2.8 | 2.5 | 2.0 | 2.9 |
| outliers | 0 | 0 | 0 | 0 | 0 | 0 | 0 |
| PDB accession code | 5HVI | 5HW1 | 5HW5 | 5KKF | 5KPU | 5I52 | 5I63 |

[a]Values parentheses refer to the highest-resolution shell of the data.
[b]$R_{merge} = \Sigma |I_h - \langle I_h \rangle|/\Sigma \langle I_h \rangle$; $I_h$ = intensity measure for reflection h; $\langle I_h \rangle$ = average intensity for reflection h calculated from replicate data.
[c]$R_{pim} = \Sigma (1/(n-1)^{1/2}|I_h - \langle I_h \rangle|/\Sigma \langle I_h \rangle$; n = number of observations (redundancy).
[d]$CC_{1/2} = \sigma_\tau^2/(\sigma_\tau^2 + \sigma_\epsilon^2)$, where $\sigma_\tau^2$ is the true measurement error variance and $\sigma_\epsilon^2$ is the independent measurement error variance.
[e]$R_{work} = \Sigma ||F_o| - |F_c||/\Sigma |F_o|$ for reflections contained in the working set. $|F_o|$ and $|F_c|$ are the observed and calculated structure factor amplitudes, respectively.
[f]$R_{free} = \Sigma ||F_o| - |F_c||/\Sigma |F_o|$ for reflections contained in the test set held aside during refinement (5% of total).
[g]per asymmetric unit
[h]calculated by MolProbity Thermal Stability Measurements CD spectroscopy experiments to measure thermal stability were performed using a Jasco J-1500 CD spectrometer equipped with a Peltier temperature controller. Protein was diluted to 10 µM in 10 mM sodium phosphate (pH 8.0) and analyzed using a quartz cuvette with a 1-mm path length. The protein sample temperature was initially increased from 10 to 90° C. at a rate of 0.5° C./min. Secondary structure was monitored at 222 nm with a step size of 1° C. and data integration time of 8 seconds. Thermal denaturation assays were repeated twice more for each protein, but with the temperature range changed to 20 to 70° C. Data were analyzed and melting temperature ($T_m$) was calculated using the Spectra Analysis tool in the J-1500 CD spectrometer software package (Jasco).

Cavity Volume Measurements

Cavity volumes of Xe-binding sites were calculated using VOIDOO (Kleywegt et al., 1994, Acta Crystallogr Sect D Biol Crystallogr, 50(2): 178-185). The probe size (1.4 Å) and grid size (0.5 Å) parameter values were the same as used by others to characterize Xe-binding sites in proteins (Rubin et al., 2002, J Mol Biol, 322(2): 425-440; Lowery, 2005, J Protein Sci, 14(4): 848-855). As was noted previously, searches using a probe size set to the van der Waals radius of Xe (2.2 Å) failed to detect any cavities in bla. Cavity volume measurements were performed using PDB coordinate files in which Xe atoms had been removed. The coordinates of the bound Xe were input as a starting point for the cavity search.

Activity Assays

The hydrolase activities of 5 nM bla(I263A) (Wang et al., 2016, Angew Chemie Int Ed, 55(31): 8984-8987) and bla (I279N) were measured in 50 mM Tris (pH 7.4), 5% (v/v) DMSO using 450 µM nitrocefin (EMD Millipore) as a substrate. Product formation was monitored at A482 using an Infinite M1000 Pro plate reader (Tecan). The assays were performed in triplicate for pre- and post-hyper CEST bla (I263A) and bla(I279N) samples.

CD Spectroscopy

The CD spectra of WT bla and pre- and post-hyper CEST bla(I263A) and bla(I279N) samples were acquired as described previously (Wang et al., 2016, Angew Chemie Int Ed, 55(31): 8984-8987). Briefly, measurements were taken using a 1 mm quartz cuvette on an AVIV model 425 circular dichroism spectrometer. The samples consisted of 10 µM enzyme in 10 mM sodium phosphate (pH 8.0) buffer. The CD spectra were acquired at 25° C. with a wavelength step of 1 nm.

The results of the experiments are now described.

Crystal Structure of Bla Complexed with Xe

Figure 23:
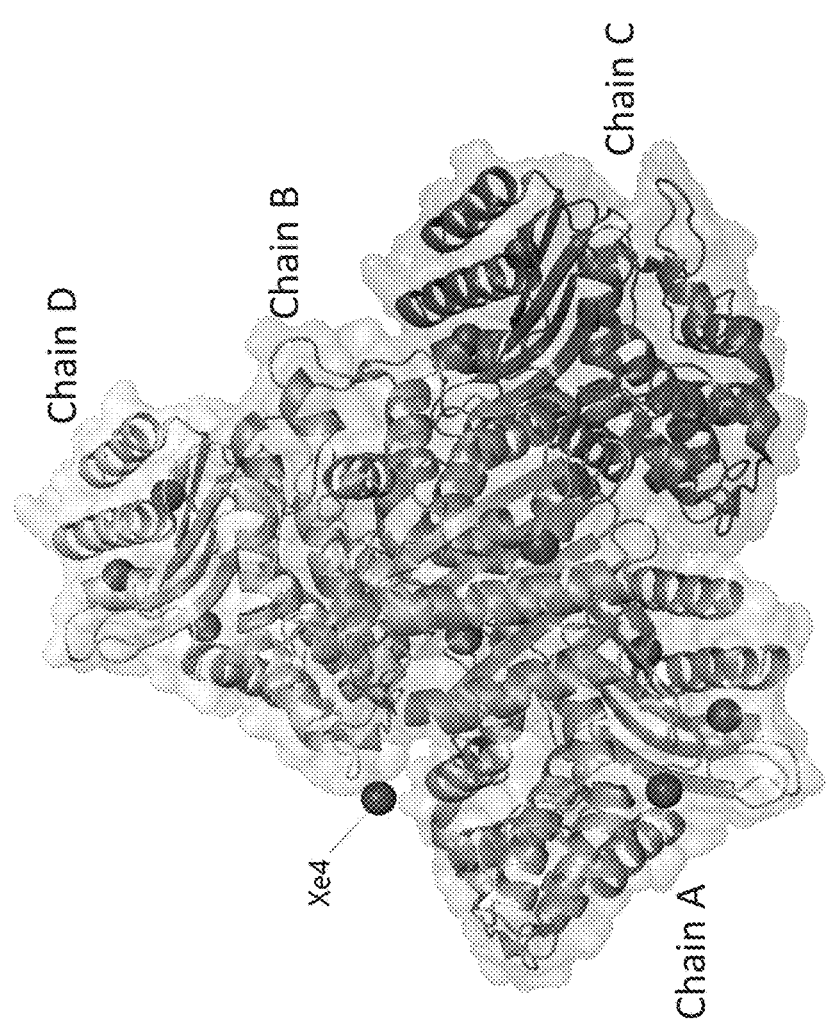
FIG. 23 illustrates the asymmetric unit of bla derivatized with Xe at 1.2 MPa.
Figure 24:
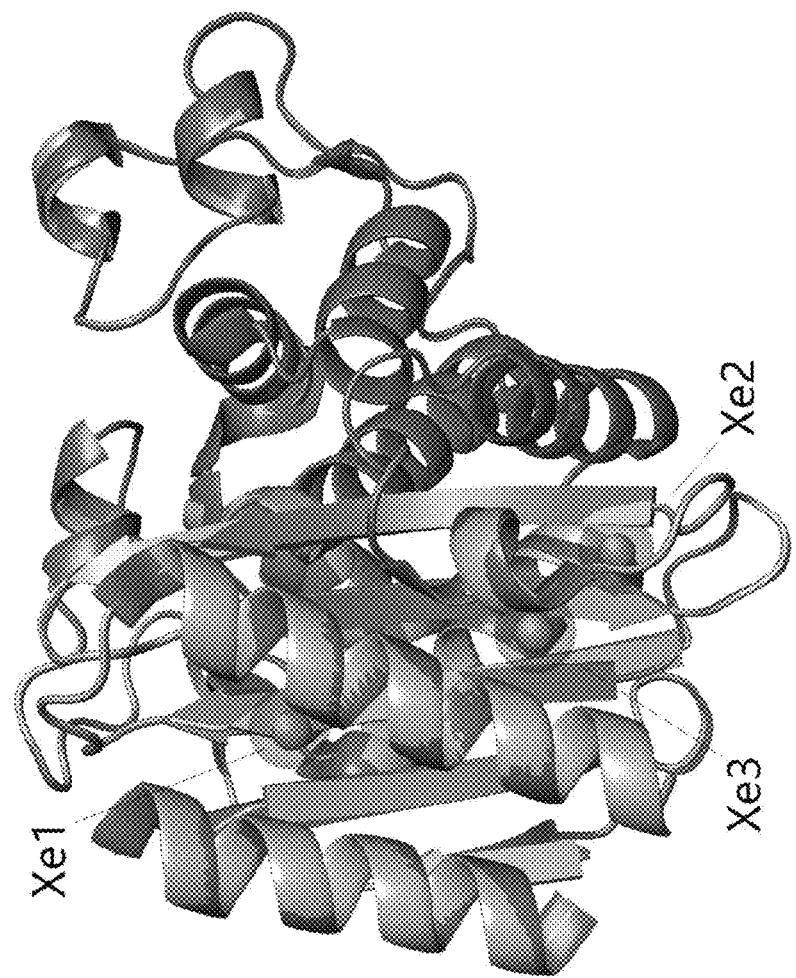
FIG. 24 depicts a comparison of Xe binding to bla at 1.2 MPa and 2.0 MPa Xe pressure. The 1.2 MPa derivative is light with Xe as large transparent spheres. The 2.0 MPa derivative is dark with Xe as small spheres.
Figures 25A, 25B, 25C:
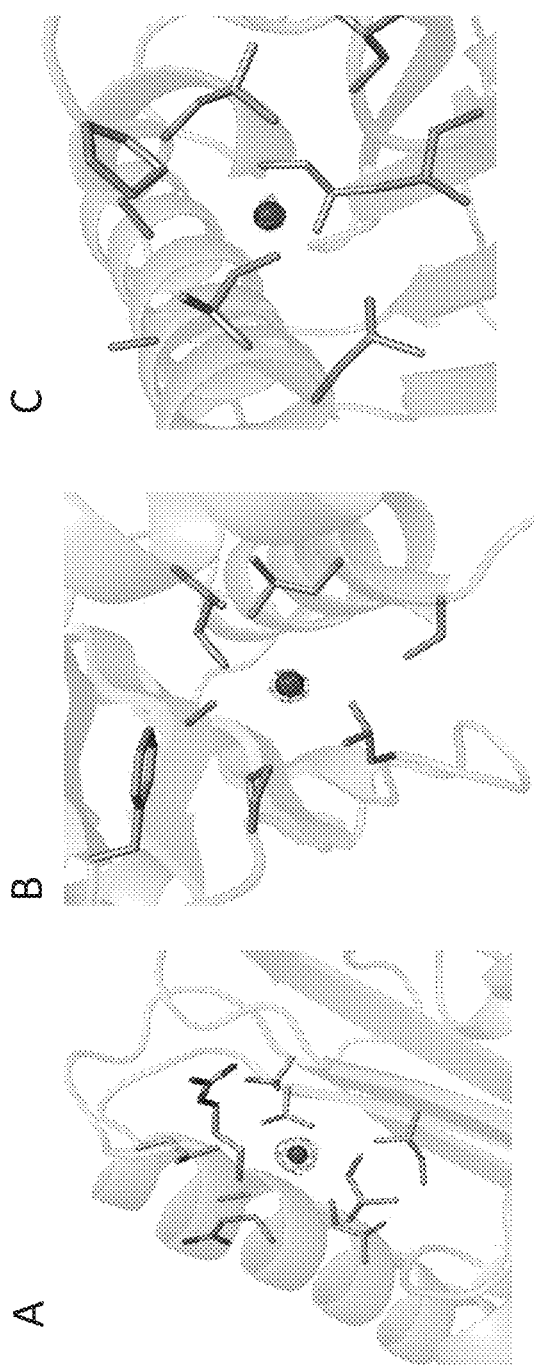
FIG. 25A through FIG. 25C, depicts anomalous Fourier maps of Xe atoms bound to bla.

Crystals of WT bla pressurized with either 1.2 or 2.0 MPa of Xe were isomorphous to native protein. The root-mean-square deviations (rmsd) of $C_\alpha$ positions from native bla were 0.11 Å for both the 1.2 MPa and 2.0 MPa Xe derivatives (Maiti et al., 2004, Nucleic Acids Res, 32: W590-4). Both Xe derivative structures showed three Xe atoms (hereafter designated Xe1, Xe2, and Xe3) bound at the same positions in all four bla chains of the asymmetric unit (FIG. 23 and FIG. 24), indicating that the presence of these Xe binding sites is independent of the Xe derivatization process used. Density present in the anomalous Fourier map further confirmed the presence of Xe at these three sites (FIG. 25). Because Xe binding was nearly identical among all four bla chains, for simplicity only chain A of the 1.2 MPa Xe derivative structure will be discussed in detail (FIG. 16A).

Figures 16A, 16B:
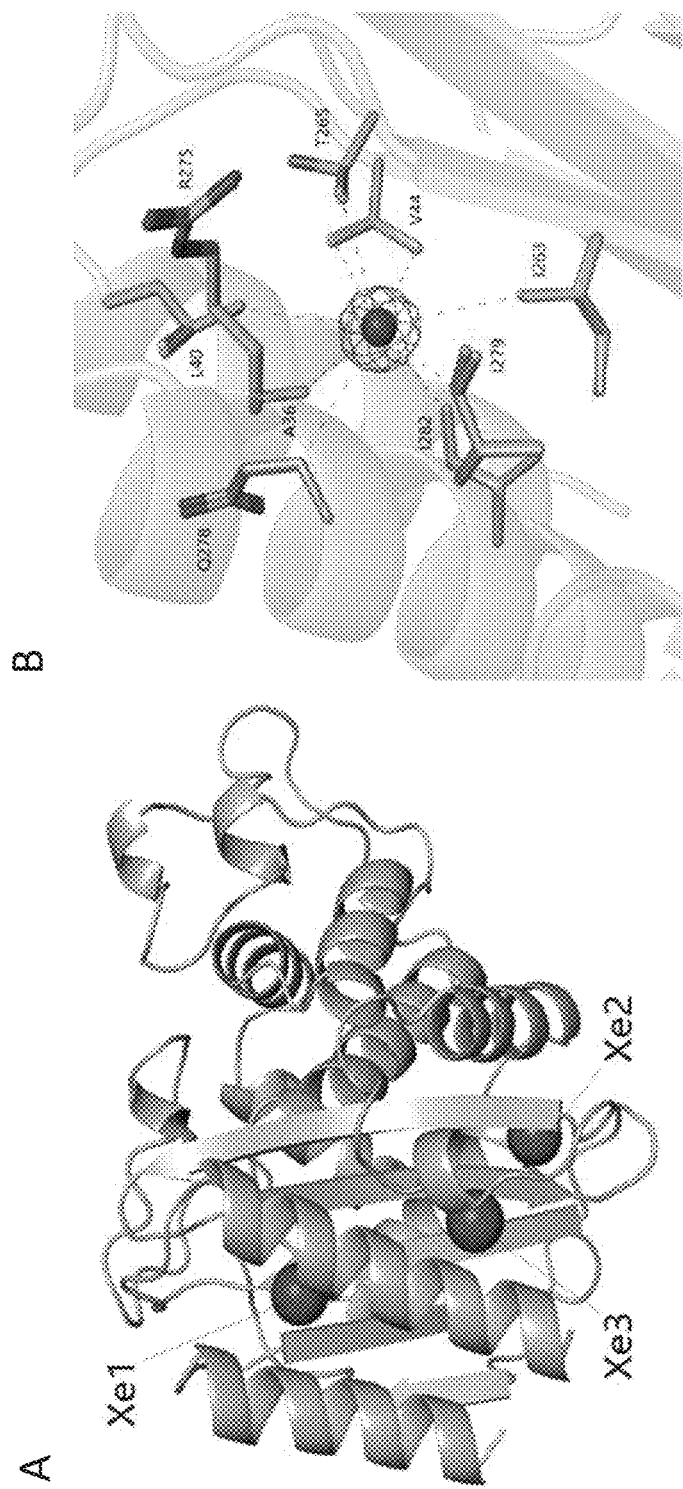
FIG. 16A and FIG. 16B, depicts an image of Chain A of the bla-Xe (1.2 MPa) complex (PDB ID 5HW1).
Figures 26A, 26B:
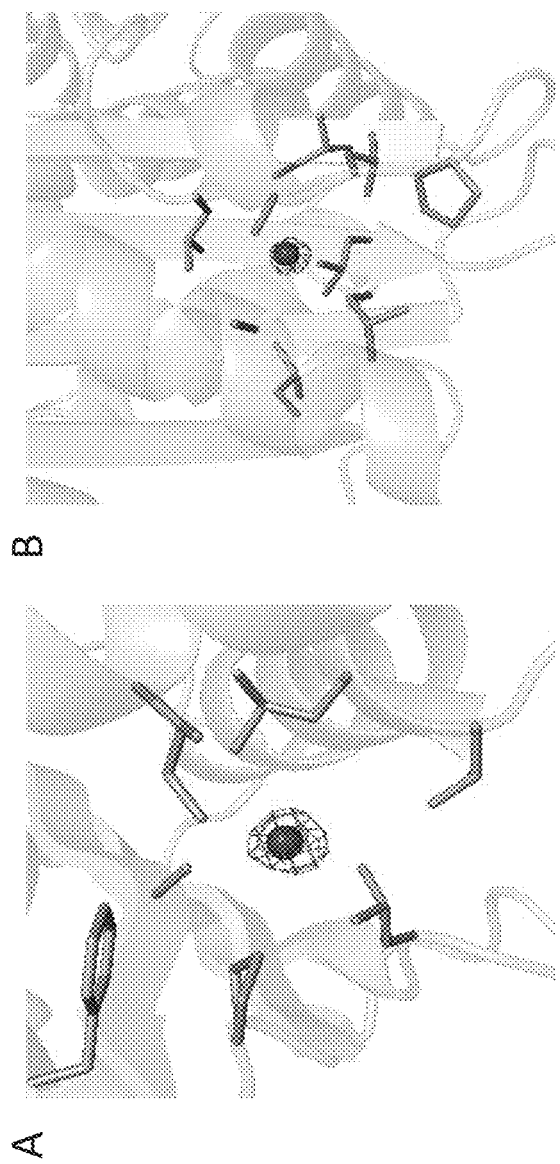
FIG. 26B depicts isomorphous difference maps of Xe2 and Xe3. Bla complexed with 1.2 MPa Xe is shown in gray with residues lining the Xe binding pockets shown as sticks.
FIG. 26A depicts Xe2 shown as a sphere. The isomorphous difference Fourier map is shown as mesh contoured at 7σ.
Figure 27:
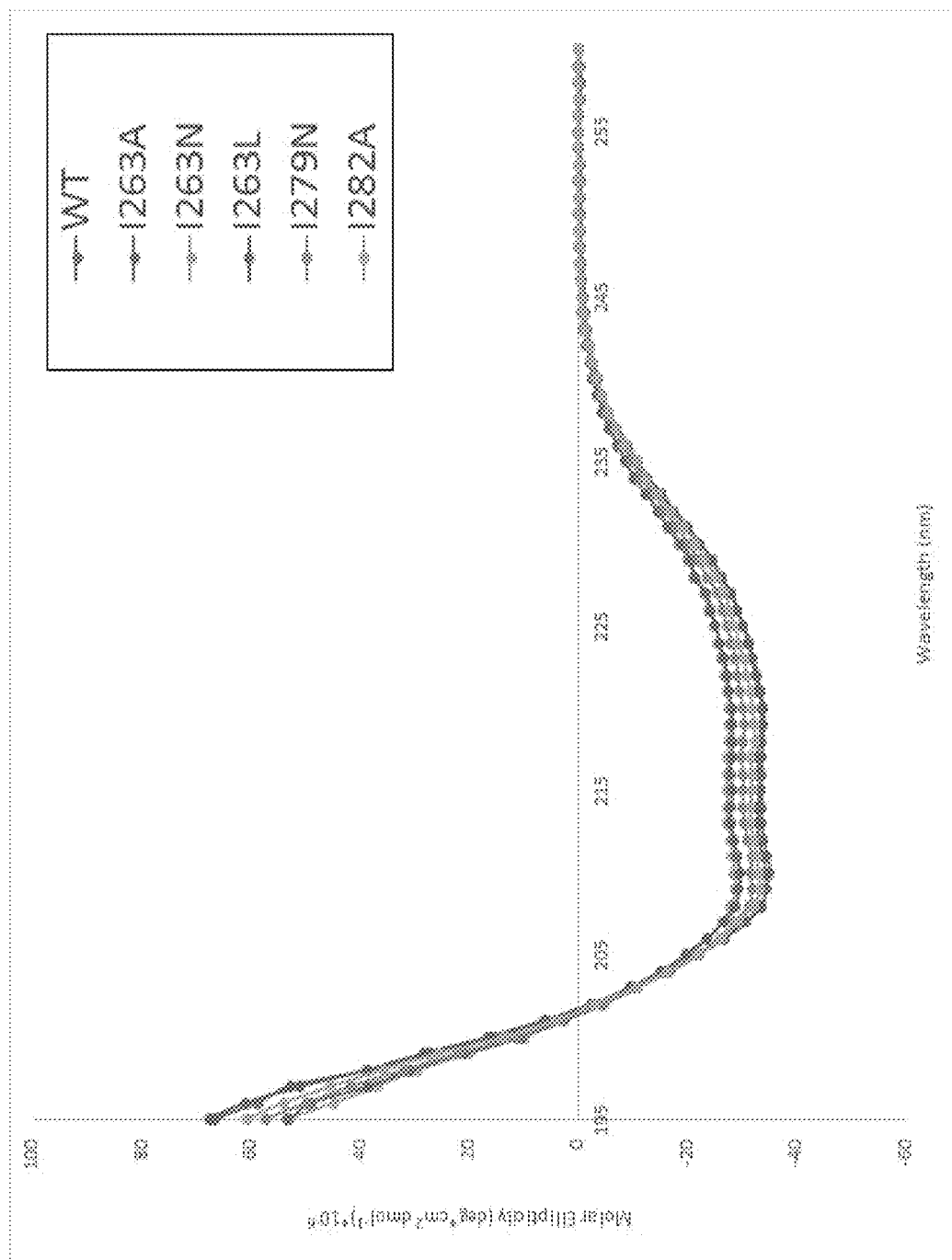
FIG. 27 depicts CD spectra of WT bla and mutants.

The residues surrounding Xe1, Xe2, and Xe3 are predominantly hydrophobic and are within van der Waals distances of the bound Xe (FIG. 16B, FIG. 26, Table 3—Table 5). Interestingly, none of the three Xe binding pockets contains water in the native bla structure, indicating that Xe binding is not driven by hydrophobic stabilization— an observation also made regarding Xe binding to myoglobin (Schoenborn et al, 1965, Nature, 207, 28-30). Additionally, computational studies of Xe binding to cryptophane concluded that the occupancy of water molecules in the hydrophobic interior of the cryptophane is anti-correlated to the free energy of Xe binding (Gao et al., 2015, Chem Sci, 6(12): 7238-7248). In the 1.2 MPa bla-Xe complex there is one additional Xe atom (Xe4) present at the interface between chains A and D, and in the 2.0 MPa bla-Xe complex there is an additional Xe atom (Xe5) present at the surface of the N-terminal α-helix. The presence of Xe4 and Xe5 are exclusive to the 1.2 MPa and 2.0 MPa derivatives, respectively. Xe4 and Xe5, however, are likely artifacts of crystal packing given their proximity to the protein surface. Indeed, inspection of bla packing in the crystal structure shows that neighboring bla molecules enclose Xe4 and Xe5.

TABLE 3

Distances from Xe1 to neighboring atoms in bla

| Residue | Atom[a] | Distance to Xe1 (Å)[b] |
|---|---|---|
| A36 | C | 6.0 |
| A36 | $C^\alpha$ | 5.8 |
| A36 | $C^\beta$ | 4.5 |
| L40 | $C^\gamma$ | 5.3 |
| L40 | $C^{\delta 1}$ | 3.9 |
| L40 | $C^{\delta 2}$ | 6.0 |
| V44 | $C^\alpha$ | 5.6 |
| V44 | $C^\beta$ | 4.7 |
| V44 | $C^{\gamma 1}$ | 4.1 |
| V44 | $C^{\gamma 2}$ | 4.0 |
| I263 | $C^\beta$ | 5.6 |
| I263 | $C^{\gamma 2}$ | 4.1 |
| Y264 | C | 5.3 |
| Y264 | O | 5.0 |
| T265 | N | 5.3 |
| T265 | $C^\alpha$ | 5.3 |
| T265 | $C^\beta$ | 4.1 |
| T265 | $O^{\gamma 1}$ | 4.8 |
| T265 | $C^{\gamma 2}$ | 4.1 |
| R275 | $C^\alpha$ | 5.8 |
| R275 | C | 5.7 |
| R275 | O | 4.7 |
| Q278 | N | 5.9 |
| Q278 | $C^\alpha$ | 5.0 |
| Q278 | $C^\beta$ | 4.0 |
| Q278 | $C^\gamma$ | 5.1 |
| Q278 | C | 4.5 |
| Q278 | O | 4.9 |
| I279 | N | 4.3 |
| I279 | $C^\alpha$ | 4.6 |
| I279 | $C^\beta$ | 4.8 |
| I279 | $C^{\gamma 1}$ | 3.7 |
| I279 | $C^{\delta 1}$ | 4.6 |
| I279 | $C^{\gamma 2}$ | 5.8 |
| I282 | $C^{\gamma 1}$ | 5.4 |
| I282 | $C^{\delta 1}$ | 4.2 |

[a]only atoms within 6 Å of Xe1 listed
[b]measured for Xe1 in chain A of 1.2 MPa structure

TABLE 4

Distances from Xe2 to neighboring atoms in bla

| Residue | Atom[a] | Distance to Xe2 (Å)[b] |
|---|---|---|
| L51 | $C^\beta$ | 5.9 |
| L51 | $C^\gamma$ | 4.6 |
| L51 | $C^{\delta 1}$ | 4.5 |

TABLE 4-continued

Distances from Xe2 to neighboring atoms in bla

| Residue | Atom[a] | Distance to Xe2 (Å)[b] |
|---|---|---|
| L51 | $C^{\delta 2}$ | 3.6 |
| L194 | $C^{\alpha}$ | 5.3 |
| L194 | $C^{\beta}$ | 4.1 |
| L194 | $C^{\gamma}$ | 4.6 |
| L194 | $C^{\delta 1}$ | 3.9 |
| L194 | $C^{\delta 2}$ | 5.1 |
| L194 | C | 5.3 |
| L194 | O | 5.2 |
| T195 | N | 5.9 |
| T195 | $C^{\beta}$ | 5.9 |
| T195 | $C^{\gamma 2}$ | 4.4 |
| I208 | $C^{\beta}$ | 4.9 |
| I208 | $C^{\gamma 1}$ | 4.0 |
| I208 | $C^{\delta 1}$ | 3.1 |
| I208 | $C^{\gamma 2}$ | 5.4 |
| F230 | $C^{\epsilon 1}$ | 5.4 |
| F230 | $C^{\zeta}$ | 5.7 |
| A249 | $C^{\alpha}$ | 5.3 |
| A249 | $C^{\beta}$ | 3.8 |
| A249 | C | 5.7 |
| A249 | O | 6.0 |
| P257 | N | 5.8 |
| P257 | $C^{\alpha}$ | 5.3 |
| P257 | $C^{\beta}$ | 3.9 |
| P257 | $C^{\gamma}$ | 3.5 |
| P257 | $C^{\delta}$ | 5.0 |
| P257 | C | 5.6 |
| P257 | O | 5.6 |

[a]only atoms within 6 Å of Xe2 listed
[b]measured for Xe1 in chain A of 1.2 MPa structure

TABLE 5

Distances from Xe3 to neighboring atoms in bla

| Residue | Atom[a] | Distance to Xe3 (Å)[b] |
|---|---|---|
| L221 | N | 5.6 |
| L221 | $C^{\alpha}$ | 4.2 |
| L221 | $C^{\beta}$ | 4.1 |
| L221 | $C^{\gamma}$ | 4.6 |
| L221 | $C^{\delta 1}$ | 5.2 |
| L221 | $C^{\delta 2}$ | 4.1 |
| L221 | C | 4.0 |
| L221 | O | 3.3 |
| R222 | N | 5.2 |
| R222 | $C^{\alpha}$ | 5.8 |
| A224 | N | 5.1 |
| A224 | $C^{\alpha}$ | 4.7 |
| A224 | $C^{\beta}$ | 4.0 |
| A224 | C | 4.3 |
| A224 | O | 4.4 |
| L225 | N | 4.4 |
| L225 | $C^{\alpha}$ | 4.5 |
| L225 | $C^{\beta}$ | 4.7 |
| L225 | $C^{\gamma}$ | 5.1 |
| L225 | $C^{\delta 1}$ | 4.2 |
| L225 | C | 6.0 |
| P226 | $C^{\delta}$ | 5.8 |
| I231 | $C^{\delta 1}$ | 5.3 |
| L250 | $C^{\beta}$ | 6.0 |
| L250 | $C^{\gamma}$ | 5.2 |
| L250 | $C^{\delta 1}$ | 3.7 |
| G283 | N | 5.5 |
| G283 | $C^{\alpha}$ | 4.1 |
| G283 | C | 4.1 |
| G283 | O | 3.8 |
| A284 | N | 5.0 |
| A284 | $C^{\alpha}$ | 5.7 |
| L286 | $C^{\beta}$ | 5.7 |
| L286 | $C^{\gamma}$ | 5.2 |
| L286 | $C^{\delta 2}$ | 4.3 |
| I287 | N | 5.4 |

TABLE 5-continued

Distances from Xe3 to neighboring atoms in bla

| Residue | Atom[a] | Distance to Xe3 (Å)[b] |
|---|---|---|
| I287 | $C^{\alpha}$ | 5.6 |
| I287 | $C^{\beta}$ | 4.8 |
| I287 | $C^{\gamma 1}$ | 3.4 |
| I287 | $C^{\delta 1}$ | 3.5 |
| I287 | $C^{\gamma 2}$ | 5.7 |

[a]only atoms within 6 Å of Xe3 listed
[b]measured for Xe1 in chain A of 1.2 MPa structure During refinement, Xe1 converged to the highest average occupancy (68%), whereas Xe2 and Xe3 converged to average occupancies of 21% and 10%, respectively (Table 6). The high occupancy of Xe1, along with its relatively large peaks in the isomorphous difference and anomalous electron density maps relative to Xe2 and Xe3, indicates that Xe1 represents the major Xe binding site in bla. From the refined occupancy of Xe1, the association constant $K_{\alpha}$ of the Xe1 binding site is estimated to be 40 $M^{-1}$, assuming a solubility of Xe in rt solution of 4.4 mM $atm^{-1}$ (Rubin et al., 2002, J Mol Biol, 322(2): 425-440). This binding affinity is comparable to the experimentally determined values for maltose-binding protein (Rubin et al., 2002, J Mol Biol, 322(2): 425-440) and T4 lysozyme (Desvaux et al, 2005, J Am Chem Soc, 127(33): 11676-11683), which are 20±10 $M^{-1}$ and 60.2±0.2 $M^{-1}$, respectively. Xe1 lies at the terminus of the cryptic hydrophobic channel previously revealed in crystal structures of allosteric ligands bound to bla (Horn et al., 2004, J Mol Biol, 336(5): 1283-1291). The far wall of the Xe1 cavity consists of residues A36, L40, and V44, flanked by T265 and Q278. The methylenes of R275 cap the binding site, shielding Xe1 from solvent. Three isoleucines—I263, I282, and I279—separate the Xe1 cavity from the hydrophobic channel and together comprise the entry portal for Xe1 binding. Notably, the conformations of the residues surrounding Xe1 are conserved between the native and Xe-derivative structures, revealing that the native conformation of bla has a pre-existing cavity suitable for Xe binding. The B-factor of Xe1 is 11.0 $Å^2$ (for chain A) and the average B-factor of protein atoms within 6 Å of Xe1 is 7.8 $Å^2$. These comparable thermal mobility values suggest that Xe1 is fairly localized in the pocket, as expected given that the van der Waals volume of Xe is 42 $Å^3$ and the Xe1 cavity volume measured by VOIDOO is 52 $Å^3$.

TABLE 6

Properties of Xe atoms in the 1.2 MPa bla-Xe complex

| Xe | Chain | Occupancy (%) | B-factor ($Å^2$) | Isomorphous difference Fourier map peak ($\sigma$) | Anomalous Fourier map peak ($\sigma$) |
|---|---|---|---|---|---|
| Xe1 | A | 65 | 11.0 | 50.5 | 19.5 |
|  | B | 72 | 9.9 | 53.0 | 22.5 |
|  | C | 67 | 12.3 | 51.6 | 17.7 |
|  | D | 67 | 11.5 | 49.7 | 18.1 |
|  | Avg. | 68 | 11.2 | 51.2 | 19.5 |
| Xe2 | A | 26 | 21.5 | 13.2 | 5.3 |
|  | B | 17 | 14.1 | 10.7 | 5.5 |
|  | C | 19 | 16.0 | 11.4 | 5.1 |
|  | D | 20 | 32.2 | 12.6 | 5.3 |
|  | Avg. | 21 | 21.0 | 12.0 | 5.3 |
| Xe3 | A | 10 | 10 | 8.2 | 3.2 |
|  | B | 6 | 6.0 | 6.7 | 0 (not observed) |
|  | C | 9 | 7.2 | 10.0 | 5.9 |

TABLE 6-continued

Properties of Xe atoms in the 1.2 MPa bla-Xe complex

| Xe | Chain | Occupancy (%) | B-factor (Å$^2$) | Isomorphous difference Fourier map peak (σ) | Anomalous Fourier map peak (σ) |
|---|---|---|---|---|---|
|  | D | 16 | 12.4 | 9.4 | 4.4 |
|  | Avg. | 10 | 8.9 | 8.6 | 3.4 |

Mechanism of Xe1 Exchange with Bla

Figure 17:
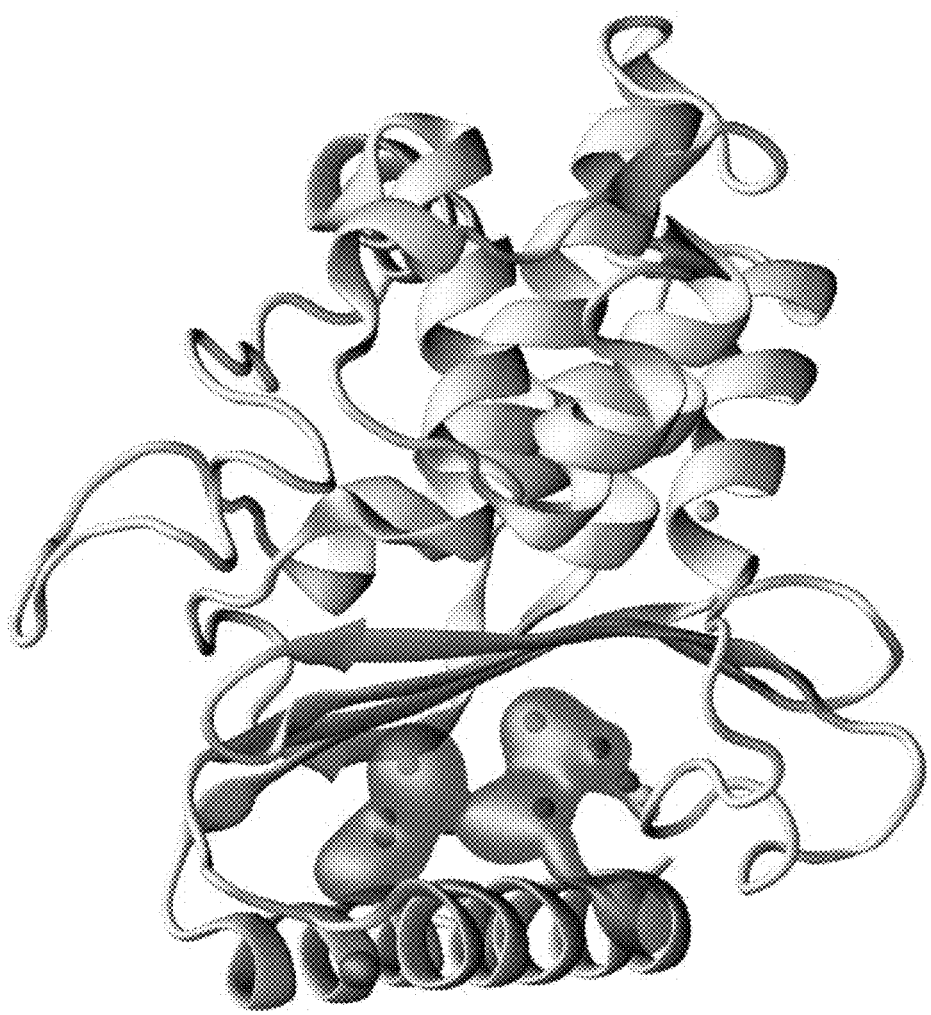
FIG. 17 depicts a Xe occupancy map calculated from a 1-µs trajectory (only the last 400 ns included in the map). Shading is the density at an arbitrary isovalue. Dark spheres are Xe atoms from a frame of the MD trajectory chosen at random. Light spheres are Xe atoms found in the crystal structure of bla.

The results of prior MD simulations (Wang et al., 2016, Angew Chemie Int Ed, 55(31): 8984-8987) were revisited to reconcile its findings with those from crystallography experiments. Briefly, the MD simulations consisted of flooding bla with Xe over a 1-μs trajectory. The atomic coordinates of unliganded bla (PDB ID 1BTL) were used as the starting point of the simulation. At the outset of the simulation, bla remains in its closed conformation with the position of the C-terminal helix (helix 12) barring Xe from accessing the interior of the hydrophobic channel. Over the course of the simulation, the C-terminal helix moves away from helix 11 and the nearby β-sheet wall to allow Xe full access to the hydrophobic channel leading to the Xe1 cavity. Inspection of the Xe density map through the final 400 ns of the trajectory reveals a continuous "Y"-shaped density throughout the channel, suggesting the pathways of Xe exchange (FIG. 17). X-ray crystallography experiments affirm the results of initial MD simulations, as Xe3 is positioned at the entrance to one of these exchange pathways and Xe1 lies at the terminus of the Xe exchange trajectory. Although the MD simulations did not predict the binding of Xe2, this binding site was recently identified as a cryptic hydrophobic site in bla using Markov State Models (Bowman et al., 2015, Proc Natl Acad Sci, 2734-2739).

There are two distinct entry points for Xe to enter the interior of the hydrophobic channel. Xe can either pass above or below the contact point between helices 11 and 12. Both pathways converge into a single route leading to the terminal cavity of the hydrophobic channel. The contours of the Xe density approximate the hydrophobic moieties of detergent-like ligands complexed with bla. The Xe density shows discrete lobes along this pathway, suggesting that the outward movement of helix 12 leads to the formation of a series of connected cavities that transiently bind Xe. The terminal cavity (i.e., the "cul-de-sac") of the hydrophobic channel is positioned between the β-sheet wall and the interface of the N- and C-terminal helices of bla, and it is within this cavity that Xe1 resides. There is a small volume of Xe density on the solvent side of the interface of the two helices, opposite the Xe1 cavity. However, the Xe density is not continuous between these two sites, suggesting that Xe exits the terminal cavity primarily via the same T-shaped channel by which it enters.

Figures 18A, 18B, 18C:
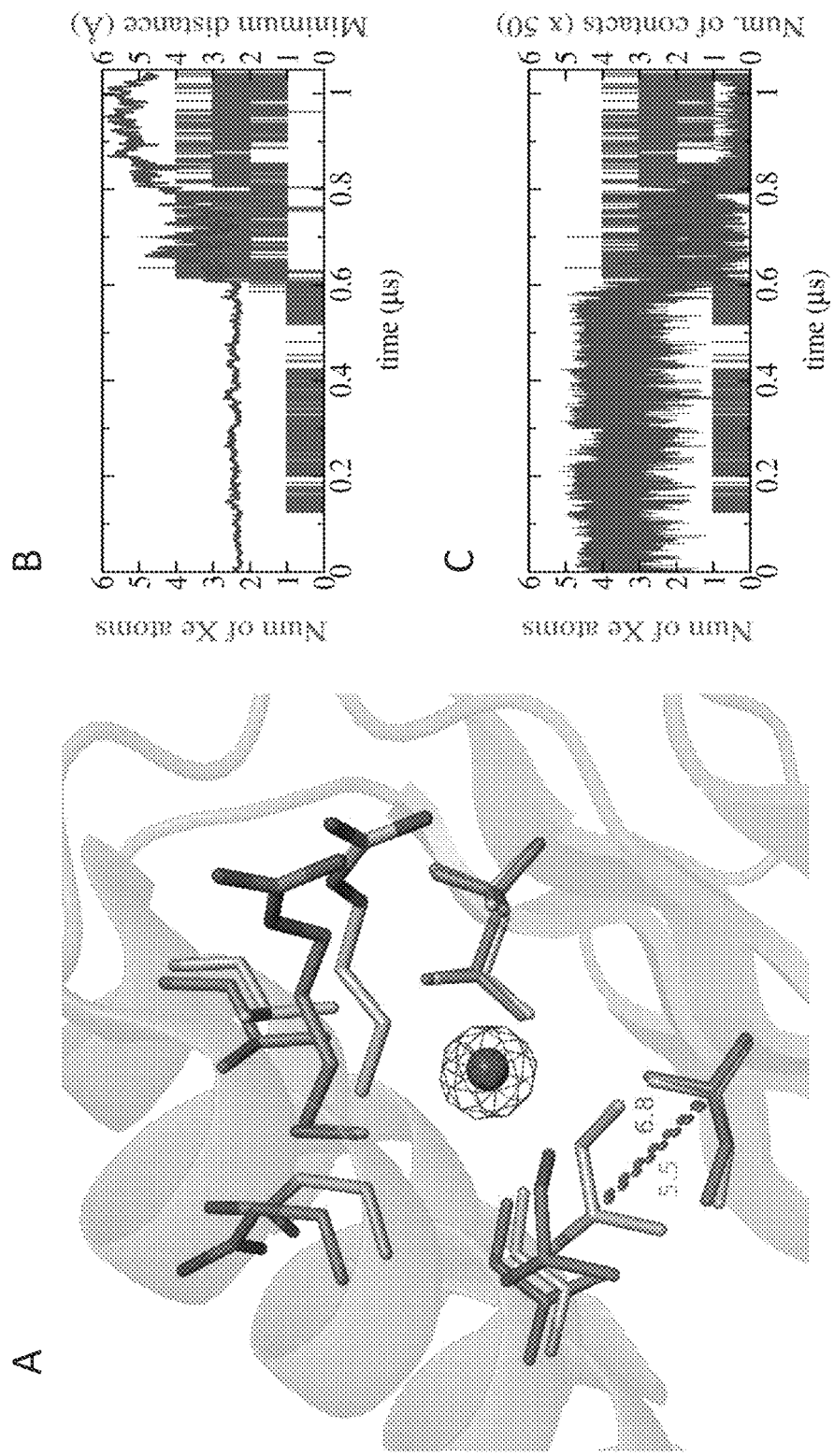
FIG. 18A illustrates Xe1 shown as a sphere, with its isomorphous difference Fourier map shown as mesh contoured at 10σ. Surrounding protein sidechains are shown as sticks (Xe-derivative in gray, liganded, "open" bla in magenta).
FIG. 18B illustrates the number of Xe atoms in the major binding site correlated to the minimum distance between Ile-263 and Ile-279 (minimum among all possible pairwise atom-atom distances).
FIG. 18C illustrates the number of Xe atoms in the major binding site anti-correlated to the number of atom-atom contacts between Ile-263 and Ile-279.

Inspection of the crystal structure of bla complexed with Xe shows no open pathway from the protein surface to the Xe1 cavity. Xe1 binding therefore involves dynamic fluctuations of the protein structure to allow access to this Xe pocket, an observation made previously to rationalize Xe binding to a serine protease (Schiltz et al., 1995, Structure, 3(3): 309-316). Comparison of an "open" bla structure complexed with an allosteric ligand (PDB ID 1PZO) to unliganded bla complexed with Xe shows that while the positions of A36, L40, V44, and I263 do not change between the open and closed conformations of bla, I279 shifts roughly 2 Å away from I263 (FIG. 18). Inspection of the dynamic distance between I263 and I279 through the MD trajectory reveals that approximately halfway through the 1-μs trajectory the distance between I263 and I279 greatly increases in a single step, an event that approximately coincides with Xe access to the terminal cavity. The transient widening of this isoleucine portal to the Xe1 cavity controls the rate of Xe1 entry and likely plays an integral role in the hyper-CEST mechanism.

Hyper-CEST Contrast Originates from Xe1

Figures 19A, 19B:
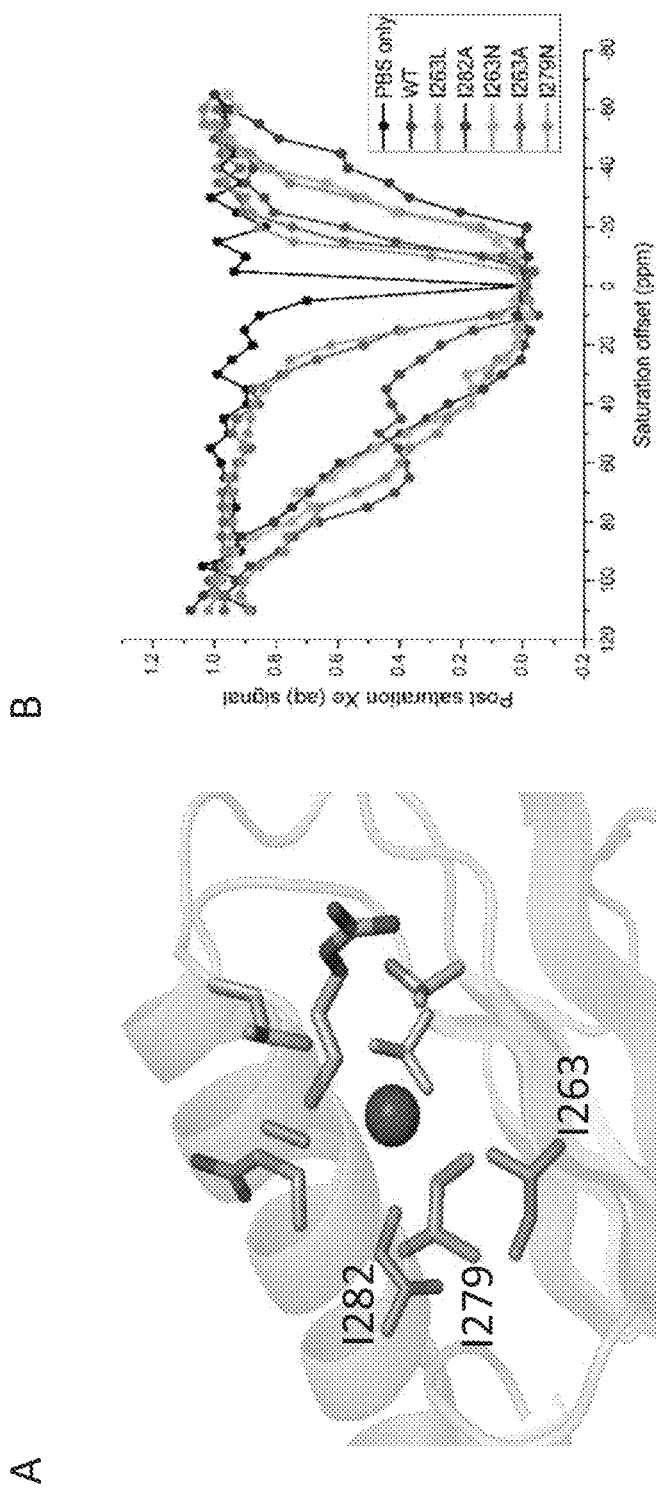
FIG. 19A depicts the Xe1 cavity with mutated residues shown as colored sticks; I263, I279, and I282.
FIG. 19B depicts the hyper-CEST z-spectra of bla mutants overlaid onto the spectrum of wild-type bla. The Xe-H$_2$O peak is set to 0 ppm.

At this point the following conclusions were drawn from the crystallography experiments and MD simulations: (1) Xe1 has a relatively high affinity for bla; (2) Xe1 is well-shielded from solvent; (3) Xe1 exchange is coupled to protein conformation and is thus relatively slow. These affirm the notion that Xe exchange at the Xe1 cavity gives rise to the unusual 60 ppm shift observed in the hyper-CEST z-spectrum of bla. To further examine Xe exchange and the Xe1 cavity, a series of single point mutations was introduced to bla to perturb Xe1 affinity and/or exchange rates and pathways (FIG. 19A). Residues I263 and I279 were targeted because they reside at the entrance of this site and likely affect Xe access as well as binding affinity (Quillin et al., 2002, Acta Crystallogr Sect D Biol Crystallogr, 58(1): 97-103; Lowery et al., 2004, Angew Chemie Int Ed, 43(46): 6320-6322). I263 was mutated to leucine, asparagine, aspartate, and alanine, and I279 was mutated to asparagine. Additionally, I282, which also makes van der Waals contacts with Xe1, was mutated to alanine. All bla mutants, with exception of I263 (which expressed exclusively as inclusion bodies), expressed at levels comparable to wild-type and were purified following the same procedure. The CD spectra of the bla mutants showed minimal changes to secondary structure (FIG. 26), suggesting that the overall bla fold is conserved among the mutants and that any changes to the hyper-CEST signal arise from local perturbations and not global structural changes.

Hyper-CEST z-spectra of all mutants were acquired following the same protocol as used for wild-type (FIG. 19B). All mutants showed either reduced contrast at 60 ppm downfield or complete loss of signal. No correlation was observed between the thermal stabilities of the mutants and their z-spectra (Table 7). As was observed previously (Wang et al., 2016, Angew Chemie Int Ed, 55(31): 8984-8987), mutating I263 into alanine resulted in loss of any appreciable hyper-CEST signal downfield of the Xe(aq) peak. A similar loss of signal was observed for the I279N mutant. The CD spectra and hydrolase activity of both mutants was measured pre- and post-CEST to verify that the loss of hyper-CEST was not the result of protein denaturation (FIG. 28; Table 8). Notably, the z-spectra of both I263A and I279N show broadening of the Xe(aq) peak, indicating that Xe is undergoing more rapid, lower affinity interactions with bla, possibly at 'site 1' with a less restrictive portal or even at 'site 2' or 'site 3'. The loss of specific downfield hyper-CEST signal from these two mutants correlates hyper-CEST response with Xe1 environment, thereby providing additional evidence that Xe1 is the origin of bla's unique hyper-CEST signal at 255 ppm.

TABLE 7

Thermal stabilities of WT bla and mutants

| Protein | $T_m$ (° C.)$^a$ |
|---|---|
| WT | 55.4 ± 0.7 |
| I263L | 51.3 ± 0.1 |
| I263A | 49.4 ± 0.5 |

TABLE 7-continued

Thermal stabilities of WT bla and mutants

| Protein | $T_m$ (° C.)[a] |
|---|---|
| I263N | 46.8 ± 0.9 |
| I279N | 47.0 ± 0.3 |
| I282A | 47.5 ± 0.5 |

[a]Data reported as mean ± standard deviation (n = 3)

TABLE 8

Specific activities of I263A and I279N mutants before and after CEST

| Protein | Initial Rate ($A_{482}$ min$^{-1}$)[a] |
|---|---|
| bla(I279N), before CEST | 0.044 ± 0.003 |
| bla(I279N), after CEST | 0.047 ± 0.002 |
| bla(I263A), before CEST | 0.142 ± 0.002 |
| bla(I263A), after CEST | 0.153 ± 0.009 |

[a]Data reported as mean ± standard deviation (n = 3)

The I282A and I263N mutants showed some appreciable level of contrast at saturation offset 60 ppm, although only about half the intensity of WT bla, suggesting that while Xe1 binding is preserved in these mutants, the alteration to Xe1 pocket adversely affects binding affinity and/or Xe exchange rates. The signal from I263L, on the other hand, is only slightly lower than from WT, as might be expected from this minor structural perturbation. An unusual feature of the hyper-CEST spectra of I282A, I263N, and I263L is the broadened signal between saturation offset 60 ppm and 0 ppm. Whereas the hyper-CEST spectrum of WT can be deconvolved into two peaks—60 ppm for Xe-bla and 0 ppm for Xe-solvent—these three mutants show only a peak at 0 ppm with significant asymmetric broadening towards 60 ppm. The signal arising from this "intermediate" range can be interpreted as resulting from Xe bound to bla but not fully shielded from solvent.

Crystal Structures of Bla Mutants Complexed with Xe

Figures 20A, 20B:
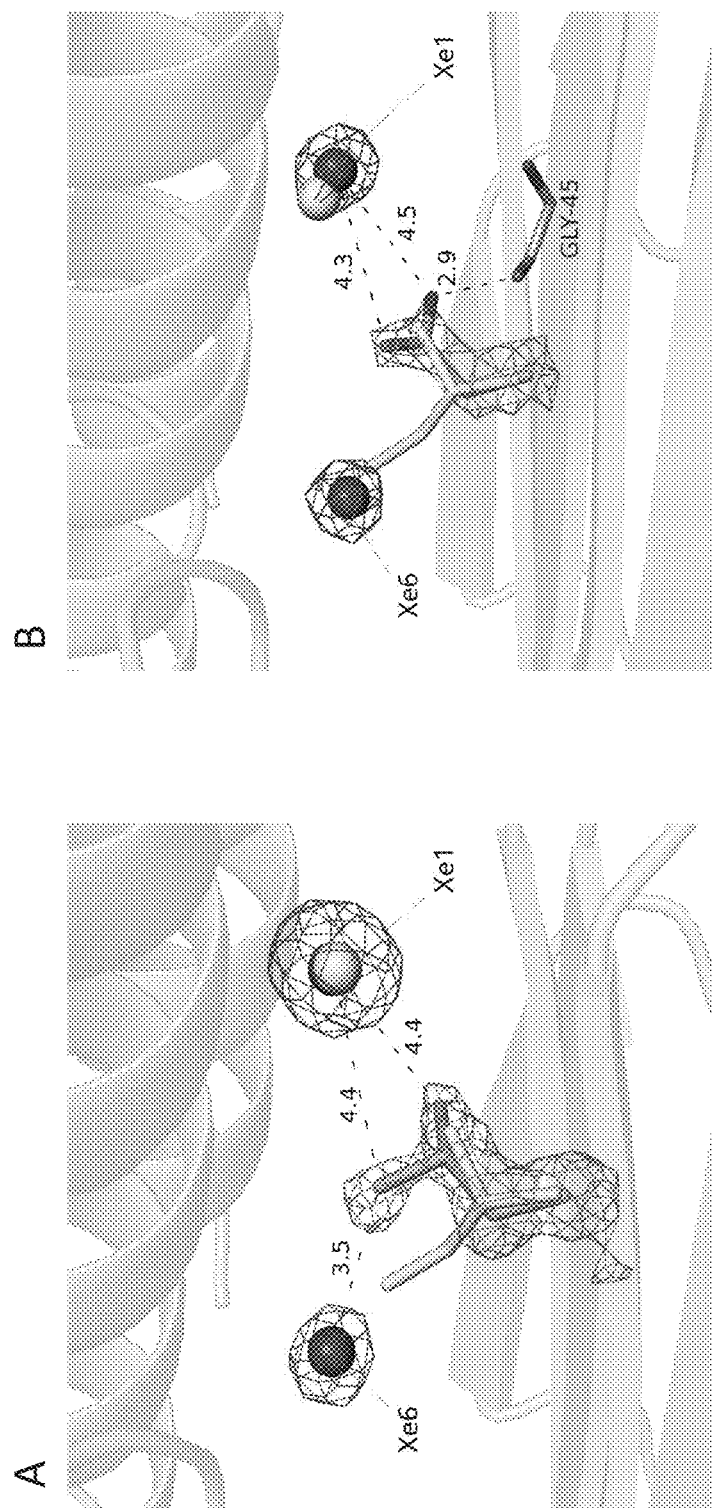
FIG. 20A depicts a cartoon representation of chain A of the bla (I263L)-Xe complex. L263 is shown as sticks with its SA omit map shown as mesh and contoured at 3σ. Ile-263 from the wild-type bla-Xe (1.2 MPa) complex shown as sticks. Xe1 and Xe6 bound in the TEM(I263L)-Xe complex are shown as spheres with their isomorphous difference Fourier maps are contoured at 5σ. The position of Xe1 bound to WT bla is shown as an enlarged transparent sphere.
FIG. 20B depicts a cartoon representation of chain A of the TEM-1 (I263N)-Xe complex. N263 is shown as sticks with its simulated annealing omit map shown as mesh and contoured at 3σ. I263 from WT bla-Xe is shown as sticks. Xe1 and Xe6 bound in the bla(I263N)-Xe complex are shown as spheres with their isomorphous difference Fourier maps contoured at 5σ. The position of Xe1 bound to WT bla is shown as an enlarged transparent sphere.

To investigate the structural basis of I263N's and I263L's unusual $^{129}$Xe hyper-CEST spectra, namely 1) the reduced signal at saturation offset 60 ppm for I263N, and 2) the signal broadening between 60 and 0 ppm, crystals of these mutants were derivatized with Xe following the same procedure as used for WT bla. As expected from the presence of hyper-CEST contrast at 60 ppm, Xe1 is observed bound to both mutants. Interestingly, the occupancy of Xe1 in I263L is higher than in WT (83% vs. 68%, Table 9), likely due to the additional van der Waals contacts made by the two methyl groups within 4.5 Å of Xe1 (FIG. 20A). This slight increase in occupancy, however, does not translate into increased CEST contrast at saturation offset 60 ppm, affirming that the mechanism of Xe1 exchange also plays a role in determining CEST contrast. In the bla(263N) mutant, the carboxamide nitrogen of Asn-263 donates a hydrogen bond to the carbonyl oxygen of G45, thereby "pinning" the asparagine side-chain to the β-sheet wall and orienting the carboxamide oxygen and nitrogen directly towards Xe1 (FIG. 20B). As a result, the position of Xe1 in the I263N mutant is shifted slightly relative to wild-type due to increased size of the asparagine side-chain. Additionally, the occupancy of Xe1 in I263N is roughly half that of WT (33% vs. 68%) (Table 10), which is unsurprising given the increased polarity introduced by the carboxamide group of Asn-263. This reduced occupancy is reflected in the hyper-CEST profile of the I263N mutant, which reports roughly half the contrast at saturation offset 60 ppm than WT. Finally, it is worth noting that despite the presence of a carbonyl oxygen inside the Xe1 pocket, no water is observed in native I263N, highlighting the extreme hydrophobicity of this cavity.

TABLE 9

Properties of Xe atoms in the bla(I263L)-Xe complex

| Xe | Chain | Occupancy (%) | B-factor (Å$^2$) |
|---|---|---|---|
| Xe1 | A | 87 | 13.4 |
| | B | 82 | 11.9 |
| | C | 76 | 13.3 |
| | D | 85 | 13.2 |
| | Avg. | 83 | 13 |
| Xe2 | A | 5 | 11.1 |
| | C | 12 | 15.9 |
| | D | 21 | 21.2 |
| | Avg. | 13 | 16 |
| Xe3 | A | 18 | 19.1 |
| | B | 17 | 24.7 |
| | Avg. | 18 | 22 |
| Xe6 | A | 25 | 14.9 |
| | B | 27 | 14.2 |
| | C | 25 | 13.9 |
| | D | 10 | 10.4 |
| | Avg. | 22 | 13 |

TABLE 10

Properties of Xe atoms in the bla(I263N)-Xe complex

| Xe | Chain | Occupancy (%) | B-factor (Å$^2$) |
|---|---|---|---|
| Xe1 | A | 47 | 29.4 |
| | B | 22 | 13.9 |
| | C | 31 | 29.6 |
| | D | 33 | 20.1 |
| | Avg. | 33 | 23 |
| Xe6 | A | 24 | 11.7 |
| | B | 32 | 15.0 |
| | C | 31 | 22.3 |
| | D | 26 | 23.7 |
| | Avg. | 28 | 18 |

Remarkably, the crystal structures of both I263L and I263N reveal a new pocket capable of binding Xe (hereafter designated Xe6). Similar to the binding sites of Xe1, Xe2, and Xe3, Xe6 is surrounded by predominately hydrophobic residues. Comparison of the sidechain conformations of residue 263 shows that Xe6 binding is blocked in WT bla by the $\gamma^1$ and δ carbons of isoleucine. The occupancies of Xe6 are low compared to Xe1; 22% and 28% in the I263L and I263N mutants, respectively (Table 9 Table 10). However, the B-factors of Xe6 are roughly the same as the residues lining the binding pocket, suggesting that Xe6 binding is fairly localized. Xe6 lies between Xe1, which is completely shielded from solvent, and Xe3, which lies at the entrance of the hydrophobic channel between helices 11 and 12. Thus, Xe6 is expected to report a chemical shift somewhere between 60 and 0 ppm. The presence of Xe6 in the I263L and I263N mutants explains the contrast observed between 60 and 0 ppm. Whereas Xe binding in WT can be approximated as a two-state system, where Xe is either aqueous or buried within the Xe1 cavity, Xe binding to I263L and I263N can transiently occupy a binding site in the middle of the hydrophobic channel that lies between the buried protein core and solvent entrance.

MD Simulations Provide Additional Insight on Xe CEST Mechanism

Figures 21A, 21B:
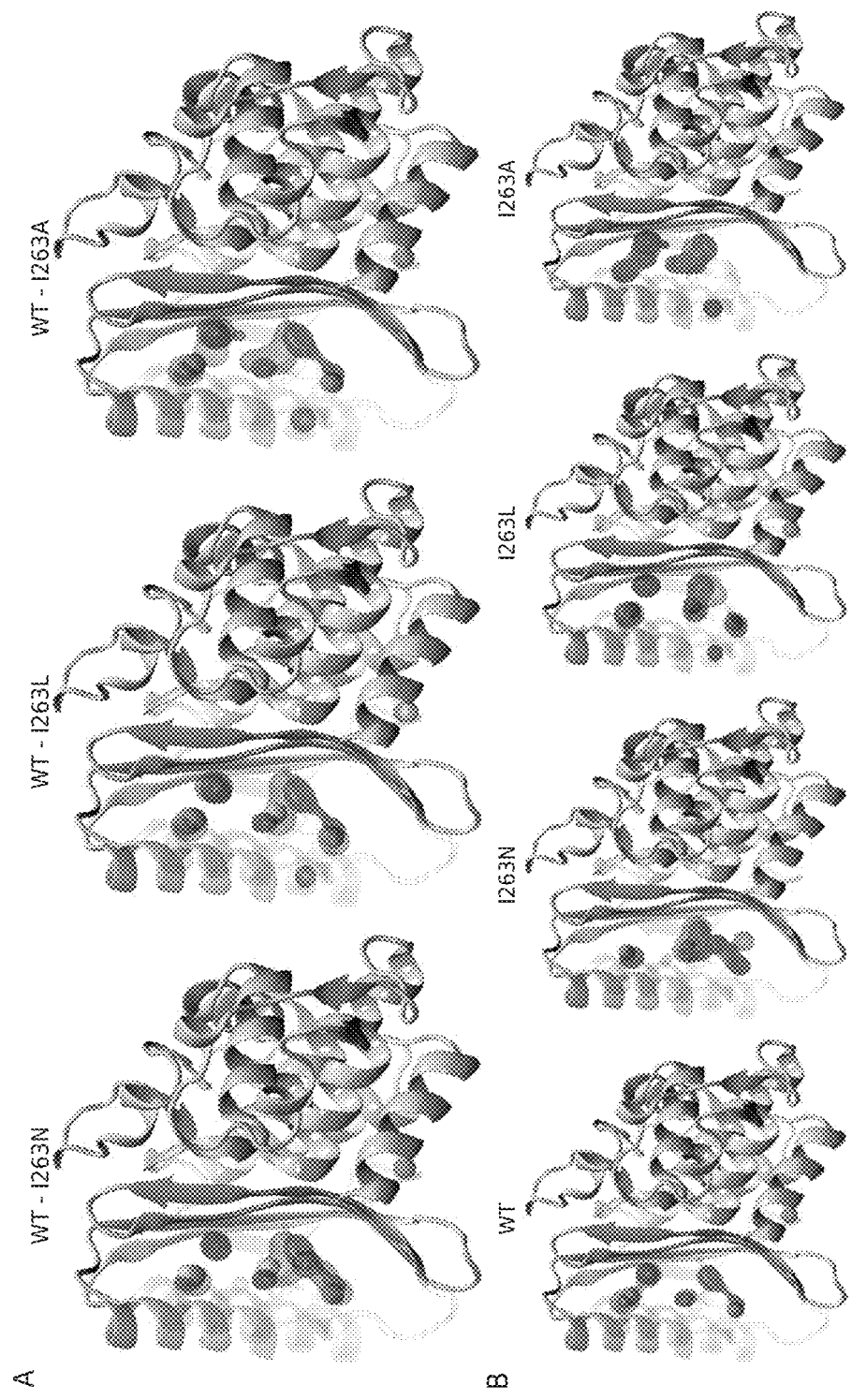
FIG. 21A and FIG. 21B, depicts the Xe binding site in WT and mutants.
Figure 28:
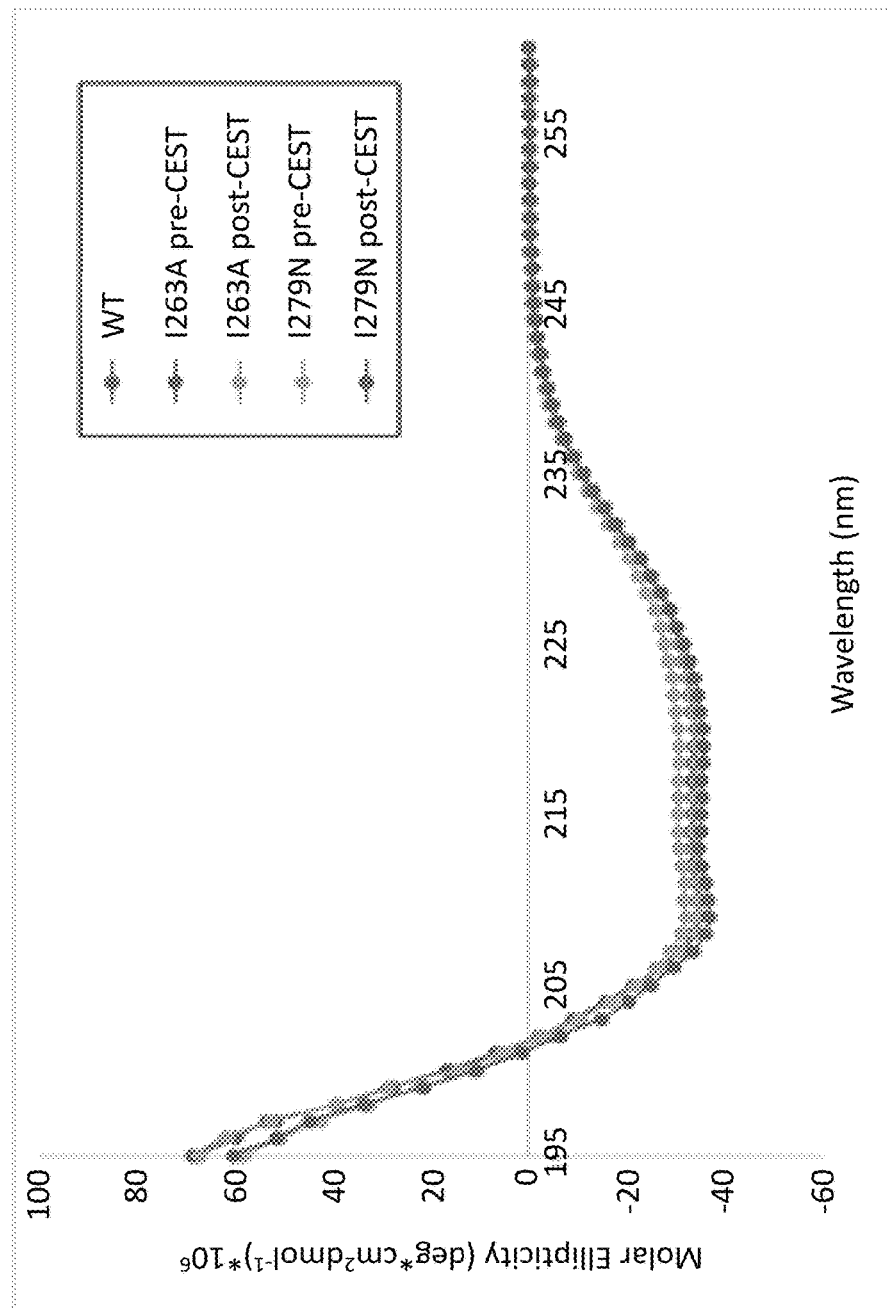
FIG. 28 depicts CD spectra of bla mutants I263A and I279N before and after Xe hyper-CEST experiment. The CD spectrum of wild-type bla is included as a reference.
Figure 29:
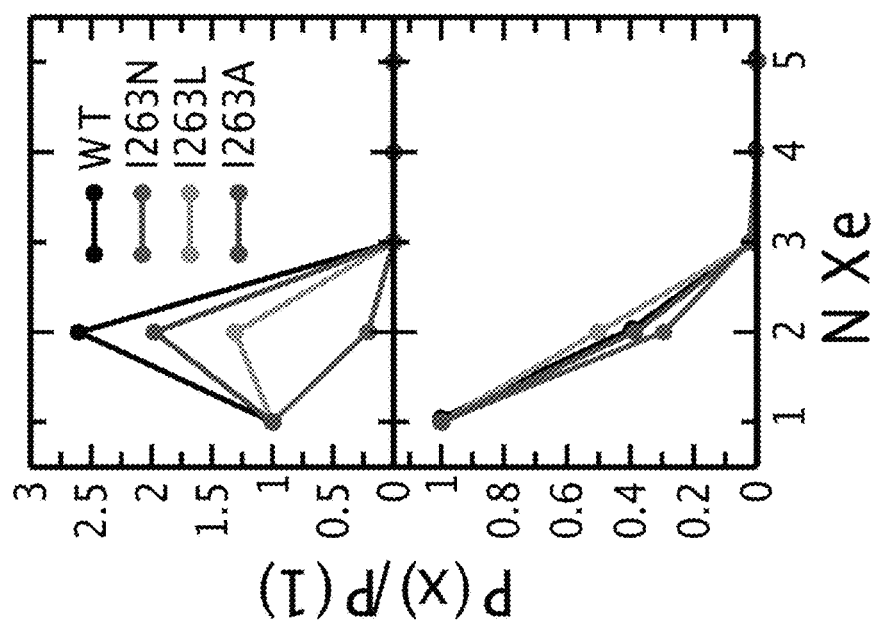
FIG. 29 depicts a graphical representation of the number of Xe atoms in the different binding sites. Relative probability (P(x)/P(1)) of finding more than one Xe atom (x) in the top binding site (top panel) and bottom binding site (bottom panel) is shown.

To further investigate the effect of the I263 mutations on the structure and dynamics of the Xe-binding cavities and to understand the molecular origins of the perturbed Xe hyper-CEST profiles, long time-scale MD simulations were performed. Mutants I263L, I263N and I263A were simulated with either a single Xe atom residing in the Xe1 site or in apo-form in the presence of a large excess of Xe atoms in solution (i.e. "flooding"). These two complementary approaches were adopted to avoid artifacts resulting from insufficient statistical sampling (single Xe simulations) and structural perturbation due to the large excess of Xe ("flooding" simulations). The patterns of occupancies calculated from these trajectories are consistent with the experimental structures (FIG. 21A) and between the two computational approaches (FIG. 21B). All I263 mutants show increased density in the region surrounding the Xe6 binding site, whereas in WT there is a density node at this site. I263N shows a more localized density within the Xe1 cavity, consistent with the decreased occupancy observed in the X-ray crystal structure and lower CEST contrast at 60 ppm. Quantitative analysis of the number of Xe atoms occupying the binding sites during the MD simulation confirms that this is indeed the case (FIG. 28). The I263A mutant, which shows the most perturbed hyper-CEST profile (i.e. complete absence of 60 ppm peak), is characterized by an occupancy map similar to that of WT but with some key differences. Notably, there is continuous Xe density within the Xe1 cavity of I263A, while WT and I263L present two spheres of density and I263N presents only one. Additionally, I263A shows no density corresponding to Xe3, suggesting that Xe exchange with this mutant occurs via a different entry point to the Xe1 cavity.

Figures 22A, 22B:
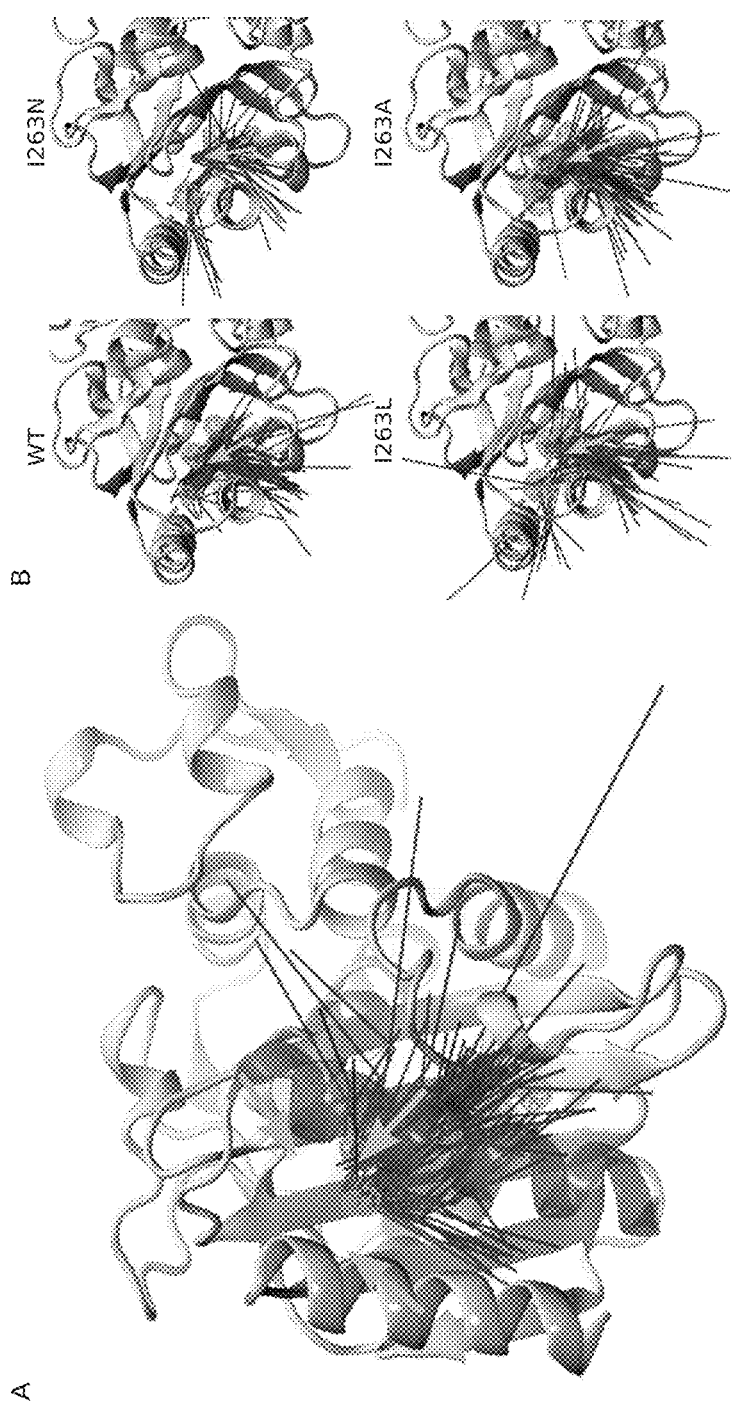
FIG. 22A and FIG. 22B, depicts Xe pathways toward the Xe1 binding site. The trajectories of all Xe binding events to WT and the mutants are shown with straight lines. The arrows highlight the major pathways followed by the Xe atoms.

To ascertain that mutations of I263 can affect accessibility as well as occupancy, all the binding events that occurred in WT bla and the mutants were analyzed (FIG. 22). This analysis provides crucial insight on the routes that Xe atoms follow to reach the protein interior. All the binding trajectories can be summarized by three major pathways: the first one has Xe3 as first entry point and proceeds between the β-sheet and α-helices 11 and 12 via Xe6 and, finally, to the Xe1 "cul de sac"; the second pathway reaches Xe1 by crossing above the interface between helices 11 and 12; finally, in the third pathway Xe atoms directly access Xe1 from the side of the β-sheet, i.e. the opposite direction with respect to helices 11 and 12. Importantly, significant differences are observed between WT and the mutants especially concerning the second and third pathways, which only in I263L and I263N are significantly populated, and are virtually absent in I263A. This marked difference suggests the following scenario: a change in the side chain of I263 causes the appearance of a novel binding site (Xe6) located within the pathway that connects the solution to Xe1 through the entry point in Xe3. Binding of Xe at Xe6 blocks the first pathway, thus I263L and I263N show alternative pathways to reach Xe1 (second and third pathways) and thus an alternative mode of Xe exchange is evident, as suggested by the z-spectra of these mutants.

From the combination of X-ray crystallography and MD simulations, general conclusions regarding the mechanism of Xe hyper-CEST with bla can be gleaned. It is evident that Xe binding within the Xe1 cavity results in the CEST peak observed 60 ppm downfield. The magnitude of the observed contrast roughly correlates to binding affinity (as measured by occupancy in crystal structures and density in MD trajectories). The I263N mutation—which lowers Xe1 binding affinity approximately half-fold—results in half the contrast at 60 ppm. Therefore, a solvent-shielded binding site with appreciable affinity for Xe is a prerequisite for observing downfield hyper-CEST contrast. Additionally, in order for the downfield CEST contrast to result in a peak resolved from the $Xe_{(aq)}$ peak, it is important that the pathway leading to the major Xe binding site consists of discrete Xe-binding cavities rather than a continuous channel. As evidenced by the I263L and I263N mutants, allowing Xe to pool in the channel outside the Xe1 cavity leads to broadening of the $Xe_{(aq)}$ peak and results in loss of resolution in the CEST z-spectra. Finally, the route of Xe entry and rate of exchange is a key determinant of CEST contrast. Inspection of the trajectories of Xe interaction with the I263A mutant shows increased rates of Xe access to the Xe1 cavity via a different route than the ones taken for WT, I263L, and I263N. Thus, it is critical that the rate of Xe exchange be slowed by the conformation of the protein in order for CEST contrast to arise.

Example 3: Maltose Binding Protein is a Genetically-Encoded Xe Hyper-CEST Reporter The large chemical shift window of $^{129}Xe$ (>300 ppm) should allow for a range of genetically encoded hyper-CEST contrast agents to be employed simultaneously, unlike standard $T_1$ or T2* MRI contrast agents. This capacity for multiplexing using hyper-CEST reporters makes them similar to optical reporter genes like fluorescent proteins (McMahon et al., 2016, Top Magn Reson Imaging, 25(5): 197-204). Since the identification of bla as a hyper-CEST gene (see Example 1 and Example 2), the search for small, monomeric bacterial proteins capable of Xe CEST at different resonance frequencies has continued. Maltose binding protein (MBP) was identified as a potential Xe hyper-CEST reporter because it possesses a single Xe-binding site that has been well-characterized by NMR (Rubin et al., 2001, J Am Chem Soc, 123(35): 8616-8617) and crystallography (Rubin et al., 2002, J Mol Biol, 322(2): 425-440). MBP is a periplasmic protein encoded by the MalE gene that serves as an initial receptor in the maltose/maltodextrin transport system in gram-negative bacteria (Boos et al., 1998, Microbiol Mol Biol Rev, 62(1): 204-229). Maltose and maltodextrins bind MBP with high affinity ($K_d$~1 μM) between two nearly symmetrical lobes that transition from an "open" to "closed" conformation (hereafter designated $MBP_{open}$ and $MBP_{closed}$) upon ligand binding. Mutations to MBP designed to shift the open-closed conformational equilibrium towards the closed state have resulted in a $K_d$ for maltose of 70 nM (Telmer et al., 2003, J Biol Chem, 278(36): 34555-34567). The large structural response to sugar binding has led to the utilization of MBP as a biosensor for the detection of target compounds in vitro and in vivo (Medintz et al., 2006, Curr Opin Biotechnol, 17(1): 17-27). Additionally, MBP is frequently used in molecular biology as solubility tag (Wood et al., 2014; Curr Opin Struct Biol, 26(1): 54-61; Kapust et al., 1999, Protein Sci, 8(8): 1668-1674), handle for protein purification (Riggs, 2000, Mol Biotechnol, 15(1): 51-63), and crystallization partner (Waugh, 2016, Protein Sci, 25(3): 559-571). MBP also functions as an expression tag in eukaryotic cells (Reuten et al., 2016, PLoS One, 11(3): e0152386).

Figures 30A, 30B, 30C:
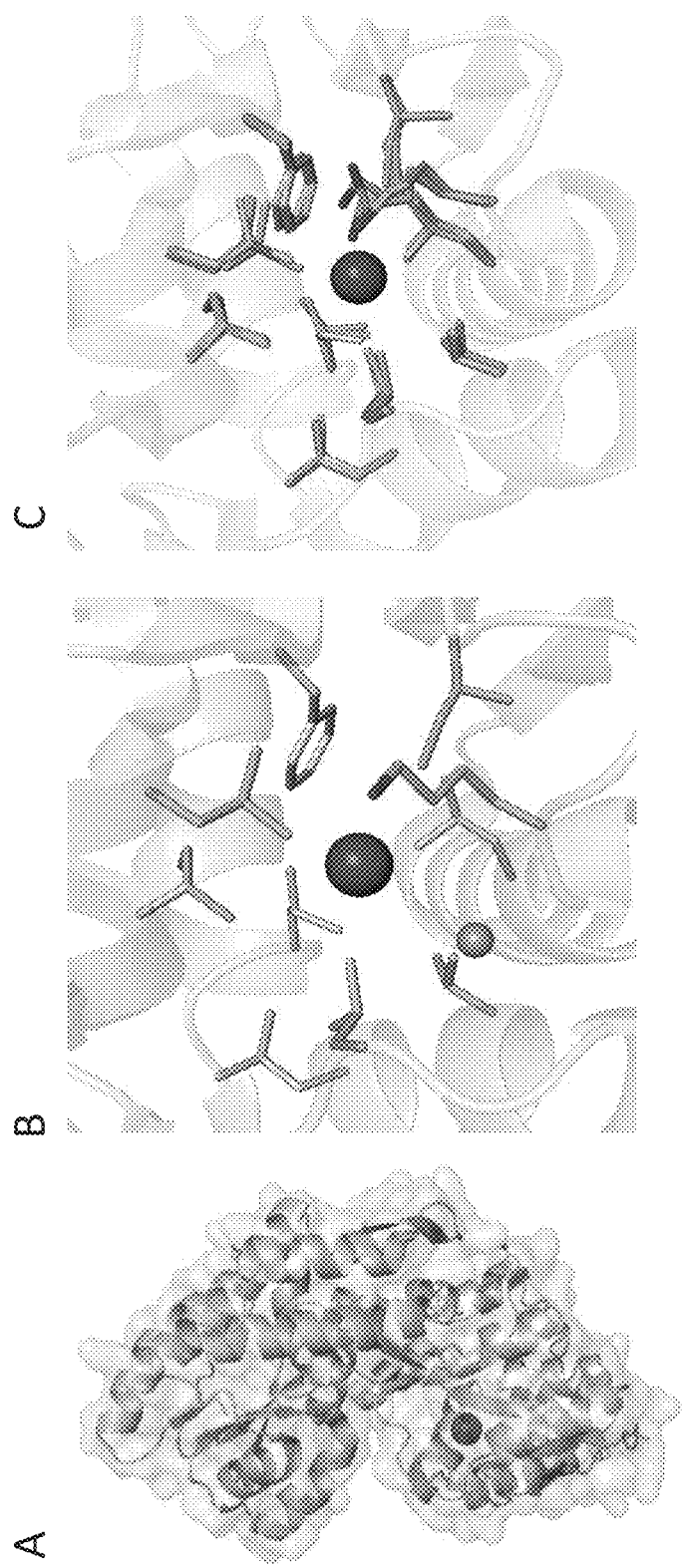
FIG. 30A through FIG. 30C, depicts maltose binding protein (MBP).

The Xe-binding site of MBP lies within the N-terminal domain, just below the surface of the sugar-binding cleft (FIG. 30A). This site is lined primarily with hydrophobic residues, specifically Ile-11, Leu-20, Phe-61, Ile-108, Leu-262, Leu-284, Leu-290, Val-293, Leu-299 (FIG. 30B), and Lys-15, which "caps" the pocket, separating the hydrophobic interior from solvent. The conformation of these residues does not significantly change in the open and closed conformations of MBP, nor does it change between $MBP_{open}$ and $MBP_{open}$ derivatized with Xe (FIG. 30C). HSQC NMR, however, determined that Xe binds at this site with a $K_a$ of 20±10 $M^1$ when MBP is in the open conformation, and binds with a lower affinity when MBP is closed. It was thus expected that $MBP_{open}$ would report greater Xe hyper-CEST contrast than $MBP_{closed}$.

The materials and methods employed in these experiments are now described.

MBP Expression and Purification

MBP was expressed from a customized pET vector (Addgene cat. no. 29656) containing the MalE gene without its N-terminal signal peptide sequence (UniProt acc. no. A0A080EQA1). The MalE gene is flanked by a N-terminal His6 tag and a C-terminal TEV cleavage sequence. The pET-MBP plasmid was transformed into BL21(DE3) competent cells (New England Biolabs) and grown in 6×1 L of LB media supplemented with 50 µg/mL kanamycin to a $OD_{600}$ of ~1. MBP expression was induced by adding isopropyl-β-D-thiogalactopyranoside (IPTG) to a final concentration of 1 mM. The induced cells were incubated overnight at 18° C., harvested by centrifugation, then frozen at −80° C. The cell pellets were resuspended in 20 mM sodium phosphate (pH 7.4), lysed with lysozyme (Sigma), and treated with benzonase nuclease (Sigma) to reduce the viscosity of the lysate. After stirring the lysate at room temperature (RT) for 30 minutes, NaCl was added to 0.5 M and imidazole was added to 20 mM. The lysate was clarified by centrifugation, and the supernatant was loaded onto a HisTrap nickel affinity column (GE Life Sciences) pre-equilibrated with 20 mM sodium phosphate (pH 7.4), 0.5 M NaCl, 20 mM imidazole. MBP was eluted from the column with 20 mM sodium phosphate (pH 7.4), 0.5 M NaCl, 500 mM imidazole. The eluate was concentrated and further purified by size-exclusion chromatography in PBS (HyClone) using a HiLoad 16/600 Superdex column (GE Life Sciences). Fractions containing pure protein (over 95% as indicated by SDS-PAGE) were pooled and concentrated. Protein concentration were determined from the absorbance at 280 nm using the extinction coefficient $\varepsilon_{280}$=67 840 $M^{-1}$ $cm^{-1}$ calculated by the PROTPARAM server. All MBP mutants were expressed and purified following the same procedure used for WT MBP.

Site-Directed Mutagenesis

Mutations were introduced to the pET-MBP plasmid via site-directed mutagenesis using the forward and reverse primers listed in (Table 11). The mutated plasmids were amplified in NEB-5α competent cells (New England Biolabs) and then purified using a miniprep kit (Qiagen). All mutated MBP genes were sequenced to verify the incorporation of the desired mutation and the integrity of the entire gene sequence.

TABLE 11

Oligonucleotide primers used in site-directed mutagenesis of MBP

| | | |
|---|---|---|
| V293L | Forward primer | 5'-GAAGGTCTGGAAGCGCTGAATAAAGACAAAC CG-3' (SEQ ID NO: 29) |
| | Reverse primer | 5'-CGGTTTGTCTTTATTCAGCGCTTCCAGACCT TC-3' (SEQ ID NO: 30) |
| V293A | Forward primer | 5'-GAAGGTCTGGAAGCGGCGAATAAAGACAAAC CG-3' (SEQ ID NO: 31) |

TABLE 11-continued

Oligonucleotide primers used in site-directed mutagenesis of MBP

| | | |
|---|---|---|
| | Reverse primer | 5'-CGGTTTGTCTTTATTCGCCGCTTCCAGACCT TC-3' (SEQ ID NO: 32) |
| M321A | Forward primer | 5'-GCGAAAGATCCACGTATTGCCGCCACTGCG GAAAACGCCCAGAAAGGTGAAATC-3' (SEQ ID NO: 33) |
| | Reverse primer | 5'-GATTTCACCTTTCTGGGCGTTTTCCGCAGTGGCG GCAATACGTGGATCTTTCGC-3' (SEQ ID NO: 34) |
| Q325A | Forward primer[a] | 5'-GCCACTGCGGAAAACGCCGCGAAAGGTGAAATCAT GCCG-3' (SEQ ID NO: 35) |
| | Reverse primer[a] | 5'-CGGCATGATTTCACCTTTCGCGGCGTTTTCCGCAG TGGC-3' (SEQ ID NO: 36) |

[a]primer also incorporates M321A mutation $^{129}$Xe Hyper-CEST $^{129}$Xe was hyperpolarized and z-spectra of bla were acquired as described previously (Wang et al., 2016, Angew Chemie Int Ed, 55(31): 8984-8987). Briefly, HP $^{129}$Xe was generated using the spin-exchange optical pumping (SEOP) method with a home-built $^{129}$Xe polarizer based on the IGI.Xe.2000 commercial model by GE. A Shark 65 W tunable ultra-narrow band diode laser (OptiGrate) set to 795 nm was used for optical pumping of Rb vapor. A gas mixture of 88% helium, 10% nitrogen, and 2% natural abundance xenon (Linde Group, N.J.) was used as the hyperpolarizer input. $^{129}$Xe hyperpolarization level was roughly 10-15%. For each data point in the hyper-CEST z-spectra, HP $^{129}$Xe was bubbled into the NMR tube through capillaries for 20 seconds, followed by a 3-second delay to allow bubbles to collapse. A Dsnob saturation pulse with 690 Hz bandwidth was used. Pulse length $t_{pulse}$=3.80 ms, field strength B1, max=77 µT, number of pulses $n_{pulse}$=400, saturation time $T_{sat}$=1.52 s. NMR experiments were performed using a Bruker BioDRX 500 MHz NMR spectrometer and 10-mm PABBO probe, at 300 K. A 900 hard pulse of this probe has a pulse length of 22 µs. Unless otherwise noted, the protein concentration used was 80 µM, with 0.1% (v/v) Pluronic L81 (Aldrich) added to mitigate foaming.

CD Spectroscopy and Thermal Stability Measurements

The CD spectra of WT MBP, V293L mutant, and V293A mutant were measured on a Jasco J-1500 CD spectrometer equipped with a Peltier temperature controller. Spectra were acquired from 10 µM of protein in 10 mM sodium phosphate (pH 8.0) buffer inside a quartz cuvette with a 1-mm path length. CD spectra were taken at 20° C. with a wavelength step of 1 nm. CD spectra were performed in triplicate and averaged. Protein thermal stability was measured by increasing temperature from 20 to 90° C. at a rate of 0.5° C./min. Secondary structure was monitored at 222 nm with a step size of 1° C. and data integration time of 8 seconds. Thermal denaturation was repeated in triplicate, and melting temperature ($T_m$) was calculated from the data using the Spectra Analysis tool in the J-1500 CD spectrometer software package (Jasco).

Fluorescence Spectroscopy

Fluorescence spectra were obtained on a Tecan Infinite M1000 PRO microplate reader using black 96 well flat-bottom microplates (Grenier Bio-One). MBP concentration was 4 µM in 20 mM HEPES (pH 7.4). Maltose was used at a final concentration of 400 µM incubated with MBP for 15 minutes prior to fluorescence readings. Excitation was at 280 nm and emission was scanned from 300 to 400 nm in 1 nm increments. All fluorescence assays were performed in triplicate and averaged. Fluorescence spectra were background corrected by subtracting the fluorescence spectrum of the well solution in the absence of protein.

The results of the experiments are now described.

To evaluate whether MBP reports any Xe hyper-CEST contrast, a hyper-CEST z-spectrum was acquired from 80 µM MBP, where multiple selective Dsnob-shaped saturation pulses were scanned over the chemical shift range of 93-358 ppm in 5 ppm steps, and the $^{129}Xe_{(aq)}$ signal was measured as a function of saturation pulse offset (FIG. 31). For $MBP_{open}$, only a single saturation response at ~195 ppm was observed, corresponding to free $^{129}Xe$ in solution. This $Xe_{(aq)}$ peak, however, was significantly broadened in comparison to the $Xe_{(aq)}$ peak observed in the absence of MBP, indicating fast Xe exchange with all specific and non-specific binding sites within MBP. This fast exchange is also evident in the direct detection Xe NMR spectra, where the addition of MBP broadens the lone $^{129}Xe$ resonance peak and alters its chemical shift slightly, but does not result in a second resolved Xe@MBP peak.

Remarkably, though, the z-spectrum of 80 µM MBP in the presence of 1 mM maltose shows a well-defined peak corresponding to $Xe@MBP_{closed}$, approximately 100 ppm downfield of the $Xe_{(aq)}$ peak. Notably, this $Xe@MBP_{closed}$ peak is 40 ppm downfield of the peak previously reported for $^{129}Xe@bla$. The z-spectrum of Xe in 1 mM maltose solution was taken as a control to verify that no Xe-maltose interactions were contributing to the downfield peak. To assess the detection sensitivity of MBP, time-dependent saturation transfer experiments were performed by measuring Xe(aq) polarization as a function of saturation time. Shaped saturation pulses were applied at the chemical shift of $Xe@MBP_{closed}$, and the residual aqueous $^{129}Xe$ signal after saturation transfer was measured as an on-resonance CEST response. Saturation frequencies of Dsnob-shaped pulses were positioned +95 ppm and -95 ppm, referenced to the $Xe_{(aq)}$ peak, for on- and off-resonance, respectively. The normalized difference between on- and off-resonance signals was represented by the saturation contrast. Using this method, 100 nM MBP reported 0.26±0.01 saturation contrast, comparable to the saturation contrast reported by 100 nM TEM-1 β-lactamase.

Figure 32:
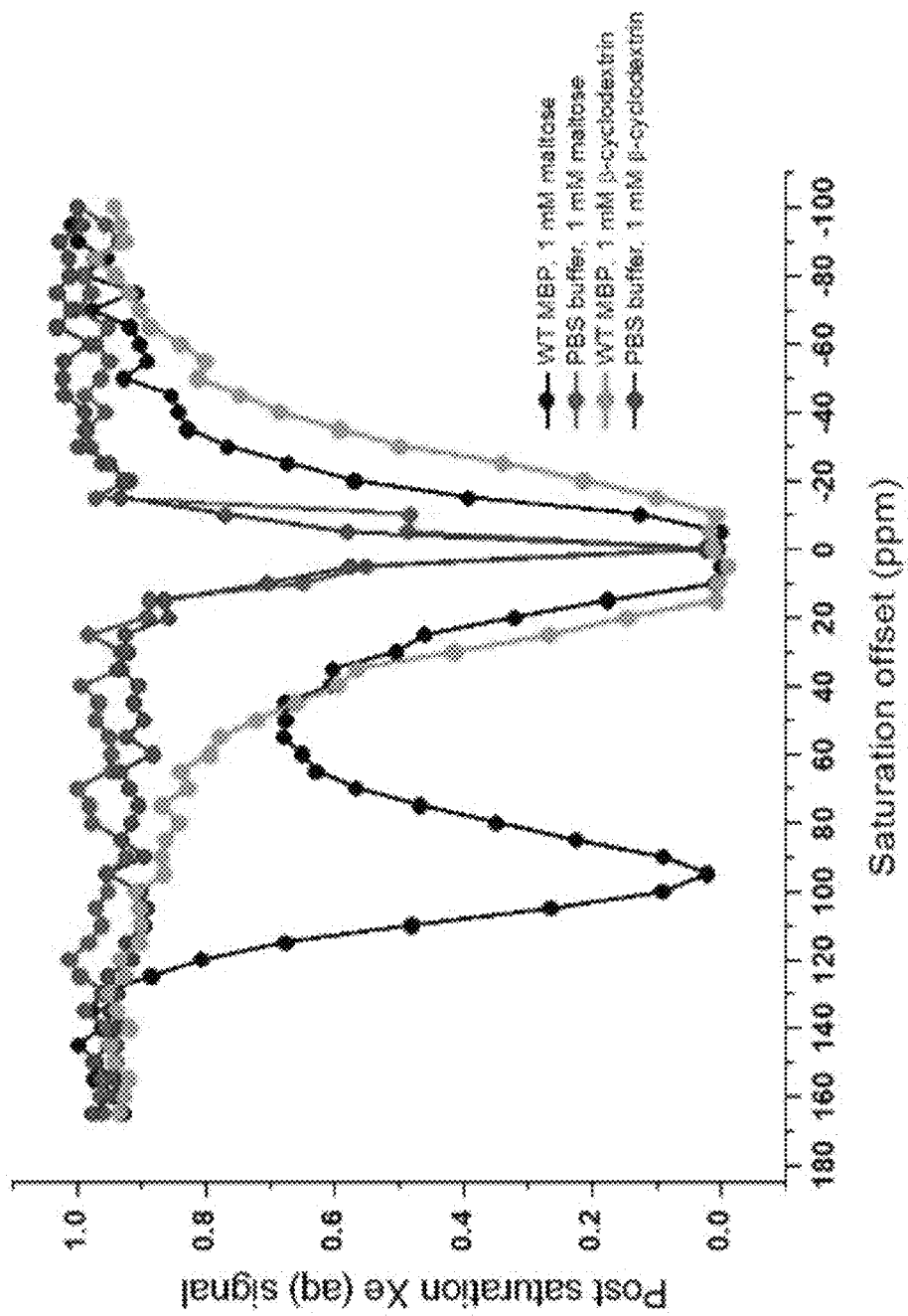
FIG. 32 depicts Xe hyper-CEST z-spectra of wt-MBP in the presence of 1 mM maltose and 1 mM O-cyclodextrin. Spectra were acquired from 80 μM protein in PBS pH 7.2. The z-spectra of PBS pH 7.2 containing 1 mM maltose and 1 mM β-cyclodextrin are shown for reference.

To test whether the CEST contrast results from the conformational change induced by sugar binding or just from sugar binding alone, the CEST spectrum of MBP in the presence of β-cyclodextrin (β-CD) was acquired. β-CD binds MBP with high affinity in the same cleft as maltose, but its larger size prevents MBP from adopting a closed conformation (Szmelcman et al., 1976, Eur J Biochem, 65(1): 13-19). Both X-ray and solution NMR data indicate that the conformation of MBP bound to β-CD closely resembles that of $MBP_{open}$ (Sharff et al., 1993, Biochemistry, 32(40: 10553-10559). The z-spectrum of MBP (FIG. 32) in the presence of β-CD reports no downfield Xe@MBP peak, thereby establishing that it is the global conformation of MBP, and not merely the presence of bound sugar, that gives rise to hyper-CEST contrast. Interestingly, though, the Xe(aq) peak is broadened by β-CD compared to maltose, suggesting that the binding of β-CD to MBP enhances its interactions with Xe, though such interactions are too fast to resolve as a separate NMR peak. The peak widths of buffer with and without β-CD are nearly identical, indicating that any interactions between Xe and β-CD do not produce any hyper-CEST contrast.

Mutagenesis to Identify Origin of Hyper-CEST Contrast

The crystal structure of MBP in the presence of Xe reveals only a single bound Xe; thus, it was examined whether this bound Xe was responsible for the hyper-CEST signal observed for MBP. To test this, the structure of this Xe-binding site was altered through site-directed mutagenesis, a strategy used by Rubin et al. to determine the effect of a specific Xe binding site in T4 lysozyme on the observed $^{129}Xe$ chemical shift in direct detection NMR (Rubin et al., 2002, J Mol Biol, 322(2): 425-440).

Figures 36A, 36B:
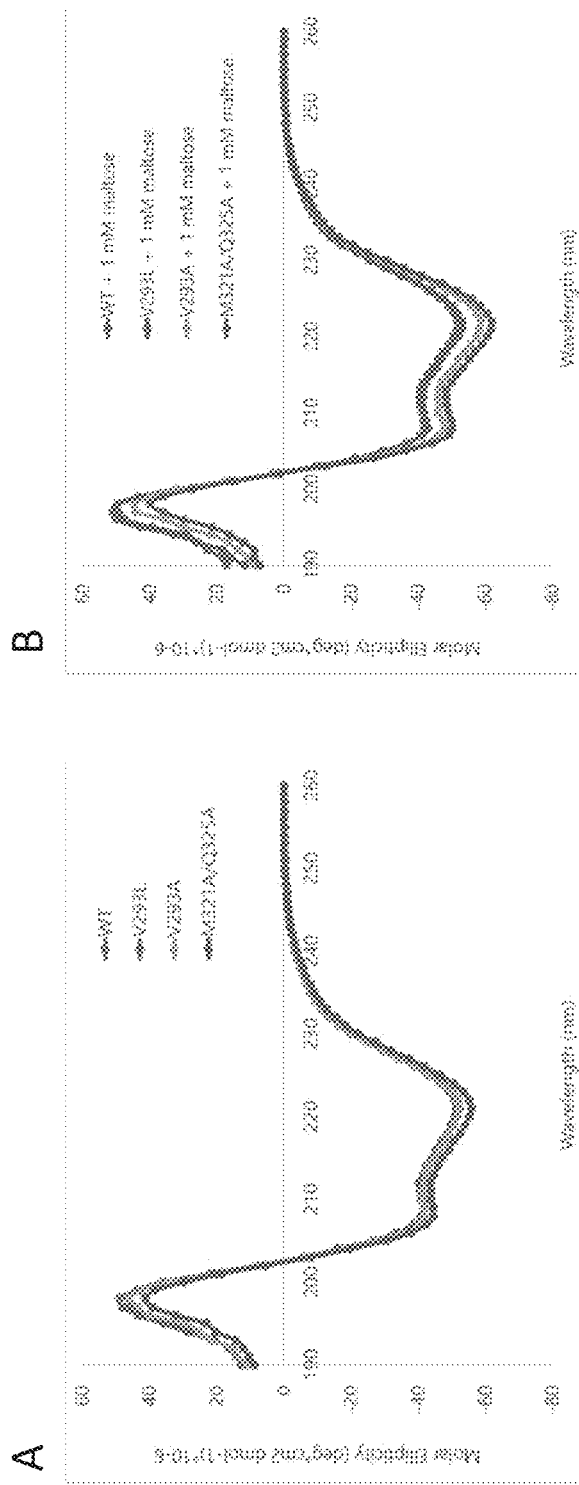
FIG. 36A and FIG. 36B, depicts CD spectra of wt MBP, MBP V293L, MBP V293A, and MBP M321A/Q325A in PBS pH 7.2.
Figure 37:
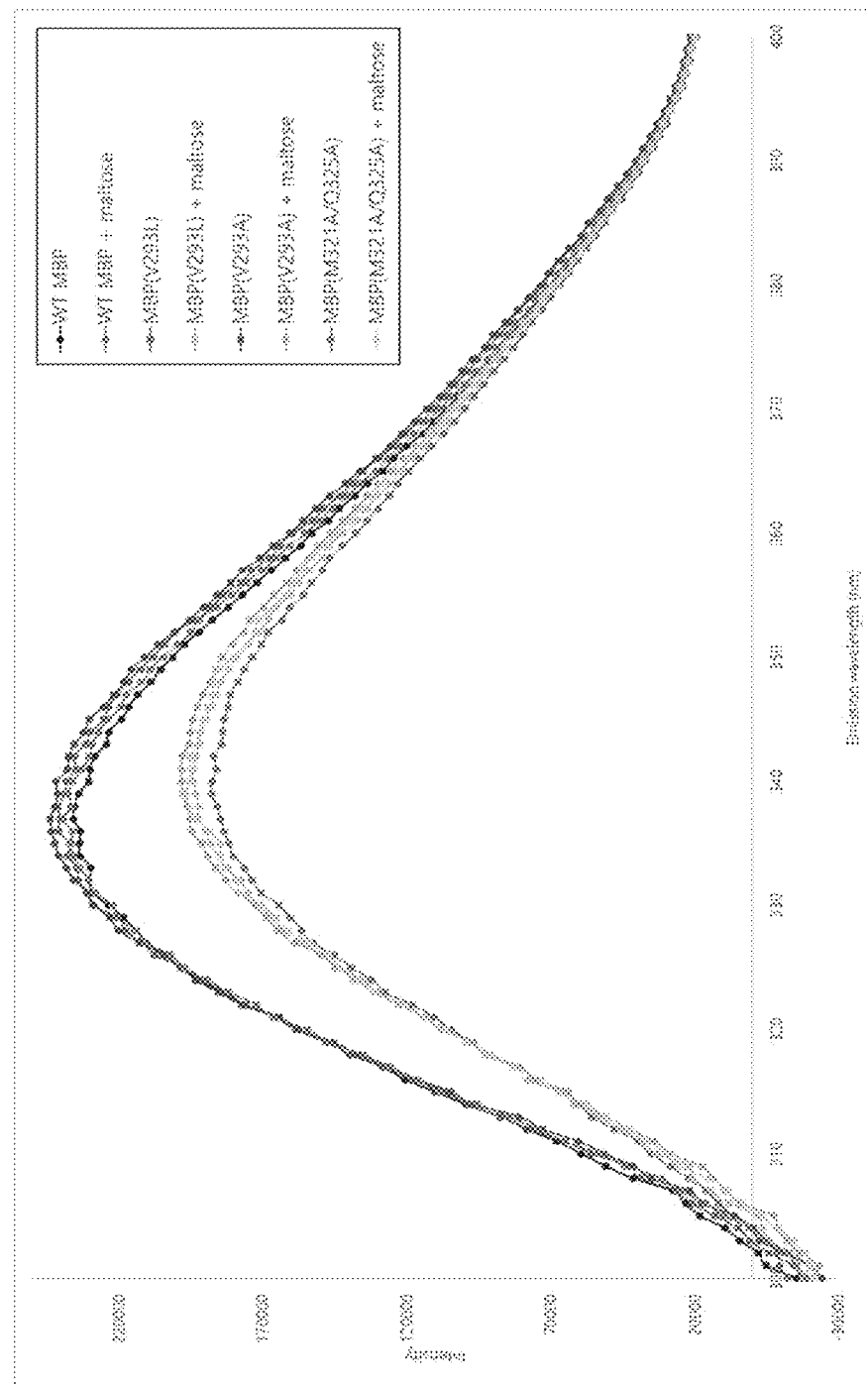
FIG. 37 depicts the fluorescence emission spectrum of MBP, and shows the quenching of fluorescence emission by maltose. The magnitude of fluorescence quenching by maltose was approximately equal among wt MBP (22%), MBP V293L (20%), MBP V293A (20%), and MBP M321A/Q325A (19%). The addition of maltose red-shifted the maximum emission wavelengths of all MBP proteins by 2-3 nm, indicating the transition from the open to the closed conformation upon ligand binding.
Figures 38A, 38B, 38C, 38D:
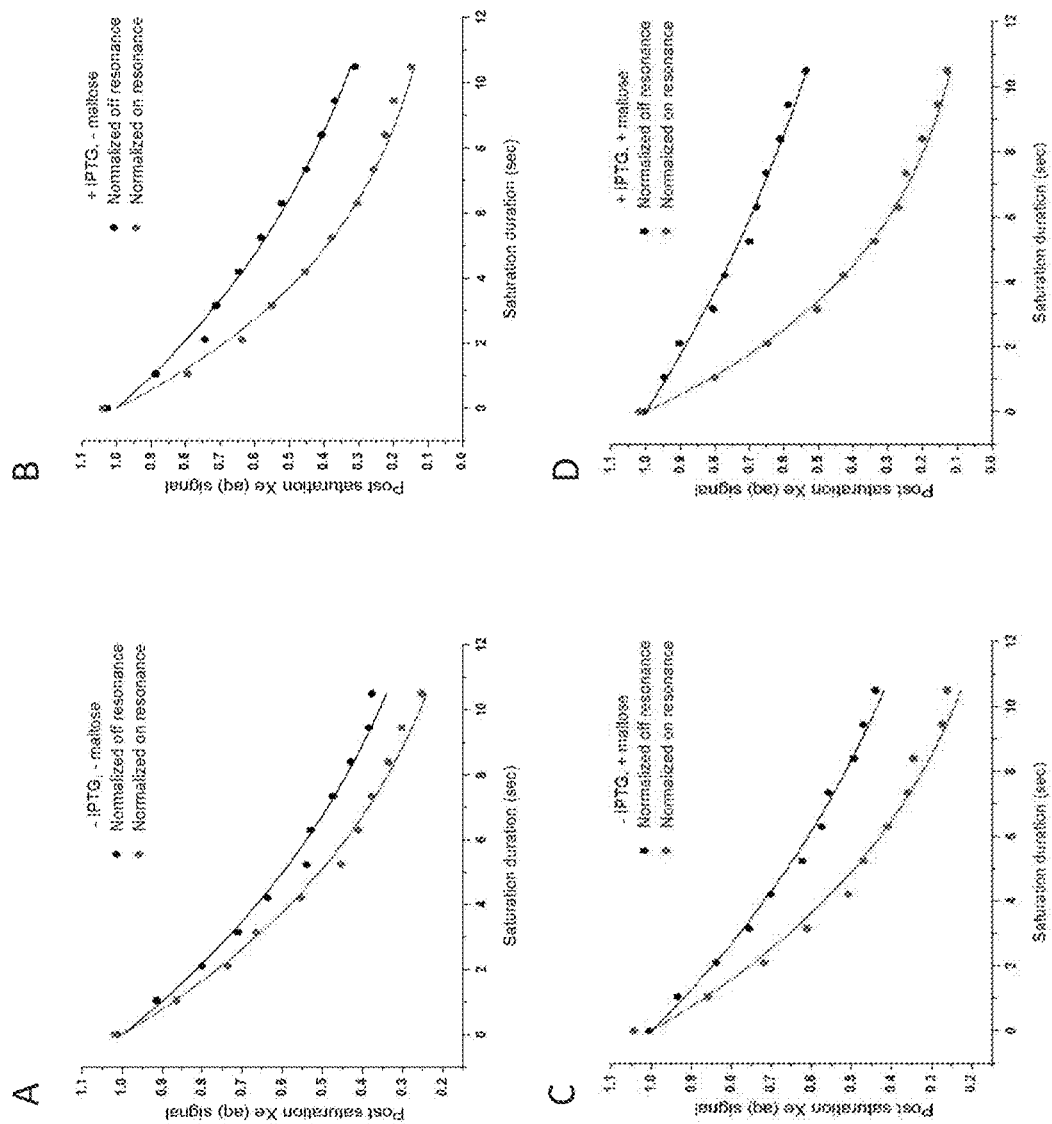
FIG. 38A through FIG. 38D, depicts the time-dependent saturation transfer data for E. coli transformed with pET-MBP plasmid. All cell solutions were normalized to OD$_{600}$=9. Saturation frequencies of Dsnob-shaped pulses were positioned at +95 ppm and −95 ppm, referenced to the Xe$_{(aq)}$ peak, for on- and off-resonance, respectively. Pulse length, $\tau_{pulse}$=1.0496 ms; field strength, B$_{1,max}$=279 μT. Both on-resonance and off-resonance data were fitted with first-order exponential decay curves.
Figure 39A:
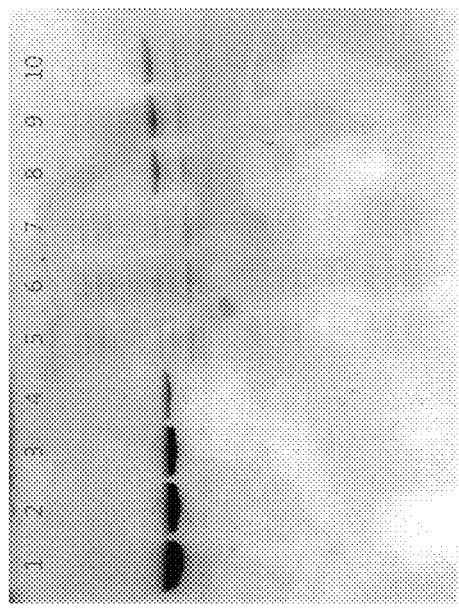
FIG. 39A and FIG. 39B, illustrates quantitative SDS-PAGE of lysate of E. coli transformed with the pET-MBP plasmid. To measure the concentration of MBP present in the E. coli cell suspensions, post-hyperCEST cells were diluted to OD$_{600}$ of 3 in B-PER lysis buffer and then lysed by five rounds of freeze/thaw lysis. The lysate was clarified and the supernatants were run on a NuPAGE 12% Bis-Tris gel (Invitrogen). Previously-purified MBP at known concentrations served as standards. The gel was stained with Coomassie Blue and imaged on a Typhoon FLA 7000 laser scanner (GE Healthcare Life Sciences). The intensities of the MBP bands were quantified using the ImageQuant TL software package (GE Healthcare Life Sciences). The lane assignments in the gel depicted in FIG. 39A are as follows: Lane 10=10 μM MBP standard; lane 9=7 μM MBP standard; lane 8=5 μM MBP standard; lane 7=2 μM MBP standard; lanes 4-6=lysate of maltose, −IPTG E. coli; lanes 1-3=lysate of −maltose, +IPTG E. coli. The lane assignments in the gel depicted in FIG. 39B are as follows: Lane 1=10 μM MBP standard; lane 2=7 μM MBP standard; lane 3=5 μM MBP standard; lane 4=2 μM MBP standard; lanes 5-7=lysate of +maltose, −IPTG E. coli; lanes 8-10=lysate of +maltose, +IPTG E. coli.
Figure 39B:
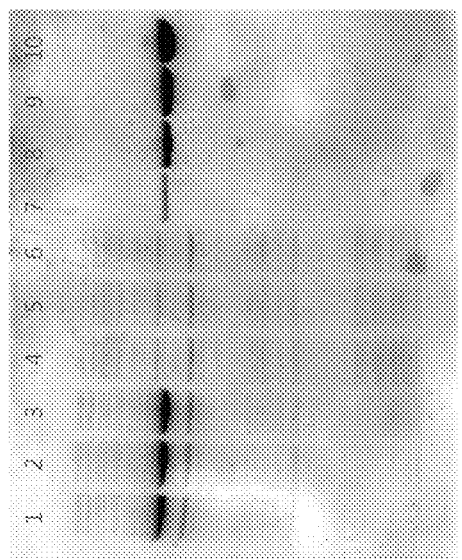

Val-293 was chosen as the site for single-point mutations due to its proximity to bound Xe identified in the maltose-free MBP structure. The methyl carbons of Val-293 are only 4.0 and 4.2 Å from Xe, respectively, thus it was expected that mutations at this position would affect Xe binding affinity and/or kinetics. Val-293 was mutated to Leu to reduce the cavity volume, and to Ala to enlarge the cavity. CD and fluorescence spectroscopy, along with thermal stability assays, confirmed that the V293L and V293A mutants retained the same global structure and maltose-binding properties as WT MBP (FIG. 36, FIG. 37, FIG. 38 Table 12).

Figure 33:
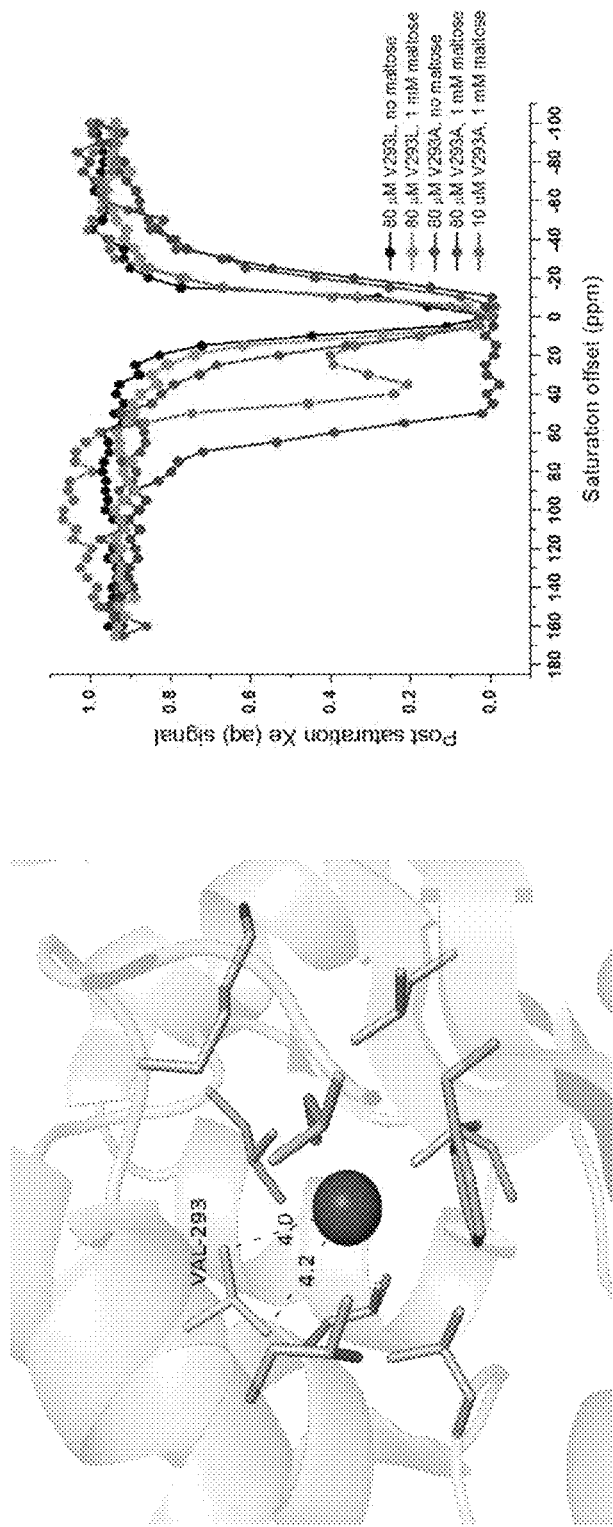
FIG. 33 depicts Xe hyper-CEST z-spectra of MBP mutants V293A and V293L. Spectra were acquired from 80 μM protein in PBS pH 7.2 without maltose and with 1 mM maltose.

Hyper-CEST z-spectra of V293L and V293A were obtained following the same protocol used for WT MBP (FIG. 33). V293L with and without maltose showed only a saturation response for $^{129}Xe_{(aq)}$, suggesting that substitution of valine for the bulkier leucine sidechain effectively blocks Xe from occupying the MBP cavity. This result helps to confirm that the crystallographically determined Xe site for $MBP_{open}$ is also the site of hyper-CEST with $MBP_{closed}$. The $^{129}Xe_{(aq)}$ peaks for V293L are narrower (19.1 ppm without maltose, 21.5 ppm with maltose) than WT MBP (41.8 ppm without maltose, 47 ppm with maltose) (see Table 15, Example 4), further confirming the overall reduction of Xe exchange with V293L relative to WT MBP. However, the $^{129}Xe_{(aq)}$ peaks for V293L are broader than PBS in the absence of protein, likely due to non-specific Xe-protein interactions elsewhere on the surface of the protein (Rubin et al., (2001), J. Magn. Reson., 152:79-86).

Figure 40:
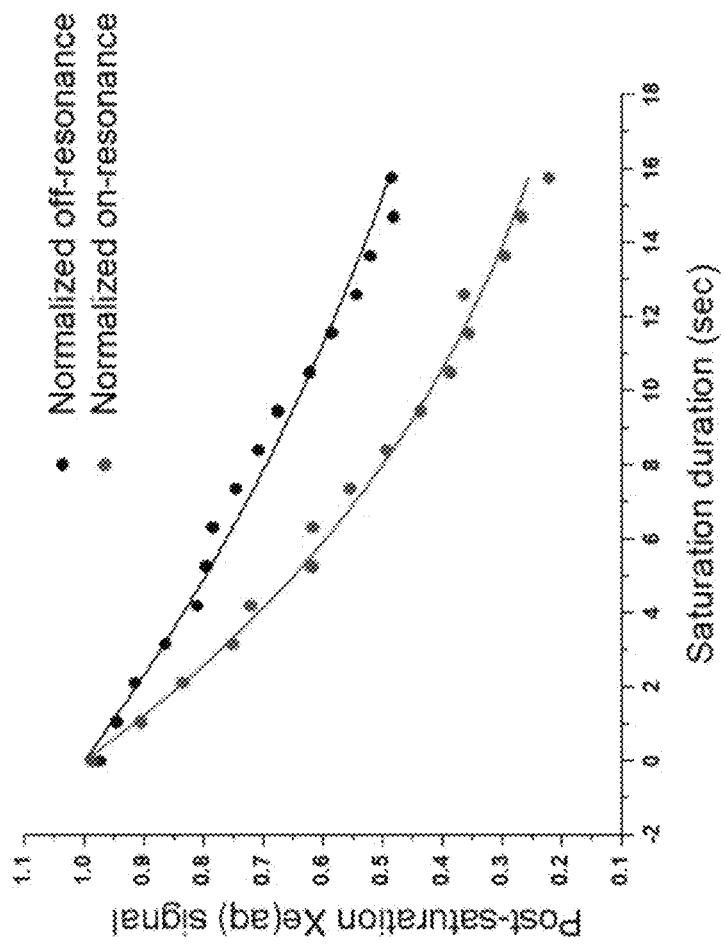
FIG. 40 depicts the time-dependent saturation transfer data for 100 nM MBP(V293A). The observed saturation contrast is 0.35±0.02. Saturation frequencies of D-SNOB-shaped pulses were positioned +36 ppm and −36 ppm, referenced to the Xe(aq) peak, for on- and off-resonance, respectively. Pulse length, $\tau_{pulse}$=1.0496 ms; field strength, B$_{1,max}$=279 μT. Both on-resonance and off-resonance data were fitted with first-order exponential decay curves, with T$_{1on}$=11.6±0.3 s and T$_{1off}$=22.0±0.7 s. Measurements taken in pH 7.2 PBS at 300 K. Pulse length, $\tau_{pulse}$=1.0496 ms; field strength, B$_{1,max}$=279 μT. The number of pulses increased linearly from 0 to 15000.

The z-spectrum of 80 µM V293A without maltose showed only the $^{129}Xe_{(aq)}$ peak, though in the presence of maltose a plateau of saturation response was observed between 50 and -10 ppm. Lowering the V293A concentration to 10 µM resolved this broad saturation response into two peaks—one at 0 ppm for $^{129}Xe_{(aq)}$, the other at 36 ppm for $Xe@V293A_{closed}$. This large change in chemical shift from 95 ppm observed for WT follows a trend observed in T4 lysozyme (Rubin et al., (2002) J. Mol. Biol., 322:425-440), clathrate cages (Ripmeester et al., (1988), J. Chem. Soc. Faraday Trans. 1 Phys. Chem. Condens. Phases, 84:3731-3745), and zeolites (Bonardet et al., (1999) Catal. Rev. Eng., 41:115-225), where it has been noted that larger cavities produce smaller downfield $^{129}Xe$ chemical shifts, and vice-versa. Notably, this mutation increased the magnitude of CEST saturation contrast with 100 nM MBP from 0.26±0.01 (WT) to 0.35±0.02 for V293A (FIG. 40). The molecular features of this signal enhancement and chemical shift change are under investigation.

TABLE 12

Thermal stabilities of MBP mutants

| Protein | $T_m$ (° C.)$^a$ |
|---|---|
| MBP-WT | 53.9 ± 0.7 |
| MBP-WT + 1 mM maltose | 61.0 ± 0.8 |
| MBP-V293L | 53.8 ± 0.8 |

TABLE 12-continued

Thermal stabilities of MBP mutants

| Protein | $T_m$ (° C.)$^a$ |
|---|---|
| MBP-V293L + 1 mM maltose | 59.5 ± 0.9 |
| MBP-V293A | 50.1 ± 0.7 |
| MBP-V293A + 1 mM maltose | 55.7 ± 0.7 |
| MBP-M321A/Q325A | 49.0 ± 0.5 |
| MBP-M321A/Q325A + 1 mM maltose | 58.8 ± 0.6 |

$^a$Data reported as mean ± standard deviation (n = 3)

Figure 34:
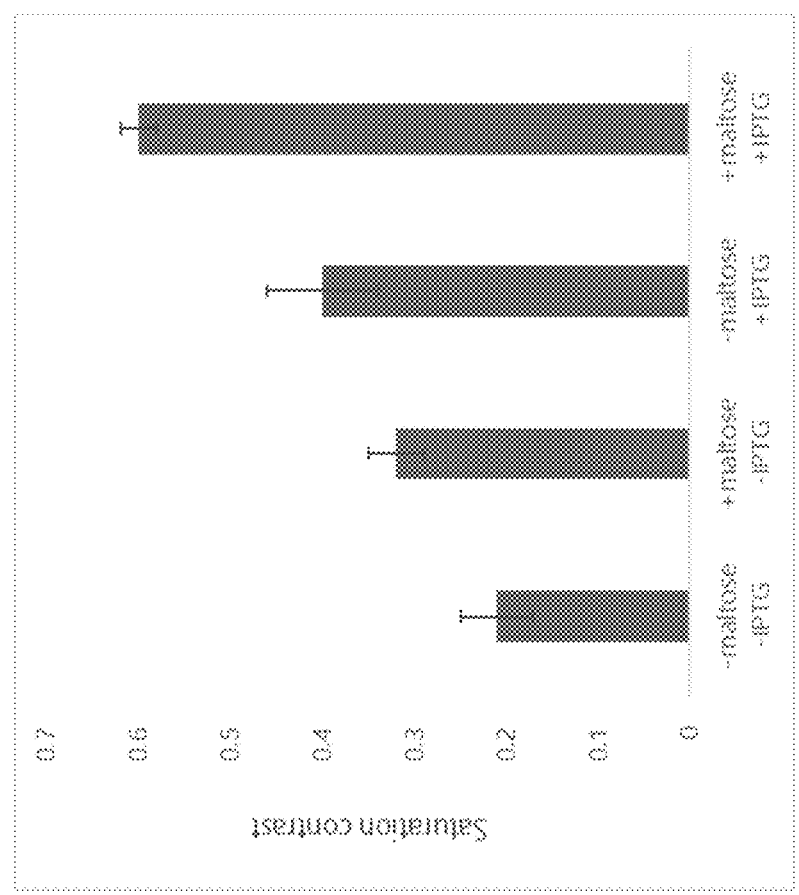
FIG. 34 depicts Xe hyper-CEST saturation contrast observed from E. coli transformed with pET-MBP plasmid. All cell solutions were normalized to OD$_{600}$=9. Saturation frequencies of Dsnob-shaped pulses were positioned at +95 ppm and −95 ppm, referenced to the Xe$_{(aq)}$ peak, for on- and off-resonance, respectively. Pulse length, $\tau_{pulse}$=1.0496 ms; field strength, B$_{1,max}$=279 μT. Both on-resonance and off-resonance data were fitted with first-order exponential decay curves.

To evaluate whether CEST contrast from MBP is observable in cells, MBP was expressed in BL21(DE3) E. coli and time-dependent saturation transfer measurements were taken (FIG. 34; FIG. 38). Cells were grown in LB and LB supplemented with 5 mM maltose, and cells not induced with IPTG served as controls to measure background CEST contrast. As expected, the saturation contrast observed from E. coli expressing MBP in the presence of maltose report the largest degree of CEST contrast. E. coli expressing MBP in the absence of maltose also report appreciable contrast, possibly due to other sugars in the cellular milieu. It is noteworthy that MBP expressed significantly better in E. coli grown in the absence of maltose. If background contrast from non-induced growths is subtracted and contrast is normalized to MBP concentration, then the data show that the presence of maltose generates a 3.7-fold increase in observed CEST contrast in E. coli (Table 13).

TABLE 13 hyper-CEST contrast from MBP expressed in E. coli

| Sample | Contrast, corrected$^a$ | [MBP] (μM)$^b$ | Contrast per μM MBP |
|---|---|---|---|
| MBP in E. coli without maltose | 0.19 | 15 ± 6 | 0.013 ± 0.005 |
| MBP in E. coli with maltose | 0.28 | 6 ± 4 | 0.05 ± 0.03 |

$^a$Corrected by subtracting contrast from non-induced E. coli grown with and without maltose, respectively
$^b$Data reported as mean ± standard deviation (n = 3)

Figure 35:
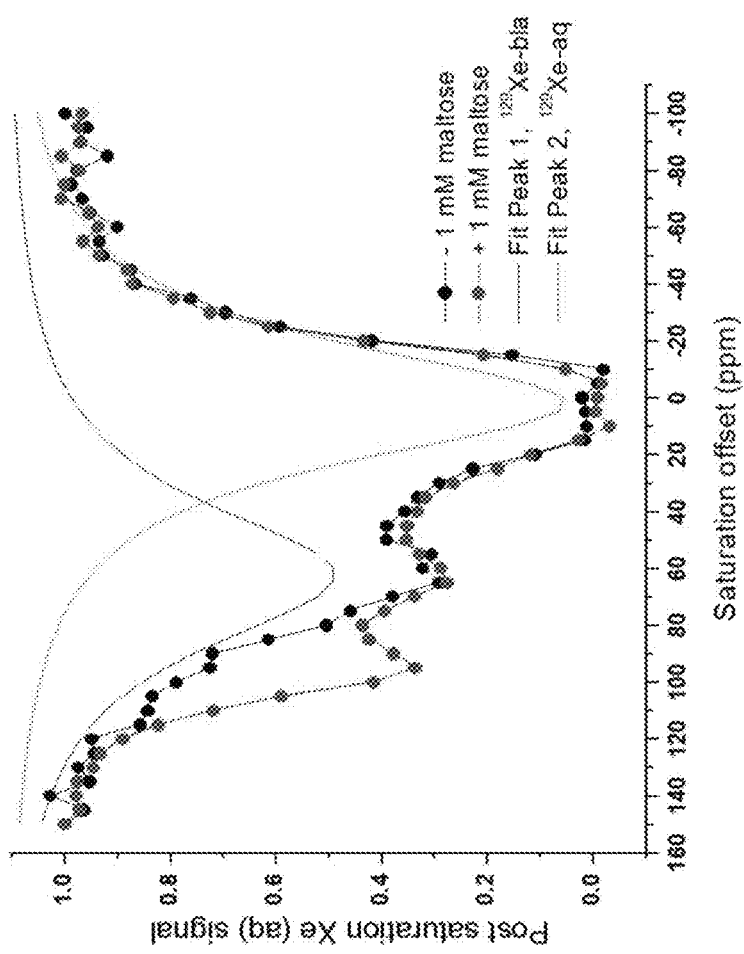
FIG. 35 depicts a Xe hyper-CEST z-spectrum of 27 μM MBP and 80 M bla in PBS (pH 7.2) with 1 mM maltose (average of 4 trials) and without maltose (average of 3 trials).

The ability of bla to serve as a hyper-CEST reporter was demonstrated both in vitro and in vivo (Example 1 and Example 2). The saturation frequency of Xe@MBP is sufficiently downfield of Xe@bla that we hypothesized that the two proteins could be detected sequentially and very sensitively with minimal crosstalk using hyper-CEST in the same solution. The hyper-CEST z-spectrum of a mixture of MBP and bla was acquired, where the ratio of MBP to bla was lowered to approximately equalize the magnitude of contrast produced by the two proteins (FIG. 35). The z-spectrum of 27 M MBP and 80 μM bla in the absence of maltose showed two peaks: Xe$_{(aq)}$ at 0 ppm, and Xe@bla at 60 ppm. In the presence of 1 mM maltose, three peaks were observed: Xe$_{(aq)}$ at 0 ppm, Xe@bla at 60 ppm, and Xe@MBP at 95 ppm. Critically, the magnitude of saturation contrast at 60 ppm for Xe@bla was not affected by maltose or whether MBP contrast was "on" or "off". The difference between Xe@MBP with and without maltose suggests that MBP can be effectively used in conjunction with bla for multiplexing experiments.

Without being bound by theory, it is envisioned that the ability to multiplex the responsive hyper-CEST agent, MBP, with a non-responsive hyper-CEST agent such as bla, should enable the in vivo quantitation of maltose via ratiometric analysis. Indeed, ratiometric approaches employing fluorescent small molecules and proteins have been widely applied for detection of ions and biomolecules in solution and in cellular studies.

Figure 41:
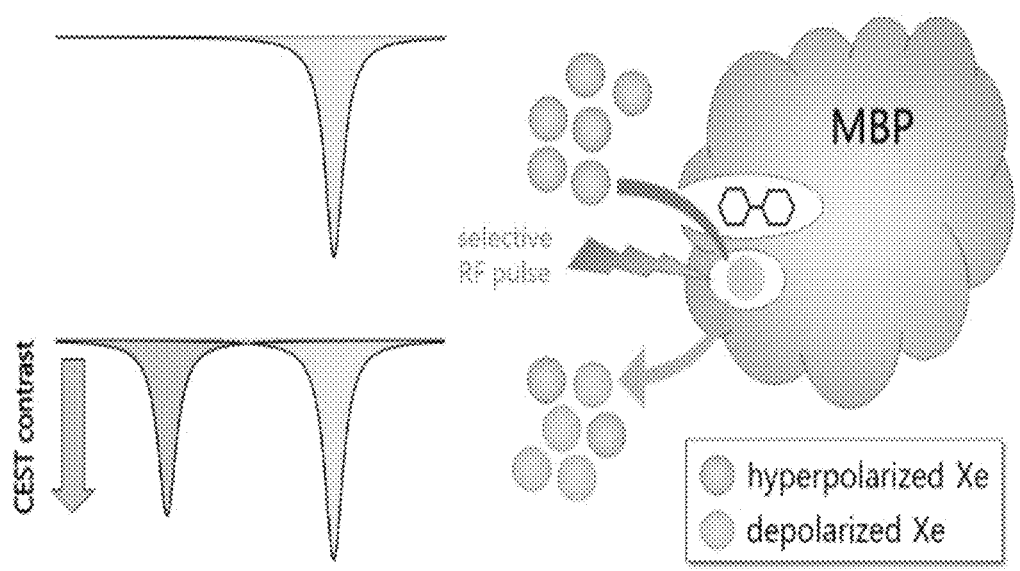
FIG. 41 illustrates ultrasensitive detection of a small molecule (maltose)-protein (MBP) interaction via hyper-CEST NMR. HP $^{129}$Xe binds maltose-bound MBP, where the unique Xe resonance frequency is saturated by shaped RF pulses. Xe exchange leads to depolarization of solution-phase Xe pool, thereby generating MR contrast.

Example 4: Nanomolar Small-Molecule Detection Using a Genetically Encoded $^{129}$Xe NMR Contrast Agent Maltose binding protein (MBP) has been developed as a small-molecule-responsive, GE xenon biosensor capable of detecting nanomolar concentrations of maltose using the hyper-CEST $^{129}$Xe NMR technique (FIG. 41).

Figure 42:
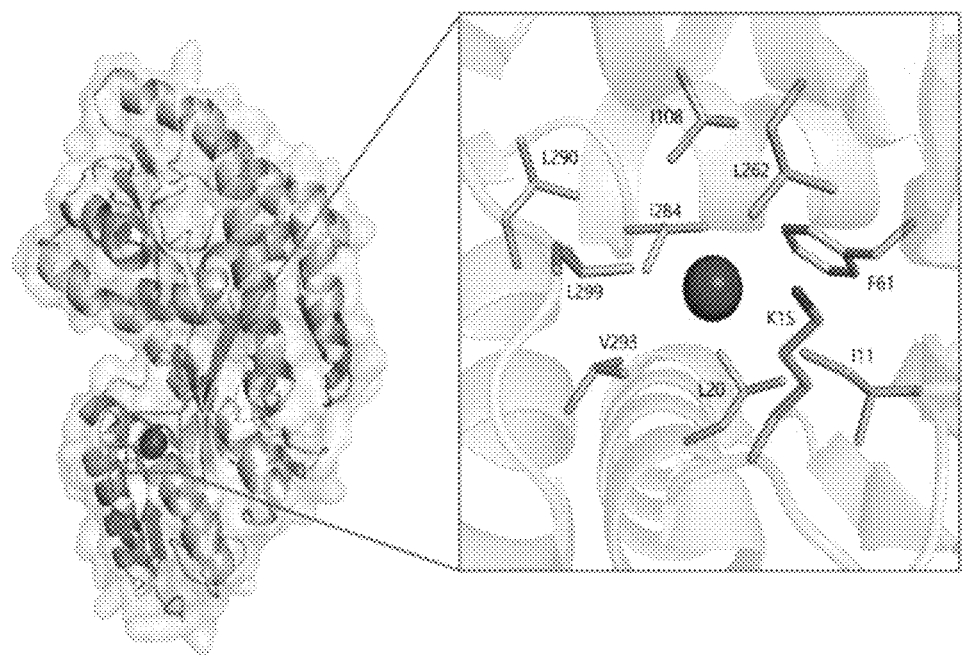
FIG. 42 illustrates Xe (sphere) bound to MBP$_{open}$ (PDB ID 1LLS), with the N-terminal domain, C-terminal domain, and linking segments. (Inset) Detailed view of the Xe-binding cavity.
Figure 43:
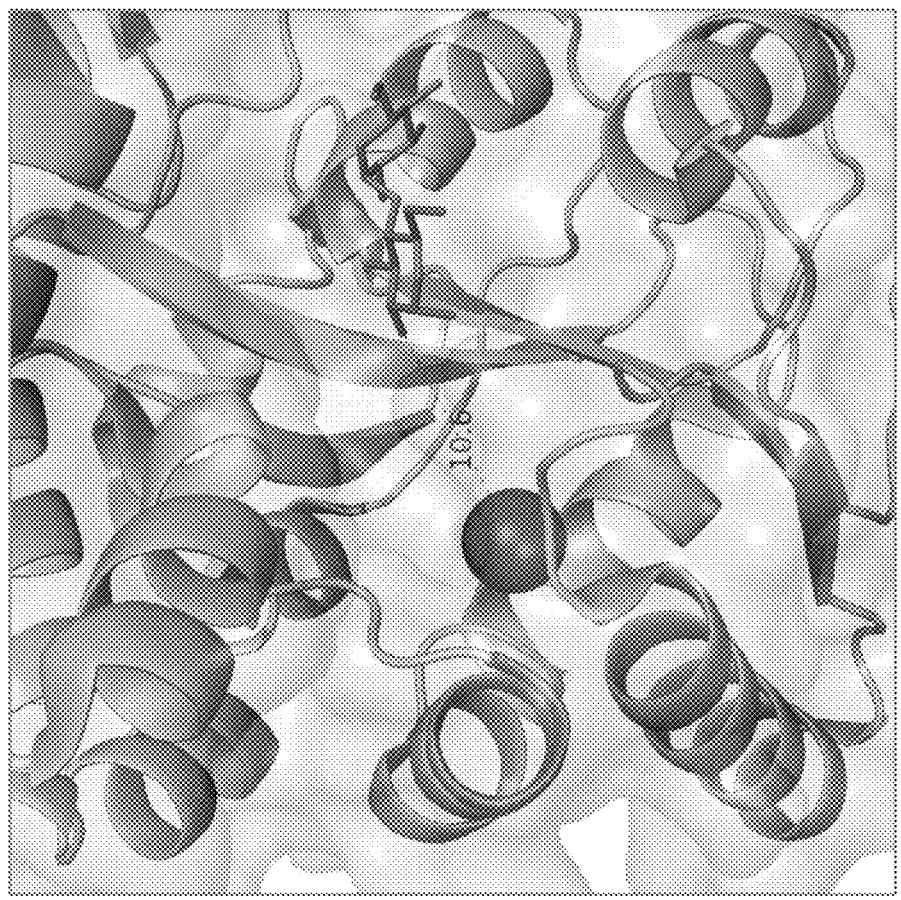
FIG. 43 illustrates a model of maltose proximity to Xe-binding site. Maltose (sticks) bound to MBP$_{closed}$ (PDB ID 1ANF) (Quiocho et al., (1997) Structure, 5:997-1015) overlaid onto the structure of MBP$_{open}$ derivatized with Xe (PDB ID 1LLS) (Rubin et al., (2002), J. Mol. Biol. 322: 425-440). Modelling was performed by aligning the N-terminal domains of the MBP$_{open}$ and MBP$_{closed}$ structures. Maltose is positioned 10.6 Å away from bound Xe.
Figures 44A, 44B:
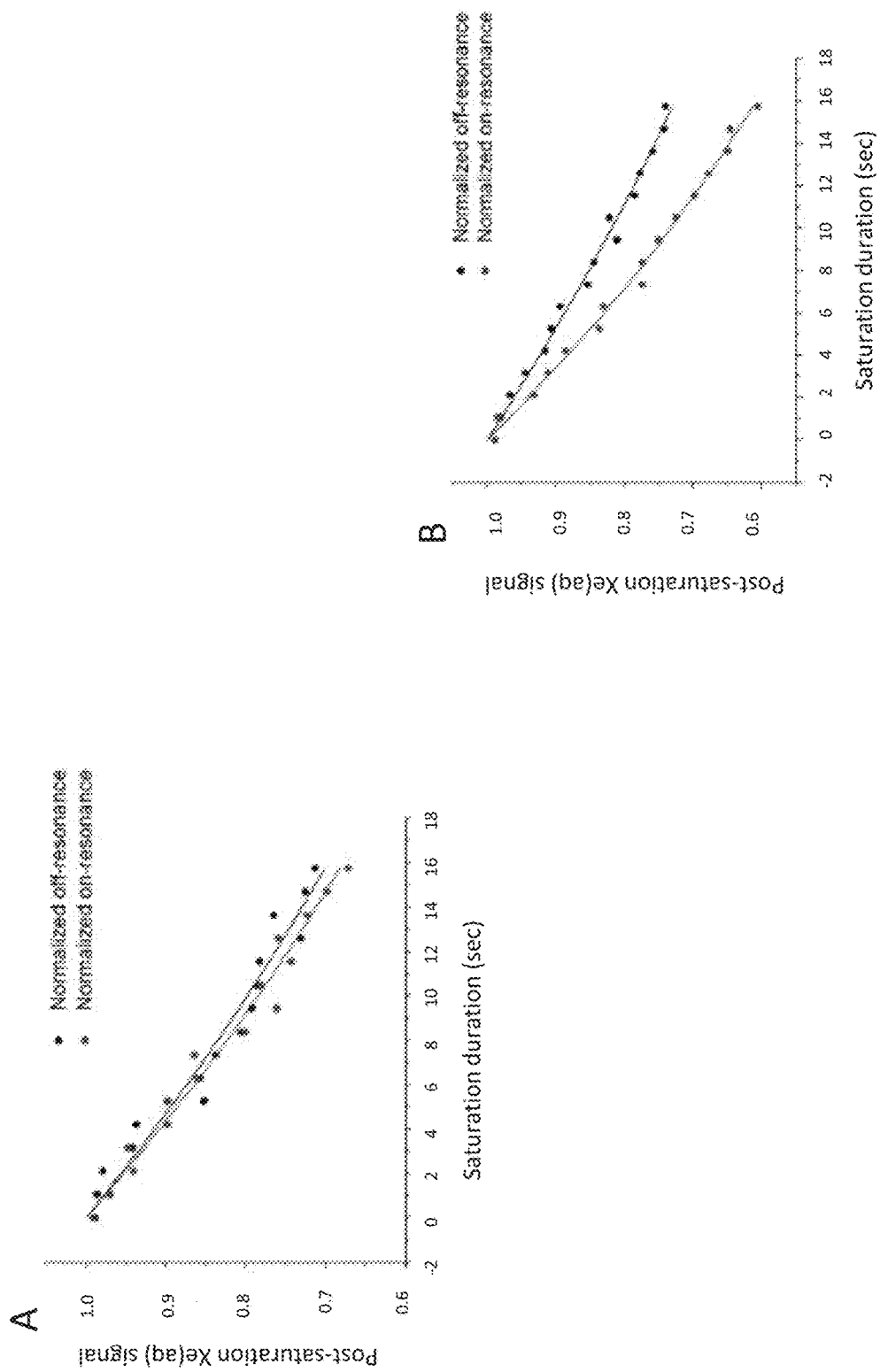
FIG. 44A through FIG. 44G, depicts time-dependent saturation transfer data for 100 nM WT MBP at varying concentrations of maltose.
Figures 44C, 44D:
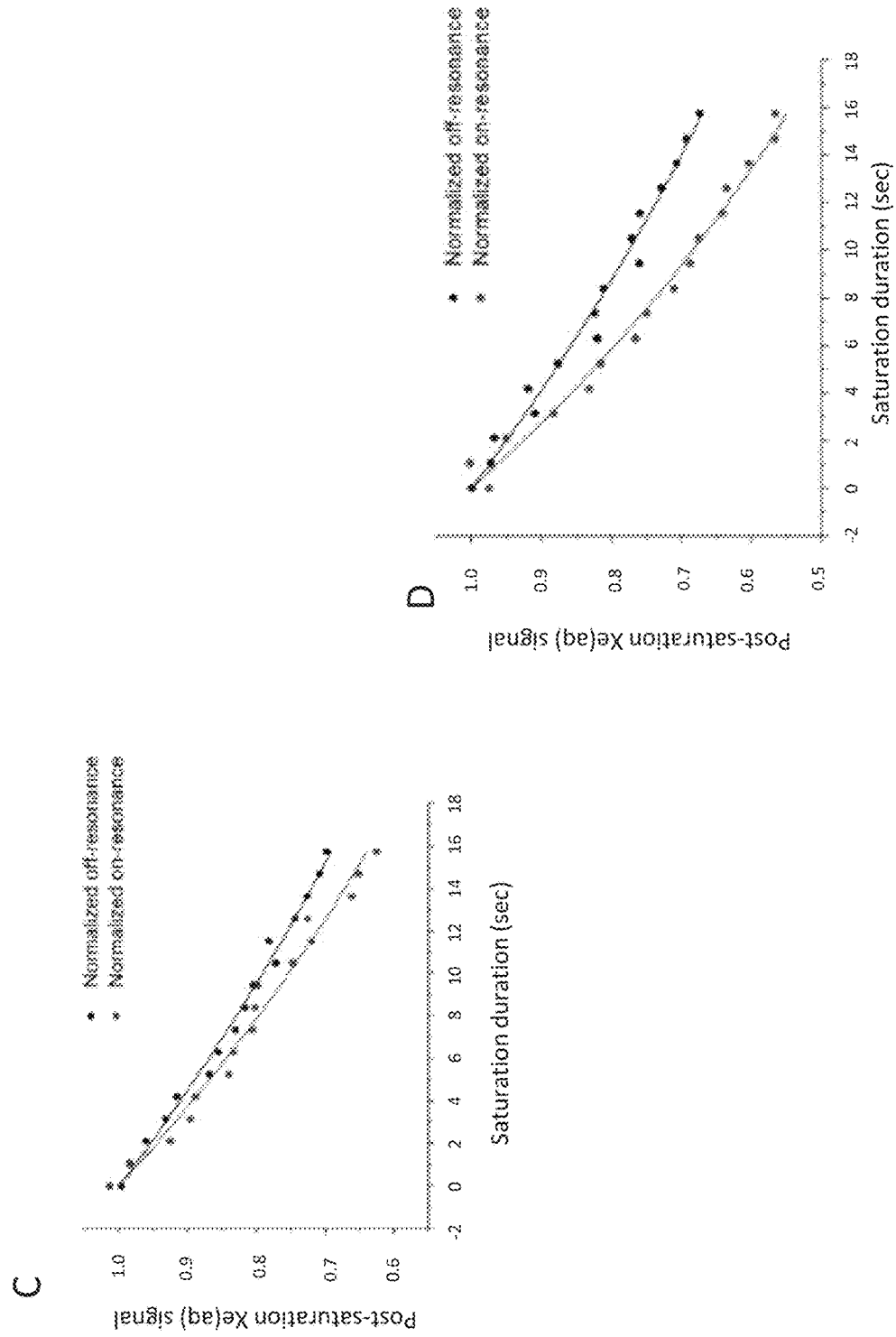
Figures 44E, 44F:
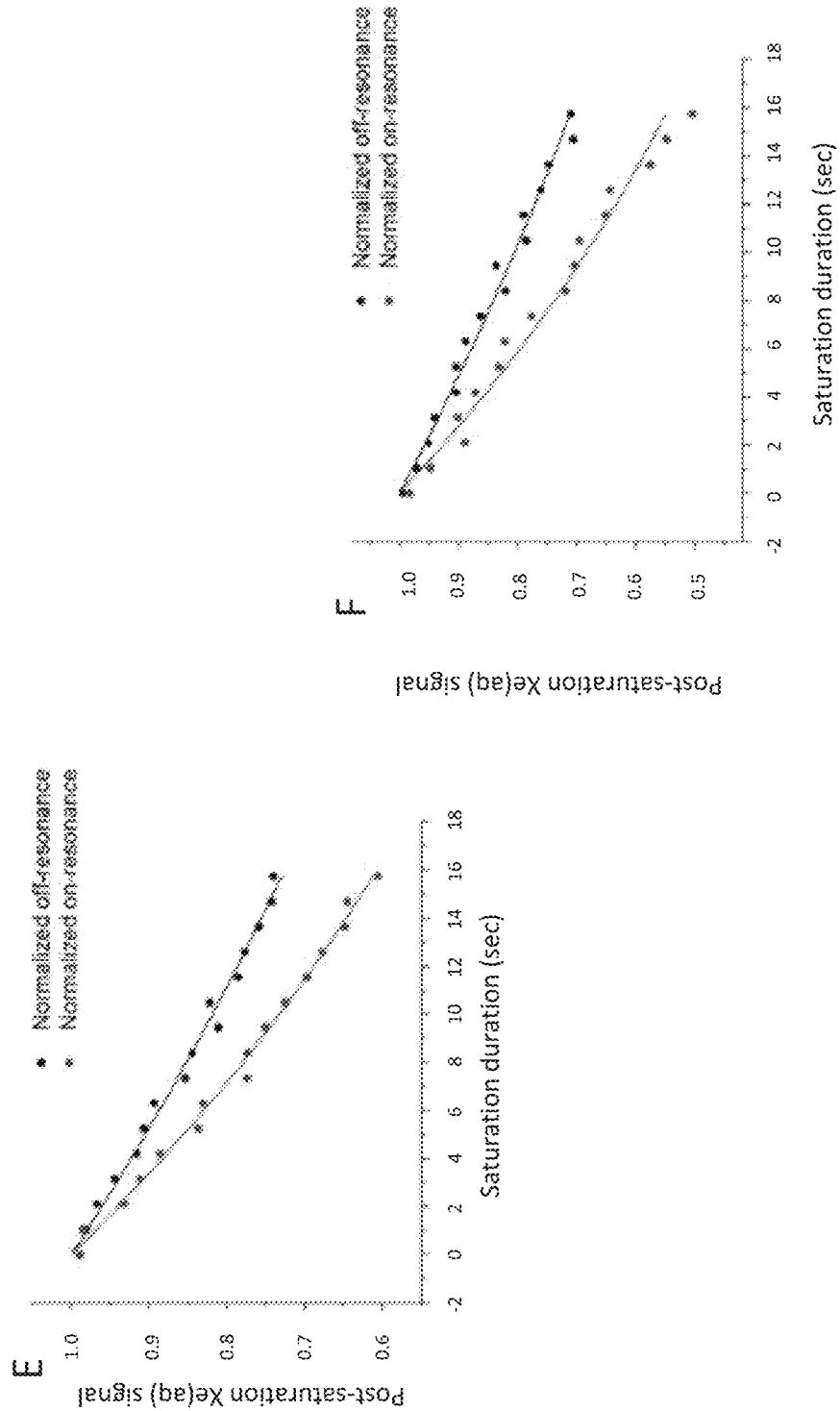
Figure 44G:
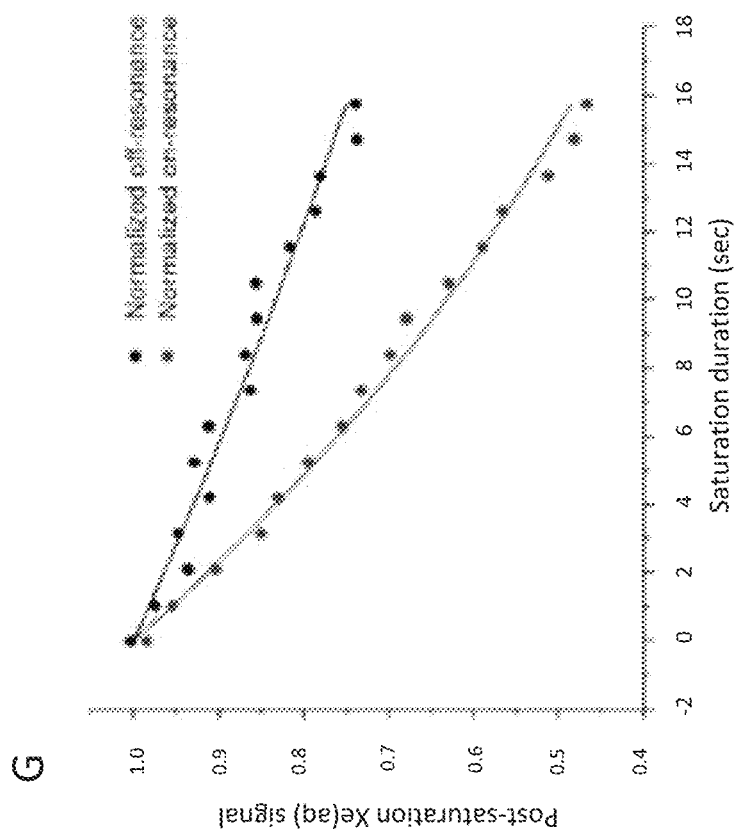

Xe binding to MBP has been well-characterized by NMR, which showed that $^{129}$Xe chemical shift depends on MBP conformation (Rubin et al., (2001), J. Am. Chem. Soc., 123:8616-8617). X-ray crystallography identified a single Xe-binding site near the maltose binding cleft of MBP (FIG. 42; FIG. 43; Rubin et al., (2002), J. Mol. Biol., 322:425-440). Small-molecule detection with MBP, as well as other periplasmic binding proteins (PBPs) (Grunewald, (2013) Advances in Chemical Bioanalysis, ed. F.-M. Matysik, Springer, Cham, vol. 6, pp. 205-235), has been achieved through a variety of signal transduction modalities, including fluorescence (Marvin et al., (2011) Proteins, 79:3025-3036), fluorescence resonance energy transfer (FRET) (Fehr et al., (2002) Proc. Natl. Acad. Sci. U.S.A, 99:9846-9851), and electrochemical response (Benson et al., (2001) Science, 293:1641-1644). Moreover, MBP has been engineered to increase ligand affinity (Seo et al., (2014) Nat. Commun., 5:3724; Marvin and Hellinga, (2001) Nat. Struct. Biol., 8, 795-798) and to bind non-maltodextrin ligands such as sucrose (Guntas et al., (2005) Proc. Natl. Acad. Sci. U.S.A, 102:11224-11229) and zinc (Marvin and Hellinga (2001) Proc. Natl. Acad. Sci. U.S.A, 98:4955-4960). The experiments presented herein evaluate the hyper-CEST NMR contrast generated by MBP as a function of maltose binding.

The materials and methods employed in these experiments are now described.

MBP Expression and Purification.

MBP was expressed from the pET His6 MBP TEV LIC cloning vector, a gift from Scott Gradia acquired via Addgene (plasmid #29656). The MBP vector was transformed into BL21(DE3) competent E. coli cells (New England Biolabs) and grown in 6×1 L of LB media supplemented with 50 μg/mL kanamycin to a $OD_{600}$ of ~1. MBP expression was induced by adding isopropyl-β-D-thiogalactopyranoside (IPTG) to a final concentration of 1 mM. The induced cells were incubated overnight at 18° C., harvested by centrifugation, then frozen at −80° C. The cell pellets were resuspended in 20 mM sodium phosphate (pH 7.4), lysed with lysozyme (Sigma), and treated with benzonase nuclease (Sigma) to reduce the viscosity of the lysate. After stirring the lysate at rt for 30 min, NaCl was added to 0.5 M and imidazole was added to 20 mM. The lysate was clarified by centrifugation, and the supernatant was loaded onto a HisTrap nickel affinity column (GE Life Sciences) pre-equilibrated with 20 mM sodium phosphate (pH 7.4), 0.5 M NaCl, 20 mM imidazole. MBP was eluted from the column with 20 mM sodium phosphate (pH 7.4), 0.5 M NaCl, 500 mM imidazole. The eluate was concentrated and further purified by size-exclusion chromatography in PBS (HyClone) using a HiLoad 16/600 Superdex column (GE Life Sciences). Fractions containing pure protein (over 95% as indicated by SDS-PAGE) were pooled and concentrated. Protein concentration were determined from the absorbance at 280 nm using the extinction coefficient $\varepsilon_{280}$=67 840 M$^{-1}$ cm$^{-1}$ calculated by the PROTPARAM server (Gasteiger et al., (2005) The Proteomics Protocols Handbook; Walker, J. M., Ed.; Humana Press: Totowa, pp. 571-607). All MBP mutants were expressed and purified following the same procedure used for WT MBP. The concentrations of MBP (V293L) and MBP(V293A) were determined from the absorbance at 280 nm using the same extinction coefficient as WT MBP, and the extinction coefficient $\varepsilon_{280}$=88 240 M$^{-1}$ cm$^{-1}$ was used for MBP(I329Y)-GFP.

Site-Directed Mutagenesis.

Mutations were introduced to either the MBP or MBP (GFP) plasmid via site-directed mutagenesis using the forward and reverse primers listed in Table 14. The mutated plasmids were amplified in NEB-5α competent E. coli cells (New England Biolabs) and then purified using a miniprep kit (Qiagen). All mutated MBP genes were sequenced at University of Pennsylvania DNA Sequencing Facility to verify the incorporation of the desired mutation and the integrity of the gene sequence.

TABLE 14

Oligonucleotide primers used

| | | |
|---|---|---|
| GFP insert | Forward primer | 5'-TACTTCCAATCCAATGCAAGCAAG GGCGAGGAGCTGTTC-3' (SEQ ID NO: 37) |
| | Reverse primer | 5'-TTATCCACTTCCAATGTTATTACTT GTACAGCTCGTCCATGCC-3' (SEQ ID NO: 38) |
| I329Y | Forward primer | 5'-CGCCCAGAAAGGTGAATACATGCC GAACATCCCGC-3' (SEQ ID NO: 39) |
| | Reverse primer | 5'-GCGGGATGTTCGGCATGTATTCACC TTTCTGGGCG-3' (SEQ ID NO: 40) |

MBP-GFP Cloning, Expression, and Purification.

The gene encoding a "superfolder" variant of GFP (Pedelacq et al., (2006) Nat. Biotechnol. 24:79-88) was amplified from the pET GFP LIC cloning vector (Addgene plasmid #29772). The primers used for amplification are listed in Table 14. The GFP insert was added to the pET His6 MBP TEV LIC cloning vector by ligation independent cloning (LIC). The resulting MBP-GFP gene was sequenced at University of Pennsylvania DNA Sequencing Facility to verify the integrity of the fusion construct. MBP-GFP was expressed and purified following the same protocol used for MBP. Protein concentration were determined from the absorbance at 280 nm using the extinction coefficient $\varepsilon_{280}$=86 875 M$^{-1}$ cm$^{-1}$.

$^{129}$Xe Hyper-CEST of Purified MBP.

$^{129}$Xe was hyperpolarized and the z-spectra of MBP were acquired as described previously (Wang et al., (2016) Angew. Chemie Int. Ed. 55:8984-8987). Briefly, hyperpolarized (hp)$^{129}$Xe was generated using the spin-exchange optical pumping (SEOP) method with a home-built $^{129}$Xe polarizer based on the IGI.Xe.2000 commercial model by GE. A Shark 65 W tunable ultra-narrow band diode laser (OptiGrate) set to 795 nm was used for optical pumping of Rb vapor. A gas mixture of 88% helium, 10% nitrogen, and 2% natural abundance xenon (Linde Group, N.J.) was used as the hyperpolarizer input. $^{129}$Xe hyperpolarization level was roughly 10-15%. For each data point in the hyper-CEST z-spectra, hp $^{129}$Xe was bubbled into the NMR tube through capillaries for 20 s, followed by a 3-s delay to allow bubbles to collapse. A d-SNOB saturation pulse with 690 Hz bandwidth was used. Pulse length, $t_{pulse}$=3.80 ms; field strength $B_{1,max}$=77 μT; number of pulses, $n_{pulse}$=400; saturation time, $T_{sat}$=1.52 s. NMR experiments were performed using a Bruker BioDRX 500 MHz NMR spectrometer and 10-mm PABBO probe, at 300 K. A 900 hard pulse of this probe has a pulse length of 22 μs. Unless otherwise noted, the protein concentration used was 80 μM, with 0.1% (v/v) Pluronic L81 (Aldrich) added to mitigate foaming. For the time-dependent saturation transfer experiments using 100 nM WT MBP, saturation frequencies of d-SNOB-shaped pulses were positioned +95 ppm and −95 ppm, referenced to the Xe$_{(aq)}$ peak, for on- and off-resonance, respectively. Pulse length, $T_{pulse}$=1.0496 ms; field strength, $B1_{max}$=279 μT. Both on-resonance and off-resonance data were fitted with first-order exponential decay curves. For the time-dependent saturation transfer experiments using 100 nM MBP(I329Y)-GFP, saturation frequencies of d-SNOB-shaped pulses were positioned +100 ppm and −100 ppm, referenced to the Xe$_{(aq)}$ peak, for on- and off-resonance, respectively. For the time-dependent saturation transfer experiments using 100 nM MBP(V293A), saturation frequencies of d-SNOB-shaped pulses were positioned +36 ppm and −36 ppm, referenced to the Xe$_{(aq)}$ peak, for on- and off-resonance, respectively.

$^{129}$Xe Hyper-CEST of WT MBP-GFP in E. coli.

BL21(DE3) E. coli competent cells were transformed with the WT MBP-GFP plasmid and cultured on a LB-agar plate supplemented with 50 μg/mL kanamycin. A single colony of transformed cells was used to inoculate 5 mL of LB medium supplemented with 50 μg/mL kanamycin. The 5 mL culture was incubated overnight at 37° C. with shaking at 250 rpm. The next morning the cells were pelleted and resuspended in 4 mL of minimal media. The resuspended cells were used to inoculate 4×1 L of minimal media supplemented with 50 μg/mL kanamycin in baffled culture flasks. Two flasks were supplemented with 1 mM maltose. The cell cultures were incubated at 37° C. with shaking at 250 rpm until OD$_{600}$ reached ~1, at which point the two control flasks was stored at 4° C. and the other two flasks were induced by adding IPTG to a final concentration of 1 mM. The induced culture flasks were incubated overnight at 18° C. with shaking at 250 rpm and then stored at 4° C. Aliquots from the control and induced cultures were centrifuged and the cell pellets were resuspended in PBS buffer with or without maltose. The concentrations of MBP-GFP in the IPTG-induced growths were measured by fluorescence spectroscopy (489 nm excitation; 510 nm emission) using a standard curve constructed from pure MBP-GFP in PBS. Cells were diluted so that the final MBP-GFP concentration was 1 μM. Cells from the control growths were diluted to match the optical densities (OD$_{600}$) of the induced cells. Saturation frequencies of d-SNOB-shaped pulses were positioned +95 ppm and −95 ppm, referenced to the Xe$_{(aq)}$ peak, for on- and off-resonance, respectively. Pulse length, $\tau_{pulse}$=1.0496 ms; field strength, $B_{1,max}$=279 μT. Both on-resonance and off-resonance data were fitted with first-order exponential decay curves. Following hyper-CEST experiment, the cell samples were gently pelleted and the fluorescence of the extracellular solution was measured to check for cell lysis caused by xenon bubbling. 21% of the −maltose/+IPTG cells were lysed, and 18% of the +maltose/+IPTG cells were lysed.

CD Spectroscopy and Thermal Stability Measurements.

The CD spectra of WT MBP, MBP V293L, and MBP V293A were measured on a Jasco J-1500 CD spectrometer equipped with a Peltier temperature controller. Spectra were acquired from 10 μM of protein in 10 mM sodium phosphate (pH 8.0) buffer inside a quartz cuvette with a 1-mm path length. CD spectra were taken at 20° C. with a wavelength step of 1 nm. CD spectra were performed in triplicate and averaged. Protein thermal stability was measured by increasing temperature from 20 to 90° C. at a rate of 0.5° C./min. Secondary structure was monitored at 222 nm with a step size of 1° C. and data integration time of 8 s. Thermal denaturation was repeated in triplicate, and melting temperature ($T_m$) was calculated from the data using the Spectra Analysis tool in the J-1500 CD spectrometer software package (Jasco).

Fluorescence Spectroscopy.

Fluorescence spectroscopy was performed to evaluate maltose binding. Maltose binding to MBP results in quenched tryptophan fluorescence and produces a 2.5 nm red shift of the intrinsic fluorescence emission spectrum (Szmelcman et al., (1976) Eur. J. Biochem. 65:13-19; Hall et al., (1997) J. Biol. Chem. 272:17605-17609). EPR spectroscopy of spin-labeled MBP showed that the red shift is indicative of MBP adopting a closed conformation (Hall et al., (1997) J. Biol. Chem. 272:17610-17614). The addition of maltose to V293L and V293A produced similar fluorescence quenching and red shifting as WT MBP, confirming maltose binding to the closed conformation. Fluorescence spectra were obtained on a Tecan Infinite M1000 PRO microplate reader using black 96 well flat-bottom microplates (Grenier Bio-One). MBP concentration was 4 M in 20 mM HEPES (pH 7.4). Maltose was added to a final concentration of 400 μM and incubated with MBP for 15 minutes prior to measuring fluorescence. Excitation was at 280 nm and emission was scanned from 300 to 400 nm in 1 nm increments. All fluorescence assays were performed in triplicate and averaged. Fluorescence spectra were background corrected by subtracting the fluorescence spectrum of the well solution in the absence of protein.

The results of the experiments are now described.

Maltose Detection by MBP

Figures 31A, 31B:
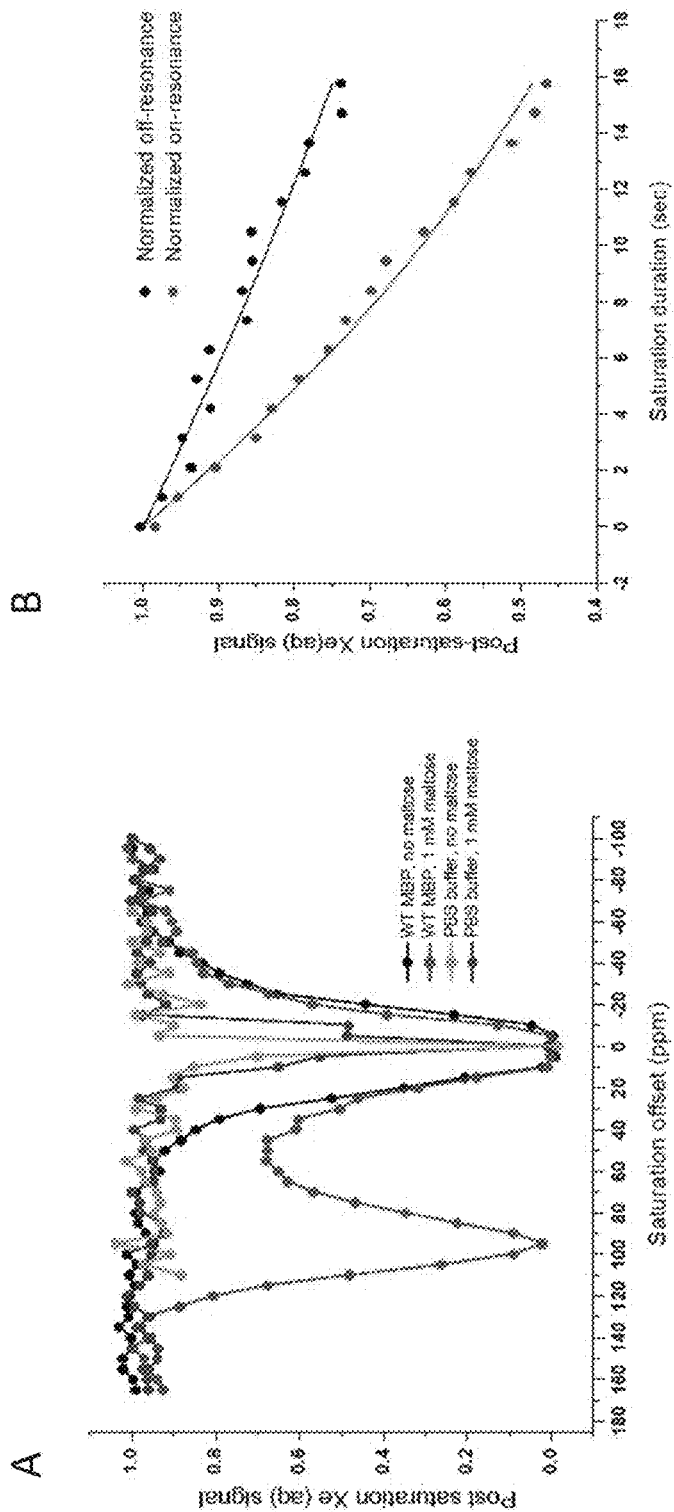
FIG. 31A depicts a Xe hyper-CEST z-spectrum of wt-MBP and wt-MBP in the presence of 1 mM maltose, acquired from 80 μM protein in PBS pH 7.2. The z-spectra of PBS pH 7.2 and PBS pH 7.2 containing 1 mM maltose are shown for reference.

Xenon hyper-CEST z-spectra were acquired from recombinant MBP in both the presence and absence of maltose to assess the magnitude and frequency of NMR saturation contrast (FIG. 31A). Multiple selective d-SNOB saturation pulses were scanned over the chemical shift range of 93 to 358 ppm in 5 ppm steps, and the $^{129}Xe_{(aq)}$ signal was measured as a function of saturation pulse offset. MBP in the absence of maltose ($MBP_{open}$) showed a single saturation response corresponding to free $^{129}Xe$ in solution centered at 0 ppm. In contrast, MBP in the presence of maltose ($MBP_{closed}$) showed a pronounced saturation response 95 ppm downfield of the $Xe_{(aq)}$ peak, corresponding to Xe@$MBP_{closed}$. This peak is 35 ppm further downfield than Xe@bla suggesting that Xe@$MBP_{closed}$ experiences a more hydrophobic environment. Also, the width of the Xe@$MBP_{closed}$ peak (35 ppm) is narrower than Xe@bla (60 ppm), indicating slower Xe exchange with MBP (Table 15).

TABLE 15

Peak widths (FWHM, in ppm) of hyper-CEST z-spectra

| z-spectrum[a] | $Xe_{(aq)}$ peak (ppm) | Xe@MBP peak (ppm) | Xe@bla peak (ppm) |
|---|---|---|---|
| PBS | 1 ± 12 | — | — |
| 1 mM maltose | 11.7 ± 0.9 | — | — |
| 80 μM MBP, no maltose | 42 ± 2 | — | — |
| 80 μM MBP, 1 mM maltose | 47 ± 2 | 35 ± 2 | — |
| 80 μM MBP(I329Y)-GFP, no maltose | 53 ± 2 | — | — |
| 80 μM MBP(I329Y)-GFP, 1 mM maltose | 39 ± 2 | 34 ± 2 | — |
| 27 μM MBP, 80 μM bla, no maltose | 52 ± 3 | — | 64 ± 7 |
| 27 μM MBP, 80 μM bla, 1 mM maltose | 53 ± 3 | 17 ± 5 | 86 ± 10 |
| 1 mM βCD | 8.9 ± 0.7 | — | — |
| 80 μM MBP, 1 mM βCD | 60 ± 2 | — | — |
| 80 μM MBP V293L, no maltose | 19.1 ± 0.1 | — | — |
| 80 μM MBP V293L, 1 mM maltose | 21.5 ± 0.9 | — | — |
| 80 μM MBP V293A, no maltose | 37 ± 2 | — | — |
| 10 μM MBP V293A, 1 mM maltose | 27 ± 2 | 20 ± 2 | — |
| 80 μM bla[b] | 47 ± 4 | — | 60 ± 7 |

[a]all spectra measured in PBS
[b]reported in Wang et al., (2016) Angew. Chemie Int. Ed, 55: 8984-8987

Figure 45:
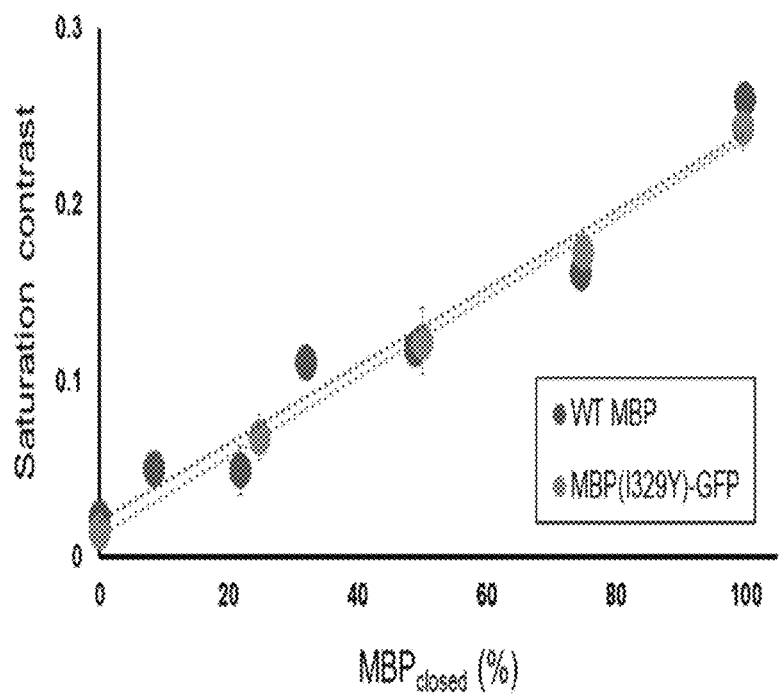
FIG. 45 depicts the saturation contrast for 100 nM WT MBP and 100 nM MBP(I329Y)-GFP as a function of percent MBP in maltose-bound closed conformation. For WT MBP, [maltose]=0, 0.1, 0.3, 0.5, 1, 3, 1000 µM. For MBP(I329Y)-GFP, [maltose]=0, 32, 72, 140, 5000 nM. Pulse length, $\tau_{pulse}$=1.0496 ms; field strength, $B_{1,max}$=279 µT. The number of pulses increased linearly from 0 to 15000.

To assess the detection sensitivity of MBP, time-dependent saturation transfer experiments were performed by measuring $Xe_{(aq)}$ polarization as a function of saturation time (FIG. 44). Saturation frequencies of d-SNOB pulses were positioned +95 ppm and −95 ppm, referenced to the $Xe_{(aq)}$ peak, for on- and off-resonance, respectively. The normalized difference between on- and off-resonance saturation transfer was measured as on-resonance hyper-CEST contrast. By this method, 100 nM MBP with 1 mM maltose reported 0.26±0.01 saturation contrast; by comparison, 0.23±0.02 saturation contrast was observed for 100 nM bla. To evaluate the responsiveness of MBP MR contrast to maltose, additional saturation contrast measurements were taken for 100 nM MBP with decreasing maltose. The lowest maltose concentration that could be readily detected by MBP was 100 nM, with an observed saturation contrast of 0.050±0.007. For each maltose concentration, the amount of $MBP_{closed}$ (i.e., contrast "ON") was calculated using a $K_d$ of 1 μM. The observed saturation contrast was linearly proportional ($R^2$=0.953) to the percentage of MBP in the maltose-bound closed conformation, which provides a measure of maltose concentration (FIG. 45).

Mutagenesis to Modulate Maltose Detection Sensitivity

Figure 46:
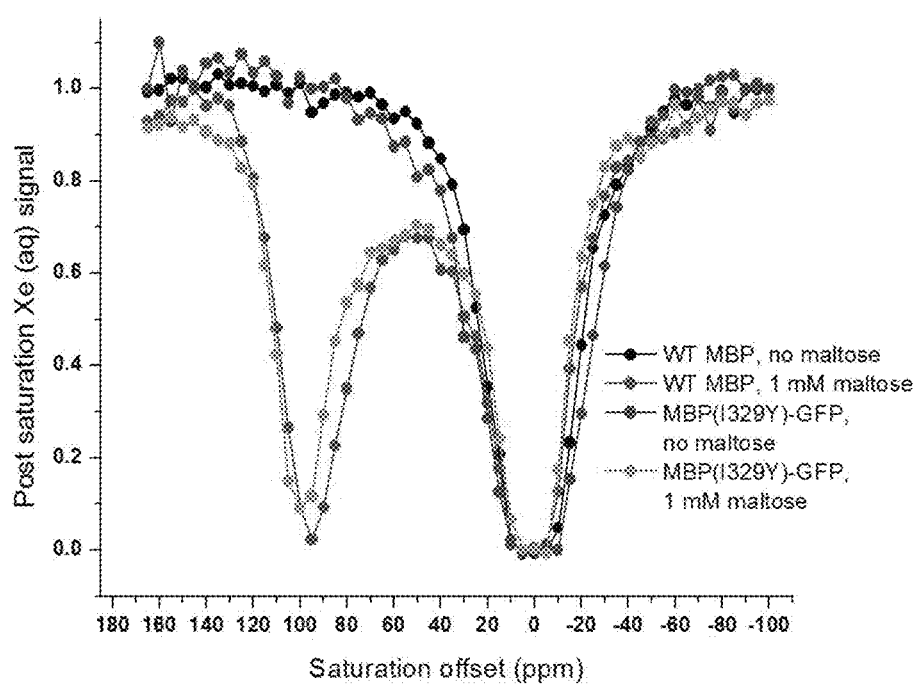
FIG. 46 depicts a comparison of CEST from WT MBP and MBP(I329Y)-GFP. Hyper-CEST z-spectra of 80 µM MBP(I329Y)-GFP with and without 1 mM maltose in pH 7.2 PBS at 300 K. The z-spectra of 80 µM WT MBP with and without 1 mM maltose shown for reference. Pulse length, $\tau_{pulse}$=3.8029 ms; field strength, $B_{1,max}$=77 µT.
Figures 47A, 47B:
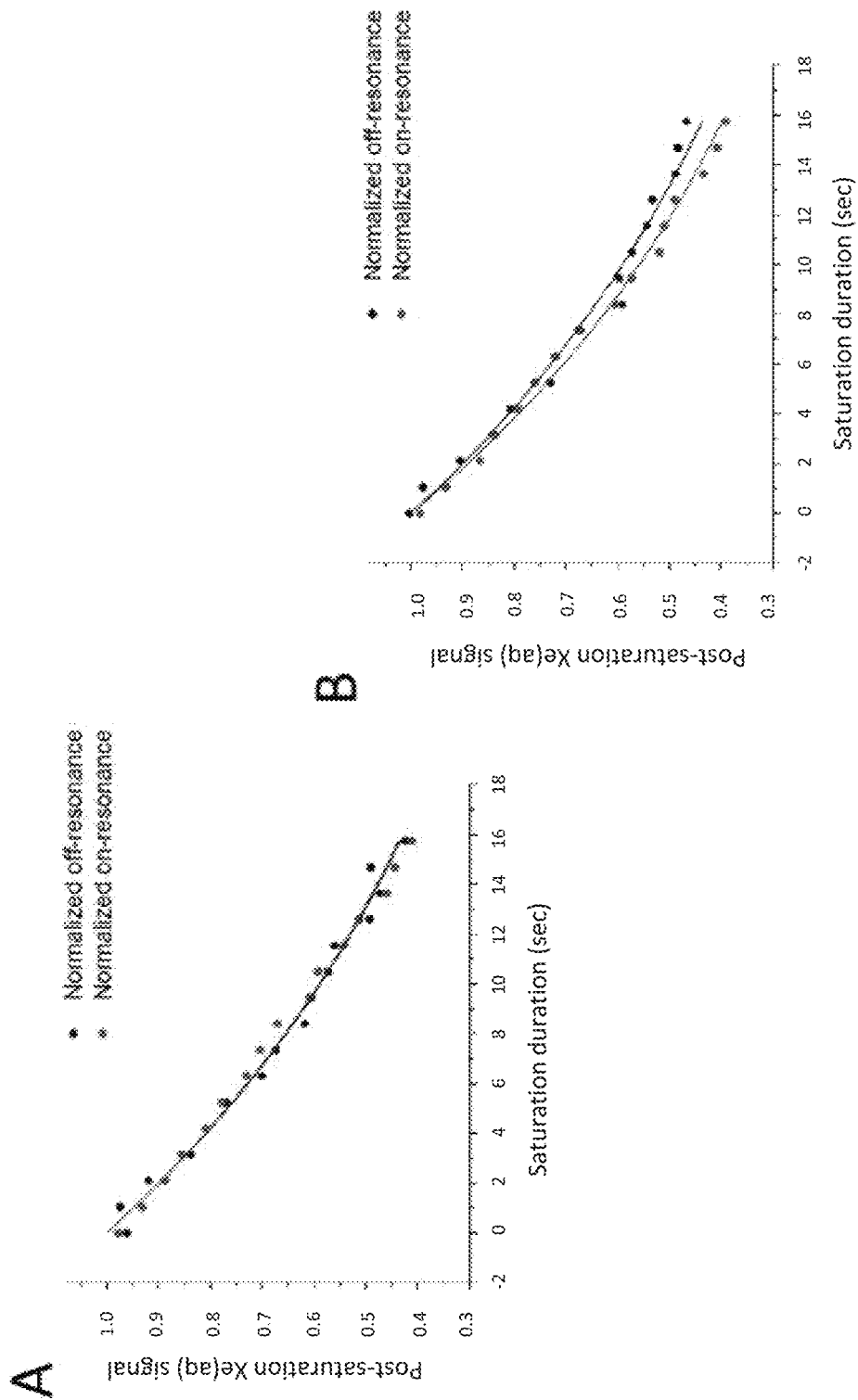
FIG. 47A through FIG. 47E, depicts time-dependent saturation transfer data for 100 nM MBP (I329Y)-GFP at varying concentrations of maltose.
Figure 47C:
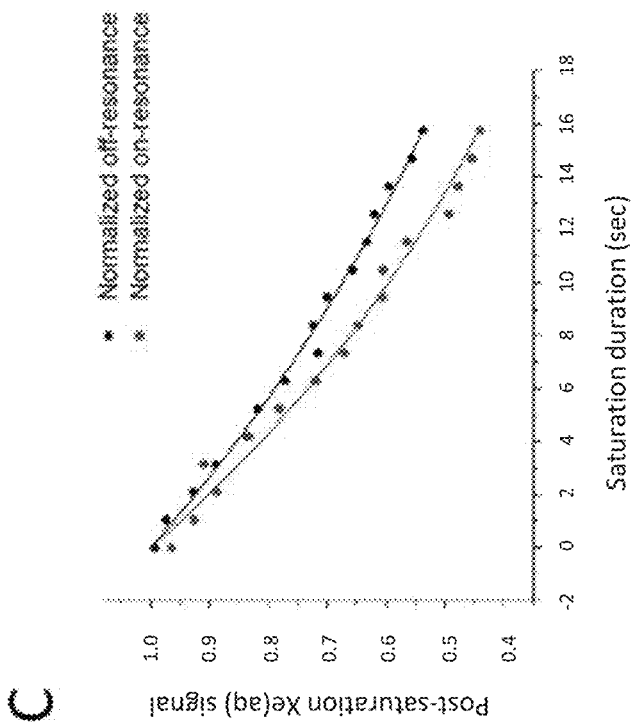
Figure 47D:
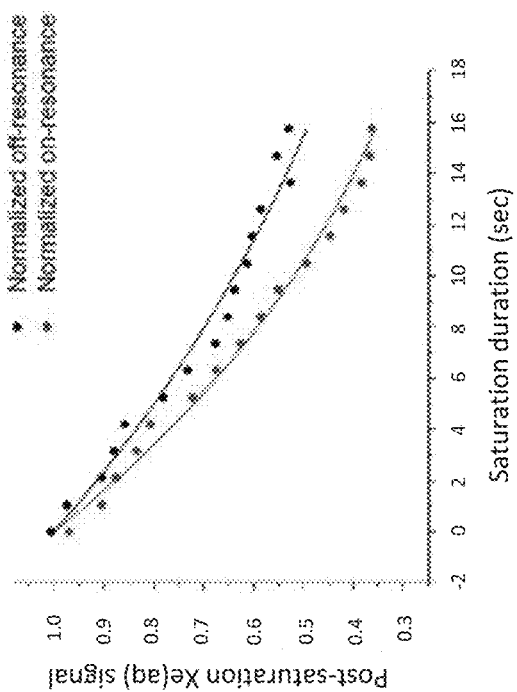
Figure 47E:
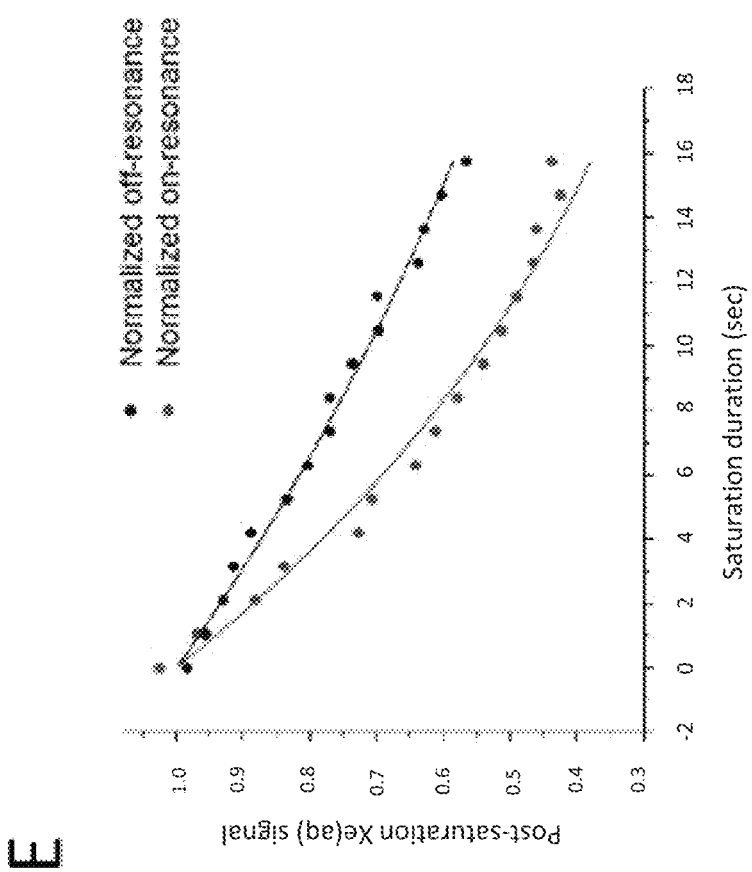

To extend the detection threshold of MBP, Ile-329 was mutated to Tyr to greatly increase maltose affinity ($K_d$=22 nM) (Seo et al., 2014, Nat. Commun., 2014, 5:3724). This mutation alters the conformational dynamics of MBP to disfavor the unliganded, open conformation, thereby promoting maltose binding through conformational coupling (Seo et al., 2014, Nat. Commun., 2014, 5:3724; Marvin and Hellinga, 2001, Nat. Struct. Biol., 8:795-798). Importantly, Ile-329 is located in a "hinge region" opposite the maltose-binding cleft, far enough away from the Xe-binding site to reasonably assume that mutations at this position should not affect Xe exchange. The I329Y mutation was introduced to MBP-GFP fusion construct to facilitate protein quantitation during cell studies (vide infra). The Xe hyper-CEST z-spectrum of MBP(I329Y)-GFP in the presence of 1 mM maltose is comparable to WT MBP (FIG. 46), though the saturation response of Xe@MBP(I329Y)-GFP is shifted 5 ppm downfield and is slightly attenuated compared to WT. Saturation contrast measurements for 100 nM MBP(I329Y)-GFP followed the same procedure used for WT MBP, but with the saturation frequencies of d-SNOB pulses positioned +100 ppm and −100 ppm (FIG. 47). As observed for WT MBP, saturation contrast was linearly proportional ($R^2$=0.997) to the percentage of MBP in the maltose-bound closed conformation (FIG. 45). The detection threshold for the I329Y mutant was 32 nM maltose, which gave rise to saturation contrast of 0.07±0.01. These saturation contrast data demonstrate that MBP can be "tuned" through mutagenesis to detect maltose across varying concentration ranges. High-affinity mutants such as I329Y can be employed for nM-tolow M maltose detection, whereas WT MBP can be used for low µM-to-mM maltose detection.

Hyper-CEST of MBP in E. coli

Figures 48A, 48B, 48C, 48D:
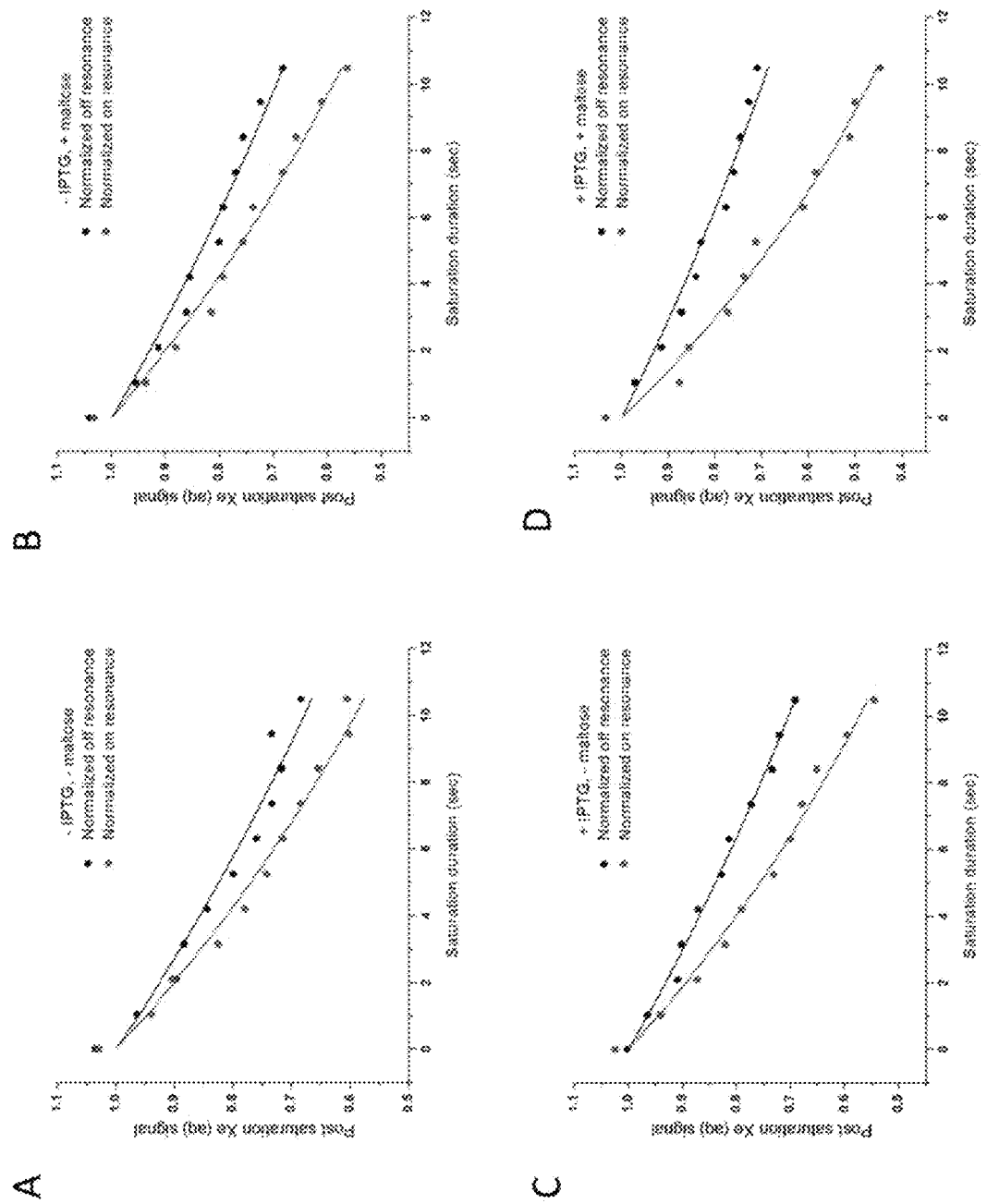
FIG. 48A through FIG. 48D, depicts time-dependent saturation transfer data for WT MBP-GFP in *E. coli*.

To evaluate the hyper-CEST contrast detectable from MBP in a cellular environment, MBP with a C-terminal GFP tag (MBP-GFP) was expressed in BL21(DE3) E. coli cells and time-dependent saturation transfer measurements were taken following the same protocol used for purified WT MBP (FIG. 48). Using the GFP tag, MBP concentration was quantified in real-time by fluorescence intensity at 510 nm ($\lambda_{ex}$=489 nm). E. coli growths not induced with IPTG served as controls to measure background contrast. Cells were washed with PBS and then transferred to an NMR tube for data collection. Control E. coli reported saturation contrasts of 0.11±0.01 and 0.09±0.01 with and without 1 mM maltose, respectively. Background contrast at 95 ppm downfield $Xe_{(aq)}$ likely arises from Xe exchanging with the hydrophobic interior of cellular membranes. E. coli expressing MBP in the presence of maltose reported 0.25±0.02 saturation contrast (Table 16), nearly five-fold higher than E. coli expressing MBP in the absence of maltose (0.14±0.01), after subtraction of background (0.11±0.01) from both. This highlights a mechanism for designing xenon-based MRI molecular imaging agents capable of detecting a specific analyte in cellular milieu.

TABLE 16

Hyper-CEST data for MBP in E. coli

| E. coli sample | $T_{1on}$ (s) | $T_{1off}$ (s) | Saturation contrast | [MBP-GFP] (µM)[a] |
|---|---|---|---|---|
| non-induced, no maltose | 19.1 ± 0.8 | 26 ± 2 | 0.09 ± 0.01 | <0.001 |
| non-induced, 1 mM maltose | 18.9 ± 0.8 | 28 ± 2 | 0.11 ± 0.01 | <0.001 |
| induced, no maltose | 17.9 ± 0.7 | 28.5 ± 0.8 | 0.14 ± 0.01 | 1 |
| induced, 1 mM maltose | 13.3 ± 0.6 | 8 ± 2 | 0.25 ± 0.02 | 1 |

[a]MBP-GFP concentration measured by fluorescence

CEST Contrast Dependence on MBP Conformation

Figure 49:
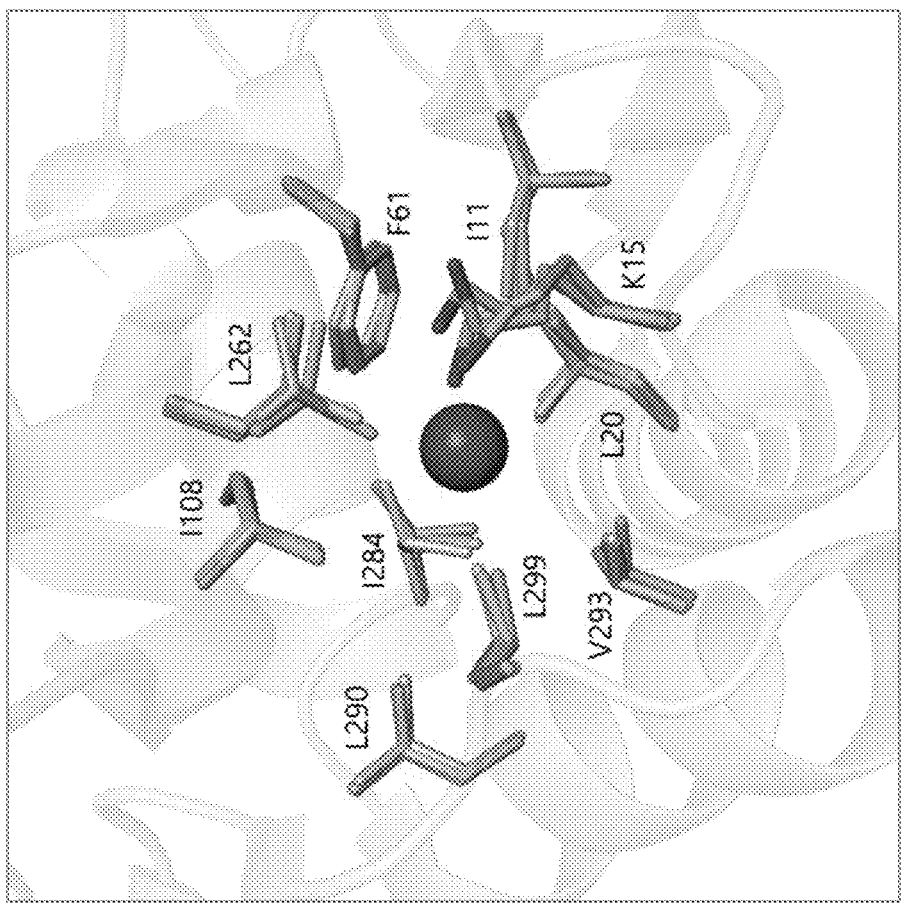
FIG. 49 depicts a comparison of the Xe-binding pocket in multiple MBP crystal structures. The conformations of the hydrophobic residues lining the pocket are conserved among $MBP_{open}$ (PDB ID 1OMP; Sharff et al., (1992) Biochemistry, 31:10657-10663, $MBP_{open}$ derivatized with Xe (PDB ID 1LLS; Rubin et al., (2002) J. Mol. Biol. 322:425-440), $MBP_{open}$ bound to βCD (PDB ID 1DMB; Sharff et al., (1993) Biochemistry, 32:10553-10559) and $MBP_{closed}$ bound to maltose (PDB ID 1ANF; Quiocho et al., (1997) Structure, 5:997-1015). There is slight variation, though, in the position of the terminal amine of Lys-15.

To ascertain whether hyper-CEST contrast with MBP results from the closed conformation induced by maltose binding or from sugar binding alone, the z-spectrum of MBP in the presence of β-cyclodextrin (βCD) was obtained (FIG. 32). βCD binds MBP with good affinity ($K_d$=1.8 µM) in the same cleft as maltose, but its larger size prevents MBP from adopting a closed conformation (Sharff et al., (1993) Biochemistry, 32:10553-10559). The z-spectrum of MBP with βCD shows no downfield saturation response, indicating that the maltose-bound closed conformation is required for producing hyper-CEST contrast. The lack of saturation contrast with MBP+βCD was unexpected given that Xe has higher affinity for MBP+βCD than MBP+maltose. Previous $^1$H-$^{15}$N HSQC NMR experiments measured a $K_a$ of 20±10 M$^1$ for Xe binding to MBP+βCD and concluded that $K_a$ was too low to measure for Xe binding to MBP+maltose: The addition of Xe to MBP+maltose produced no measurable changes in the $^1$H-$^{15}$N HSQC resonances (Rubin et al., 2002, J. Mol. Biol., 322:425-440). Indeed, the fact that the $Xe_{(aq)}$ peak is broadened more by βCD (FWHM=60 ppm) than by maltose (47 ppm) reveals a greater degree of Xe exchange with MBP+βCD than MBP+maltose (Table 15). The structural basis for a difference in Xe affinity is not obvious, however, as the contours of the Xe-binding cavity are largely conserved among several MBP complexes (FIG. 49). It therefore appears that the primary determinant of hyper-CEST contrast in MBP is rate of Xe exchange, not Xe affinity. Xe exchange is likely too fast (~MHz frequency) with $MBP_{open}$ (with or without βCD), but the binding of maltose and the conformational change to $MBP_{closed}$ slows the rate of Xe exchange to resolve a separate peak in the z-spectrum.

These experiments have demonstrated that 100 nM MBP generates significant saturation contrast in vitro and that observed contrast is proportional to % $MBP_{closed}$, thereby characterizing MBP as a "smart" analyte-sensitive biosensor. The I329Y MBP sensor at 100 nM concentration detected maltose in the range 32 nM to 5 M, whereas 100 nM WT MBP detected maltose in the range 100 nM to 1 mM. Notably, the large (+95 ppm)$^{129}$Xe NMR chemical shift was generated within the GE MBP molecule and did not require post-translational modification or cofactor such as a lanthanide or other paramagnetic shift agent. Additionally, WT MBP appended with GFP was readily detected at 1 µM via hyper-CEST NMR when expressed in E. coli. The large downfield shift of WT MBP (δ=95 ppm) makes it compatible with bla (δ=60 ppm) for multiplexing applications and ratiometric analysis. Notably, Xe-bla was cleanly detected in the multiplexing experiment with minimal crosstalk from Xe-MBP, by withholding maltose until Xe-MBP signal was desired. Experiments with I329Y MBP confirm 3-4 orders-of-magnitude higher small-molecule sensitivity than that achieved with available GE $T_1$ or $^1$H-CEST contrast agents. Indeed, nM maltose detection via MBP hyper-CEST NMR rivals the small-molecule detection sensitivity of many GE fluorescent sensors.

The increased contrast generated by V293A (and loss of contrast observed for V293L; see Example 3) confirms that MBP-CEST efficiency can be enhanced with mutations to the xenon binding site: coupling this with mutations promoting the maltose-bound, MBP-closed conformation (Seo et al., 2014, Nat. Commun., 5:3724; Marvin and Hellinga, 2011, Nat. Struct. Biol., 8:795-798) should yield a superior biosensor. Furthermore, the modulated saturation frequency of V293A (δ=36 ppm, shifted 59 ppm upfield from WT MBP) suggests that rational mutagenesis will yield MBP variants with a broad range of $^{129}$Xe NMR chemical shifts, akin to the palette of fluorescent proteins such as GFP and mCherry commonly used for multiplexed cellular imaging (Shaner et al., 2005, Nat. Methods, 2:905-909). Similar attempts to engineer bla through site-directed mutagenesis have so far failed to improve or modulate its CEST signal, which makes MBP a particularly versatile protein system for elucidating the hyper-CEST mechanism. Finally, MBP variants that have been engineered previously to bind different ligands (Guntas et al., 2005, Proc. Natl. Acad. Sci. U.S.A, 102:11224-11229; Marvin and Hellinga, 2001, Proc. Natl. Acad. Sci. U.S.A, 98:4955-4960) highlight the exciting potential for employing MBP-enhanced $^{129}$Xe NMR/MRI to detect bioactive molecules present in mammalian cells.

Example 5: Zinc Sensor

Figure 50:
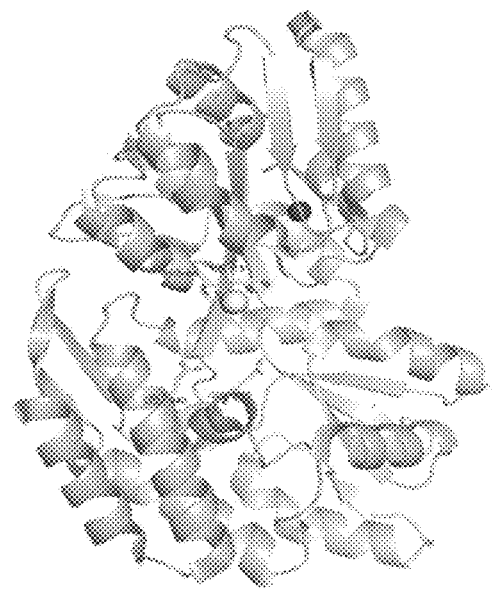
FIG. 50 illustrates that MBP-based zinc sensor binds $Zn^{2+}$ in its open conformation. The structure contains multiple engineered metal binding ligands; central sphere: $Zn^{2+}$; upper sphere: potential Xe binding site.

Zinc biosensors were developed based on maltose binding protein (MBP) by protein engineering (Marvin et al., 2001, Proc Natl Acad Sci USA, 98:4955-4960). Four key residues at maltose binding site (A63, R66, Y155, W340) were mutated to convert the specificity of MBP. Additional mutations at the hinge region (A96, I329) and ligand binding cleft (E111, K15) of MBP may be helpful to improve Hyper-CEST signal. The crystal structure of an MBP-based zinc sensor (MBP-A63H/R66H/E111M/Y155E/W340E) (Telmer et al., 2005, J Mol Biol, 354:829-840 is shown in FIG. 50, with a potential Xe site indicated. In order to serve as a $^{129}$Xe MRI contrast agent, MBP-based zinc sensor is expected to undergo a conformational change similar to MBP when binding its substrate.

All zinc sensor variants (ZSFs) constructed to date are listed in Table 17 with their $Zn^{2+}$ affinity (measured by ITC).

TABLE 17

Zinc sensors and their $Zn^{2+}$ binding affinity

| Name | Mutations to MBP | $K_d$ for $Zn^{2+}/\mu M$ |
|---|---|---|
| ZSF | A63H/R66H/Y155E/W340E/I329F | 1.43 ± 0.15 |
| ZSF-A96F | A63H/R66H/Y155E/W340E/A96F/I329F | 3.13 ± 0.16 |
| ZSF-His$_2$GluCys | A63H/R66H/Y155E/W340C/I329F | 6.62 ± 0.64 |
| ZSF-His$_2$Cys$_2$ | A63H/R66H/Y155C/W340C/I329F | 13.74 ± 3.30 |
| ZSF-His$_3$Glu | A63H/R66H/Y155H/W340E/I329F | 0.36 ± 0.13 |
| ZSF-His$_4$ | A63H/R66H/Y155H/W340H/I329F | 6.06 ± 1.59 |

Figure 51:
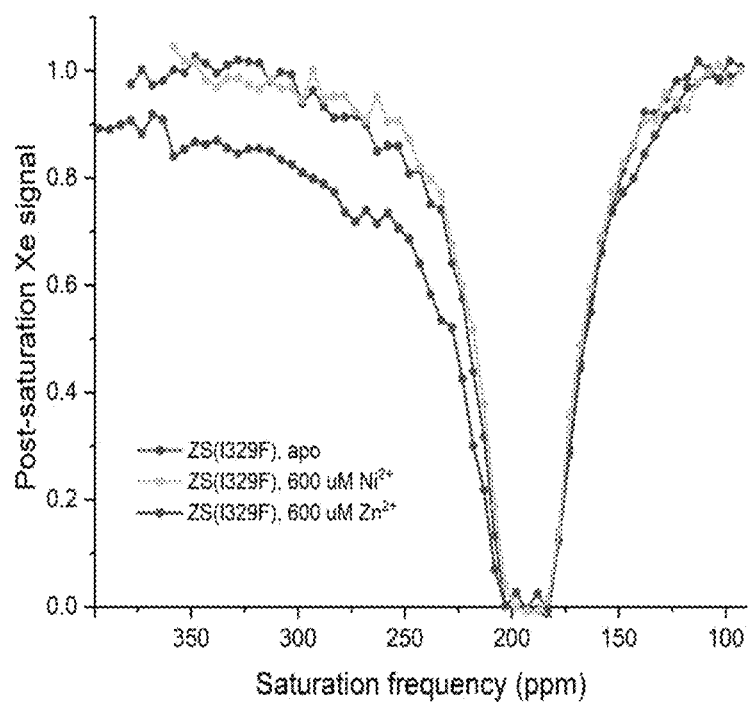
FIG. 51 depicts z-spectra of 80 µM ZSF in 20 mM Tris, pH 7.4 buffer, in absence and presence of $Ni^{2+}$ and $Zn^{2+}$.

The first version, ZSF, had no detectable affinity for maltose and cellularly abundant $Ca^{2+}$ and $Mg^{2+}$. However, it had comparable affinity for other transition metals, such as $Ni^{2+}$ (3.75±0.16 μM) and $Fe^{3+}$ (2.22±0.52 μM). Despite its affinity for other transition metals, ZSF only showed CEST effect with zinc binding (FIG. 51). Without being bound by theory, it is hypothesized that this is probably due to different conformations of the protein sensor.

Figure 52:
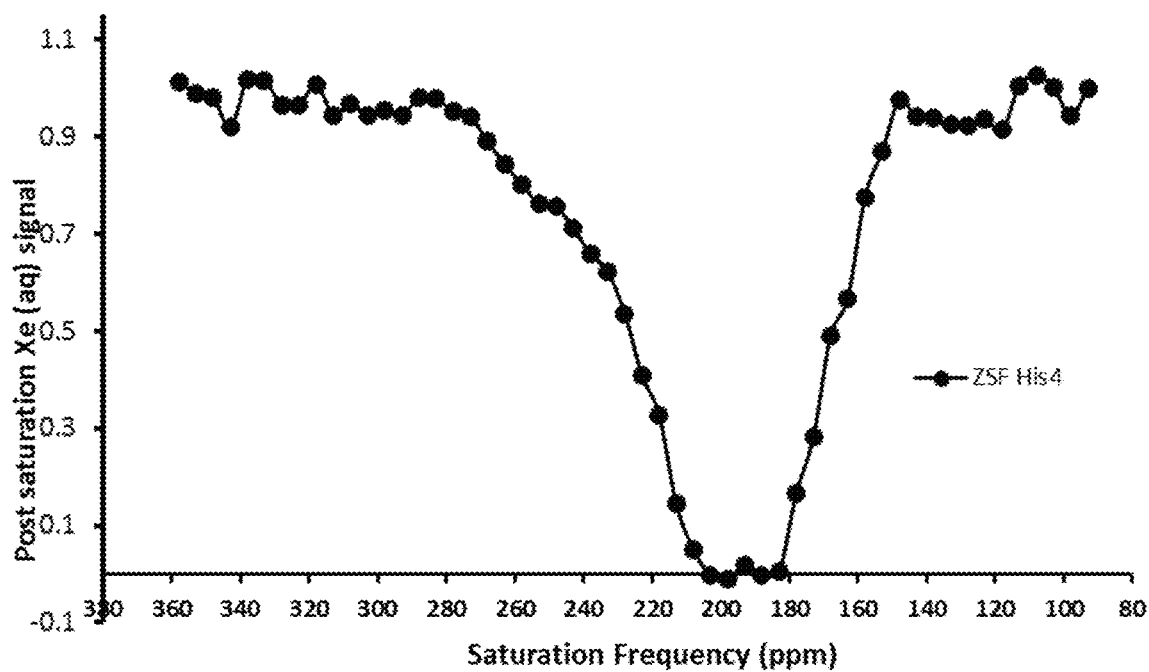
FIG. 52 depicts z-spectra of 80 µM ZSF-His$_4$ in 20 mM Tris, 100 mM NaCl, pH 7.4 buffer, in presence of 400 µM $Zn^{2+}$.

The Xe@aq peaks of other zinc sensors did look asymmetric to some degree, indicating a weak CEST effect (FIG. 52).

To further improve the CEST signal, mutations (L262M, D14C/W230C) that constrict Xe exchange pathways are also envisioned.

Example 6: Ribose Binding Protein

Ribose binding protein (RBP), like MBP, is a member of the periplasmic binding protein (PBP) superfamily and mediates ribose import and chemotaxis in gram-negative bacteria (Bjorkman et al., 1994, J. Biol. Chem, 269:30206-30211). RBP from *E. coli* binds ribose with high affinity ($K_d$=130 nM) (Willis and Furlong, (1974) J. Biol. Chem. 249:6926-6929) in a hinge region between two globular lobes. In the absence of ribose, RBP exists in an open conformation, but upon binding ribose RBP adopts a closed conformation. As with other PBPs (Moschou et al., 2006, Anal. Chem. 2006, 78 (19), 6692-6700; Advances in Chemical Bioanalysis; Grunewald, 2013, Springer International Publishing: Cham, Vol. 6, pp 205-235), RBP's ligand selectivity has made it a popular platform for biosensing applications. Lager and coworkers developed an optical biosensor for ribose by attaching fluorescent proteins to the N- and C-termini of RBP and monitoring ribose binding via changes in FRET fluorescence (Lager et al., 2003, FEBS Lett, 553:85-89). Similarly, a fluorescent probe attached to the hinge region of RBP was shown to effectively transduce ribose binding into optical contrast (Vercillo et al., 2007, Protein Sci, 16:362-368). Interest in ribose biosensors is motivated by ribose's involvement in metabolism and disease. Extracellular free ribose is imported into mammalian cells through a process known as "ribose salvage", where it is then phosphorylated to ribose-5-phosphate before entering either the nucleotide synthesis or pentose-phosphate pathways (Barsotti and Ipata, 2002, Biochem. Pharmacol, 63:117-122; Park et al., 2007, FEBS Lett, 581:3211-3216).

Without being bound by theory, it has been hypothesized that different cell types and cancer cells utilize ribose salvage to provide precursors for distinct cellular pathways (Clark et al., 2014, Proc. Natl. Acad. Sci. U.S.A 111:E2866-E2874). The ability to monitor free ribose concentration in vivo would be a useful tool for understanding the association between ribose salvage and cell metabolism in healthy and diseased states.

Figure 53:
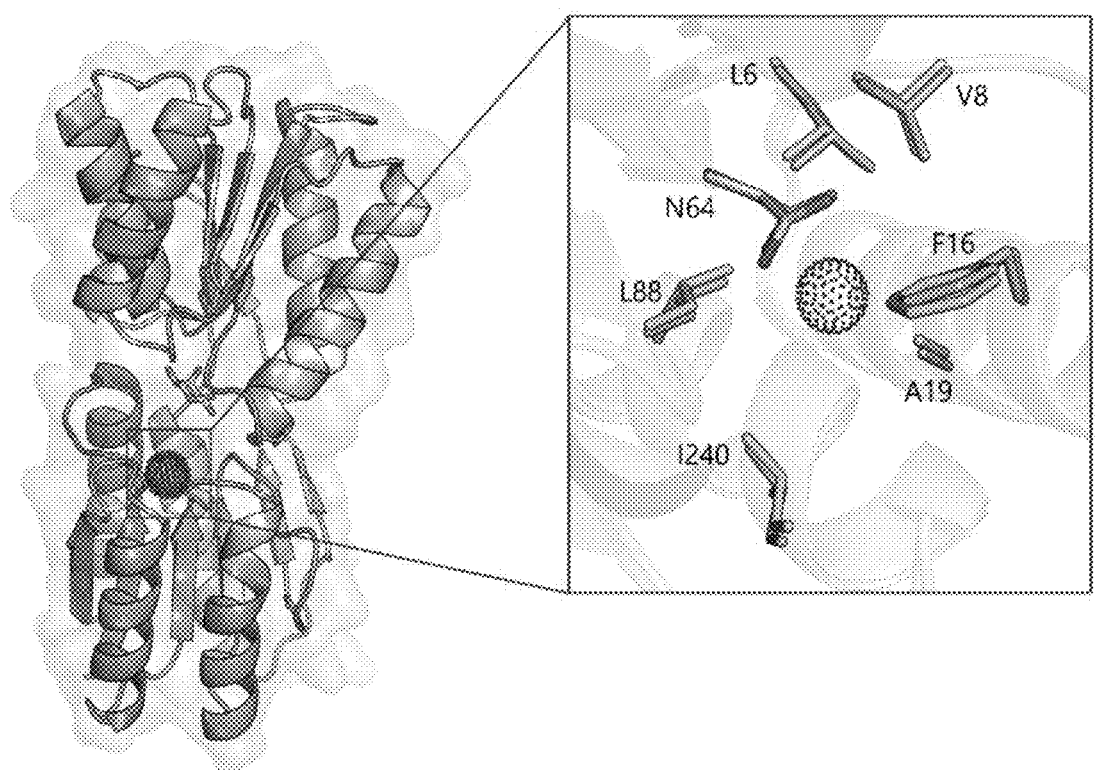
FIG. 53 depicts the purported Xe binding site in RBP (L19A). The protein model is based on the crystal structure of ribose-bound wild-type RBP in its closed conformation (PDB ID 2DRI; Bjorkman et al., (1994) J. Biol. Chem. 269:30206-30211). Xe was modeled at the center of the cavity created by the L19A mutation. Bound ribose shown as sticks. (Inset) Close-up view of the Xe binding site of RBP(L19A) in its closed and open (PDB ID 1URP; Bjorkman et al., (1998) J. Mol. Biol. 279:651-664) conformations. Open and closed RBP structures were aligned from residues 1 to 100 using PyMOL.

A xenon binding site has been previously engineered into RBP through a leucine-to-alanine truncation at residue 19 (FIG. 53) (Lowery et al., (2004) Angew. Chem. Int. Ed. Engl, 43:6320-6322). $^1$H-$^{15}$N HSQC NMR experiments determined the xenon binding affinities of open and closed RBP(L19A) to be 70±30 $M^{-1}$ and 40±20 M-1, respectively. Direct detection Xe NMR experiments showed that the chemical shift of Xe is sensitive to the conformational state of RBP(L19A) and, therefore, to the presence or absence of ribose in solution. This prior work, along with RBP's structural similarity to MBP, motivated us to develop RBP as a genetically encoded hyper-CEST biosensor for ribose.

The materials and methods employed in these experiments are now described.

A codon-optimized gene encoding *E. coli* RBP (UniProt ID P02925) incorporating the L19A mutation was obtained. The RBP(L19A) gene was then cloned into a pET expression vector encoding an N-terminal His6-GFP tag Addgene plasmid no. 29663. GFP-RBP was expressed and purified following a protocol similar to the one used to prepare MBP. The GFP-RBP plasmid was transformed into BL21(DE3) competent *E. coli* cells (New England Biolabs) and grown in 6×1 L of LB media supplemented with 50 μg/mL kanamycin to an $OD_{600}$ of ~1. Protein expression was induced by adding isopropyl-β-D-thiogalactopyranoside (IPTG) to a final concentration of 1 mM. The induced cells were incubated overnight at 18° C., harvested by centrifugation, then frozen at −80° C.

Figure 54:
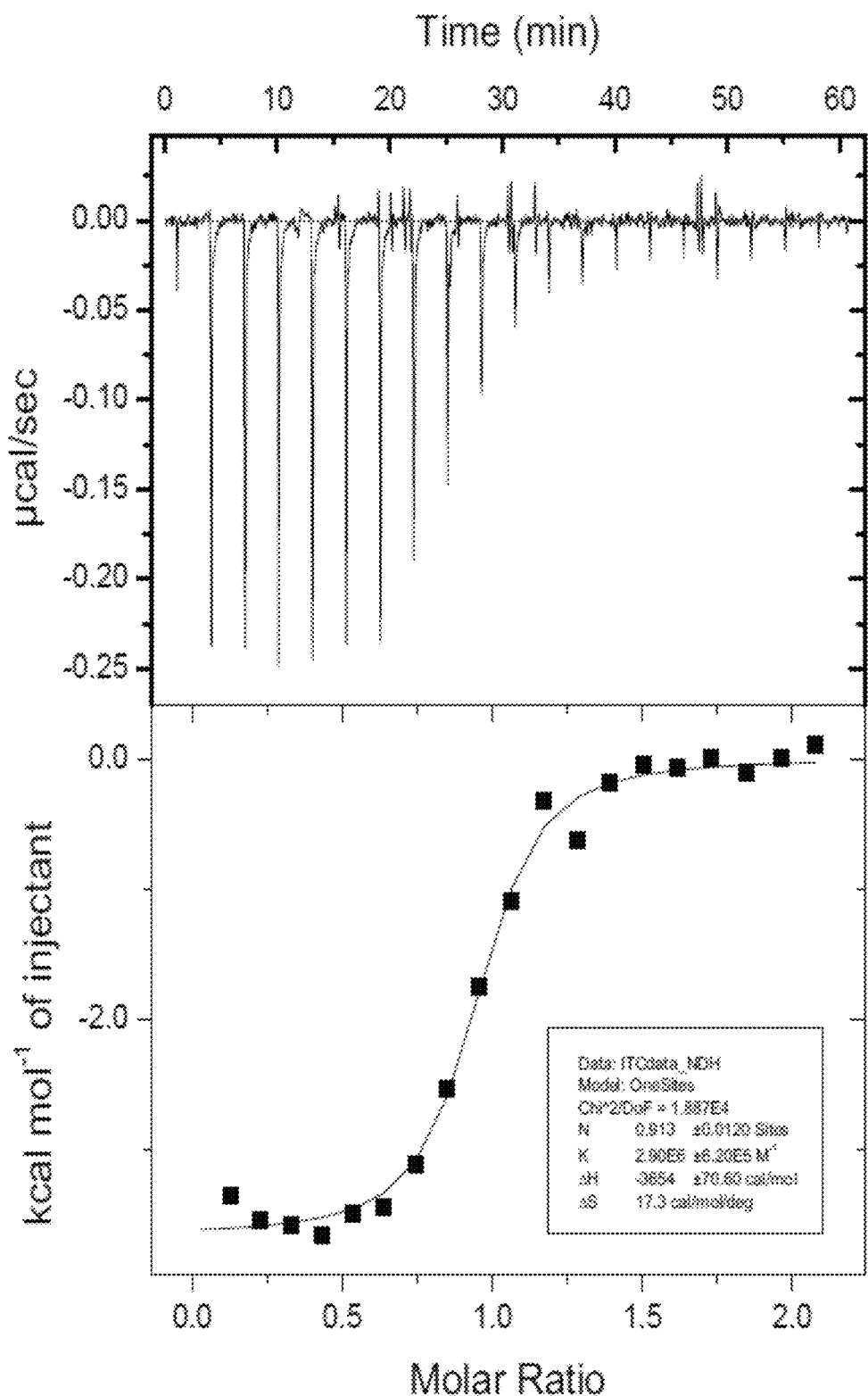
FIG. 54 depicts an enthalpogram of ribose binding to GFP-RBP(L19A) measured by ITC. ITC was performed at 298 K in PBS.

The cell pellet was resuspended in 20 mM sodium phosphate (pH 7.4), lysed with lysozyme (Sigma), and treated with benzonase nuclease (Sigma). After stirring the lysate at room temperature for 30 minutes, NaCl was added to 0.5 M and imidazole was added to 20 mM. The lysate was clarified by centrifugation, and the supernatant was loaded onto a HisTrap nickel affinity column (GE Life Sciences) pre-equilibrated with 20 mM sodium phosphate (pH 7.4), 0.5 M NaCl, 20 mM imidazole. The column was washed with 20 column volumes (CVs) of 20 mM sodium phosphate (pH 7.4), 0.5 M NaCl, 20 mM imidazole, 8 M urea to unfold GFP-RBP(L19A) and remove bound ribose. GFP-RBP (L19A) was refolded via a 12 CV gradient to 20 mM sodium phosphate (pH 7.4), 0.5 M NaCl, 20 mM imidazole. GFP-RBP(L19A) was eluted from the column with 20 mM sodium phosphate (pH 7.4), 0.5 M NaCl, 500 mM imidazole. The eluate was concentrated and further purified by size-exclusion chromatography in PBS (HyClone) using a HiLoad 16/600 Superdex column (GE Life Sciences). Fractions containing pure protein (over 95% as indicated by SDS-PAGE) were pooled and concentrated. Protein concentration was determined from measuring the absorbance at 280 nm using the extinction coefficient $\varepsilon_{280}$=27 850 $M^{-1}$ $cm^{-1}$ calculated by the PROTPARAM server. Protein concentration was confirmed by Bradford Assay. The integrity of GFP-RBP(L19A) and binding affinity for ribose was validated by ITC (FIG. 54). ITC was performed by titrating 300 μM ribose into 30 μM GFP-RBP(L19A). ITC was conducted at 298 K in PBS using a MicroCal ITC 200 instrument (GE Healthcare).

The L19V mutation was introduced to the GFP-RBP (L19A) gene via site-directed mutagenesis using the forward and reverse primers listed in Table 18. The mutated plasmid was amplified in NEB-5α competent cells (New England Biolabs) and then purified using a miniprep kit (New England Biolabs). The mutated gene was sequenced to verify the incorporation of the L19V mutation and the integrity of the entire gene sequence.

TABLE 18

Oligonucleotide primers used in site-directed mutagenesis of RBP

| L19V | Forward primer | 5'-GTTCTTTGTCTCTGTGAAGGACGGCGCGC-3' (SEQ ID NO: 41) |
|---|---|---|
| | Reverse primer | 5'-GCGCGCCGTCCTTCACAGAGACAAAGAAC-3' (SEQ ID NO: 42) |

The results of the experiments are now described.

Figure 55:
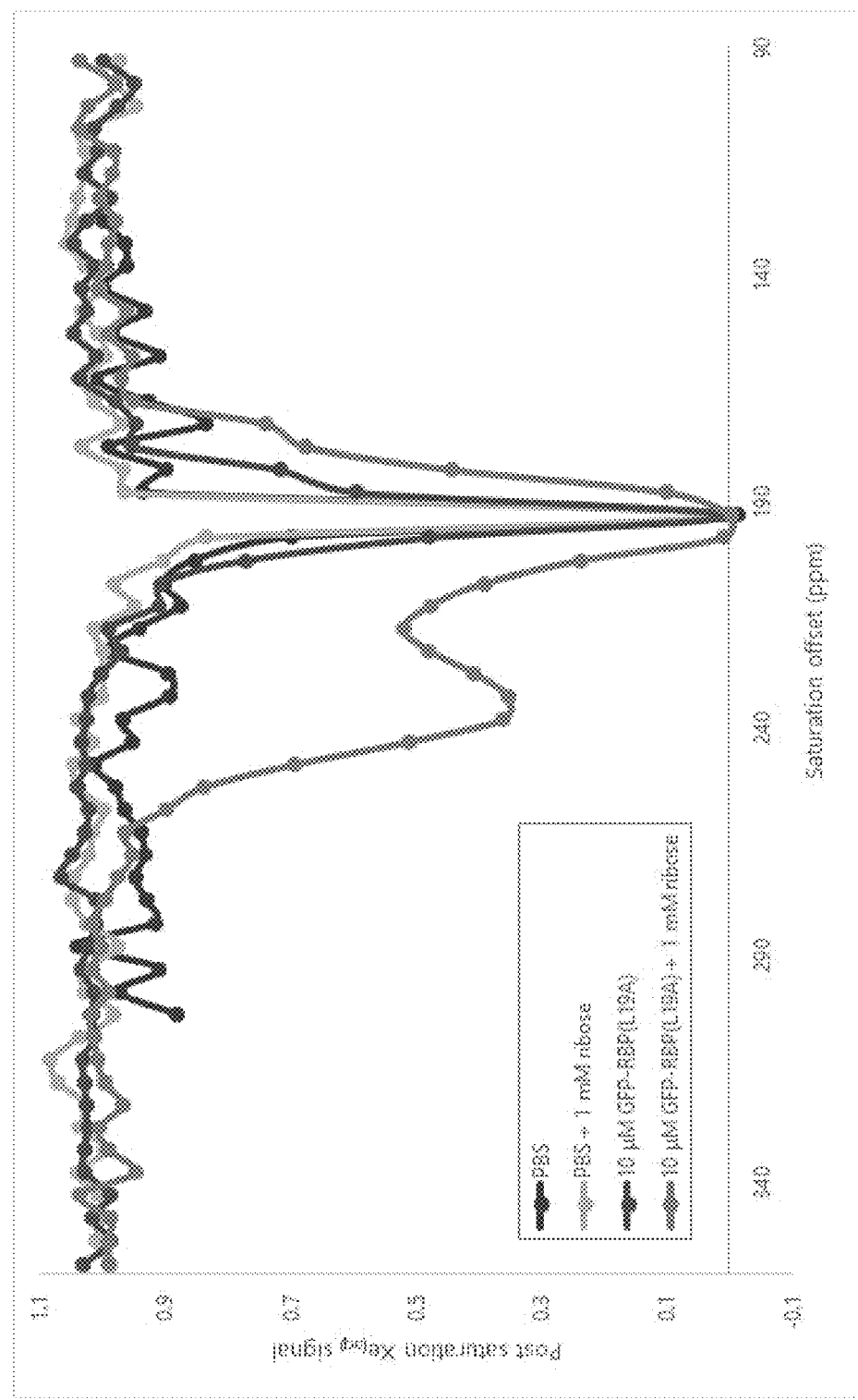
FIG. 55 depicts a hyper-CEST z-spectra of 10 µM GFP-RBP(L19A) with and without 1 mM ribose in pH 7.2 PBS at 300 K. The z-spectra of PBS with and without ribose is shown for reference.

To evaluate whether GFP-RBP(L19A) reports any Xe hyper-CEST contrast, a hyper-CEST z-spectrum was acquired from 10 μM GFP-RBP(L19A) in the presence and absence of ribose. Multiple selective Dsnob-shaped saturation pulses were scanned over the chemical shift range of 93-358 ppm in 5 ppm steps, and the $^{129}Xe_{(aq)}$ signal was measured as a function of saturation pulse offset (FIG. 55). Unliganded GFP-RBP(L19A) showed only a single saturation response at ~195 ppm, corresponding to free $^{129}Xe_{(aq)}$ in solution. However, in the presence of 1 mM ribose, the z-spectrum of GFP-RBP(L19A) shows two peaks—the first at ~195 ppm corresponding to $^{129}Xe_{(aq)}$, and the second at ~235 ppm corresponding to $^{129}Xe$ exchange with ribose-bound RBP(L19A).

Figure 56:
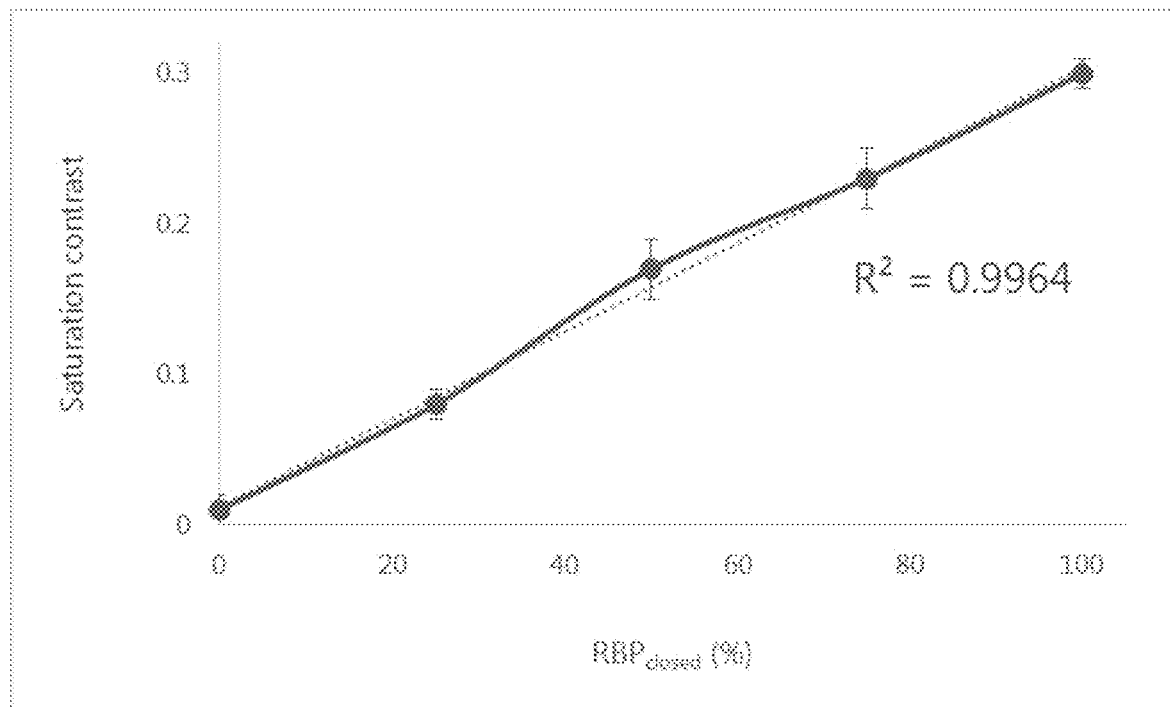
FIG. 56 depicts the saturation contrast for 100 nM GFP-RBP(L19A) as a function of percent RBP in ribose-bound closed conformation. [Ribose]=0 nM, 150 nM, 350 nM, 975 nM, and 1 mM.

To assess the detection sensitivity of GFP-RBP(L19A), time-dependent saturation transfer experiments were performed by measuring $Xe_{(aq)}$ polarization as a function of saturation time. Shaped saturation pulses were applied at the chemical shift of Xe@RBP(L19A)$_{closed}$, and the residual aqueous $^{129}Xe$ signal after saturation transfer was measured as an on-resonance CEST response. Saturation frequencies of $D_{snob}$-shaped pulses were positioned at +42.5 and −42.5 ppm, referenced to the $Xe_{(aq)}$ peak, for on- and off-resonance, respectively. The pulse length was 1.727 ms, and the field strength was 170 μT. The normalized difference between on- and off-resonance signals was represented by the saturation contrast. Using this method, 100 nM GFP-RBP(L19A) reported a maximum of 0.30±0.01 saturation contrast, comparable to the contrast reported by 100 nM MBP$_{closed}$ and 100 nM TEM-1 β-lactamase. Measuring saturation contrast as a function of percent RBP(L19A) it its closed conformation showed a linear relationship (FIG. 56), indicating that GFP-RBP(L19A) can serve as a ribose biosensor in the high-nanomolar to low-micromolar range.

Figure 57:
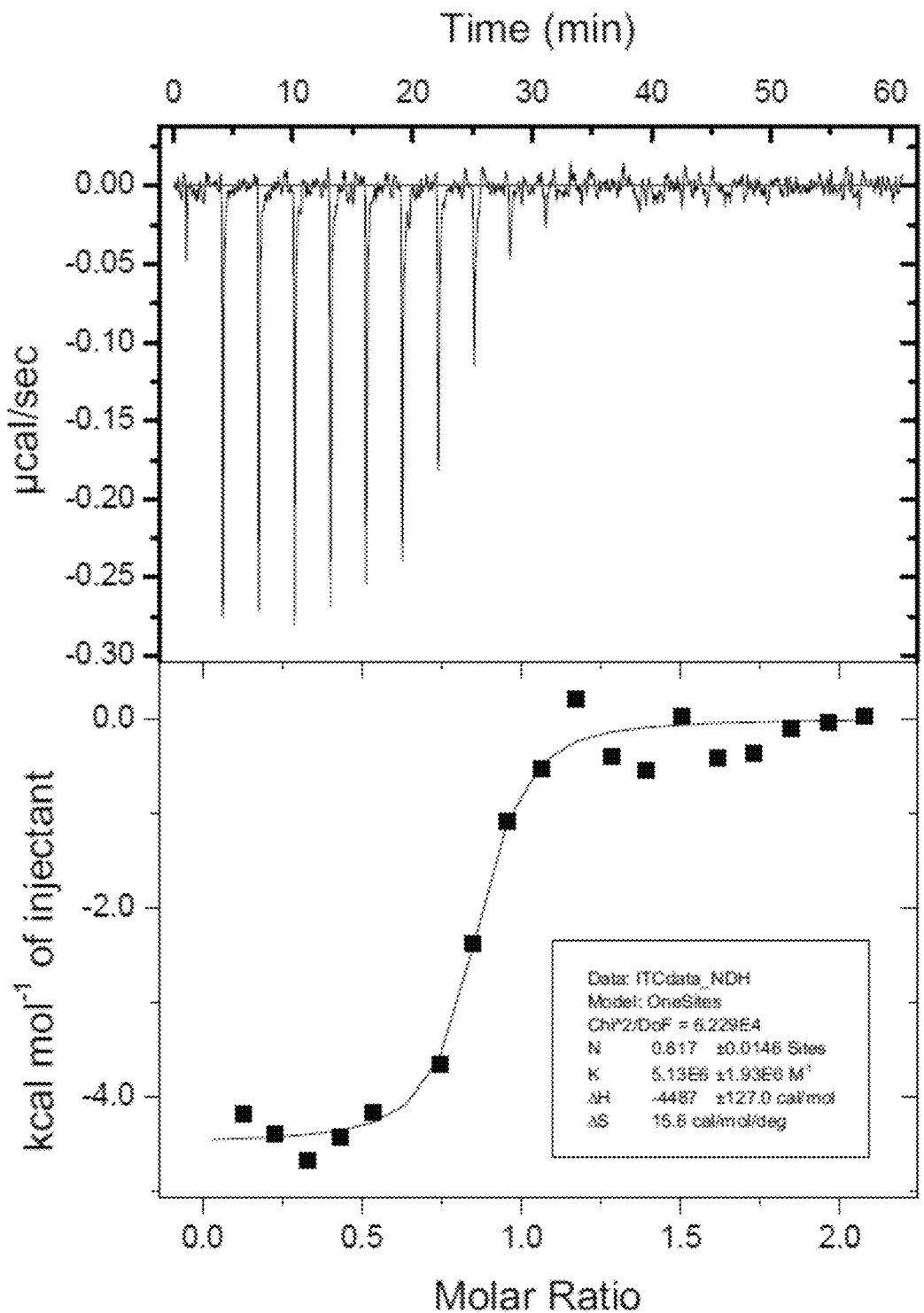
FIG. 57 depicts an enthalpogram of ribose binding to GFP-RBP(L19V) measured by ITC. ITC was performed at 298 K in PBS.
Figure 58:
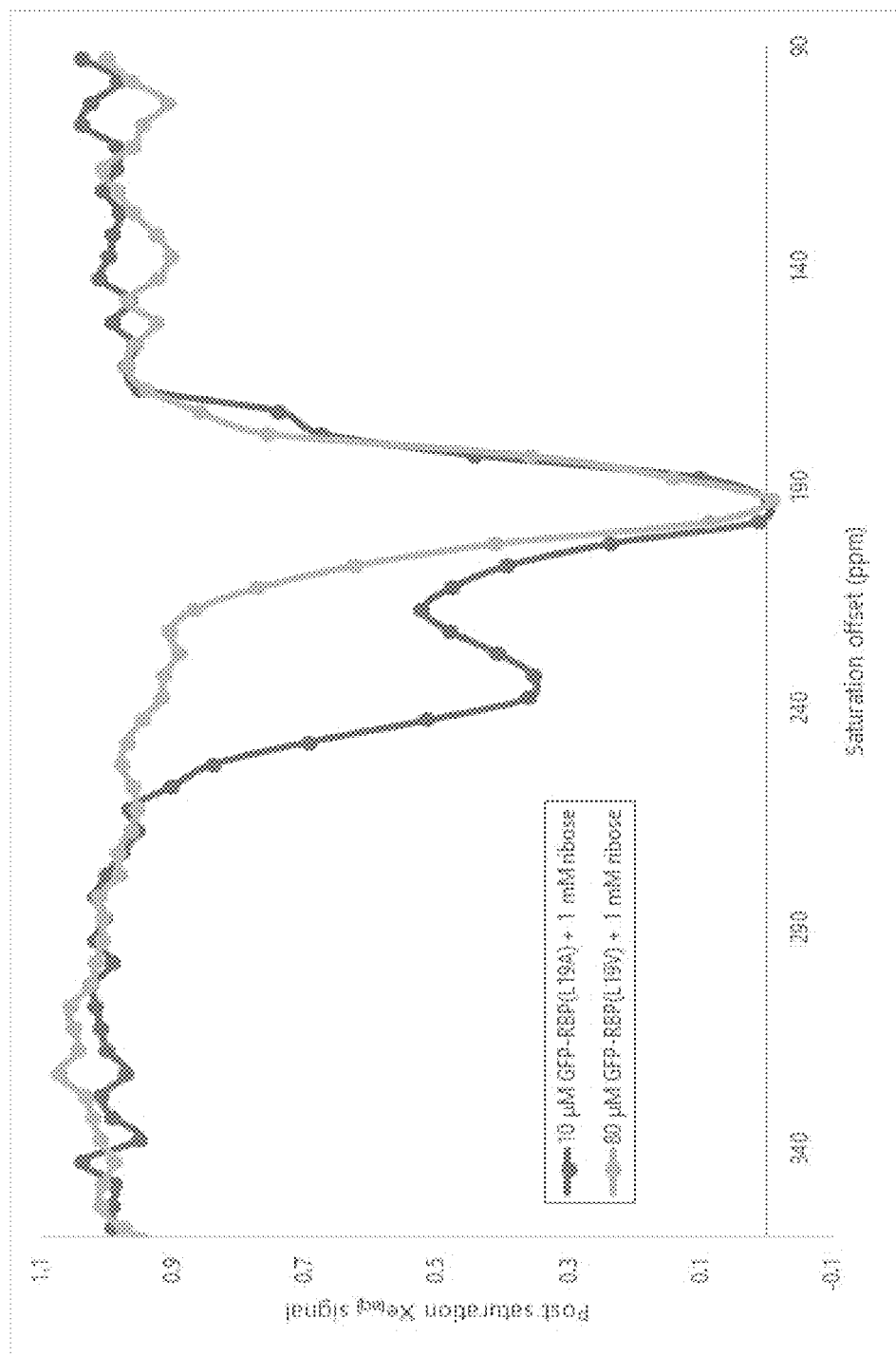
FIG. 58 depicts a hyper-CEST z-spectrum of 80 µM GFP-RBP(L19V) with 1 mM ribose in pH 7.2 PBS at 300 K. The z-spectrum of 10 µM GFP-RBP(L19A) with 1 mM ribose shown for reference.

To ascertain whether CEST contrast originates from the Xe cavity engineered via the L19A mutation, the GFP-RBP (L19V) mutant was prepared via site-directed mutagenesis. It was expected that reducing the cavity volume would either modulate the chemical shift of saturation contrast or block Xe binding entirely. The GFP-RBP(L19V) mutant was expressed and purified following the same procedure used to prepare GFP-RBP(L19A). As before, ITC was performed to validate the integrity of the purified protein (FIG. 57). Notably, the z-spectrum of 80 μM GFP-RBP(L19V) shows no downfield saturation contrast, indicating that the cavity created by the L19A is indeed responsible for generating the MR contrast observed by Xe hyper-CEST.

Biosensing Prospects with Other PBPs

Figure 59:
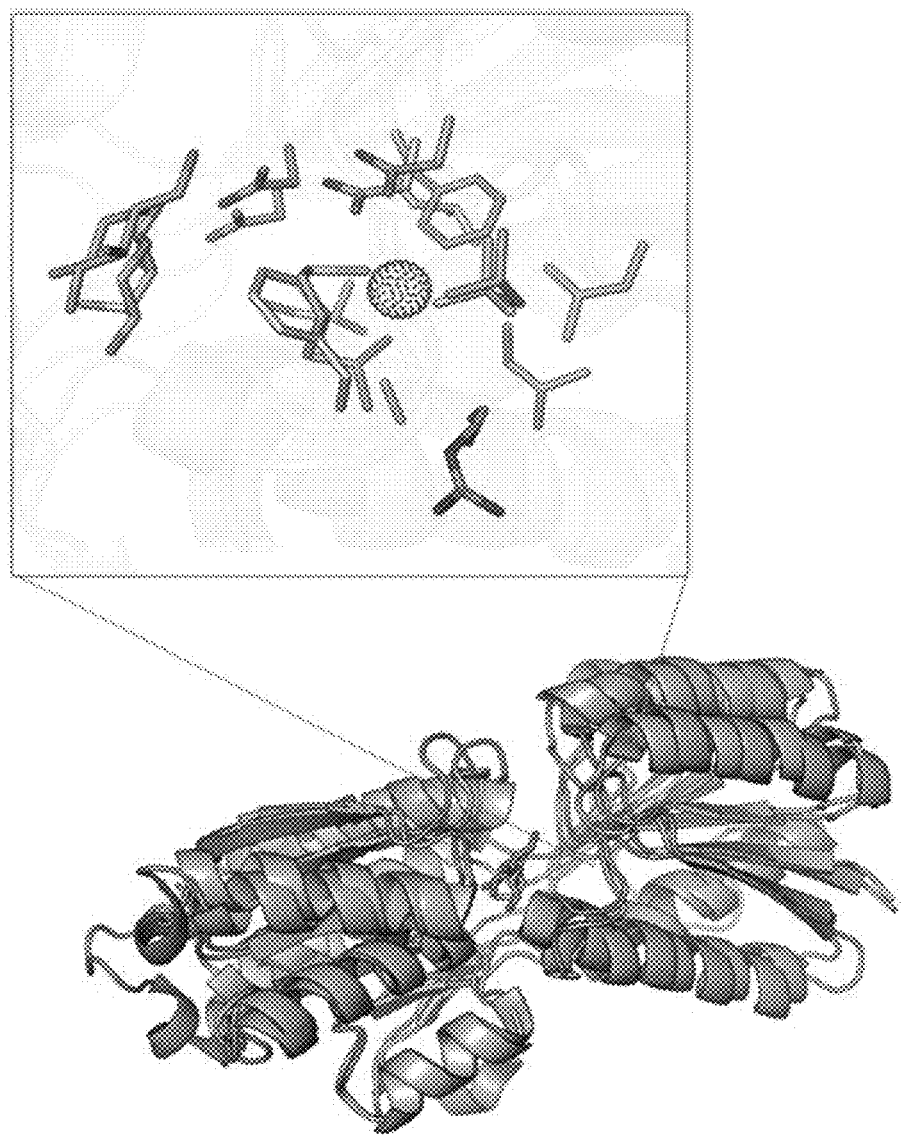
FIG. 59 depicts a comparison of ribose binding protein (RBP) and glucose/galactose binding protein (GGBP). Ribose-bound RBP with a L19A truncation (PDB ID 2DRI) and glucose-bound GGBP (PDB ID 2FVY; Borrok et al., (2007) Protein Sci. 16:1032-1041). (Inset) Close-up view of the purported Xe binding site of RBP(L19A), with the center of the cavity indicated with dots. GGBP side chains shown for comparison.

The periplasmic binding proteins (PBPs) share a common fold, consisting of a ligand-binding hinge region located between two globular domains (Dwyer and Hellinga, 2004, Curr. Opin. Struct. Biol. 14:495-504). The PBPs can be divided into two subclasses depending on the topological arrangement of the central β-sheet in their core structures (Fukami-Kobayashi et al., 1999, J. Mol. Biol. 286:279-290). Hyper-CEST contrast has been observed from both class I (RBP) and class II (MBP) PBPs. It is thus expected that other members of the PBP family can be engineered to serve as Xe hyper-CEST biosensors. For example, glucose/galactose binding protein from *E. coli* (GGBP; UniProt ID P0AEE5) is a class I PBP whose structure is nearly identical to RBP (rmsd=1.8 Å) (FIG. 59). It is likely that a Xe cavity can be engineered into the protein near the ligand binding cleft following the same rational-design strategy used for RBP.

The range of analytes detectable by PBP-based biosensors can be expanded even further by mutating the active sites of naturally-occurring PBPs. Several approaches for altering protein specificity are well-established, including computational design and directed evolution (Antikainen and Martin, 2005, Bioorg. Med. Chem. 13:2701-2716). By these methods, MBP has been converted to bind zinc (Marvin and Hellinga, 2001, Proc. Natl. Acad. Sci. U.S.A 98:4955-4960) as well as sucrose (Guntas et al., 2005, Proc. Natl. Acad. Sci. U.S.A 102:11224-11229). Moreover, the in silico approach has been extended to remodel the ligand-binding pockets of other PBPs, including ribose binding protein, glucose/galactose binding protein, arabinose binding protein, glutamine binding protein, and histidine binding protein (Looger et al., 2003, Nature 423:185-190). The ligand-binding pockets of these five PBPs were redesigned to bind trinitrotoluene (TNT), L-lactate, or serotonin instead of the natural sugar or amino-acid ligand. Collectively, these examples demonstrate the versatility of PBPs as a platform for biosensing exotic, non-natural ligands.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An 129Xe NMR imaging agent comprising one or more protein reporters selected from the group consisting of TEM-1 β-lactamase (bla), and a mutant of bla, wherein the mutant of bla comprises a point mutation located at a residue selected from the group consisting of 1263, 1279, 1282, M182 and a combination thereof.

2. The imaging agent of claim 1, wherein the one or more protein reporters comprise an amino acid sequence selected from the group consisting of SEQ ID NO: 1, SEQ ID NO: 2, SEQ ID NO: 3, SEQ ID NO: 4, SEQ ID NO: 5, and SEQ ID NO: 6.

3. The imaging agent of claim 1, wherein the one or more protein reporters comprise a targeting domain that binds to a biomolecule of interest.

4. A method of 129Xe NMR imaging comprising the steps of:
  a. administering to a cell or subject a 129Xe NMR imaging agent comprising one or more protein reporters selected from the group consisting of bla and a mutant of bla, wherein the mutant of bla comprises a point mutation located at a residue selected from the group consisting of I263, I279, I282, M182 and a combination thereof;
  b. administering hyperpolarized xenon to the cell or subject;
  c. obtaining magnetic resonance data of a target site of the cell or subject; and
  d. analyzing the data to produce a magnetic resonance image of the target site.

5. The method of claim 4, wherein the method further comprises administering a saturating radio frequency pulse to the target site.

6. The method of claim 4, wherein the data comprises a chemical shift of about 60 ppm indicating the presence and location of said bla or said mutant of bla at the target site.

7. The method of claim 4, wherein the protein reporter is administered at a concentration in the range of about 0.001 µM 100 µM.

8. The method of claim 4, wherein the cell is in an in vitro or ex vivo environment.

9. The method of claim 4, wherein the subject is a mammal.

10. The method of claim 4, wherein the protein reporter further comprises a targeting domain that binds a biomolecule of interest.

11. The method of claim 4, wherein the method is used to detect the presence of a tumor in the subject.

* * * * *